US008133734B2

(12) United States Patent
Shi et al.

(10) Patent No.: US 8,133,734 B2
(45) Date of Patent: *Mar. 13, 2012

(54) KIT COMPRISING AN ANTIBODY TO INTERLEUKIN 17 RECEPTOR-LIKE PROTEIN

(75) Inventors: Yanggu Shi, Gaithersburg, MD (US); Stephen M. Ruben, Brookeville, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/618,178

(22) Filed: Nov. 13, 2009

(65) Prior Publication Data
US 2010/0143246 A1 Jun. 10, 2010

Related U.S. Application Data

(60) Division of application No. 11/567,524, filed on Dec. 6, 2006, now Pat. No. 7,638,603, which is a continuation of application No. 10/645,702, filed on Aug. 22, 2003, now abandoned, which is a division of application No. 09/796,844, filed on Mar. 2, 2001, now Pat. No. 6,849,719, and a continuation-in-part of application No. PCT/US00/05759, filed on Mar. 6, 2000, and a continuation-in-part of application No. PCT/US99/21048, filed on Sep. 15, 1999, and a continuation-in-part of application No. 09/268,311, filed on Mar. 16, 1999, now Pat. No. 6,482,923, said application No. PCT/US00/05759 is a continuation-in-part of application No. 09/268,311, said application No. PCT/US99/21048 is a continuation-in-part of application No. 09/268,311.

(60) Provisional application No. 60/187,015, filed on Mar. 6, 2000.

(51) Int. Cl.
*C07K 16/00* (2006.01)
*C07K 17/00* (2006.01)

(52) U.S. Cl. ............... 435/810; 530/387.1; 530/387.3; 530/387.9; 530/388.1; 530/388.22; 436/808

(58) Field of Classification Search ............. None
See application file for complete search history.

(56) References Cited

U.S. PATENT DOCUMENTS

| 5,194,596 | A | 3/1993 | Tischer et al. |
| 5,350,836 | A | 9/1994 | Kopchick et al. |
| 5,869,286 | A | 2/1999 | Yao et al. |
| 6,482,923 | B1 | 11/2002 | Shi et al. |
| 6,635,443 | B1 | 10/2003 | Shi et al. |
| 6,849,719 | B2 | 2/2005 | Shi et al. |
| 7,094,886 | B2 | 8/2006 | Shaughnessy |
| 7,638,603 | B2 | 12/2009 | Shi et al. |

FOREIGN PATENT DOCUMENTS

| WO | WO 95-14772 A | 6/1995 |
| WO | WO 96-29408 A1 | 9/1996 |
| WO | WO 98-20165 A1 | 5/1998 |
| WO | WO 98-58529 A1 | 12/1998 |
| WO | WO 99-14240 A1 | 3/1999 |
| WO | WO 99-35263 A1 | 7/1999 |
| WO | WO 00-15959 A1 | 3/2000 |
| WO | WO 00-55204 A1 | 9/2000 |
| WO | WO 01/68848 A2 | 9/2001 |

OTHER PUBLICATIONS

Benjamin, L.E., et al., "A plasticity window for blood vessel remodelling is defined by pericyte coverage of the preformed endothelial network and is regulated by PDGF-B and VEGF," *Development* 125:1591-1598, Company Of Biologists Limited (1987).
Bork, P., "Powers and Pitfalls in Sequence Analysis: The 70% Hurdle," *Genome Res.* 10:398-400, Cold Spring Harbor Laboratory Press (Apr. 2000).
Bork, P. and Bairoch, A., "Go hunting in sequence databases but watch out for the traps," *Trends Genet.* 12: 425-427, Elsevier Trends Journals (Oct. 1996).
Brenner, S.E., "Errors in genome annotation," *Trends Genet.* 15:132-133, Elsevier Trends Journals (Apr. 1999).
Doerks, T., et al., "Protein annotation: detective work for function prediction," *Trends Genet.* 14:248-250, Elsevier Trends Journals (Jun. 1998).
Ji, T.H. and Grossmann, M., "G protein-coupled receptors. I. Diversity of receptor-ligand interactions," *J. Biol. Chem.* 10:17299-17302, American Society for Biochemistry and Molecular Biology (1998).
Massagué, J., "The TGF-β family of growth and differentiation factors," *Cell* 49:437-438, Cell Press (1987).
Murdoch, C. and Finn, A., "Chemokine receptors and their role in inflammation and infectious diseases," *Blood* 95:3032-3043, American Society of Hematology (May 2000).
Parnet, P., et al., "IL-1Rrp is a novel receptor-like molecule similar to the type I interleukin-1 receptor and its homologues T1/ST2 and IL-1R AcP," *J. Biol. Chem.* 271:3967-3970, American Society for Biochemistry and Molecular Biology (Feb. 1996).
Pilbeam, C.C., et al., "Comparison of the effects of various lengths of synthetic human parathyroid hormone-related peptide (hPTHrP) of malignancy on bone resorption and formation in organ culture," *Bone* 14:717-720, Elsevier Science (1993).
Skolnick, J., et al., "From genes to protein structure and function: novel applications of computational approaches in the genomic era," *Trends Biotechnol.* 18:34-39, Elsevier Science Publishers (Jan. 2000).
Smith, T.F., et al., "The challenges of genome sequence annotations or 'the devil is in the details,'" *Nat. Biotech.* 15:1222-1223, Nature America Publishing (Nov. 1997).
Vukicevic, S., et al., "Induction of nephrogenic mesenchyme by osteogenic protein 1 (bone morphogenetic protein 7)," *Proc. Natl. Acad. Sci. USA* 93:9021-9026, National Academy of Sciences (Aug. 1996).

(Continued)

*Primary Examiner* — Dong Jiang

(74) *Attorney, Agent, or Firm* — Sterne, Kessler, Goldstein & Fox P.L.L.C.

(57) ABSTRACT

The present invention relates to a novel IL17RLP protein which is a member of the interleukin (IL)-17 receptor family. In particular, isolated nucleic acid molecules are provided encoding the human IL17RLP protein. IL17RLP polypeptides are also provided as are vectors, host cells and recombinant methods for producing the same. The invention further relates to screening methods for identifying agonists and antagonists of IL17RLP activity. Also provided are diagnostic methods for detecting immune system-related disorders and therapeutic methods for treating, diagnosing, detecting, and/or preventing immune system-related disorders.

11 Claims, 5 Drawing Sheets

OTHER PUBLICATIONS

Yao, Z., et al., "Herpesvirus Saimiri encodes a new cytokine, IL-17, which binds to a novel cytokine receptor," *Immunity* 3:811-821, Cell Press (Dec. 1995).
Tian et al., Locus Q9NRM6, Oct. 1, 2002.
Genbank Accession No. AQ309936 (Dec. 21, 1998).
Genbank Accession No. AQ240146 (Sep. 28, 1998).
Genbank Accession No. AQ113232 (Aug. 28, 1998).
Genbank Accession No. AA514396 (Aug. 18, 1997).
Genbank Accession No. AA287951 (Aug. 14, 1997).
Genbank Accession No. W61239 (Oct. 15, 1996).
Genbank Accession No. R74129 (Jun. 5, 1995).
Genbank Accession No. H25941 (Jul. 10, 1995).
Genbank Accession No. T96740 (Mar. 27, 1995).
Genbank Accession No. H25975 (Jul. 10, 1995).
Genbank Accession No. T96629 (Mar. 27, 1995).
Genbank Accession No. N56060 (Feb. 20, 1996).
Genbank Accession No. AA007528 (May 9, 1997).
Genbank Accession No. AA007529 (May 9, 1997).
Genbank Accession No. T97745 (Mar. 29, 1995).
Genbank Accession No. R74038 (Jun. 5, 1995).
Genbank Accession No. T98361 (Mar. 31, 1995).
Genbank Accession No. D25960 (Nov. 30, 1995).
Genbank Accession No. T97852 (Mar. 31, 1995).
Genbank Accession No. T98360 (Mar. 31, 1995).
Genbank Accession No. W61238 (Oct. 15, 1996).
Genbank Accession No. AA677205 (Dec. 19, 1997).
Genbank Accession No. AI032064 (Aug. 29, 1998).
Genbank Accession No. AA847767 (Mar. 31, 1998).
Genbank Accession No. AA832389 (Mar. 18, 1998).
Genbank Accession No. AA836217 (Aug. 28, 1998).
Genbank Accession No. AI034244 (Aug. 28, 1998).
Genbank Accession No. 732635 (Jan. 23, 1998).
Genbank Accession No. AI033911 (Aug. 28, 1998).
U.S. Appl. No. 09/912,293, not published, Rosen et al., pp. 1-75 (pp. 1 and 2 partially redacted): portion of Table 2: Seq ID No. 229467.
PCT International Search Report, International Appl. No. PCT/US00/05759, mailed Jun. 9, 2000.
Pan et al., "Forced expression of murine IL-17E induces growth retardation, jaundice, a TH2-biased response and multiorgan inflammation in mice," *J. Immunol.* 167: 6559-6567 The American Association of Immunologists (2001).
Kim et al., "Transgenic overexpression of human IL-17E results in eosinophilia, B-lymphocyte hyperplasia, and altered antibody production," *Blood* 100: 2330-2340 American Society of Hematology (Oct. 2002).
Lee et al., "IL-17E, a novel proinflammatory ligand for the IL-17 receptor homolog IL-17Rh1", *J. Biol. Chem.* 276: 1660-1664 American Society for Biochemistry and Molecular Biology (Jan. 2001).
Moseley et al., "Interleukin-17 family and IL-17 receptors" *Cytokine and Growth Factor Reviews* 14:155-174 Elsevier B.V. (2003).
Yokote et al., "Structural determinants in the platelet-derived growth factor alpha-receptor implicated in modulation of chemotaxis," *J. Biol. Chem.* 271: 5101-5111 American Society for Biochemistry and Molecular Biology (Mar. 1996).
Stoltz et al., "The role of NF-kappaB in the angiogenic response of coronary microvessel endothelial cells," *Proc. Natl. Acad. Sci. USA* 93:2832-2837, National Academy of Sciences (Apr. 1996).
Tian et al., "Evi27 encodes a novel membrane protein with homology to the IL17 receptor" *Oncogene* 19: 2098-2109 Nature Publishing Group (2000).
Maezawa et al., "Involvement of TNF receptor-associated factor 6 in IL-25 receptor signaling," *J. Immunol.* 176: 1013-1018 The American Association of Immunologists (Jan. 2006).
Database EMBL EST [Online] Apr. 12, 1997 "zs55b03.r1 NCI_CGAP_GCBI Homo sapiens cDNA clone IMAGE:701357 5', mRNA sequence" retrieved from EBI Database accession No. AA287951 XP002235142.
Database EMBL__EST [Online] Apr. 14, 1995 "ye51g03.r1 Soares fetal liver spleen INFLS Homo sapiens cDNA clone IMAGE: 121300 5', mRNA sequence" retrieved from EBI Database accession No. T96740 XP002235143.
Database EMBL_EST [Online] Jul. 15, 1997 "nf57c01.s1 NCI_CGAP_Co3 Homo sapiens cDNA clone IMAGE:924000 3',mRNA sequence" retrieved from EBI Database accession No. AA514369 XP002235144.
Shi et al., "A novel cytokine receptor-ligand pair: Identification, molecular characterization and in vivo immunomodulatory activity" *J. Biol. Chem.* 275:19167-17176 American Society for Biochemistry and Molecular Biology (Jun. 2000).
Spriggs, Melanic K., "Interleukin-17 and its receptor." *J.Clin.Immunology* 17: 366-369 Springer (Sep. 1997).
Office Action for U.S. Appl. No. 11/567,524, filed Dec. 6, 2006, mailed on Jan. 23, 2009.

IL17RLP Nucleotide and Amino Acid Sequence

```
  1  GCACGAGCGATGTCGCTCGTGCTGCTAAGCCTGGCCGCGCTGTGCAGGAGCGCCGTACCC   60
  1             M  S  L  V  L  L  S  L  A  A  L  C  R  S  A  V  P     17

61  CGAGAGCCGACCGTTCAATGTGGCTCTGAAACTGGCCATCTCCAGAGTGGATGCTACAA  120
 18  R  E  P  T  V  Q  C  G  S  E  T  G  P  S  P  E  W  M  L  Q    37

121  CATGATCTAATCCCCGGAGACTTGAGGGACCTCCGAGTAGAACCTGTTACAACTAGTGTT  180
 38  H  D  L  I  P  G  D  L  R  D  L  R  V  E  P  V  T  T  S  V    57

181  GCAACAGGGGACTATTCAATTTTGATGAATGTAAGCTGGGTACTCCGGGCAGATGCCAGC  240
 58  A  T  G  D  Y  S  I  L  M  N  V  S  W  V  L  R  A  D  A  S    77
                                        Domain I 241  ATCCGCTTGTTGAAGGCCACCAAGATTTGTGTGACGGGCAAAAGCAACTTCCAGTCCTAC  300
 78  I  R  L  L  K  A  T  K  I  C  V  T  G  K  S  N  F  Q  S  Y    97
     Domain I 301  AGCTGTGTGAGGTGCAATTACACAGAGGCCTTCCAGACTCAGACCAGACCCTCTGGTGGT  360
 98  S  C  V  R  C  N  Y  T  E  A  F  Q  T  Q  T  R  P  S  G  G   117

361  AAATGGACATTTTCCTACATCGGCTTCCCTGTAGAGCTGAACACAGTCTATTTCATTGGG  420
118  K  W  T  F  S  Y  I  G  F  P  V  E  L  N  T  V  Y  F  I  G   137

421  GCCCATAATATTCCTAATGCAAATATGAATGAAGATGGCCCTTCCATGTCTGTGAATTTC  480
138  A  H  N  I  P  N  A  N  M  N  E  D  G  P  S  M  S  V  N  F   157

481  ACCTCACCAGGCTGCCTAGACCACATAATGAAATATAAAAAAAAGTGTGTCAAGGCCGGA  540
158  T  S  P  G  C  L  D  H  I  M  K  Y  K  K  K  C  V  K  A  G   177
                                                Domain II 541  AGCCTGTGGGATCCGAACATCACTGCTTGTAAGAAGAATGAGGAGACAGTAGAAGTGAAC  600
178  S  L  W  D  P  N  I  T  A  C  K  K  N  E  E  T  V  E  V  N   197
         Domain II 601  TTCACAACCACTCCCCTGGGAAACAGATACATGGCTCTTATCCAACACAGCACTATCATC  660
198  F  T  T  T  P  L  G  N  R  Y  M  A  L  I  Q  H  S  T  I  I   217

661  GGGTTTTCTCAGGTGTTTGAGCCACACCAGAAGAAACAAACGCGAGCTTCAGTGGTGATT  720
218  G  F  S  Q  V  F  E  P  H  Q  K  K  Q  T  R  A  S  V  V  I   237
             Domain III
```

FIG. 1A

IL17RLP Nucleotide and Amino Acid Sequence

```
 721  CCAGTGACTGGGGATAGTGAAGGTGCTACGGTGCAGCTGACTCCATATTTTCCTACTTGT   780
 238   P   V   T   G   D   S   E   G   A   T   V   Q   L   P   Y   F   P   T   C    257

781  GGCAGCGACTGCATCCGACATAAAGGAACAGTTGTGCTCTGCCCACAAACAGGCGTCCCT   840
 258   G   S   D   C   I   R   H   K   G   T   V   V   L   C   P   Q   T   G   V   P    277
               Domain IV                                    Domain V 841  TTCCCTCTGGATAACAACAAAAGCAAGCCGGGAGGCTGGCTGCCTCTCCTCCTGCTGTCT   900
 278   F   P   L   D   N   N   K   S   K   P   G   G   W   L   P   L   L   L   L   S    297
       Domain V 901  CTGCTGGTGGCCACATGGGTGCTGGTGGCAGGGATCTATCTAATGTGGAGGCACGAAAGG   960
 298   L   L   V   A   T   W   V   L   V   A   G   I   Y   L   M   W   R   H   E   R    317

961  ATCAAGAAGACTTCCTTTTCTACCACCACACTACTGCCCCCCATTAAGGTTCTTGTGGTT  1020
 318   I   K   K   T   S   F   S   T   T   T   L   L   P   P   I   K   V   L   V   V    337
                                                           Domain VI 1021  TACCCATCTGAAATATGTTTCCATCACACAATTTGTTACTTCACTGAATTTCTTCAAAAC  1080
 338   Y   P   S   E   I   C   F   H   H   T   I   C   Y   F   T   E   F   L   Q   N    357
       Domain VI 1081  CATTGCAGAAGTGAGGTCATCCTTGAAAAGTGGCAGAAAAAGAAAATAGCAGAGATGGGT  1140
 358   H   C   R   S   E   V   I   L   E   K   W   Q   K   K   K   I   A   E   M   G    377
           Domain VII                                    Domain VIII 1141  CCAGTGCAGTGGCTTGCCACTCAAAAGAAGGCAGCAGACAAAGTCGTCTTCCTTCTTTCC  1200
 378   P   V   Q   W   L   A   T   Q   K   K   A   A   D   K   V   V   F   L   L   S    397

1201  AATGACGTCAACAGTGTGTGCGATGGTACCTGTGGCAAGAGCGAGGGCAGTCCCAGTGAG  1260
 398   N   D   V   N   S   V   C   D   G   T   C   G   K   S   E   G   S   P   S   E    417

1261  AACTCTCAAGACTCTTCCCCTTGCCTTTAACCTTTTCTGCAGTGATCTAAGAAGCCAGAT  1320
 418   N   S   Q   D   S   S   P   C   L                                              426

1321  TCATCTGCACAAATACGTGGTGGTCTACTTTAGAGAGATTGATACAAAAGACGATTACAA  1380

1381  TGCTCTCAGTGTCTGCCCCAAGTACCACCTCATGAAGGATGCCACTGCTTTCTGTGCAGA  1440

1441  ACTTCTCCATGTCAAGTAGCAGGTGTCAGCAGGAAAAAGATCACAAGCCTGCCACGATGG  1500
```

FIG. 1B

IL17RLP Nucleotide and Amino Acid Sequence

```
1501  CTGCTGCTCCTTGTAGCCCACCCATGAGAAGCAAGWGACCTTAAAGGCTTCCTATCCCAC  1560

1561  CAATTACAGGGAAAAAACGTGTGATGATCCTGAAGCTTACTATGCAGCCTACAAACAGCC  1620

1621  TTAGTAATTAAAACATTTTATACCAATAAAATTTTCAAATATTGCTAACTAATGTAGCAT  1680

1681  TAACTAACGATTGGAAACTACATTTACAACTTCAAAGCTGTTTTATACATAGAAATCAAT  1740

1741  TACAGTTTTAATTGAAAACTATAACCATTTTGATAATGCAACAATAAAGCATCTTCAGCC  1800

1801  AAAAAAAAAAAAAAAA  1816
```

FIG. 1C

IL17RLP vs. murine IL17R

Percent Similarity: 49.879    Percent Identity: 28.571

IL17RLP.aa
x
mIL17R.aa

```
  1 MSLVLLSLAALCRS.AVPRE...PTVQCGSE.........TGPSPEWMLQ  37
    ::::||  |..|..:  |  ||     |..  :  |        |. ...|: .
 16 LGWLLLLLNVLAPGRASPRLLDFPAPVCAQEGLSCRVKNSTCLDDSWIHP  65

38 HDLIPGDLRDLRVEPVTTSVATGDYSILMNVSWVLRADASIRLLKATKIC  87
    .:|.|:.  :::  ::    ..|..  |:.   :::|.|.|..||||  .|.:..::
 66 KNLTPSSPKNIYINLSVSSTQHGELVPVLHVEWTLQTDASILYLEGAELS 115

88 VTGKSNFQSYSCVRCNYTEAFQTQTRPSGGKWTFSYIGFPVELNTVYFIG 137
    |   . .. :..   ||:  .:  .  :|   :  :     :| || : |.|  .  |  :..
116 VLQLNTNERL.CVKFQFLSMLQHHRK....RWRFSFSHFVVDPGQEYEVT 160

138 AHNIPNAMMNEDGPSMSVNFTSPGCLDHIMKYKKKCVKAGSLWDPNITAC 187
    .|::|..:   ::|.   .|   :    |:|  |   ||  ...||..||||||||.
161 VHHLPKPIPDGDPNHKSKIIFVPDCEDSKMKMTTSCVSSGSLWDPNITVE 210

188 KKNEETVEVNFTTTPLGNRYMALIQ.......HSTIIGFSQVFEPHQKK. 229
    .  :.:  :   |:||      :..|  .|::           ||.:  ...|:|.|:|..
211 TLDTQHLRVDFTLWNESTPYQVLLESFSDSENHSCFDVVKQIFAPRQEEF 260

230 QTRASVVIPVTGD..SEGATVQLTPYFPTCGSDCIRHKGTV..VLCPQTG 275
    :  ||.|.:.:.    :       ||:  |:|..|   .||:||  .||      .:..|.
261 HQRANVTFTLSKFHWCCHHHVQVQPFFSSCLNDCLRHAVTVPCPVISNTT 310

276 VPFPLDNNKSKPGGWLPLL......LLSLLVATWVLVAGIYLMWRHERIK 319
    ||  |:      :::: ||         |:.:|:...|:|  |:: ||  .  .
311 VPKPV.......ADYIPLWVYGLITLIAILLVGSVIVLIICMTWRLSGAD 353

320 KTSFS...............TTTLLPPIKVLVVYPSEICFHHTICY.FTEF 354
    ...  :              |..  |.|  ||::||..:   .:.. .:.. |.:|
354 QEKHGDDSKINGILPVADLTPPPLRPRKVWIVYSADHPLYVEVVLKFAQF 403

355 LQNHCRSEVILEKWQKKKIAEMGPVQWLATQKK....AADKVVFLLSNDV 400
    | . | .|| |:  :::..  |.|:|.:  |:-  ||.       ...|:::| |.:.
404 LITACGTEVALDLLEEQVISEVGVMTWVSRQKQEMVESNSKIIILCSRGT 453

401 NSVCDGTCGKSEGSPSENSQDSSPC 425
    ..  .:.  |..|...  .:...|.
454 QAKWKAILGWAEPAVQLRCDHWKPA 478
```

FIG. 2

KIT COMPRISING AN ANTIBODY TO INTERLEUKIN 17 RECEPTOR-LIKE PROTEIN

This application is a divisional of U.S. application Ser. No. 11/567,524, filed Dec. 6, 2006 (now U.S. Pat. No. 7,638,603, issued Dec. 29, 2009), which is a continuation of U.S. application Ser. No. 10/645,702, filed Aug. 22, 2003 now abandoned, which is a divisional of U.S. application Ser. No. 09/796,844, filed Mar. 2, 2001 (now U.S. Pat. No. 6,849,719, issued Feb. 1, 2005), which claims benefit under 35 U.S.C. §119(e) of U.S. Provisional Application No. 60/187,015, filed Mar. 6, 2000; U.S. application Ser. No. 09/796,844 is also a continuation-in-part of International Application No. PCT/US00/05759, filed Mar. 6, 2000 (now abandoned), and a continuation-in-part of International Application No. PCT/US99/21048, filed Sep. 15, 1999, and a continuation-in-part of U.S. application Ser. No. 09/268,311, filed Mar. 16, 1999 (now U.S. Pat. No. 6,482,923, issued Nov. 19, 2002); International Application No. PCT/US00/05759 is a continuation-in-part of U.S. application Ser. No. 09/268,311, filed Mar. 16, 1999 (now U.S. Pat. No. 6,482,923, issued Nov. 19, 2002); International Application No. PCT/US99/21048 is a continuation-in-part of U.S. application Ser. No. 09/268,311 (now U.S. Pat. No. 6,482,923, issued Nov. 19, 2002). Each of these applications is hereby incorporated by reference in its entirety.

REFERENCE TO A SEQUENCE LISTING SUBMITTED ELECTRONICALLY VIA EFS-WEB

The content of the electronically submitted substitute sequence listing (Name: SubstituteSequenceListing.txt, Size: 37,686 kilobytes; and Date of Creation: Dec. 30, 2010) is herein incorporated by reference in its entirety.

FIELD OF THE INVENTION

The present invention relates to a novel human gene encoding a polypeptide which is a member of the interleukin (IL)-17 receptor family. More specifically, isolated nucleic acid molecules are provided encoding a human polypeptide named Interleukin 17-Receptor-Like Protein, hereinafter referred to as IL17RLP. IL17RLP polypeptides are also provided, as are vectors, host cells and recombinant methods for producing the same. Also provided are diagnostic methods for diagnosing and/or detecting disorders related to the immune system and therapeutic methods for treating and/or preventing such disorders. The invention further relates to screening methods for identifying agonists and antagonists of IL17RLP activity.

BACKGROUND OF THE INVENTION

Cytokines typically exert their respective biochemical and physiological effects by binding to specific receptor molecules. Receptor binding will then stimulate specific signal transduction pathways (Kishimoto, T., et al., *Cell* 76:253-262 (1994). The specific interactions of cytokines with their receptors are often the primary regulators of a wide variety of cellular process including activation, proliferation, and differentiation (Arai, K.-I, et al., *Ann. Rev. Biochem.* 59:783-836 (1990); Paul, W. and Seder, R., *Cell* 76:241-251 (1994)).

Human interleukin (IL)-17 was only recently identified. IL-17 is a 155 amino acid polypeptide which was molecularly cloned from a CD4+ T-cell cDNA library (Yao, Z., et al., *J. Immunol.* 155:5483-5486 (1995)). The IL-17 polypeptide contains an N-terminal signal peptide and contains approximately 72% identity at the amino acid level with a T-cell trophic herpesvirus saimiri (HVS) gene designated HVS13. High levels of IL-17 are secreted from CD4-positive primary peripheral blood leukocytes (PBL) upon stimulation (Yao, Z., et al., *Immunity* 3:811-821 (1995)). Treatment of fibroblasts with IL-17, HVS13, or another murine homologue, designated CTLA8, activate signal transduction pathways and result in the stimulation of the NF-kappaB transcription factor family, the secretion of IL-6, and the costimulation of T-cell proliferation (Yao, Z., et al., *Immunity* 3:811-821 (1995)).

An HVS13-Fc fusion protein was used to isolate a murine IL-17 receptor molecule which does not appear to belong to any of the previously described cytokine receptor families (Yao, Z., et al., *Immunity* 3:811-821 (1995)). The murine IL-17 receptor (mIL-17R) is predicted to encode a type I transmembrane protein of 864 amino acids with an apparent molecular mass of 97.8 kDa. mIL-17R is predicted to possess an N-terminal signal peptide with a cleavage site between alanine-31 and serine-32. The molecule also contains a 291 amino acid extracellular domain, a 21 amino acid transmembrane domain, and a 521 amino acid cytoplasmic tail. A soluble recombinant IL-17R molecule consisting of 323 amino acids of the extracellular domain of IL-17R fused to the Fc portion of human IgG1 was able to significantly inhibit IL-17-induced IL-6 production by murine NIH-3T3 cells (supra).

Interestingly, the expression of the IL-17 gene is highly restricted. It is typically observed primarily in activated T-lymphocyte memory cells (Broxmeyer, H. *J. Exp. Med.* 183:2411-2415 (1996); Fossiez, F., et al., *J. Exp. Med.* 183: 2593-2603 (1996)). Conversely, the IL-17 receptor appears to be expressed in a large number of cells and tissues including (Rouvier, E., et al., *J. Immunol.* 150:5445-5456 (1993); Yao, Z., et al., *J. Immunol.* 155:5483-5486 (1995)). It remains to be seen, however, if IL-17 itself can play an autocrine role in the expression of IL-17. IL-17 has been implicated as a causitive agent in the expression of IL-6, IL-8, G-CSF, Prostaglandin E ($PGE_2$), and intracellular adhesion molecule (ICAM)-1 (Fossiez, F., supra; Yao, Z., et al., *Immunity* 3:811-821 (1995)). Each of these molecules possesses highly relevant and potentially therapeutically valuable properties. For instance, IL-6 is involved in the regulation of hematopoietic stem and progenitor cell growth and expansion (Ikebuchi, K., et al., *Proc. Natl. Acad. Sci. USA* 84:9035-9039 (1987); Gentile, P. and Broxmeyer, H. E. *Ann. N.Y. Acad. Sci. USA* 628: 74-83 (1991)). IL-8 exhibits a myelosuppressive activity for stem and immature subsets of myeloid progenitors (Broxmeyer, H. E., et al., *Ann. Hematol.* 71:235-246 (1995); Daly, T. J., et al., *J. Biol. Chem.* 270:23282-23292 (1995)). G-CSF acts early and late to activate and stimulate hematopoiesis in general (more specifically, neutrophil hematopoiesis) while $PGE_2$ enhances erythropoiesis, suppresses lymphopoiesis and myelopoiesis in general, and strongly suppresses monocytopoiesis (Broxmeyer, H. E. *Amer. J. Ped. Hematol./Oncol.* 14:22-30 (1992); Broxmeyer, H. E. and Williams, D. E. *CRC Crit. Rev. Oncol./Hematol.* 8:173-226 (1988)).

IL-17 receptor appears to be structurally unrelated to any previously described cytokine receptor family. Despite the existence of 12 cysteine residues in the extracellular domain, their relative positions are not characteristic of receptor molecules classified as members of the immunoglobulin superfamily (Williams, A. and Barclay, A. *Annu. Rev. Immunol.* 6:381-405 (1988)), the TNFR family (Smith, C., et al., *Science* 248:1019-1023 (1990)), the hematopoietin receptor family (Cosman, D. *Cytokine* 5:95-106 (1993)), or any previously described tyrosine kinase receptors (Hanks, S., et al., *Science* 241:42-52 (1988)).

Thus, there is a need for polypeptides that function as receptor molecules for cytokines and, thereby, function in the transfer of an extracellular signal ultimately to the nucleus of the cell, since disturbances of such regulation may be involved in disorders relating to cellular activation, hemostasis, angiogenesis, tumor metastasis, cellular migration and ovulation, as well as neurogenesis. Therefore, there is a need for identification and characterization of such human polypeptides which can play a role in detecting, preventing, ameliorating or correcting such disorders.

SUMMARY OF THE INVENTION

The present invention provides isolated nucleic acid molecules comprising a polynucleotide encoding at least a portion of the IL17RLP polypeptide having the complete amino acid sequence shown in SEQ ID NO:2 or the complete amino acid sequence encoded by the cDNA clone deposited as plasmid DNA with the American Type Culture Collection (ATCC™) as ATCC™ Deposit Number 209198 on Aug. 8, 1997. The ATCC™ is located at 10801 University Boulevard, Manassas, Va. 20110-2209, USA. The nucleotide sequence determined by sequencing the deposited IL17RLP clone, which is shown in FIGS. 1A, 1B, and 1C (SEQ ID NO:1), contains an open reading frame encoding a complete polypeptide of 426 amino acid residues, including an initiation codon encoding an N-terminal methionine at nucleotide positions 10-12, and a predicted molecular weight of about 47.1 kDa. Nucleic acid molecules of the invention include those encoding the complete amino acid sequence excepting the N-terminal methionine shown in SEQ ID NO:2, or the complete amino acid sequence excepting the N-terminal methionine encoded by the cDNA clone in ATCC™ Deposit Number 209198, which molecules also can encode additional amino acids fused to the N-terminus of the IL17RLP amino acid sequence.

The encoded polypeptide has a predicted leader sequence of 19 amino acids underlined in FIGS. 1A, 1B, and 1C; and the amino acid sequence of the predicted mature IL17RLP protein is also shown in FIGS. 1A, 1B, and 1C as amino acid residues 20-426, and as residues IL-407 in SEQ ID NO:2.

In another embodiment, the encoded polypeptide has a predicted leader sequence from Met-(−19) to Ser-(−6) of SEQ ID NO:2 (i.e., from Met-1 to Ser-14 of the amino acid sequence presented in FIGS. 1A, 1B, and 1C); an extracellular domain from Ala-(−5) to Trp-271 of SEQ ID NO:2 (i.e., from Ala-15 to Tyr-290 of the amino acid sequence presented in FIGS. 1A, 1B, and 1C); a transmembrane domain from Leu-272 to Leu-292 of SEQ ID NO:2 (i.e., from Leu-291 to Leu-311 of the amino acid sequence presented in FIGS. 1A, 1B, and 1C); and an intracellular domain from Met-293 to Leu-407 of SEQ ID NO:2 (i.e., from Met-312 to Leu-426 of the amino acid sequence presented in FIGS. 1A, 1B, and 1C). The predicted length of the leader peptide in this embodiment is within the originally predicted range of 14-19 amino acids.

In an additional embodiment, the IL17RLP transmembrane domain may have an N-terminal boundary beginning at amino acid residue Pro-268, Gly-269, Gly-270, Trp-271 or Leu-272 of the IL17RLP sequence as shown in SEQ ID NO:2 (i.e., amino acid residues Pro-287, Gly-288, Gly-289, Trp-290 or Leu-291 of the IL17RLP sequence as shown in FIGS. 1A, 1B, and 1C) and a C-terminal boundary including amino acid residue Tyr-291, Leu-292, Met-293 or Trp-294 of the IL17RLP sequence as shown in SEQ ID NO:2 (i.e., amino acid residues Tyr-310, Leu-311, Met-312 or Trp-313 of the IL17RLP sequence as shown in FIGS. 1A, 1B, and 1C).

Thus, one aspect of the invention provides an isolated nucleic acid molecule comprising, or alternatively consisting of, a polynucleotide comprising a nucleotide sequence selected from the group consisting of: (a) a nucleotide sequence encoding the IL17RLP polypeptide having the complete amino acid sequence in SEQ ID NO:2 (i.e., positions −19 to 407 of SEQ ID NO:2); (b) a nucleotide sequence encoding the IL17RLP polypeptide having the complete amino acid sequence in SEQ ID NO:2 excepting the N-terminal methionine (i.e., positions −18 to 407 of SEQ ID NO:2); (c) a nucleotide sequence encoding the predicted mature IL17RLP polypeptide having the amino acid sequence at positions 1 to 407 in SEQ ID NO:2; (d) a nucleotide sequence encoding a polypeptide comprising the predicted extracellular domain of the IL17RLP polypeptide having the amino acid sequence at positions 1 to 271 in SEQ ID NO:2; (e) a nucleotide sequence encoding a soluble IL17RLP polypeptide having the predicted extracellular and intracellular domains, but lacking the predicted transmembrane domain; (f) a nucleotide sequence encoding the IL17RLP polypeptide having the complete amino acid sequence encoded by the cDNA clone contained in ATCC™ Deposit No. 209198; (g) a nucleotide sequence encoding the IL17RLP polypeptide having the complete amino acid sequence excepting the N-terminal methionine encoded by the cDNA clone contained in ATCC™ Deposit No. 209198; (h) a nucleotide sequence encoding the mature IL17RLP polypeptide having the amino acid sequence encoded by the cDNA clone contained in ATCC™ Deposit No. 209198; (i) a nucleotide sequence encoding the extracellular domain of the IL17RLP polypeptide having the amino acid sequence encoded by the cDNA clone contained in ATCC™ Deposit No. 209198; and (j) a nucleotide sequence complementary to any of the nucleotide sequences in (a), (b), (c), (d), (e), (f), (g), (h) or (i) above.

Further embodiments of the invention include isolated nucleic acid molecules that comprise, or alternatively consist of, a polynucleotide having a nucleotide sequence at least 80%, 85%, or 90% identical, and more preferably at least 95%, 96%, 97%, 98%, 99% or 100% identical, to any of the nucleotide sequences in (a), (b), (c), (d), (e), (f), (g), (h) or (i), above, or a polynucleotide which hybridizes under stringent hybridization conditions to a polynucleotide in (a), (b), (c), (d), (e), (f), (g), (h) or (i), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a IL17RLP polypeptide having an amino acid sequence in (a), (b), (c), (d), (e), (f), (g) or (h), above.

An additional nucleic acid embodiment of the invention relates to an isolated nucleic acid molecule comprising, or alternatively consisting of, a polynucleotide which encodes the amino acid sequence of an epitope-bearing portion of a IL17RLP polypeptide having an amino acid sequence in (a), (b), (c), (d), (e), (f) or (g), above. A further embodiment of the invention relates to an isolated nucleic acid molecule comprising a polynucleotide which encodes the amino acid sequence of a IL17RLP polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polynucleotide which encodes the amino acid sequence of a IL17RLP polypeptide to have an amino acid sequence which contains not more than 10, 9, 8, 7, 6, 5, 4, 3, 2 or 1 amino acid substitutions. Conservative substitutions are preferable.

In another embodiment, the present invention includes a polynucleotide of 1,918 nucleotides (SEQ ID NO:17) which encodes the IL17RLP polypeptide provided in SEQ ID NO:18. The IL17RLP of SEQ ID NO:18 differs from the IL17RLP provided in SEQ ID NO:2 only by the deletion of the C-terminal two residues (Cys-406 and Leu-407 of SEQ ID NO:2) and the addition of nine amino acid residues (Leu-425 through Ile-433 of SEQ ID NO:18). The extracellular domain of IL17RLP is identical in SEQ ID NO:2 and SEQ ID NO:18. The IL17RLP polynucleotide sequence shown in SEQ ID NO:17 was derived from sequencing the HAPOR40 cDNA clone deposited with the ATCC™ with ATCC™ Deposit No. 209198 on Aug. 8, 1997.

The present invention also relates to recombinant vectors, which include the isolated nucleic acid molecules of the present invention, and to host cells containing the recombinant vectors, as well as to methods of making such vectors and host cells and for using them for production of IL17RLP polypeptides or peptides by recombinant techniques.

In accordance with a further aspect of the present invention, there is provided a process for producing such polypeptide by recombinant techniques comprising culturing recombinant prokaryotic and/or eukaryotic host cells, containing an IL17RLP nucleic acid sequence, under conditions promoting expression of said protein and subsequent recovery of said protein.

The invention further provides an isolated IL17RLP polypeptide comprising, or alternatively consisting of, an amino acid sequence selected from the group consisting of: (a) the amino acid sequence of the full-length IL17RLP polypeptide having the complete amino acid sequence shown in SEQ ID NO:2 (i.e., positions −19 to 407 of SEQ ID NO:2); (b) the amino acid sequence of the full-length IL17RLP polypeptide having the complete amino acid sequence shown in SEQ ID NO:2 excepting the N-terminal methionine (i.e., positions −18 to 407 of SEQ ID NO:2); (c) the amino acid sequence of the mature IL17RLP polypeptide having the complete amino acid sequence shown in SEQ ID NO:2 (i.e., positions 1 to 407 of SEQ ID NO:2); (d) the amino acid sequence of the predicted extracellular domain of the IL17RLP polypeptide having the complete amino acid sequence shown in SEQ ID NO:2 (i.e., positions 1 to 271 of SEQ ID NO:2); (e) the amino acid sequence of a soluble IL17RLP polypeptide having the predicted extracellular and intracellular domains, but lacking the predicted transmembrane domain; (f) the complete amino acid sequence encoded by the cDNA clone contained in the ATCC™ Deposit No. 209198; (g) the complete amino acid sequence excepting the N-terminal methionine encoded by the cDNA clone contained in the ATCC™ Deposit No. 209198; (h) the complete amino acid sequence of the mature IL17RLP encoded by the cDNA clone contained in the ATCC™ Deposit No. 209198, and; (i) the complete amino acid sequence of the extracellular domain of the IL17RLP encoded by the cDNA clone contained in the ATCC™ Deposit No. 209198. The polypeptides of the present invention also include polypeptides having an amino acid sequence at least 80% or 85% identical, more preferably at least 90% identical, and still more preferably 95%, 96%, 97%, 98%, 99% or 100% identical to those described in (a), (b), (c), (d), (e), (f), (g), (h) or (i) above, as well as polypeptides having an amino acid sequence with at least 90% similarity, and more preferably at least 95% similarity, to those above.

An additional embodiment of this aspect of the invention relates to a peptide or polypeptide which comprises, or alternatively consists of, the amino acid sequence of an epitope-bearing portion of a IL17RLP polypeptide having an amino acid sequence described in (a), (b), (c), (d), (e), (f), (g), (h) or (i), above. Peptides or polypeptides having the amino acid sequence of an epitope-bearing portion of an IL17RLP polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

A further embodiment of the invention relates to a polypeptide which comprises, or alternatively consists of, the amino acid sequence of an IL17RLP polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of an IL17RLP polypeptide, which contains at least one, but not more than 20, 10, 9, 8, 7, 6, 5, 4, 3, 2 or 1 amino acid substitutions. In specific embodiments, the number of additions, substitutions, and/or deletions in the amino acid sequence of FIGS. 1A, 1B, and 1C, or fragments thereof (e.g., the mature form and/or other fragments described herein), is 1-5, 5-10, 5-25, 5-50, 10-50, 50-150, 50-200 or 100-250, conservative amino acid substitutions are preferable.

In another embodiment, the invention provides an isolated antibody that binds specifically to a IL17RLP polypeptide having an amino acid sequence described in (a), (b), (c), (d), (e), (f), (g), (h) or (i) above. The invention further provides methods for isolating antibodies that bind specifically to a IL17RLP polypeptide having an amino acid sequence as described herein. Such antibodies are useful diagnostically or therapeutically as described below.

The invention also provides for pharmaceutical compositions comprising IL17RLP polynucleotides or polypeptides, particularly human IL17RLP polynucleotides or polypeptides, which may be employed, for instance, to treat, diagnose, detect, and/or prevent disorders relating to cellular activation, hemostasis, angiogenesis, tumor metastasis, cellular migration and ovulation, as well as neurogenesis. Methods of treating, diagnosing, and/or detecting individuals in need of IL17RLP polynucleotides or polypeptides are also provided.

The invention further provides compositions comprising an IL17RLP polynucleotide or an IL17RLP polypeptide for administration to cells in vitro, to cells ex vivo and to cells in vivo, or to a multicellular organism. In certain particularly preferred embodiments of this aspect of the invention, the compositions comprise an IL17RLP polynucleotide for expression of an IL17RLP polypeptide in a host organism for treatment, diagnosis, detection, and/or prevention of disease. Particularly preferred in this regard is expression in a human patient for treatment, diagnosis, detection, and/or prevention of a dysfunction associated with aberrant endogenous activity of an IL17RLP polypeptide.

The present invention also provides a screening method for identifying compounds capable of enhancing or inhibiting a biological activity of the IL17RLP polypeptide, which involves contacting a ligand which is inhibited by the IL17RLP polypeptide with the candidate compound in the presence of an IL17RLP polypeptide, assaying receptor-binding activity of the ligand in the presence of the candidate compound and of IL17RLP polypeptide, and comparing the ligand activity to a standard level of activity, the standard being assayed when contact is made between the ligand itself in the presence of the IL17RLP polypeptide and the absence of the candidate compound In this assay, an increase in ligand activity over the standard indicates that the candidate compound is an agonist of IL17RLP activity and a decrease in ligand activity compared to the standard indicates that the compound is an antagonist of IL17RLP activity.

In another aspect, a screening assay for agonists and antagonists is provided which involves determining the effect a candidate compound has on IL17RLP binding to a ligand. In particular, the method involves contacting the ligand with an IL17RLP polypeptide and a candidate compound and determining whether IL17RLP polypeptide binding to the ligand is increased or decreased due to the presence of the candidate compound. In this assay, an increase in binding of IL17RLP over the standard binding indicates that the candidate compound is an agonist of IL17RLP binding activity and a decrease in IL17RLP binding compared to the standard indicates that the compound is an antagonist of IL17RLP binding activity.

It has been discovered that IL17RLP is expressed not only in adult pulmonary tissue, but also in Crohn's Disease tissue, kidney pyramid, cortex, and medulla tissues, hippocampus, frontal cortex of the brain from a patient with epilepsy, adrenal gland tumor, striatum depression, osteclastoma, endometrial tumor, and hypothalamus from a patient with Schizophrenia. Therefore, nucleic acids of the invention are useful as hybridization probes for differential identification of the tissue(s) or cell type(s) present in a biological sample. Similarly, polypeptides and antibodies directed to those polypeptides are useful to provide immunological probes for differential identification of the tissue(s) or cell type(s). In addition, for a number of disorders of the above tissues or cells, particularly of the immune system, significantly higher or lower levels of IL17RLP gene expression may be detected in certain tissues (e.g., cancerous and wounded tissues) or bodily fluids (e.g., serum, plasma, urine, synovial fluid or spinal fluid) taken from an individual having such a disorder, relative to a "standard" IL17RLP gene expression level, i.e., the IL17RLP expression level in healthy tissue from an individual not having the immune system disorder. Thus, the invention provides a diagnostic method useful during diagnosis of such a disorder, which involves: (a) assaying IL17RLP gene expression level in cells or body fluid of an individual; (b) comparing the IL17RLP gene expression level with a standard IL17RLP gene expression level, whereby an increase or decrease in the assayed IL17RLP gene expression level compared to the standard expression level is indicative of disorder in the immune system.

An additional aspect of the invention is related to a method for treating, diagnosing, and/or detecting an individual in need of an increased level of IL17RLP activity in the body comprising administering to such an individual a composition comprising a therapeutically effective amount of an isolated IL17RLP polypeptide of the invention or an agonist thereof.

A still further aspect of the invention is related to a method for treating, diagnosing, and/or detecting an individual in need of a decreased level of IL17RLP activity in the body comprising, administering to such an individual a composition comprising a therapeutically effective amount of an IL17RLP antagonist. Preferred antagonists for use in the present invention are IL17RLP-specific antibodies.

BRIEF DESCRIPTION OF THE FIGURES

FIGS. 1A, 1B, and 1C show the nucleotide sequence (SEQ ID NO:1) and deduced amino acid sequence (SEQ ID NO:2) of IL17RLP.

Figure 3:
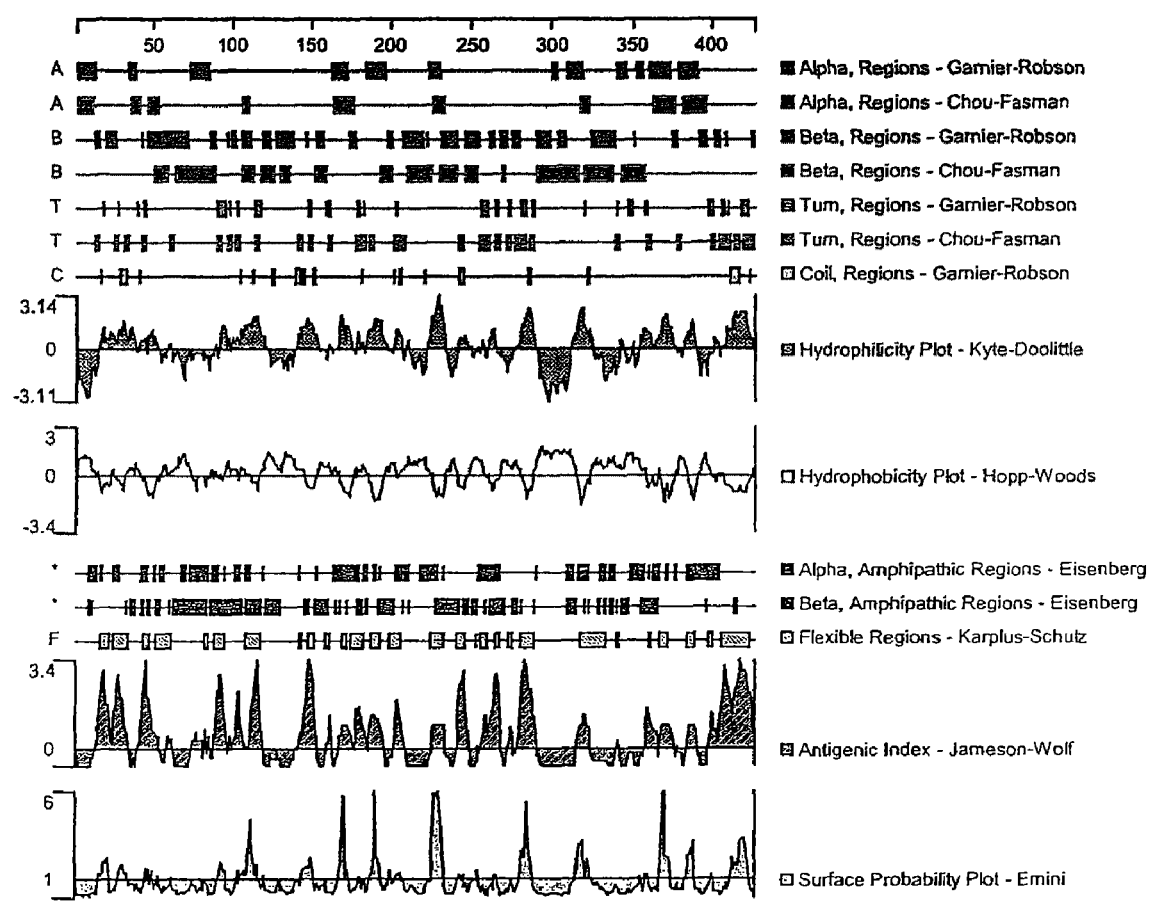

The predicted leader sequence of about 19 amino acids is underlined. Note that the methionine residue at the beginning of the leader sequence in FIGS. 1A, 1B, and 1C is shown in position number (positive) 1, whereas the leader positions in the corresponding sequence of SEQ ID NO:2 are designated with negative position numbers. Thus, the leader sequence positions 1 to 19 in FIGS. 1A, 1B, and 1C correspond to positions −19 to −1 in SEQ ID NO:2.

Six potential asparagine-linked glycosylation sites are marked in the amino acid sequence of IL17RLP. The sites are marked with the bold pound symbol (#) above the nucleotide sequence coupled with a bolded one letter abbreviation for the asparagine (N) in the amino acid sequence in FIGS. 1A, 1B, and 1C; that is, the actual asparagine residues which are potentially glycosylated is bolded in FIGS. 1A, 1B, and 1C. The potential N-linked glycosylation sequences are found at the following locations in the IL17RLP amino acid sequence: N-67 through W-70 (N-67, V-68, S-69, W-70); N-103 through E-106 (N-103, Y-104, T-105, E-106; N-156 through S-159 (N-156, F-157, T-158, S-159); N-183 through A-186 (N-183, I-184, T-185, A-186); N-197 through T-200 (N-197, F-198, T-199, T-200); and N-283 through K-286 (N-283, K-284, S-285, K-286). Two potential cAMP- and cGMP-dependent protein kinase phosphorylation sites are also marked in FIGS. 1A, 1B, and 1C with a bolded lysine symbol (K) in the IL17RLP amino acid sequence and an asterisk (*) above the first nucleotide encoding that lysine residue in the IL17RLP nucleotide sequence. The potential cAMP- and cGMP-dependent protein kinase phosphorylation sequences are found in the IL17RLP amino acid sequence at the following locations: K-141 through threonine-231 (K-228, K-229, Q-230, T-231) and K-319 through S-322 (K-319, K-320, T-321, S-322). Three potential Protein Kinase C (PKC) phosphorylation sites are also marked in FIGS. 1A, 1B, and 1C with a bolded serine or tyrosine symbol (S or T) in the IL17RLP amino acid sequence and an asterisk (*) above the first nucleotide encoding that serine tyrosine residue in the IL17RLP nucleotide sequence. The potential PKC phosphorylation sequences are found in the IL17RLP amino acid sequence at the following locations: S-77 through R-79 (S-77, 1-78, R-79); T-89 through K-91 (T-89, G-90, K-91); and T-384 through K-386 (T-384, Q-385, K-386). Three potential Casein Kinase II (CK2) phosphorylation sites are also marked in FIGS. 1A, 1B, and 1C with a bolded serine symbol (S) in the IL17RLP amino acid sequence and an asterisk (*) above the first nucleotide encoding the appropriate serine residue in the IL17RLP nucleotide sequence. The potential CK2 phosphorylation sequences are found at the following locations in the IL17RLP amino acid sequence: S-178 through D-181 (S-178, L-179, W-180, D-181); S-402 through D-405 (S-402, V-403, C-404, D-405); and S-414 through E-417 (S-414, P-415, S-416, E-417). A single potential myristylation site is found in the IL17RLP amino acid sequence shown in FIGS. 1A, 1B, and 1C. The potential myristylation site is marked in FIGS. 1A, 1B, and 1C with a double underline delineating the amino acid residues representing the potential myristolation site in the IL17RLP amino acid sequence. The potential myristolation site is located at the following position in the IL17RLP amino acid sequence: G-116 through F-121 (G-116, G-117, K-118, W-119, T-120, F-121).

Mutations in one or more of the amino acid residues in the above-recited potential structural features of the IL17RLP polypeptide are contemplated as mutations which may affect biological, structural, binding or other characteristics of an IL17RLP DNA or polypeptide of the invention.

FIG. 2 shows the regions of identity between the amino acid sequences of the IL17RLP protein and translation product of the murine mRNA for IL-17 receptor (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

FIG. 3 shows an analysis of the IL17RLP amino acid sequence. Alpha, beta, turn and coil regions; hydrophilicity and hydrophobicity; amphipathic regions; flexible regions; antigenic index and surface probability are shown. In the "Antigenic Index or Jameson-Wolf" graph, the positive peaks indicate locations of the highly antigenic regions of the IL17RLP protein, i.e., regions from which epitope-bearing peptides of the invention can be obtained.

In the "Antigenic Index or Jameson-Wolf" graph, the positive peaks indicate locations of the highly antigenic regions of the IL17RLP protein, i.e., regions from which epitope-bearing peptides of the invention can be obtained. Non-limiting examples of antigenic polypeptides or peptides that can be used to generate IL17RLP-specific antibodies include: a polypeptide comprising amino acid residues from about a polypeptide comprising amino acid residues from about Ser-14 to about Val-22 in SEQ ID NO:2, a polypeptide comprising amino acid residues from about Cys-24 to about Pro-32 in SEQ ID NO:2, a polypeptide comprising amino acid residues from about Ile-41 to about Arg-49 in SEQ ID NO:2, a polypeptide comprising amino acid residues from about Thr-89 to about Val-97 in SEQ ID NO:2, a polypeptide comprising amino acid residues from about Thr-110 to about Lys-118 in SEQ ID NO:2, a polypeptide comprising amino acid residues from about Ala-144 to about Ser-152 in SEQ ID NO:2, a polypeptide comprising amino acid residues from about Thr-240 to about Val-248 in SEQ ID NO:2, a polypeptide comprising amino acid residues from about Gly-258 to about Thr-267 in SEQ ID NO:2, a polypeptide comprising amino acid residues from about Leu-280 to about Gly-288 in SEQ ID NO:2, a polypeptide comprising amino acid residues from about Cys-404 to about Glu-412 in SEQ ID NO:2, a polypeptide comprising amino acid residues from about Pro-415 to about Ser-423 in SEQ ID NO:2, a polypeptide comprising amino acid residues from about Gly-409 to about Glu-417 in SEQ ID NO:2, and a polypeptide comprising amino acid residues from about Cys-404 to about Leu-426 in FIGS. 1A, 1B, and 1C (which is identical to the sequence shown in SEQ ID NO:2 with exception to the numbering schemes as detailed above).

The data presented in FIG. 3 are also represented in tabular form in Table I. The data presented in Table I is identical to that originally presented in FIG. 3. The columns are labeled with the headings "Res", "Position", and Roman Numerals I-XIV. The column headings refer to the following features of the amino acid sequence presented in FIG. 3 and Table I: "Res": amino acid residue of SEQ ID NO:2 or FIGS. 1A, 1B, and 1C (which is the identical sequence shown in SEQ ID NO:2, with the exception that the residues are numbered 1-426 in FIGS. 1A, 1B, and 1C and −19 through 407 in SEQ ID NO:2); "Position": position of the corresponding residue within SEQ ID NO:2 or FIGS. 1A, 1B, and 1C (which is the identical sequence shown in SEQ ID NO:2, with the exception that the residues are numbered 1-366 in FIGS. 1A, 1B, and 1C and −19 through 407 in SEQ ID NO:2); I: Alpha, Regions—Garnier-Robson; II: Alpha, Regions—Chou-Fasman; III: Beta, Regions—Garnier-Robson; IV: Beta, Regions—Chou-Fasman; V: Turn, Regions—Garnier-Robson; VI: Turn, Regions—Chou-Fasman; VII: Coil, Regions—Garnier-Robson; VIII: Hydrophilicity Plot—Kyte-Doolittle; IX: Hydrophobicity Plot—Hopp-Woods; X: Alpha, Amphipathic Regions—Eisenberg; XI: Beta, Amphipathic Regions—Eisenberg; XII: Flexible Regions—Karplus-Schulz; XIII: Antigenic Index—Jameson-Wolf; and XIV: Surface Probability Plot—Emini.

DETAILED DESCRIPTION

The present invention provides isolated nucleic acid molecules comprising, or alternatively consisting of, a polynucleotide encoding a IL17RLP polypeptide having the amino acid sequence shown in SEQ ID NO:2, which was determined by sequencing a cloned cDNA. The nucleotide sequence shown in FIGS. 1A, 1B, and 1C (SEQ ID NO:1) was obtained by sequencing the HAPOR40 clone, which was deposited on Aug. 8, 1997 at the American Type Culture Collection, 10801 University Boulevard, Manassas, Va. 20110-2209, and given accession number ATCC™ 209198. The deposited clone is contained in the pBLUESCRIPT™ SK(−) plasmid (STRATAGENE™, La Jolla, Calif.).

The IL17RLP protein of the present invention shares sequence homology with the translation product of the murine mRNA for IL-17 receptor (FIG. 2; SEQ ID NO:3). Murine IL-17 receptor is thought to be an important component of the IL-17 cytokine signal transduction pathway. IL-17 receptor appears to be structurally unrelated to any members of previously described cytokine receptor families. The IL-17/IL-17 receptor complex activates NF-kappaB activity. NF-kappaB is a transcription factor known to regulate a large number of gene products involved in growth control. NF-kappaB-induced gene products include molecules involved in immune, inflammatory, or acute phase responses, such as immunoglobulin light chain, major histocompatibility complex (MHC), IL-2R alpha chain, and cytokines such as IL-1beta, IL-6, and TNFalpha. NF-kappaB directly stimulates the HIV enhancer in T-cells and can itself be activated by different viral proteins with oncogenic potential, such as the hepatitis B virus HBX protein, EBV LMP1, and HTLV-1 Tax protein. The induction of NF-kappaB by Tax results in up-regulation of IL-2 and IL-2R and subsequently uncontrolled T-cell growth. IL-17 and HVS13, a gene product of HVS and a murine counterpart of IL-17, strongly induce IL-6 expression. IL-6 is a potent growth factor for myelomas, plasmacytomas, and hybridomas and is involved in the growth of Lennert's Lymphoma T-cells.

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIGS. 1A, 1B, and 1C (SEQ ED NO:1), a nucleic acid molecule of the present invention encoding a IL17RLP polypeptide may be obtained using standard cloning and screening procedures, such as those for cloning cDNAs using mRNA as starting material. Illustrative of the invention, the nucleic acid molecule described in FIGS. 1A, 1B, and 1C (SEQ ID NO:1) was discovered in a cDNA library derived from human adult pulmonary tissue.

Additional clones of the same gene were also identified in cDNA libraries from the following tissues: Crohn's Disease tissue, kidney pyramid, cortex, and medulla tissues, hippocampus, frontal cortex of the brain from a patient with epilepsy, adrenal gland tumor, striatum depression, osteclastoma, endometrial tumor, and hypothalamus from a patient with Schizophrenia.

The determined nucleotide sequence of the IL17RLP cDNA of FIGS. 1A, 1B, and 1C (SEQ ID NO:1) contains an open reading frame encoding a protein of 426 amino acid residues, with an initiation codon at nucleotide positions 10-12 of the nucleotide sequence in FIGS. 1A, 1B, and 1C (SEQ ID NO:1), and a deduced molecular weight of about 47.1 kDa. The amino acid sequence of the IL17RLP protein shown in SEQ ID NO:2 is about 28.6% identical to the murine mRNA for IL-17 receptor (FIG. 2; Yao, Z., et al, *Immunity* 3:811-821 (1995); GenBank Accession No. U31993).

The open reading frame of the IL17RLP gene shares sequence homology with the translation product of the murine mRNA for IL-17 receptor (FIG. 2; SEQ ID NO:3). The murine IL-17 receptor is thought to be important in regulation of immune cell signal transduction cascades and the resulting regulation of cell growth, differentiation, and activation-state. The homology between the murine IL-17 receptor and IL17RLP indicates that IL17RLP may also be involved in regulation of immune cell signal transduction cascades and the resulting regulation of cell growth, differentiation, and activation-state.

As one of ordinary skill would appreciate, due to the possibilities of sequencing errors discussed above, the actual complete IL17RLP polypeptide encoded by the deposited cDNA, which comprises about 426 amino acids, may be somewhat longer or shorter. More generally, the actual open reading frame may be anywhere in the range of ±20 amino acids, more likely in the range of ±10 amino acids, of that predicted from either the first methionine codon from the N-terminus shown in FIGS. 1A, 1B, and 1C (SEQ ID NO:1). It will further be appreciated that, depending on the analytical criteria used for identifying various functional domains, the exact "address" of the extracellular, intracellular and transmembrane domains of the IL17RLP polypeptide may differ slightly from the predicted positions above. For example, the exact location of the IL17RLP extracellular domain in SEQ ID NO:2 may vary slightly (e.g., the address may "shift" by about 1 to about 20 residues, more likely about 1 to about 5 residues) depending on the criteria used to define the domain. In this case, the ends of the transmembrane domain and the beginning of the extracellular domain were predicted on the basis of the identification of the hydrophobic amino acid sequence in the above indicated positions, as shown in FIG. 3. In any event, as discussed further below, the invention further provides polypeptides having various residues deleted from the N-terminus of the complete polypeptide, including polypeptides lacking one or more amino acids from the N-terminus of the extracellular domain described herein, which constitute soluble forms of the extracellular domain of the IL17RLP protein.

In another embodiment, the present invention includes a polynucleotide of 1,918 nucleotides (SEQ ID NO:17) which encodes the IL17RLP polypeptide provided in SEQ ID NO:18. The IL17RLP of SEQ ID NO:18 differs from the IL17RLP provided in SEQ ID NO:2 only by the deletion of the C-terminal two residues (Cys-406 and Leu-407 of SEQ ID NO:2) and the addition of nine amino acid residues (Leu-425 through Ile-433 of SEQ ID NO:18). The extracellular domain of IL17RLP is identical in SEQ ID NO:2 and SEQ ID NO:18. The IL17RLP polynucleotide sequence shown in SEQ ID NO:17 was derived from sequencing the HAPOR40 cDNA clone deposited with the ATCC™ with ATCC™ Deposit No. 209198 on Aug. 8, 1997.

It will further be appreciated that, depending on the analytical criteria used for identifying the exact location of the cleavage site of the precursor form of the mature IL17RLP molecule shown in SEQ ID NO:2 may vary slightly, depending on the criteria used to define the cleavage site. In this case, the ends of the signal peptide and the beginning of the mature IL17RLP molecule were predicted using the HGSI SignalP computer algorithm. One of skill in the art will realize that another widely accepted computer algorithm used to predict potential sites of polypeptide cleavage, PSORT, will predict the cleavage of an N-terminal signal peptide from the IL17RLP polypeptide at a point slightly different from that predicted by the HGSI SignalP algorithm. In either case, as discussed further below, the invention further provides polypeptides having various residues deleted from the N-terminus of the complete polypeptide, including polypeptides corresponding to either of the predicted mature IL17RLP polypeptides described herein.

Leader and Mature Sequences

The amino acid sequence of the complete IL17RLP protein includes a leader sequence and a mature protein, as shown in SEQ ID NO:2. More in particular, the present invention provides nucleic acid molecules encoding a mature form of the IL17RLP protein. Thus, according to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature IL17RLP polypeptide having the amino acid sequence encoded by the cDNA clone identified as ATCC™ Deposit No. 209198. By the "mature IL17RLP polypeptide having the amino acid sequence encoded by the cDNA clone in ATCC™ Deposit No. 209198" is meant the mature form(s) of the IL17RLP protein produced by expression in a mammalian cell (e.g., COS cells, as described below) of the complete open reading frame encoded by the human DNA sequence of the clone contained in the deposited clone HAPOR40.

In addition, methods for predicting whether a protein has a secretory leader as well as the cleavage point for that leader sequence are available. For instance, the method of McGeoch (*Virus Res.* 3:271-286 (1985)) uses the information from a short N-terminal charged region and a subsequent uncharged region of the complete (uncleaved) protein. The method of von Heinje (*Nucleic Acids Res.* 14:4683-4690 (1986)) uses the information from the residues surrounding the cleavage site, typically residues −13 to +2 where +1 indicates the amino terminus of the mature protein. The accuracy of predicting the cleavage points of known mammalian secretory proteins for each of these methods is in the range of 75-80% (von Heinje, supra). However, the two methods do not always produce the same predicted cleavage point(s) for a given protein.

In the present case, the deduced amino acid sequence of the complete IL17RLP polypeptide was analyzed by a variation of the computer program "PSORT", available from Dr. Kenta Nakai of the Institute for Chemical Research, Kyoto University (Nakai, K. and Kanehisa, M. *Genomics* 14:897-911 (1992)), which is an expert system for predicting the cellular location of a protein based on the amino acid sequence. As part of this computational prediction of localization, the methods of McGeoch and von Heinje are incorporated. Thus, the computation analysis above predicted a single cleavage site within the complete amino acid sequence shown in SEQ ID NO:2 (see above discussion).

As one of ordinary skill would appreciate from the above discussions, due to the possibilities of sequencing errors as well as the variability of cleavage sites in different known proteins, the mature IL17RLP polypeptide encoded by the deposited cDNA is expected to consist of about 407 amino acids (presumably residues 1 to 407 of SEQ ID NO:2, but may consist of any number of amino acids in the range of about 407-412 amino acids (e.g., 407, 408, 409, 410, 411, and/or 412); and the actual leader sequence(s) of this protein is expected to be 14-19 amino acids (presumably residues −19 through −1 of SEQ ID NO:2), but may consist of any number of amino acids in the range of 14-19 amino acids (e.g., 14, 15, 16, 17, 18 and/or 19).

In another embodiment, the encoded polypeptide has a predicted leader sequence from Met-(−19) to Ser-(−6) of SEQ ID NO:2 (i.e., from Met-1 to Ser-14 of the amino acid sequence presented in FIGS. 1A, 1B, and 1C); an extracellular domain from Ala-(−5) to Trp-271 of SEQ ID NO:2 (i.e., from Ala-15 to Trp-290 of the amino acid sequence presented in FIGS. 1A, 1B, and 1C); a transmembrane domain from Leu-272 to Leu-292 of SEQ ID NO:2 (i.e., from Leu-291 to Leu-311 of the amino acid sequence presented in FIGS. 1A, 1B, and 1C); and an intracellular domain from Met-293 to Leu-407 of SEQ ID NO:2 (i.e., from Met-312 to Leu-426 of the amino acid sequence presented in FIGS. 1A, 1B, and 1C). The predicted leader peptide in this embodiment is within the originally predicted range of 14-19 amino acids.

In an additional embodiment, the IL17RLP transmembrane domain may have an N-terminal boundary beginning at amino acid residue Pro-268, Gly-269, Gly-270, Trp-271 or Leu-272 of the IL17RLP sequence as shown in SEQ ID NO:2 (i.e., amino acid residues Pro-287, Gly-288, Gly-289, Trp-290 or Leu-291 of the IL17RLP sequence as shown in FIGS. 1A, 1B, and 1C) and a C-terminal boundary including amino acid residue Tyr-291, Leu-292, Met-293 or Trp-294 of the IL17RLP sequence as shown in SEQ ID NO:2 (i.e., amino acid residues Tyr-310, Leu-311, Met-312 or Trp-313 of the IL17RLP sequence as shown in FIGS. 1A, 1B, and 1C).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically. However, a nucleic acid contained in a clone that is a member of a library (e.g., a genomic or cDNA library) that has not been isolated from other members of the library (e.g., in the form of a homogeneous solution containing the clone and other members of the library) or which is contained on a chromosome preparation (e.g., a chromosome spread) or a nucleic acid present in a preparation of genomic DNA (e.g., intact, sheared, and/or cut with one or more restriction enzymes) that has not been isolated from other nucleic acids in the preparation, is not "isolated" for the purposes of this invention.

Isolated nucleic acid molecules of the present invention include DNA molecules comprising an open reading frame (ORF) with an initiation codon at positions 10-12 of the nucleotide sequence shown in FIGS. 1A, 1B, and 1C (SEQ ID NO:1).

Also included are DNA molecules comprising the coding sequence for the predicted mature IL17RLP protein shown at positions 1-407 of SEQ ID NO:2.

In addition, isolated nucleic acid molecules of the invention include DNA molecules which comprise a sequence substantially different from those described above but which, due to the degeneracy of the genetic code, still encode the IL17RLP protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

In another aspect, the invention provides isolated nucleic acid molecules encoding the IL17RLP polypeptide having an amino acid sequence encoded by the cDNA clone contained in the plasmid deposited as ATCC™ Deposit No. 209198 on Aug. 8, 1997.

Preferably, this nucleic acid molecule will encode the mature polypeptide encoded by the above-described deposited cDNA clone. Also preferably, this nucleic acid molecule will encode the extracellular domain encoded by the above-described cDNA clone.

The invention further provides an isolated nucleic acid molecule having the nucleotide sequence shown in FIGS. 1A, 1B, and 1C (SEQ ID NO:1) or the nucleotide sequence of the IL17RLP cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the IL17RLP gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1-1290 of SEQ ID NO:1.

In addition, the invention provides nucleic acid molecules having nucleotide sequences related to extensive portions of SEQ ID NO:1 which have been determined from the following related cDNA clones: HHPCH63R (SEQ ID NO:4) and HETCC45RA (SEQ ID NO:5). Such polynucleotides may preferably be excluded from the invention.

Further, the invention includes a polynucleotide comprising, or alternatively consisting of, any portion of at least about 25 nucleotides, at least about 30 nucleotides, at least about 35 nucleotides, at least about 40 nucleotides, at least about 45 nucleotides, preferably at least about 50 nucleotides, at least about 60 nucleotides, at least about 70 nucleotides, at least about 80 nucleotides, at least about 90 nucleotides, or at least about 100 nucleotides of SEQ ID NO:1 from residue 50-1800, 100-1800, 200-1800, 300-1800, 400-1800, 500-1800, 600-1800, 50-650, 100-650, 200-650, 300-650, 400-650, 500-650, 50-500, 100-500, 200-500, 300-500, 400-500, 50-400, 100-400, 200-400, 300-400, 50-300, 100-300, 200-300, 50-200, 100-200, and 50-100.

More generally, by a fragment of an isolated nucleic acid molecule having the nucleotide sequence of the deposited cDNA or the nucleotide sequence shown in FIGS. 1A, 1B, and 1C (SEQ ID NO:1) is intended fragments at least about 15 nt, and more preferably at least about 20 nt, more preferably at least about 25 nt, still more preferably at least about 30 nt, more preferably at least about 35 nt, and even more preferably, at least about 40 nt, more preferably at least about 45 nt, in length which are useful as diagnostic probes and primers as discussed herein. Of course, larger fragments 50-300 nt in length (e.g., 50 nt, 55 nt, 60 nt, 65 nt, 70 nt, 75 nt, 80 nt, 85 nt, 90 nt, 95 nt, 100 nt, 125 nt, 150 nt, 175 nt, 200 nt, 225 nt, 250 nt, 275 nt, and/or 300 nt (of course, fragment lengths in addition to those recited herein are also useful)) are also useful according to the present invention as are fragments corresponding to most, if not all, of the nucleotide sequence of the deposited cDNA or as shown in FIGS. 1A, 1B, and 1C (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A, 1B, and 1C (SEQ ID NO:1). Preferred nucleic acid fragments of the present invention include nucleic acid molecules encoding epitope-bearing portions of the IL17RLP polypeptide as identified, for example, in FIG. 3 and described in more detail below.

In specific embodiments, the polynucleotide fragments of the invention encode a polypeptide which demonstrates a functional activity. By a polypeptide demonstrating "functional activity" is meant, a polypeptide capable of displaying one or more known functional activities associated with a complete, mature, extracellular domain, or active form of the IL17RLP polypeptide. Such functional activities include, but are not limited to, biological activity ((e.g., activation of signal transduction pathways resulting in the stimulation of the NF-kappaB transcription factor family, the secretion of IL-6, and the costimulation of T-cell proliferation; induction of IL-6, IL-8, G-CSF, Prostaglandin E ($PGE_2$), and intracellular adhesion molecule (ICAM)-1 expression; regulation of hematopoietic stem and progenitor cell growth and expansion; myelosuppressive activity for stem and immature subsets of myeloid progenitors; activation and stimulation of hematopoiesis in general (more specifically, neutrophil hematopoiesis); enhancement of erythropoiesis; suppression of lymphopoiesis and myelopoiesis; and strong suppression of monocytopoiesis)), antigenicity [ability to bind (or compete with a IL17RLP polypeptide for binding) to an anti-IL17RLP antibody], immunogenicity (ability to generate antibody which binds to an IL17RLP polypeptide), the ability to form polymers with other IL17RLP or IL17RLP-like polypeptides, and ability to bind to a receptor or ligand for an IL17RLP polypeptide.

Preferred nucleic acid fragments of the present invention also include nucleic acid molecules encoding polypeptides comprising, or alternatively consisting of, one or more of the following domains of IL17RLP: Domain I (i.e., Val-49 through Leu-62 of SEQ ID NO:2 (Val-68 through Leu-81 of FIGS. 1A, 1B, and 1C)); Domain II (Cys-154 through Thr-166 of SEQ ID NO:2 (i.e., Cys-173 through Thr-185 of FIGS. 1A, 1B, and 1C)); Domain III (Gln-202 through Gln-208 of SEQ ID NO:2 (i.e., Gln-221 through Gln-227 of FIGS. 1A, 1B, and 1C)); Domain IV (Asp-241 through Val-249 of SEQ ID NO:2 (i.e., Asp-260 through Val-268 of FIGS. 1A, 1B, and 1C)); Domain V (Thr-255 through Leu-261 of SEQ ID NO:2 (i.e., Thr-274 through Leu-280 of FIGS. 1A, 1B, and 1C)); Domain VI (Leu-310 through Tyr-319 of SEQ ID NO:2 (i.e., Leu-329 through Tyr-338 of FIGS. 1A, 1B, and 1C)); Domain VII (Cys-340 through Leu-346 of SEQ ID NO:2 (i.e., Cys-359 through Leu-365 of FIGS. 1A, 1B, and 1C)); and Domain VIII (Ile-354 through Gly-358 of SEQ ID NO:2 (i.e., Ile-373 through Gly-377 of FIGS. 1A, 1B, and 1C)).

In specific embodiments, the polynucleotide fragments of the invention encode antigenic regions. Non-limiting examples of antigenic polypeptides or peptides that can be used to generate IL17RLP-specific antibodies include: a polypeptide comprising, or alternatively consisting of, amino acid residues from about from about Ser-14 to about Val-22, from about Cys-24 to about Pro-32, from about Ile-41 to about Arg-49, from about Thr-89 to about, from about Thr-110 to about Lys-118, from about Ala-144 to about Ser-152, from about Thr-240 to about Val-248, from about Gly-258 to about Thr-267, from about Leu-280 to about Gly-288, from about Cys-404 to about Glu-412, from about Pro-415 to about Ser-423, from about Gly-409 to about Glu-417, and from about Cys-404 to about Leu-426 in FIGS. 1A, 1B, and 1C (which is the identical sequence to that shown in SEQ ID NO:2, with the exception of the numbering schemes as described above).

Additional preferred polypeptide fragments comprise, or alternatively consist of, the amino acid sequence of residues: M-1 to A-15; S-2 to V-16; L-3 to P-17; V-4 to R-18; L-5 to E-19; L-6 to P-20; S-7 to T-21; L-8 to V-22; A-9 to Q-23; A-10 to C-24; L-11 to G-25; C-12 to S-26; R-13 to E-27; S-14 to T-28; A-15 to G-29; V-16 to P-30; P-17 to S-31; R-18 to P-32; E-19 to E-33; P-20 to W-34; T-21 to M-35; V-22 to L-36; Q-23 to Q-37; C-24 to H-38; G-25 to D-39; S-26 to L-40; E-27 to I-41; T-28 to P-42; G-29 to G-43; P-30 to D-44; S-31 to L-45; P-32 to R-46; E-33 to D-47; W-34 to L-48; M-35 to R-49; L-36 to V-50; Q-37 to E-51; H-38 to P-52; D-39 to V-53; L-40 to T-54; I-41 to T-55; P-42 to S-56; G-43 to V-57; D-44 to A-58; L-45 to T-59; R-46 to G-60; D-47 to D-61; L-48 to Y-62; R-49 to S-63; V-50 to I-64; E-51 to L-65; P-52 to M-66; V-53 to N-67; T-54 to V-68; T-55 to S-69; S-56 to W-70; V-57 to V-71; A-58 to L-72; T-59 to R-73; G-60 to A-74; D-61 to D-75; Y-62 to A-76; S-63 to S-77; I-64 to I-78; L-65 to R-79; M-66 to L-80; N-67 to L-81; V-68 to K-82; S-69 to A-83; W-70 to T-84; V-71 to K-85; L-72 to I-86; R-73 to C-87; A-74 to V-88; D-75 to T-89; A-76 to G-90; S-77 to K-91; I-78 to S-92; R-79 to N-93; L-80 to F-94; L-81 to Q-95; K-82 to S-96; A-83 to Y-97; T-84 to S-98; K-85 to C-99; I-86 to V-100; C-87 to R-101; V-88 to C-102; T-89 to N-103; G-90 to Y-104; K-91 to T-105; S-92 to E-106; N-93 to A-107; F-94 to F-108; Q-95 to Q-109; S-96 to T-110; Y-97 to Q-111; S-98 to T-112; C-99 to R-113; V-100 to P-114; R-101 to S-115; C-102 to G-116; N-103 to G-117; Y-104 to K-118; T-105 to W-119; E-106 to T-120; A-107 to F-121; F-108 to S-122; Q-109 to Y-123; T-110 to I-124; Q-111 to G-125; T-112 to F-126; R-113 to P-127; P-114 to V-128; S-115 to E-129; G-116 to L-130; G-117 to N-131; K-118 to T-132; W-119 to V-133; T-120 to Y-134; F-121 to F-135; S-122 to I-136; Y-123 to G-137; I-124 to A-138; G-125 to H-139; F-126 to N-140; P-127 to I-141; V-128 to P-142; E-129 to N-143; L-130 to A-144; N-131 to N-145; T-132 to M-146; V-133 to N-147; Y-134 to E-148; F-135 to D-149; I-136 to G-150; G-137 to P-151; A-138 to S-152; H-139 to M-153; N-140 to S-154; I-141 to V-155; P-142 to N-156; N-143 to F-157; A-144 to T-158; N-145 to S-159; M-146 to P-160; N-147 to G-161; E-148 to C-162; D-149 to L-163; G-150 to D-164; P-151 to H-165; S-152 to I-166; M-153 to M-167; S-154 to K-168; V-155 to Y-169; N-156 to K-170; F-157 to K-171; T-158 to K-172; S-159 to C-173; P-160 to V-174; G-161 to K-175; C-162 to A-176; L-163 to G-177; D-164 to S-178; H-165 to L-179; I-166 to W-180; M-167 to D-181; K-168 to P-182; Y-169 to N-183; K-170 to I-184; K-171 to T-185; K-172 to A-186; C-173 to C-187; V-174 to K-188; K-175 to K-189; A-176 to N-190; G-177 to E-191; S-178 to E-192; L-179 to T-193; W-180 to V-194; D-181 to E-195; P-182 to V-196; N-183 to N-197; I-184 to F-198; T-185 to T-199; A-186 to T-200; C-187 to T-201; K-188 to P-202; K-189 to L-203; N-190 to G-204; E-191 to N-205; E-192 to R-206; T-193 to Y-207; V-194 to M-208; E-195 to A-209; V-196 to L-210; N-197 to I-211; F-198 to Q-212; T-199 to H-213; T-200 to S-214; T-201 to T-215; P-202 to I-216; L-203 to I-217; G-204 to G-218; N-205 to F-219; R-206 to S-220; Y-207 to Q-221; M-208 to V-222; A-209 to F-223; L-210 to E-224; I-211 to P-225; Q-212 to H-226; H-213 to Q-227; S-214 to K-228; T-215 to K-229; I-216 to Q-230; I-217 to T-231; G-218 to R-232; F-219 to A-233; S-220 to S-234; Q-221 to V-235; V-222 to V-236; F-223 to I-237; E-224 to P-238; P-225 to V-239; H-226 to T-240; Q-227 to G-241; K-228 to D-242; K-229 to S-243; Q-230 to E-244; T-231 to G-245; R-232 to A-246; A-233 to T-247; S-234 to V-248; V-235 to Q-249; V-236 to L-250; I-237 to T-251; P-238 to P-252; V-239 to Y-253; T-240 to F-254; G-241 to P-255; D-242 to T-256; S-243 to C-257; E-244 to G-258; G-245 to S-259; A-246 to D-260; T-247 to C-261; V-248 to I-262; Q-249 to R-263; L-250 to H-264; T-251 to K-265; P-252 to G-266; Y-253 to T-267; F-254 to V-268; P-255 to V-269; T-256 to L-270; C-257 to C-271; G-258 to P-272; S-259 to Q-273; D-260 to T-274; C-261 to G-275; I-262 to V-276; R-263 to P-277; H-264 to F-278; K-265 to P-279; G-266 to L-280; T-267 to D-281; V-268 to N-282; V-269 to N-283; L-270 to K-284; C-271 to S-285; P-272 to K-286; Q-273 to P-287; T-274 to G-288; G-275 to G-289; V-276 to W-290; P-277 to L-291; F-278 to P-292; P-279 to L-293; L-280 to L-294; D-281 to L-295; N-282 to L-296; N-283 to S-297; K-284 to L-298; S-285 to L-299; K-286 to V-300; P-287 to A-301; G-288 to T-302; G-289 to W-303; W-290 to V-304; L-291 to L-305; P-292 to V-306; L-293 to A-307; L-294 to G-308; L-295 to I-309; L-296 to Y-310; S-297 to L-311; L-298 to M-312; L-299 to W-313; V-300 to R-314; A-301 to H-315; T-302 to E-316; W-303 to R-317; V-304 to I-318; L-305 to K-319; V-306 to K-320; A-307 to T-321; G-308 to S-322; I-309 to F-323; Y-310 to S-324; L-311 to T-325; M-312 to T-326; W-313 to T-327; R-314 to L-328; H-315 to L-329; E-316 to P-330; R-317 to P-331; I-318 to I-332; K-319 to K-333; K-320 to V-334; T-321 to L-335; S-322 to V-336; F-323 to V-337; S-324 to Y-338; T-325 to P-339; T-326 to S-340; T-327 to E-341; L-328 to I-342; L-329 to C-343; P-330 to F-344; P-331 to H-345; I-332 to H-346; K-333 to T-347; V-334 to I-348; L-335 to C-349; V-336 to Y-350; V-337 to F-351; Y-338 to T-352; P-339 to E-353; S-340 to F-354; E-341 to L-355; I-342 to Q-356; C-343 to N-357; F-344 to H-358; H-345 to C-359; H-346 to R-360; T-347 to S-361; I-348 to E-362; C-349 to V-363; Y-350 to I-364; F-351 to L-365; T-352 to E-366; E-353 to K-367; F-354 to W-368; L-355 to Q-369; Q-356 to K-370; N-357 to K-371; H-358 to C-372; C-359 to I-373; R-360 to A-374; S-361 to E-375; E-362 to M-376; V-363 to G-377; I-364 to P-378; L-365 to V-379; E-366 to Q-380; K-367 to W-381; W-368 to L-382; Q-369 to A-383; K-370 to T-384; K-371 to Q-385; K-372 to K-386; I-373 to K-387; A-374 to A-388; E-375 to A-389; M-376 to D-390; G-377 to K-391; P-378 to V-392; V-379 to V-393; Q-380 to F-394; W-381 to L-395; L-382 to L-396; A-383 to S-397; T-384 to N-398; Q-385 to D-399; K-386 to V-400; K-387 to N-401; A-388 to S-402; A-389 to V-403; D-390 to C-404; K-391 to D-405; V-392 to G-406; V-393 to T-407; F-394 to C-408; L-395 to 0-409; L-396 to K-410; S-397 to S-411; N-398 to E-412; D-399 to G-413; V-400 to S-414; N-401 to P-415; S-402 to S-416; V-403 to E-417; C-404 to N-418; D-405 to S-419; G-406 to Q-420; I-407 to D-421; C-408 to S-422; G-409 to S-423; K-410 to P-424; S-411 to C-425; and E-412 to L-426 of the amino acid sequence in shown in SEQ ID NO:2. These polypeptide fragments may retain the biological activity of IL17RLP polypeptides of the invention and/or may be useful to generate or screen for antibodies, as described further below. Polynucleotides encoding these polypeptide fragments are also encompassed by the invention.

Preferably, the polynucleotide fragments of the invention encode a polypeptide which demonstrates a IL17RLP functional activity. By a polypeptide demonstrating a IL17RLP "functional activity" is meant, a polypeptide capable of displaying one or more known functional activities associated with a full-length (complete) IL17RLP protein. Such functional activities include, but are not limited to, biological activity, antigenicity [ability to bind (or compete with a IL17RLP polypeptide for binding) to an anti-IL17RLP antibody], immunogenicity (ability to generate antibody which binds to a IL17RLP polypeptide), ability to form multimers with IL17RLP polypeptides of the invention, and ability to bind to a receptor or ligand for a IL17RLP polypeptide.

The functional activity of IL17RLP polypeptides, and fragments, variants derivatives, and analogs thereof, can be assayed by various methods.

In additional embodiments, the polynucleotides of the invention encode functional attributes of IL17RLP. Preferred embodiments of the invention in this regard include fragments that comprise, or alternatively consist of, alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of IL17RLP.

The data representing the structural or functional attributes of IL17RLP set forth in FIG. 3 and/or Table I, as described above, was generated using the various modules and algorithms of the DNA*STAR set on default parameters. In a preferred embodiment, the data presented in columns VIII, IX, XIII, and XIV of Table I can be used to determine regions of IL17RLP which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIG. 3, but may, as shown in Table I, be represented or identified by using tabular representations of the data presented in FIG. 3. The DNA*STAR computer algorithm used to generate FIG. 3 (set on the original default parameters) was used to present the data in FIG. 3 in a tabular format (See Table I). The tabular format of the data in FIG. 3 may be used to easily determine specific boundaries of a preferred region.

The above-mentioned preferred regions set out in FIG. 3 and in Table I include, but are not limited to, regions of the aforementioned types identified by analysis of the amino acid sequence set out in FIGS. 1A, 1B, and 1C. As set out in FIG. 3 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index.

TABLE I

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | A | . | . | . | . | . | −1.43 | 0.61 | . | . | . | −0.60 | 0.30 |
| Ser | 2 | A | A | . | . | . | . | . | −1.86 | 0.87 | . | . | . | −0.60 | 0.20 |
| Leu | 3 | A | A | . | . | . | . | . | −1.77 | 1.13 | . | . | . | −0.60 | 0.13 |
| Val | 4 | A | A | . | . | . | . | . | −2.19 | 1.09 | . | . | . | −0.60 | 0.17 |
| Leu | 5 | A | A | . | . | . | . | . | −2.39 | 1.16 | . | . | . | −0.60 | 0.11 |
| Leu | 6 | A | A | . | . | . | . | . | −2.38 | 1.27 | . | . | . | −0.60 | 0.13 |
| Ser | 7 | A | A | . | . | . | . | . | −2.89 | 1.09 | . | . | . | −0.60 | 0.18 |
| Leu | 8 | A | A | . | . | . | . | . | −2.74 | 1.13 | * | * | . | −0.60 | 0.18 |
| Ala | 9 | A | A | . | . | . | . | . | −1.78 | 1.01 | * | * | . | −0.60 | 0.11 |
| Ala | 10 | A | A | . | . | . | . | . | −1.27 | 0.33 | * | . | . | −0.30 | 0.17 |
| Leu | 11 | A | A | . | . | . | . | . | −1.04 | 0.33 | * | * | . | −0.30 | 0.27 |
| Cys | 12 | A | . | B | . | . | T | . | −1.60 | 0.14 | * | . | . | 0.10 | 0.27 |
| Arg | 13 | . | . | B | . | . | T | . | −1.00 | 0.29 | * | . | . | 0.40 | 0.20 |
| Ser | 14 | . | . | B | . | . | T | . | −0.30 | 0.21 | . | . | . | 0.70 | 0.37 |
| Ala | 15 | . | . | B | . | . | T | . | 0.29 | −0.47 | . | . | . | 1.75 | 1.37 |
| Val | 16 | . | . | . | . | . | . | C | 0.89 | −1.04 | * | . | F | 2.50 | 1.21 |
| Pro | 17 | . | . | . | . | T | . | . | 1.24 | −0.61 | * | . | F | 3.00 | 1.39 |
| Arg | 18 | . | . | . | . | T | . | . | 0.28 | −0.51 | . | . | F | 2.70 | 1.99 |
| Glu | 19 | . | . | B | . | . | . | . | 0.58 | −0.37 | . | . | F | 1.70 | 1.99 |
| Pro | 20 | . | . | B | . | . | . | . | 0.50 | −0.61 | . | . | F | 1.70 | 2.23 |
| Thr | 21 | . | . | B | . | . | . | . | 1.01 | −0.47 | . | . | F | 0.95 | 0.61 |
| Val | 22 | . | . | B | . | . | . | . | 0.92 | −0.04 | . | . | . | 0.50 | 0.35 |
| Gln | 23 | . | . | B | . | . | . | . | 0.81 | 0.34 | . | . | . | 0.18 | 0.30 |
| Cys | 24 | . | . | B | . | . | T | . | 0.50 | −0.09 | * | . | F | 1.41 | 0.36 |
| Gly | 25 | . | . | B | . | . | T | . | 0.37 | −0.09 | * | . | F | 1.69 | 0.71 |
| Ser | 26 | . | . | . | . | T | T | . | 0.47 | −0.30 | * | . | F | 2.37 | 0.40 |
| Glu | 27 | . | . | . | . | T | T | . | 1.02 | −0.27 | * | . | F | 2.80 | 1.16 |
| Thr | 28 | . | . | . | . | . | . | C | 0.81 | −0.46 | * | . | F | 2.12 | 1.57 |
| Gly | 29 | . | . | . | . | . | . | C | 1.48 | −0.46 | . | . | F | 1.84 | 1.82 |
| Pro | 30 | . | . | . | . | . | . | C | 1.53 | −0.84 | . | . | F | 1.86 | 1.82 |
| Ser | 31 | . | . | . | . | . | T | C | 1.23 | 0.07 | . | . | F | 0.88 | 1.32 |
| Pro | 32 | . | . | . | . | . | T | C | 0.42 | 0.20 | . | * | F | 0.60 | 1.32 |
| Glu | 33 | A | . | . | . | . | T | . | 0.73 | 0.46 | . | . | F | −0.05 | 0.71 |
| Trp | 34 | A | . | . | . | . | T | . | 1.04 | 0.43 | . | * | . | −0.20 | 0.91 |
| Met | 35 | A | A | . | . | . | . | . | 1.26 | 0.54 | . | * | . | −0.60 | 0.80 |
| Leu | 36 | A | A | . | . | . | . | . | 0.74 | 0.11 | . | * | . | −0.30 | 0.77 |
| Gln | 37 | A | A | . | . | . | . | . | 0.07 | 0.80 | . | * | . | −0.60 | 0.61 |
| His | 38 | . | A | B | . | . | . | . | −0.14 | 0.57 | . | * | . | −0.60 | 0.43 |
| Asp | 39 | . | A | . | . | T | . | . | −0.20 | 0.39 | . | . | . | 0.10 | 0.81 |
| Leu | 40 | . | A | . | . | . | . | C | 0.40 | 0.13 | . | . | . | 0.24 | 0.46 |
| Ile | 41 | . | . | B | . | . | T | . | 0.40 | −0.27 | * | * | . | 1.38 | 0.57 |
| Pro | 42 | . | . | B | . | . | T | . | 0.51 | −0.09 | * | * | F | 1.87 | 0.28 |
| Gly | 43 | . | . | . | . | T | T | . | 0.54 | −0.09 | * | * | F | 2.61 | 0.66 |
| Asp | 44 | . | . | . | . | T | T | . | −0.27 | −0.77 | * | . | F | 3.40 | 1.58 |
| Leu | 45 | . | A | B | . | . | . | . | 0.66 | −0.77 | * | * | F | 2.11 | 0.84 |
| Arg | 46 | . | A | B | . | . | . | . | 0.69 | −1.20 | * | * | F | 1.92 | 1.67 |
| Asp | 47 | . | A | B | . | . | . | . | 0.90 | −0.99 | . | * | F | 1.43 | 0.74 |
| Leu | 48 | . | A | B | . | . | . | . | 1.03 | −0.99 | . | . | . | 1.09 | 1.56 |
| Arg | 49 | . | A | B | . | . | . | . | 0.18 | −1.24 | . | . | . | 0.75 | 1.23 |
| Val | 50 | . | A | B | B | . | . | . | 0.68 | −0.60 | * | . | . | 0.60 | 0.55 |
| Glu | 51 | . | A | B | B | . | . | . | 0.26 | −0.11 | * | * | F | 0.45 | 0.96 |
| Pro | 52 | . | A | B | B | . | . | . | −0.04 | −0.31 | . | * | F | 0.45 | 0.70 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Val | 53 | . | . | B | B | . | . | . | −0.09 | 0.07 | * | * | F | 0.00 | 1.27 |
| Thr | 54 | . | . | B | B | . | . | . | −0.79 | 0.07 | * | * | F | −0.15 | 0.55 |
| Thr | 55 | . | . | B | B | . | . | . | −0.24 | 0.57 | * | . | F | −0.45 | 0.36 |
| Ser | 56 | . | . | B | B | . | . | . | −0.59 | 0.63 | * | . | F | −0.45 | 0.69 |
| Val | 57 | . | . | B | B | . | . | . | −0.38 | 0.41 | . | . | F | −0.45 | 0.47 |
| Ala | 58 | . | . | B | B | . | . | . | 0.23 | −0.07 | . | . | F | 0.45 | 0.55 |
| Thr | 59 | . | . | B | . | . | . | T | 0.24 | 0.20 | . | * | F | 0.25 | 0.64 |
| Gly | 60 | . | . | B | . | . | T | . | −0.33 | 0.20 | . | . | F | 0.40 | 1.16 |
| Asp | 61 | . | . | B | . | . | T | . | −0.84 | 0.24 | . | . | F | 0.25 | 0.80 |
| Tyr | 62 | . | . | B | . | . | T | . | −0.59 | 0.43 | . | * | . | −0.20 | 0.46 |
| Ser | 63 | . | . | B | B | . | . | . | −0.00 | 0.56 | . | * | . | −0.60 | 0.46 |
| Ile | 64 | . | . | B | B | . | . | . | −0.54 | 0.53 | . | * | . | −0.60 | 0.44 |
| Leu | 65 | . | . | B | B | . | . | . | −0.50 | 1.17 | . | * | . | −0.60 | 0.21 |
| Met | 66 | . | . | B | B | . | . | . | −0.79 | 0.80 | . | * | . | −0.60 | 0.21 |
| Asn | 67 | . | . | B | B | . | . | . | −1.40 | 1.33 | * | * | . | −0.60 | 0.31 |
| Val | 68 | . | . | B | B | . | . | . | −1.91 | 1.29 | * | * | . | −0.60 | 0.28 |
| Ser | 69 | . | . | B | B | . | . | . | −0.91 | 1.29 | * | * | . | −0.60 | 0.24 |
| Trp | 70 | . | . | B | B | . | . | . | −0.69 | 0.67 | * | * | . | −0.60 | 0.29 |
| Val | 71 | . | . | B | B | . | . | . | −0.09 | 0.77 | . | * | . | −0.60 | 0.39 |
| Leu | 72 | A | . | . | B | . | . | . | −0.68 | 0.13 | * | * | . | −0.30 | 0.49 |
| Arg | 73 | A | . | . | B | . | . | . | −0.12 | 0.24 | * | * | . | −0.30 | 0.47 |
| Ala | 74 | A | . | . | B | . | . | . | −0.71 | −0.29 | * | * | . | 0.30 | 0.85 |
| Asp | 75 | A | . | . | B | . | . | . | −0.31 | −0.24 | * | * | . | 0.30 | 0.72 |
| Ala | 76 | A | . | . | B | . | . | . | −0.27 | −0.93 | * | * | . | 0.60 | 0.72 |
| Ser | 77 | A | . | . | B | . | . | . | −0.27 | −0.24 | * | * | . | 0.30 | 0.59 |
| Ile | 78 | A | . | . | B | . | . | . | −0.33 | −0.06 | * | * | . | 0.30 | 0.29 |
| Arg | 79 | A | . | . | B | . | . | . | −0.33 | −0.06 | * | * | . | 0.30 | 0.57 |
| Leu | 80 | A | . | . | B | . | . | . | −0.64 | −0.06 | * | * | . | 0.30 | 0.43 |
| Leu | 81 | A | . | . | B | . | . | . | −0.01 | 0.04 | * | * | . | −0.30 | 0.89 |
| Lys | 82 | A | . | . | B | . | . | . | −0.60 | −0.64 | * | * | F | 0.75 | 0.91 |
| Ala | 83 | A | . | . | B | . | . | . | −0.38 | 0.04 | * | * | F | −0.15 | 0.77 |
| Thr | 84 | A | . | . | B | . | . | . | −1.34 | −0.07 | * | . | F | 0.45 | 0.50 |
| Lys | 85 | . | . | B | B | . | . | . | −0.84 | −0.11 | * | . | F | 0.45 | 0.19 |
| Ile | 86 | . | . | B | B | . | . | . | −0.38 | 0.37 | . | * | . | −0.30 | 0.27 |
| Cys | 87 | . | . | B | B | . | . | . | −0.38 | 0.30 | * | * | . | −0.30 | 0.18 |
| Val | 88 | . | . | B | B | . | . | . | −0.09 | −0.19 | * | * | . | 0.58 | 0.18 |
| Thr | 89 | . | . | B | B | . | . | . | 0.22 | 0.20 | * | * | F | 0.41 | 0.35 |
| Gly | 90 | . | . | . | . | . | T | T | −0.52 | −0.09 | * | * | F | 2.24 | 1.05 |
| Lys | 91 | . | . | . | . | . | T | T | 0.37 | 0.13 | * | * | F | 1.92 | 1.22 |
| Ser | 92 | . | . | . | . | . | T | T | 0.73 | −0.11 | . | * | F | 2.80 | 1.47 |
| Asn | 93 | . | . | . | . | . | T | T | 1.34 | −0.21 | . | * | F | 2.52 | 1.99 |
| Phe | 94 | . | . | . | . | . | T | . | 1.36 | 0.11 | . | * | F | 1.44 | 1.56 |
| Gln | 95 | . | . | . | . | . | T | . | 1.03 | 0.50 | * | * | F | 0.86 | 1.56 |
| Ser | 96 | . | . | . | . | . | T | T | 0.13 | 0.69 | . | * | . | 0.48 | 0.52 |
| Tyr | 97 | . | . | B | . | . | . | T | 0.54 | 0.93 | . | * | . | −0.20 | 0.44 |
| Ser | 98 | . | . | . | . | . | T | T | −0.12 | 0.14 | . | * | . | 0.50 | 0.50 |
| Cys | 99 | . | . | B | . | . | . | T | 0.58 | 0.31 | . | * | . | 0.10 | 0.20 |
| Val | 100 | . | . | B | . | . | . | . | 0.33 | 0.33 | . | * | . | 0.12 | 0.21 |
| Arg | 101 | . | . | B | . | . | . | . | 0.32 | 0.33 | . | * | . | 0.34 | 0.24 |
| Cys | 102 | . | . | B | . | . | . | T | 0.57 | 0.43 | * | * | . | 0.46 | 0.65 |
| Asn | 103 | . | . | . | . | . | T | T | 0.28 | −0.14 | * | * | . | 2.13 | 1.52 |
| Tyr | 104 | . | . | . | . | . | T | T | 0.24 | −0.29 | * | * | . | 2.20 | 0.78 |
| Thr | 105 | . | . | . | . | . | T | C | 1.10 | 0.50 | * | * | . | 1.03 | 1.26 |
| Glu | 106 | . | A | B | B | . | . | . | 0.68 | 0.33 | . | * | . | 0.51 | 1.36 |
| Ala | 107 | . | A | B | B | . | . | . | 1.34 | 0.41 | . | . | . | −0.01 | 1.25 |
| Phe | 108 | . | A | B | B | . | . | . | 1.03 | 0.06 | * | * | F | 0.22 | 1.50 |
| Gln | 109 | . | A | B | B | . | . | . | 1.39 | 0.06 | * | * | F | 0.00 | 1.25 |
| Thr | 110 | . | A | B | B | . | . | . | 1.49 | 0.06 | * | * | F | 0.00 | 2.43 |
| Gln | 111 | . | . | B | B | . | . | . | 1.19 | −0.01 | * | * | F | 0.94 | 4.34 |
| Thr | 112 | . | . | . | B | . | . | C | 1.43 | −0.41 | * | * | F | 1.48 | 3.36 |
| Arg | 113 | . | . | . | B | . | . | C | 1.79 | −0.39 | . | * | F | 1.82 | 2.30 |
| Pro | 114 | . | . | . | . | . | T | T | 1.83 | −0.44 | . | * | F | 2.76 | 1.32 |
| Ser | 115 | . | . | . | . | . | T | T | 1.86 | −0.84 | . | * | F | 3.40 | 1.82 |
| Gly | 116 | . | . | . | . | . | T | T | 1.54 | −0.41 | . | * | F | 2.61 | 0.98 |
| Gly | 117 | . | . | . | . | . | T | T | 1.16 | 0.07 | . | * | F | 1.67 | 0.91 |
| Lys | 118 | . | . | . | B | . | . | T | 0.74 | 0.43 | . | * | F | 0.63 | 0.59 |
| Trp | 119 | . | . | B | B | . | . | . | 0.71 | 0.43 | * | . | . | −0.26 | 0.80 |
| Thr | 120 | . | . | B | B | . | . | . | 0.12 | 0.76 | * | * | . | −0.45 | 1.26 |
| Phe | 121 | . | . | B | B | . | . | . | 0.12 | 1.01 | . | * | . | −0.60 | 0.44 |
| Ser | 122 | . | . | B | B | . | . | . | −0.23 | 1.44 | . | * | . | −0.60 | 0.42 |
| Tyr | 123 | . | . | B | B | . | . | . | −0.49 | 1.31 | . | * | . | −0.60 | 0.25 |
| Ile | 124 | . | . | . | B | T | . | . | −1.06 | 1.26 | . | * | . | −0.20 | 0.45 |
| Gly | 125 | . | . | . | B | . | . | C | −0.74 | 1.11 | . | * | . | −0.40 | 0.25 |
| Phe | 126 | . | . | . | B | . | . | C | −0.86 | 0.73 | . | * | . | −0.40 | 0.27 |
| Pro | 127 | . | . | B | . | . | . | . | −0.56 | 0.66 | . | * | . | −0.40 | 0.32 |
| Val | 128 | . | . | B | . | . | . | . | −0.62 | 0.37 | . | * | . | −0.10 | 0.52 |
| Glu | 129 | . | . | B | . | . | . | . | −0.59 | 0.43 | . | * | . | −0.40 | 0.87 |
| Leu | 130 | . | . | B | B | . | . | . | −0.49 | 0.29 | . | * | . | −0.30 | 0.42 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Asn | 131 | . | . | B | B | . | . | . | −0.49 | 0.61 | . | * | . | −0.60 | 0.88 |
| Thr | 132 | . | . | B | B | . | . | . | −1.17 | 0.76 | . | . | . | −0.60 | 0.44 |
| Val | 133 | . | . | B | B | . | . | . | −0.66 | 1.44 | . | . | . | −0.60 | 0.38 |
| Tyr | 134 | . | . | B | B | . | . | . | −1.24 | 1.19 | . | . | . | −0.60 | 0.23 |
| Phe | 135 | . | . | B | B | . | . | . | −0.47 | 1.29 | . | . | . | −0.60 | 0.16 |
| Ile | 136 | . | . | B | B | . | . | . | −0.47 | 1.30 | . | . | . | −0.60 | 0.30 |
| Gly | 137 | . | . | B | . | . | . | . | −1.04 | 1.06 | . | . | . | −0.40 | 0.30 |
| Ala | 138 | . | . | B | . | . | . | . | −0.40 | 0.99 | . | . | . | −0.40 | 0.25 |
| His | 139 | . | . | . | . | . | . | C | −0.16 | 0.63 | * | . | . | −0.20 | 0.54 |
| Asn | 140 | . | . | . | . | . | . | C | −0.04 | 0.34 | . | . | . | 0.10 | 0.88 |
| Ile | 141 | . | . | . | . | . | T | C | 0.84 | 0.41 | . | . | . | 0.00 | 0.88 |
| Pro | 142 | . | . | . | . | . | T | C | 0.59 | 0.31 | * | . | F | 0.60 | 1.04 |
| Asn | 143 | . | . | . | . | T | T | . | 1.18 | 0.43 | * | . | F | 0.35 | 0.64 |
| Ala | 144 | . | . | . | . | . | T | C | 1.21 | 0.43 | . | . | F | 0.64 | 1.47 |
| Asn | 145 | . | . | . | . | . | . | C | 1.21 | −0.26 | . | * | . | 1.53 | 1.65 |
| Met | 146 | . | . | . | B | . | . | . | 1.76 | −0.69 | . | * | . | 1.97 | 1.71 |
| Asn | 147 | . | . | . | . | . | T | C | 1.76 | −0.66 | . | * | F | 2.86 | 1.68 |
| Glu | 148 | . | . | . | . | T | T | . | 1.46 | −0.73 | . | * | F | 3.40 | 1.61 |
| Asp | 149 | . | . | . | . | T | T | . | 1.44 | −0.74 | . | . | F | 3.06 | 2.19 |
| Gly | 150 | . | . | . | . | . | T | C | 1.14 | −0.74 | . | . | F | 2.52 | 1.35 |
| Pro | 151 | . | . | . | . | . | . | C | 0.89 | −0.76 | . | . | F | 1.98 | 1.04 |
| Ser | 152 | . | . | . | B | . | . | C | 0.89 | −0.11 | . | * | F | 0.99 | 0.46 |
| Met | 153 | . | . | B | B | . | . | . | 0.19 | 0.29 | * | * | . | −0.30 | 0.75 |
| Ser | 154 | . | . | B | B | . | . | . | −0.12 | 0.64 | . | * | . | −0.60 | 0.42 |
| Val | 155 | . | . | B | B | . | . | . | −0.08 | 0.70 | . | * | . | −0.60 | 0.45 |
| Asn | 156 | . | . | B | B | . | . | . | −0.08 | 0.70 | . | * | . | −0.60 | 0.61 |
| Phe | 157 | . | . | B | B | . | . | . | −0.12 | 0.51 | . | * | . | −0.60 | 0.71 |
| Thr | 158 | . | . | . | B | T | . | . | −0.19 | 0.56 | . | * | F | −0.05 | 0.94 |
| Ser | 159 | . | . | . | . | . | T | C | −0.70 | 0.49 | . | * | F | 0.15 | 0.31 |
| Pro | 160 | . | . | . | . | T | T | . | 0.16 | 0.77 | . | * | F | 0.35 | 0.30 |
| Gly | 161 | . | . | . | . | T | T | . | 0.12 | −0.01 | . | . | F | 1.25 | 0.35 |
| Cys | 162 | A | . | . | . | . | T | . | −0.07 | −0.00 | . | . | . | 0.70 | 0.35 |
| Leu | 163 | A | A | . | . | . | . | . | −0.36 | 0.30 | * | . | . | −0.30 | 0.16 |
| Asp | 164 | A | A | . | . | . | . | . | −0.01 | 0.49 | * | . | . | −0.60 | 0.16 |
| His | 165 | A | A | . | . | . | . | . | −0.04 | 0.06 | * | * | . | −0.30 | 0.60 |
| Ile | 166 | A | A | . | . | . | . | . | 0.34 | 0.24 | * | . | . | −0.15 | 1.13 |
| Met | 167 | A | A | . | . | . | . | . | 1.06 | −0.44 | * | * | . | 0.45 | 1.36 |
| Lys | 168 | A | A | . | . | . | . | . | 1.91 | −0.44 | * | * | . | 0.45 | 1.99 |
| Tyr | 169 | A | A | . | . | . | . | . | 1.24 | −0.94 | * | . | F | 0.90 | 5.69 |
| Lys | 170 | A | A | . | . | . | . | . | 0.42 | −1.06 | * | . | F | 0.90 | 3.08 |
| Lys | 171 | A | A | . | . | . | . | . | 1.36 | −1.03 | * | . | F | 0.90 | 1.14 |
| Lys | 172 | A | A | . | . | . | . | . | 1.37 | −1.03 | * | * | F | 0.90 | 1.46 |
| Cys | 173 | . | A | B | . | . | . | . | 0.98 | −1.29 | * | . | . | 0.60 | 0.74 |
| Val | 174 | . | A | B | . | . | . | . | 0.92 | −0.86 | * | . | . | 0.60 | 0.36 |
| Lys | 175 | . | A | B | . | . | . | . | 0.07 | −0.47 | * | . | F | 0.45 | 0.24 |
| Ala | 176 | . | A | B | . | . | . | . | −0.27 | 0.21 | * | . | F | 0.01 | 0.38 |
| Gly | 177 | . | . | B | . | . | T | . | −0.31 | 0.56 | * | . | F | 0.27 | 0.53 |
| Ser | 178 | . | . | . | . | . | T | C | 0.14 | −0.09 | . | * | F | 1.53 | 0.44 |
| Leu | 179 | . | . | . | . | T | T | . | 1.00 | 0.34 | * | * | F | 1.29 | 0.68 |
| Trp | 180 | . | . | . | . | T | T | . | 0.07 | 0.24 | * | * | F | 1.60 | 1.11 |
| Asp | 181 | . | . | . | . | . | T | C | 0.34 | 0.50 | . | * | F | 0.79 | 0.58 |
| Pro | 182 | . | . | . | . | T | T | . | 0.10 | 0.60 | . | * | F | 0.98 | 1.01 |
| Asn | 183 | . | . | . | . | T | T | . | −0.27 | 0.41 | * | * | F | 0.67 | 0.97 |
| Ile | 184 | A | . | . | . | . | T | . | 0.59 | 0.07 | * | * | . | 0.26 | 0.31 |
| Thr | 185 | A | . | . | . | . | . | . | 0.92 | 0.07 | * | * | . | −0.10 | 0.40 |
| Ala | 186 | A | . | . | . | . | . | . | 0.92 | −0.36 | . | * | . | 0.50 | 0.50 |
| Cys | 187 | A | . | . | . | . | T | . | 1.13 | −0.36 | . | . | . | 0.85 | 1.15 |
| Lys | 188 | A | . | . | . | . | T | . | 1.13 | −1.04 | . | . | F | 1.30 | 1.38 |
| Lys | 189 | A | . | . | . | . | T | . | 1.71 | −1.53 | * | . | F | 1.30 | 2.37 |
| Asn | 190 | A | . | . | . | . | T | . | 1.17 | −1.54 | * | . | F | 1.30 | 6.38 |
| Glu | 191 | A | . | . | . | . | . | . | 1.76 | −1.47 | . | . | F | 1.10 | 2.37 |
| Glu | 192 | A | . | . | . | . | . | . | 1.57 | −1.47 | . | * | F | 1.10 | 2.05 |
| Thr | 193 | A | . | . | B | . | . | . | 1.52 | −0.83 | * | * | F | 0.75 | 0.95 |
| Val | 194 | A | . | . | B | . | . | . | 0.78 | −0.83 | . | * | F | 0.75 | 0.88 |
| Glu | 195 | A | . | . | B | . | . | . | 0.47 | −0.04 | . | * | . | 0.30 | 0.44 |
| Val | 196 | A | . | . | B | . | . | . | 0.16 | 0.44 | . | * | . | −0.60 | 0.44 |
| Asn | 197 | . | . | B | B | . | . | . | −0.16 | 0.44 | . | * | . | −0.60 | 0.85 |
| Phe | 198 | . | . | B | B | . | . | . | −0.06 | 0.29 | . | * | . | −0.30 | 0.71 |
| Thr | 199 | . | . | B | B | . | . | . | −0.01 | 0.71 | . | * | F | −0.30 | 1.48 |
| Thr | 200 | . | . | B | B | . | . | . | −0.36 | 0.76 | . | * | F | −0.33 | 0.76 |
| Thr | 201 | . | . | . | . | . | T | C | 0.50 | 0.79 | . | * | F | 0.39 | 0.87 |
| Pro | 202 | . | . | . | . | . | T | C | 0.61 | 0.40 | . | . | F | 0.81 | 0.97 |
| Leu | 203 | . | . | . | . | T | T | . | 1.07 | −0.09 | * | . | F | 1.88 | 1.32 |
| Gly | 204 | . | . | . | . | . | T | C | 0.78 | 0.19 | * | . | F | 1.20 | 1.43 |
| Asn | 205 | . | . | . | . | . | T | C | 0.50 | 0.31 | * | . | F | 0.93 | 0.91 |
| Arg | 206 | . | . | B | . | . | T | . | 0.00 | 0.39 | . | . | . | 0.61 | 1.12 |
| Tyr | 207 | . | . | B | . | . | T | . | −0.68 | 0.39 | * | * | . | 0.34 | 0.93 |
| Met | 208 | . | . | B | . | . | T | . | 0.13 | 0.64 | * | . | . | −0.08 | 0.41 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Ala | 209 | . | . | B | B | . | . | . | 0.44 | 0.64 | * | . | . | −0.60 | 0.36 |
| Leu | 210 | . | . | B | B | . | . | . | 0.14 | 1.14 | * | . | . | −0.60 | 0.31 |
| Ile | 211 | . | . | B | B | . | . | . | −0.28 | 0.77 | * | * | . | −0.60 | 0.42 |
| Gln | 212 | . | . | B | B | . | . | . | −0.92 | 0.64 | . | . | . | −0.60 | 0.60 |
| His | 213 | . | . | B | B | . | . | . | −1.21 | 0.83 | . | . | . | −0.60 | 0.51 |
| Ser | 214 | . | . | B | B | . | . | . | −0.97 | 0.83 | . | . | . | −0.60 | 0.51 |
| Thr | 215 | . | . | B | B | . | . | . | −0.86 | 0.57 | . | . | . | −0.60 | 0.29 |
| Ile | 216 | . | . | B | B | . | . | . | −0.27 | 0.96 | . | . | . | −0.60 | 0.19 |
| Ile | 217 | . | . | B | B | . | . | . | −0.27 | 0.84 | . | . | . | −0.60 | 0.19 |
| Gly | 218 | . | . | B | B | . | . | . | −1.09 | 0.86 | * | . | . | −0.60 | 0.22 |
| Phe | 219 | . | . | B | B | . | . | . | −1.49 | 1.01 | * | . | . | −0.60 | 0.24 |
| Ser | 220 | . | . | . | B | . | . | C | −1.18 | 1.11 | * | . | . | −0.40 | 0.29 |
| Gln | 221 | . | . | B | B | . | . | . | −0.50 | 0.43 | * | . | . | −0.60 | 0.51 |
| Val | 222 | . | . | B | B | . | . | . | 0.36 | 0.43 | * | . | . | −0.60 | 0.92 |
| Phe | 223 | A | . | . | B | . | . | . | 0.70 | 0.14 | * | . | . | −0.30 | 0.93 |
| Glu | 224 | A | . | . | B | . | . | . | 1.44 | 0.16 | * | . | F | −0.15 | 0.93 |
| Pro | 225 | A | A | . | . | . | . | . | 1.79 | −0.24 | * | . | F | 0.60 | 2.51 |
| His | 226 | A | A | . | . | . | . | . | 1.79 | −0.89 | * | . | F | 0.90 | 5.79 |
| Gln | 227 | A | A | . | . | . | . | . | 2.33 | −1.27 | * | * | F | 0.90 | 5.79 |
| Lys | 228 | A | A | . | . | . | . | . | 3.14 | −0.79 | * | * | F | 0.90 | 5.40 |
| Lys | 229 | A | A | . | B | . | . | . | 2.56 | −1.21 | * | * | F | 0.90 | 7.77 |
| Gln | 230 | A | A | . | B | . | . | . | 2.47 | −1.21 | . | * | F | 0.90 | 4.53 |
| Thr | 231 | . | A | B | B | . | . | . | 1.64 | −1.23 | . | * | F | 0.90 | 3.04 |
| Arg | 232 | . | A | B | B | . | . | . | 0.79 | −0.59 | * | * | F | 0.90 | 1.13 |
| Ala | 233 | . | A | B | B | . | . | . | −0.14 | 0.06 | * | * | F | −0.15 | 0.48 |
| Ser | 234 | . | . | B | B | . | . | . | −0.40 | 0.34 | . | * | . | −0.30 | 0.23 |
| Val | 235 | . | . | B | B | . | . | . | −1.26 | 0.29 | . | * | . | −0.30 | 0.19 |
| Val | 236 | . | . | B | B | . | . | . | −1.26 | 0.93 | . | * | . | −0.60 | 0.14 |
| Ile | 237 | . | . | B | B | . | . | . | −1.71 | 0.91 | * | * | . | −0.60 | 0.15 |
| Pro | 238 | . | . | B | B | . | . | . | −1.12 | 0.96 | . | * | . | −0.60 | 0.20 |
| Val | 239 | . | . | B | B | . | . | . | −1.12 | 0.31 | . | * | . | −0.30 | 0.44 |
| Thr | 240 | . | . | B | B | . | . | . | −0.27 | 0.06 | * | F | . | 0.15 | 0.84 |
| Gly | 241 | . | . | . | B | . | . | C | 0.24 | −0.63 | . | * | F | 1.55 | 0.94 |
| Asp | 242 | . | . | . | . | . | T | C | 0.54 | −0.63 | . | * | F | 2.40 | 1.26 |
| Ser | 243 | . | . | . | . | . | T | C | 0.44 | −0.77 | . | . | F | 2.55 | 0.88 |
| Glu | 244 | . | . | . | . | . | T | C | 0.44 | −0.77 | . | . | F | 3.00 | 1.28 |
| Gly | 245 | . | . | B | . | . | T | . | 0.76 | −0.56 | . | * | F | 2.35 | 0.57 |
| Ala | 246 | . | . | B | B | . | . | . | 0.29 | −0.16 | . | * | F | 1.35 | 0.74 |
| Thr | 247 | . | . | B | B | . | . | . | −0.02 | 0.14 | . | * | . | 0.30 | 0.35 |
| Val | 248 | . | . | B | B | . | . | . | 0.07 | 0.63 | . | * | . | −0.30 | 0.51 |
| Gln | 249 | . | . | B | B | . | . | . | −0.18 | 0.63 | . | * | . | −0.60 | 0.78 |
| Leu | 250 | . | . | B | B | . | . | . | −0.53 | 0.89 | . | * | . | −0.60 | 0.85 |
| Thr | 251 | . | . | B | B | . | . | . | −0.16 | 1.19 | . | * | . | −0.60 | 0.99 |
| Pro | 252 | . | . | B | B | . | . | . | −0.16 | 0.97 | . | * | F | −0.45 | 0.89 |
| Tyr | 253 | . | . | . | B | T | . | . | 0.03 | 1.06 | * | * | F | 0.10 | 1.55 |
| Phe | 254 | . | . | B | . | . | T | . | −0.31 | 0.94 | * | . | . | −0.20 | 0.58 |
| Pro | 255 | . | . | . | . | T | T | . | 0.20 | 0.89 | * | . | F | 0.35 | 0.37 |
| Thr | 256 | . | . | . | . | T | T | . | 0.51 | 0.84 | * | . | F | 0.35 | 0.31 |
| Cys | 257 | . | . | . | . | T | T | . | 0.06 | 0.09 | * | . | F | 0.65 | 0.61 |
| Gly | 258 | . | . | . | . | T | T | . | −0.59 | −0.13 | * | * | F | 1.25 | 0.21 |
| Ser | 259 | . | . | . | . | T | T | . | 0.22 | 0.13 | * | . | F | 0.65 | 0.10 |
| Asp | 260 | . | . | B | . | . | T | . | 0.40 | −0.36 | * | * | F | 0.85 | 0.37 |
| Cys | 261 | . | . | B | . | . | T | . | 0.76 | −0.43 | * | * | . | 0.98 | 0.51 |
| Ile | 262 | . | . | B | . | . | . | . | 1.08 | −0.86 | * | * | . | 1.36 | 0.77 |
| Arg | 263 | . | . | B | . | . | . | . | 1.11 | −0.81 | * | * | . | 1.64 | 0.45 |
| His | 264 | . | . | . | . | T | T | . | 0.56 | −0.33 | * | * | . | 2.37 | 1.22 |
| Lys | 265 | . | . | . | . | T | T | . | −0.30 | −0.26 | * | * | F | 2.80 | 1.30 |
| Gly | 266 | . | . | . | . | T | T | . | −0.44 | −0.30 | * | * | F | 2.37 | 0.49 |
| Thr | 267 | . | . | B | . | . | T | . | −0.22 | 0.39 | * | * | F | 1.09 | 0.30 |
| Val | 268 | . | . | B | B | . | . | . | −0.54 | 0.46 | . | * | . | −0.04 | 0.08 |
| Val | 269 | . | . | B | B | . | . | . | −0.51 | 0.89 | . | * | . | −0.32 | 0.12 |
| Leu | 270 | . | . | B | B | . | . | . | −0.87 | 0.86 | . | * | . | −0.60 | 0.15 |
| Cys | 271 | . | . | B | . | . | T | . | −0.87 | 0.86 | . | . | . | −0.20 | 0.29 |
| Pro | 272 | . | . | B | . | . | T | . | −1.41 | 0.64 | . | . | F | −0.05 | 0.39 |
| Gln | 273 | . | . | B | . | . | T | . | −0.77 | 0.64 | . | . | F | 0.35 | 0.35 |
| Thr | 274 | . | . | . | . | T | T | . | −0.61 | 0.39 | . | . | F | 0.80 | 1.01 |
| Gly | 275 | . | . | B | . | . | . | . | −0.01 | 0.60 | . | * | F | −0.25 | 0.56 |
| Val | 276 | . | . | B | . | . | T | . | −0.16 | 0.60 | . | * | . | −0.20 | 0.50 |
| Pro | 277 | . | . | B | . | . | T | . | 0.06 | 0.89 | . | * | . | −0.20 | 0.29 |
| Phe | 278 | . | . | B | . | . | T | . | 0.06 | 0.40 | . | * | . | 0.14 | 0.49 |
| Pro | 279 | . | . | B | . | . | T | . | 0.37 | 0.37 | . | . | . | 0.93 | 1.05 |
| Leu | 280 | . | . | B | . | . | . | . | 0.76 | 0.13 | . | . | F | 1.22 | 1.09 |
| Asp | 281 | . | . | . | . | T | T | . | 1.31 | −0.30 | . | * | F | 2.76 | 2.52 |
| Asn | 282 | . | . | . | . | T | T | . | 1.57 | −0.70 | . | . | F | 3.40 | 2.19 |
| Asn | 283 | . | . | . | . | T | T | . | 2.06 | −1.13 | . | . | F | 3.06 | 5.31 |
| Lys | 284 | . | . | . | . | T | T | . | 1.92 | −1.39 | . | . | F | 2.85 | 4.91 |
| Ser | 285 | . | . | . | . | . | . | C | 2.39 | −0.96 | . | . | F | 2.24 | 3.02 |
| Lys | 286 | . | . | . | . | . | T | C | 2.10 | −0.93 | . | . | F | 2.23 | 1.86 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 287 | . | . | . | . | T | T | . | 1.29 | −0.41 | . | . | F | 1.77 | 0.98 |
| Gly | 288 | . | . | . | . | T | T | . | 1.08 | 0.27 | . | . | F | 1.30 | 0.60 |
| Gly | 289 | . | . | . | . | T | T | . | 0.22 | 0.31 | . | * | F | 1.17 | 0.47 |
| Trp | 290 | . | . | B | B | . | . | . | −0.29 | 1.00 | * | . | . | −0.21 | 0.25 |
| Leu | 291 | . | . | B | B | . | . | . | −1.14 | 1.26 | . | . | . | −0.34 | 0.21 |
| Pro | 292 | . | . | B | B | . | . | . | −1.74 | 1.51 | . | . | . | −0.47 | 0.17 |
| Leu | 293 | . | . | B | B | . | . | . | −1.70 | 1.77 | . | . | . | −0.60 | 0.14 |
| Leu | 294 | . | . | B | B | . | . | . | −2.17 | 1.24 | . | . | . | −0.60 | 0.22 |
| Leu | 295 | . | . | B | B | . | . | . | −2.69 | 1.24 | . | . | . | −0.60 | 0.12 |
| Leu | 296 | . | . | B | B | . | . | . | −2.73 | 1.50 | . | . | . | −0.60 | 0.12 |
| Ser | 297 | . | . | B | B | . | . | . | −3.11 | 1.46 | . | . | . | −0.60 | 0.11 |
| Leu | 298 | . | . | B | B | . | . | . | −2.61 | 1.27 | . | . | . | −0.60 | 0.13 |
| Leu | 299 | A | . | . | B | . | . | . | −2.09 | 1.07 | . | . | . | −0.60 | 0.23 |
| Val | 300 | A | . | . | B | . | . | . | −2.13 | 1.30 | . | . | . | −0.60 | 0.18 |
| Ala | 301 | A | . | . | B | . | . | . | −2.13 | 1.56 | . | . | . | −0.60 | 0.16 |
| Thr | 302 | A | . | . | B | . | . | . | −2.69 | 1.56 | . | . | . | −0.60 | 0.16 |
| Trp | 303 | . | . | B | B | . | . | . | −2.47 | 1.51 | . | . | . | −0.60 | 0.16 |
| Val | 304 | . | . | B | B | . | . | . | −2.00 | 1.37 | . | . | . | −0.60 | 0.16 |
| Leu | 305 | . | . | B | B | . | . | . | −2.03 | 1.30 | . | . | . | −0.60 | 0.11 |
| Val | 306 | . | . | B | B | . | . | . | −1.69 | 1.50 | . | . | . | −0.60 | 0.07 |
| Ala | 307 | . | . | B | B | . | . | . | −2.19 | 1.34 | . | . | . | −0.60 | 0.15 |
| Gly | 308 | . | . | B | B | . | . | . | −2.50 | 1.39 | . | . | . | −0.60 | 0.15 |
| Ile | 309 | A | . | . | B | . | . | . | −1.93 | 1.31 | * | * | . | −0.60 | 0.21 |
| Tyr | 310 | A | . | . | B | . | . | . | −1.01 | 1.59 | * | * | . | −0.60 | 0.21 |
| Leu | 311 | A | . | . | B | . | . | . | −0.19 | 1.09 | * | * | . | −0.60 | 0.42 |
| Met | 312 | A | . | . | B | . | . | . | 0.40 | 1.16 | * | * | . | −0.60 | 0.82 |
| Trp | 313 | A | . | . | B | . | . | . | 0.86 | 0.47 | * | * | . | −0.60 | 0.91 |
| Arg | 314 | A | . | . | B | . | . | . | 0.86 | −0.29 | . | * | . | 0.45 | 2.16 |
| His | 315 | A | . | . | B | . | . | . | 1.14 | −0.29 | * | . | . | 0.45 | 1.53 |
| Glu | 316 | A | . | . | B | . | . | . | 2.00 | −0.90 | * | . | . | 0.75 | 2.91 |
| Arg | 317 | A | A | . | . | . | . | . | 2.29 | −1.81 | * | . | F | 0.90 | 2.97 |
| Ile | 318 | A | A | . | . | . | . | . | 2.28 | −1.33 | * | . | F | 0.90 | 3.15 |
| Lys | 319 | . | A | . | . | T | . | . | 1.47 | −1.44 | * | . | F | 1.30 | 2.43 |
| Lys | 320 | . | A | . | B | T | . | . | 1.20 | −0.66 | * | * | F | 1.30 | 1.08 |
| Thr | 321 | . | A | . | B | . | . | C | 0.89 | −0.27 | * | . | F | 0.80 | 2.06 |
| Ser | 322 | . | A | . | B | . | . | C | 0.47 | −0.47 | * | * | F | 0.80 | 1.48 |
| Phe | 323 | . | . | B | B | . | . | . | 1.04 | 0.01 | * | . | F | 0.00 | 1.07 |
| Ser | 324 | . | . | B | B | . | . | . | 0.19 | 0.50 | . | . | F | −0.30 | 1.07 |
| Thr | 325 | . | . | B | B | . | . | . | −0.67 | 0.70 | . | . | F | −0.45 | 0.66 |
| Thr | 326 | . | . | B | B | . | . | . | −0.57 | 1.00 | . | . | F | −0.45 | 0.63 |
| Thr | 327 | . | . | B | B | . | . | . | −0.48 | 0.64 | . | . | F | −0.45 | 0.72 |
| Leu | 328 | . | . | B | B | . | . | . | −0.67 | 0.69 | . | * | F | −0.45 | 0.78 |
| Leu | 329 | . | . | B | B | . | . | . | −0.32 | 0.89 | * | * | F | −0.45 | 0.38 |
| Pro | 330 | . | . | B | B | . | . | . | −0.87 | 0.40 | * | . | F | −0.15 | 0.52 |
| Pro | 331 | . | . | B | B | . | . | . | −1.37 | 0.56 | * | * | F | −0.45 | 0.47 |
| Ile | 332 | . | . | B | B | . | . | . | −1.91 | 0.56 | * | * | F | −0.45 | 0.47 |
| Lys | 333 | . | . | B | B | . | . | . | −1.96 | 0.51 | * | * | F | −0.45 | 0.23 |
| Val | 334 | . | . | B | B | . | . | . | −1.39 | 0.73 | . | . | . | −0.60 | 0.11 |
| Leu | 335 | . | . | B | B | . | . | . | −1.39 | 1.06 | . | * | . | −0.60 | 0.24 |
| Val | 336 | . | . | B | B | . | . | . | −1.48 | 0.80 | * | * | . | −0.60 | 0.19 |
| Val | 337 | . | . | B | B | . | . | . | −0.59 | 1.19 | * | * | . | −0.60 | 0.34 |
| Tyr | 338 | . | . | B | . | . | . | T | −1.52 | 0.54 | * | . | . | −0.20 | 0.71 |
| Pro | 339 | A | . | . | . | . | T | . | −1.33 | 0.54 | . | . | F | −0.05 | 0.67 |
| Ser | 340 | A | . | . | . | T | T | . | −1.22 | 0.47 | . | * | F | 0.35 | 0.48 |
| Glu | 341 | A | . | . | . | . | T | . | −0.40 | 0.61 | . | . | F | −0.05 | 0.27 |
| Ile | 342 | A | . | . | B | . | . | . | 0.42 | 0.36 | . | . | . | −0.30 | 0.24 |
| Cys | 343 | A | . | . | B | . | . | . | 0.36 | 0.43 | . | * | . | −0.60 | 0.24 |
| Phe | 344 | A | . | . | B | . | . | . | −0.32 | 0.53 | . | . | . | −0.60 | 0.20 |
| His | 345 | A | . | . | B | . | . | . | −0.69 | 1.21 | . | * | . | −0.60 | 0.20 |
| His | 346 | . | . | B | B | . | . | . | −0.93 | 1.10 | . | * | . | −0.60 | 0.20 |
| Thr | 347 | . | . | . | B | T | . | . | −0.74 | 1.29 | . | * | . | −0.20 | 0.36 |
| Ile | 348 | . | . | . | B | T | . | . | −0.39 | 1.29 | * | . | . | −0.20 | 0.23 |
| Cys | 349 | . | . | . | B | T | . | . | 0.31 | 1.27 | * | . | . | −0.20 | 0.24 |
| Tyr | 350 | . | . | . | B | T | . | . | −0.36 | 0.77 | * | . | . | −0.20 | 0.29 |
| Phe | 351 | . | . | B | B | . | . | . | −1.13 | 1.07 | * | . | . | −0.60 | 0.36 |
| Thr | 352 | A | . | . | B | . | . | . | −0.82 | 1.07 | * | . | . | −0.60 | 0.56 |
| Glu | 353 | A | . | . | B | . | . | . | 0.07 | 0.90 | * | . | . | −0.60 | 0.61 |
| Phe | 354 | A | . | . | B | . | . | . | 0.70 | 0.54 | * | . | . | −0.45 | 1.14 |
| Leu | 355 | A | . | . | B | . | . | . | 0.28 | 0.26 | * | . | . | −0.15 | 1.07 |
| Gln | 356 | A | . | . | B | . | . | . | 1.09 | 0.34 | * | * | . | −0.30 | 0.33 |
| Asn | 357 | . | . | . | B | T | . | . | 1.10 | 0.34 | * | * | . | 0.10 | 0.75 |
| His | 358 | . | . | . | B | . | . | C | 1.10 | −0.06 | * | * | . | 0.65 | 1.22 |
| Cys | 359 | . | . | . | . | T | T | . | 0.94 | −0.74 | . | * | . | 1.55 | 1.22 |
| Arg | 360 | A | . | . | . | . | T | . | 0.87 | −0.50 | * | * | F | 1.15 | 0.56 |
| Ser | 361 | A | . | . | . | . | T | . | 0.06 | −0.21 | . | * | F | 0.85 | 0.29 |
| Glu | 362 | A | . | . | . | . | T | . | 0.06 | −0.03 | . | * | F | 0.85 | 0.45 |
| Val | 363 | A | A | . | . | . | . | . | 0.13 | −0.60 | * | * | . | 0.60 | 0.40 |
| Ile | 364 | A | A | . | . | . | . | . | 0.51 | −0.60 | * | * | . | 0.60 | 0.59 |

TABLE I-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 365 | A | A | . | . | . | . | . | 0.40 | −0.07 | * | * | . | 0.30 | 0.36 |
| Glu | 366 | A | A | . | . | . | . | . | 0.74 | 0.33 | * | . | . | −0.30 | 0.84 |
| Lys | 367 | A | A | . | . | . | . | . | 0.79 | −0.31 | * | . | F | 0.60 | 2.38 |
| Trp | 368 | A | A | . | . | . | . | . | 1.69 | −1.00 | . | . | F | 0.90 | 5.78 |
| Gln | 369 | A | A | . | . | . | . | . | 1.69 | −1.69 | . | . | F | 0.90 | 6.68 |
| Lys | 370 | A | A | . | . | . | . | . | 1.91 | −1.00 | * | . | F | 0.90 | 2.34 |
| Lys | 371 | A | A | . | . | . | . | . | 1.91 | −0.50 | * | . | F | 0.90 | 2.25 |
| Lys | 372 | A | A | . | . | . | . | . | 1.27 | −1.41 | * | . | F | 0.90 | 2.25 |
| Ile | 373 | A | A | . | . | . | . | . | 1.21 | −1.20 | . | . | . | 0.75 | 1.11 |
| Ala | 374 | . | A | B | . | . | . | . | 1.00 | −0.77 | . | . | . | 0.60 | 0.55 |
| Glu | 375 | . | A | B | . | . | . | . | 0.10 | −0.34 | . | . | . | 0.30 | 0.43 |
| Met | 376 | . | A | B | . | . | . | . | 0.06 | 0.30 | * | . | . | −0.30 | 0.45 |
| Gly | 377 | . | . | B | . | . | T | . | −0.28 | 0.01 | * | . | . | 0.10 | 0.77 |
| Pro | 378 | A | . | . | . | . | T | . | −0.20 | 0.43 | . | . | . | −0.20 | 0.47 |
| Val | 379 | A | . | . | . | . | T | . | −0.20 | 1.11 | . | . | . | −0.20 | 0.39 |
| Gln | 380 | A | . | . | . | . | T | . | −0.51 | 1.00 | . | . | . | −0.20 | 0.40 |
| Trp | 381 | A | A | . | . | . | . | . | 0.09 | 1.06 | . | . | . | −0.60 | 0.37 |
| Leu | 382 | A | A | . | . | . | . | . | 0.48 | 1.03 | . | . | . | −0.60 | 0.87 |
| Ala | 383 | A | A | . | . | . | . | . | 0.73 | 0.39 | . | . | . | −0.15 | 1.00 |
| Thr | 384 | A | A | . | . | . | . | . | 1.00 | −0.01 | * | . | F | 0.60 | 1.91 |
| Gln | 385 | A | A | . | . | . | . | . | 0.41 | −0.43 | * | . | F | 0.60 | 2.34 |
| Lys | 386 | A | A | . | . | . | . | . | 0.70 | −0.61 | * | . | F | 0.90 | 2.34 |
| Lys | 387 | A | A | . | . | . | . | . | 1.56 | −1.11 | * | . | F | 0.90 | 2.71 |
| Ala | 388 | A | A | . | . | . | . | . | 1.29 | −1.60 | * | . | F | 0.90 | 3.12 |
| Ala | 389 | A | A | . | . | . | . | . | 0.74 | −1.36 | * | . | F | 0.90 | 1.16 |
| Asp | 390 | A | A | . | . | . | . | . | 0.04 | −0.71 | * | . | F | 0.75 | 0.43 |
| Lys | 391 | A | A | . | . | . | . | . | −0.81 | 0.07 | * | . | . | −0.30 | 0.37 |
| Val | 392 | . | A | B | . | . | . | . | −1.67 | 0.26 | * | . | . | −0.30 | 0.30 |
| Val | 393 | . | A | B | . | . | . | . | −1.38 | 0.44 | * | . | . | −0.60 | 0.15 |
| Phe | 394 | . | A | B | . | . | . | . | −0.79 | 0.83 | * | . | . | −0.60 | 0.10 |
| Leu | 395 | . | A | B | . | . | . | . | −0.79 | 1.23 | * | . | . | −0.60 | 0.22 |
| Leu | 396 | . | A | B | . | . | . | . | −1.69 | 0.59 | * | * | . | −0.60 | 0.49 |
| Ser | 397 | . | A | . | . | T | . | . | −0.83 | 0.59 | * | . | F | −0.05 | 0.42 |
| Asn | 398 | . | . | . | . | T | . | . | −0.28 | 0.20 | * | . | F | 0.45 | 0.81 |
| Asp | 399 | . | . | . | . | T | T | . | −0.43 | −0.10 | * | . | F | 1.40 | 1.32 |
| Val | 400 | . | . | . | . | T | T | . | −0.29 | −0.14 | * | . | F | 1.25 | 0.73 |
| Asn | 401 | . | . | B | . | T | T | . | 0.52 | 0.04 | * | * | F | 0.65 | 0.24 |
| Ser | 402 | . | . | B | . | . | T | . | 0.48 | −0.36 | * | . | . | 0.70 | 0.24 |
| Val | 403 | . | . | B | . | . | . | . | 0.17 | 0.07 | * | . | . | 0.21 | 0.32 |
| Cys | 404 | . | . | B | . | . | . | . | −0.50 | −0.09 | * | . | . | 1.32 | 0.29 |
| Asp | 405 | . | . | B | . | . | T | . | 0.01 | 0.09 | . | . | F | 1.18 | 0.12 |
| Gly | 406 | . | . | . | . | T | T | . | 0.06 | 0.13 | . | . | F | 1.89 | 0.16 |
| Thr | 407 | . | . | . | . | T | T | . | 0.06 | −0.51 | . | . | F | 3.10 | 0.58 |
| Cys | 408 | . | . | B | . | . | T | . | 0.91 | −0.70 | . | . | F | 2.39 | 0.47 |
| Gly | 409 | . | . | . | . | T | T | . | 1.23 | −0.70 | . | . | F | 2.48 | 0.81 |
| Lys | 410 | . | . | . | . | T | T | . | 0.93 | −0.70 | . | . | F | 2.17 | 0.56 |
| Ser | 411 | . | . | . | . | . | T | C | 1.07 | −0.80 | . | . | F | 1.81 | 1.40 |
| Glu | 412 | . | . | . | . | . | . | C | 1.08 | −0.94 | . | . | F | 1.30 | 2.18 |
| Gly | 413 | . | . | . | . | . | . | C | 1.74 | −0.99 | . | * | F | 1.64 | 1.46 |
| Ser | 414 | . | . | . | . | . | T | C | 2.09 | −0.99 | . | * | F | 2.18 | 1.89 |
| Pro | 415 | . | . | . | . | . | T | C | 1.74 | −0.97 | . | * | F | 2.52 | 1.75 |
| Ser | 416 | . | . | . | . | . | T | C | 2.04 | −0.59 | . | . | F | 2.86 | 2.38 |
| Glu | 417 | . | . | . | . | T | T | . | 2.04 | −0.61 | . | . | F | 3.40 | 3.07 |
| Asn | 418 | . | . | . | . | T | . | . | 2.09 | −1.00 | . | . | F | 2.86 | 3.32 |
| Ser | 419 | . | . | . | . | T | T | . | 2.09 | −1.04 | . | . | F | 2.93 | 3.32 |
| Gln | 420 | . | . | . | . | T | T | . | 2.09 | −1.04 | . | . | F | 2.80 | 2.57 |
| Asp | 421 | . | . | . | . | T | T | . | 1.72 | −0.61 | . | . | F | 2.67 | 2.47 |
| Ser | 422 | . | . | . | . | T | T | . | 0.91 | −0.44 | . | . | F | 2.09 | 0.99 |
| Ser | 423 | . | . | . | . | . | T | C | 0.52 | −0.14 | . | . | F | 2.10 | 0.47 |
| Pro | 424 | . | . | B | . | . | T | . | 0.43 | −0.11 | . | . | . | 1.54 | 0.36 |
| Cys | 425 | . | . | B | . | . | T | . | 0.04 | 0.31 | . | . | . | 0.73 | 0.34 |
| Leu | 426 | . | . | B | . | . | T | . | −0.34 | 0.36 | . | . | . | 0.52 | 0.33 |

Among highly preferred fragments in this regard are those that comprise regions of IL17RLP that combine several structural features, such as several features set out above.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC™ Deposit No. 209198. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, more preferably at least about 25 nt, still more preferably at least about 30 nt, and even more preferably about 30-70 (e.g., 30, 35, 40, 45, 50, 55, 60, 65, and/or 70 (of course, fragment lengths in addition to those recited herein are also useful)) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A, 1B, and 1C (SEQ ID NO:1)). Of course, a polynucleotide which hybridizes only to a poly A sequence (such as the 3' terminal poly(A) tract of the IL17RLP cDNA shown in FIGS. 1A, 1B, and 1C (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

In preferred embodiments, polynucleotides which hybridize to the reference polynucleotides disclosed herein encode polypeptides which either retain substantially the same biological function or activity as the mature form of the IL17RLP polypeptide encoded by the polynucleotide sequence depicted in FIGS. 1A, 1B, and 1C (SEQ ID NO:1) or the clone contained in the deposit (HAPOR40).

Alternative embodiments are directed to polynucleotides which hybridize to the reference polynucleotide (i.e., a polynucleotide sequence disclosed herein), but do not retain biological activity. While these polynucleotides do not retain biological activity, they have uses, such as, for example, as probes for the polynucleotides of SEQ ID NO:1, for recovery of the polynucleotides, as diagnostic probes, and as PCR primers.

As indicated, nucleic acid molecules of the present invention which encode a IL17RLP polypeptide may include, but are not limited to those encoding the amino acid sequence of the mature polypeptide, by itself; and the coding sequence for the mature polypeptide and additional sequences, such as those encoding the about 19 amino acid leader or secretory sequence, such as a pre-, or pro- or prepro-protein sequence; the coding sequence of the mature polypeptide, with or without the aforementioned additional coding sequences.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described by Gentz and colleagues (*Proc. Natl. Acad. Sci. USA* 86:821-824 (1989)), for instance, hexa-histidine provides for convenient purification of the fusion protein. The "HA" tag is another peptide useful for purification which corresponds to an epitope derived from the influenza hemagglutinin protein, which has been described by Wilson and coworkers (*Cell* 37:767 (1984)). As discussed below, other such fusion proteins include the IL17RLP fused to Fc at the N- or C-terminus.

The present invention further relates to variants of the nucleic acid molecules of the present invention, which encode portions, analogs or derivatives of the IL17RLP protein. Variants may occur naturally, such as a natural allelic variant. By an "allelic variant" is intended one of several alternate forms of a gene occupying a given locus on a chromosome of an organism (*Genes II*, Lewin, B., ed., John Wiley & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the IL17RLP protein or portions thereof. Also especially preferred in this regard are conservative substitutions.

Most highly preferred are nucleic acid molecules encoding the mature protein having the amino acid sequence shown in SEQ ID NO:2, SEQ ID NO:18, or the mature IL17RLP amino acid sequence encoded by the deposited cDNA clone.

Most highly preferred are nucleic acid molecules encoding the extracellular domain of the protein having the amino acid sequence shown in SEQ ID NO:2, SEQ ID NO:18, or the extracellular domain of the IL17RLP amino acid sequence encoded by the deposited cDNA clone.

Thus, one aspect of the invention provides an isolated nucleic acid molecule comprising a polynucleotide having a nucleotide sequence selected from the group consisting of: (a) a nucleotide sequence encoding the IL17RLP polypeptide having the complete amino acid sequence in SEQ ID NO:2 (i.e., positions −19 to 407 of SEQ ID NO:2); (b) a nucleotide sequence encoding the IL17RLP polypeptide having the complete amino acid sequence in SEQ ID NO:2 excepting the N-terminal methionine (i.e., positions −18 to 407 of SEQ ID NO:2); (c) a nucleotide sequence encoding the predicted mature IL17RLP polypeptide having the amino acid sequence at positions 1 to 407 in SEQ ID NO:2; (d) a nucleotide sequence encoding a polypeptide comprising the predicted extracellular domain of the IL17RLP polypeptide having the amino acid sequence at positions 1 to 271 in SEQ ID NO:2; (e) a nucleotide sequence encoding a soluble IL17RLP polypeptide having the predicted extracellular and intracellular domains, but lacking the predicted transmembrane domain; (f) a nucleotide sequence encoding the IL17RLP polypeptide having the complete amino acid sequence encoded by the human cDNA contained in ATCC™ Deposit No. 209198; (g) a nucleotide sequence encoding the IL17RLP polypeptide having the complete amino acid sequence excepting the N-terminal methionine encoded by the human cDNA contained in ATCC™ Deposit No. 209198; (h) a nucleotide sequence encoding the mature IL17RLP polypeptide having the amino acid sequence encoded by the human cDNA contained in ATCC™ Deposit No. 209198; (i) a nucleotide sequence encoding the extracellular domain of the IL17RLP polypeptide having the amino acid sequence encoded by the human cDNA contained in ATCC™ Deposit No. 209198; and (j) a nucleotide sequence complementary to any of the nucleotide sequences in (a), (b), (c), (d), (e), (0, (g), (h) or (i) above.

Further embodiments of the invention include isolated nucleic acid molecules that comprise a polynucleotide having a nucleotide sequence at least 80%, 85%, 90% identical, and more preferably at least 92%, 95%, 96%, 97%, 98%, 99% or 100% identical, to any of the nucleotide sequences in (a), (b), (c), (d), (e), (f), (g), (h) or (i), above, or a polynucleotide which hybridizes under stringent hybridization conditions to a polynucleotide in (a), (b), (c), (d), (e), (f), (g), (h) or (i), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a IL17RLP polypeptide having an amino acid sequence in (a), (b), (c), (d), (e), (f), (g) or (h), above. A further nucleic acid embodiment of the invention relates to an isolated nucleic acid molecule comprising a polynucleotide which encodes the amino acid sequence of a IL17RLP polypeptide having an amino acid sequence which contains at least one conservative amino acid substitution, but not more than 50 conservative amino acid substitutions, even more preferably, not more than 40 conservative amino acid substitutions, still more preferably not more than 30 conservative amino acid substitutions, and still even more preferably not more than 20 conservative amino acid substitutions. Of course, in order of ever-increasing preference, it is highly preferable for a polynucleotide which encodes the amino acid sequence of a IL17RLP polypeptide to have an amino acid sequence which contains not more than 10-20, 10-15, 7-15, 7-10, 5-10, 3-7, 3-5, 2-5, 1-5, 1-3, 10, 9, 8, 7, 6, 5, 4, 3, 2 or 1 conservative amino acid substitutions.

The present invention also relates to recombinant vectors, which include the isolated nucleic acid molecules of the present invention, and to host cells containing the recombinant vectors, as well as to methods of making such vectors and host cells and for using them for production of IL17RLP polypeptides or peptides by recombinant techniques.

By a polynucleotide having a nucleotide sequence at least, for example, 95% "identical" to a reference nucleotide sequence encoding a IL17RLP polypeptide is intended that the nucleotide sequence of the polynucleotide is identical to the reference sequence except that the polynucleotide sequence may include up to five point mutations per each 100 nucleotides of the reference nucleotide sequence encoding the IL17RLP polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80%, 85%, 90%, 92%, 95%, 96%, 97%, 98%, 99% or 100° A identical to, for instance, the nucleotide sequence shown in FIGS. 1A, 1B, and 1C or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711).

Bestfit uses the local homology algorithm of Smith and Waterman to find the best segment of homology between two sequences (*Advances in Applied Mathematics* 2:482-489 (1981)). When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed. A preferred method for determining the best overall match between a query sequence (a sequence of the present invention) and a subject sequence, also referred to as a global sequence alignment, can be determined using the FASTDB computer program based on the algorithm of Brutlag and colleagues (*Comp. App. Biosci.* 6:237-245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

In certain preferred embodiments, IL17RLP proteins of the invention comprise fusion proteins as described herein wherein the IL17RLP polypeptides are those described as $n^1$-$m^1$, $n^2$-$m^2$, and/or $n^3$-$m^3$ herein. In preferred embodiments, the application is directed to nucleic acid molecules at least 80%, 85%, 90%, 92%, 95%, 96%, 97%, 98%, 99%, or 100% identical to the nucleic acid sequences encoding polypeptides having the amino acid sequence of the specific N- and C-terminal deletions recited herein. Polynucleotides encoding these polypeptides are also encompassed by the invention.

The present application is directed to nucleic acid molecules at least 80%, 85%, 90%, 92%, 95%, 96%, 97%, 98%, 99% or 100% identical to the nucleic acid sequence shown in FIGS. 1A, 1B, and 1C (SEQ ID NO:1) or to the nucleic acid sequence of the deposited cDNA, irrespective of whether they encode a polypeptide having IL17RLP activity. This is because even where a particular nucleic acid molecule does not encode a polypeptide having IL17RLP activity, one of skill in the art would still know how to use the nucleic acid molecule, for instance, as a hybridization probe or a polymerase chain reaction (PCR) primer. Uses of the nucleic acid molecules of the present invention that do not encode a polypeptide having IL17RLP activity include, inter alia, (1) isolating the IL17RLP gene or allelic variants thereof in a cDNA library; (2) in situ hybridization (e.g., "FISH") to metaphase chromosomal spreads to provide precise chromosomal location of the IL17RLP gene, as described by Verma and colleagues (*Human Chromosomes: A Manual of Basic Techniques*, Pergamon Press, New York (1988)); and Northern Blot analysis for detecting IL17RLP mRNA expression in specific tissues.

Preferred, however, are nucleic acid molecules comprising, or alternatively consisting of, sequences at least 80%, 85%, 90%, 92%, 95%, 96%, 97%, 98%, 99% or 100% identical to the nucleic acid sequence shown in FIGS. 1A, 1B, and 1C (SEQ ID NO:1) or to the nucleic acid sequence of the deposited cDNA which do, in fact, encode a polypeptide having IL17RLP protein activity. By "a polypeptide having IL17RLP activity" is intended polypeptides exhibiting activity similar, but not necessarily identical, to an activity of the mature or soluble form of the IL17RLP protein of the invention, as measured in a particular biological assay. For example, the IL17RLP protein of the present invention modulates IL-6 secretion from NIH-3T3 cells. An in vitro ELISA assay which quantitates the amount of IL-6 secreted from cells in response to treatment with cytokines or the soluble extracellular domains of cytokine receptors has been described (Yao, Z., et al., *Immunity* 3:811-821 (1995)). Briefly, the assay involves plating the target cells at a density of approximately $5\times10^6$ cells/mL in a volume of 500 microliters in the wells of a 24 well flat-bottomed culture plate (Costar). The cultures are then treated with various concentrations of the cytokine or the soluble extracellular domain of cytokine receptor in question The cells are then cultured for 24 hours at 37° C. At this time, 50 microliters of supernatant is removed and assayed for the quantity of IL-6 essentially as described by the manufacturer (Genzyme, Boston, Mass.). IL-6 levels are then calculated by reference to a standard curve constructed with recombinant IL-17 cytokine. Such activity is useful for determining the level of IL17RLP-mediated IL-6 secretion.

IL17RLP protein modulates immune system cell proliferation and differentiation in a dose-dependent manner in the above-described assay. Thus, "a polypeptide having IL17RLP protein activity" includes polypeptides that also exhibit any of the same stimulatory activities in the above-described assays in a dose-dependent manner. Although the degree of dose-dependent activity need not be identical to that of the IL17RLP protein, preferably, "a polypeptide having IL17RLP protein activity" will exhibit substantially similar dose-dependence in a given activity as compared to the IL17RLP protein (i.e., the candidate polypeptide will exhibit greater activity or not more than about 25-fold less and, preferably, not more than about tenfold less activity relative to the reference IL17RLP protein).

Lymphocyte proliferation is another in vitro assay which may be performed to determine the activity of IL17RLP, soluble, extracellular domains of IL17RLP, and agonists and antagonists (e.g., anti-IL17RLP antibodies). For example, Yao and colleagues (*Immunity* 3:811-821 (1995)) have recently described an in vitro assay for determining the effects of various cytokines and soluble cytokine receptors on the proliferation of murine leukocytes. Briefly, lymphoid organs are harvested aseptically, lymphocytes are isolated from the harvested organs, and the resulting collection of lymphoid cells are suspended in standard culture medium as described by Fanslow and coworkers (J. Immunol. 147:535-5540 (1991)). The lymphoid cell suspensions may then be divided into several different subclasses of lymphoid cells including splenic T-cells, lymph node B-cells, $CD4^+$ and $CD8^+$ T-cells, and mature adult thymocytes. For splenic T-cells, spleen cell suspensions ($200\times10^6$ cells) are incubated with CD11 b mAb and class II MHC mAb for 30 min at 4° C., loaded on a T-cell purification column (Pierce, Rockford, Ill.), and the T-cells eluted according to the manufacturer's instructions. Using this method, purity of the resulting T-cell populations should be >95% $CD3^+$ and <1% $sIgM^+$. For purification of lymph node subsets, B-cells are removed from by adherence to tissue culture dishes previously coated with goat anti-mouse IgG (10 μg/mL). Remaining cells were then incubated with anti-CD4 or anti-CD8 for 30 min at 4° C. then washed and placed on tissue culture dishes previously coated with goat anti-rat IgG (20 micrograms per milliliter). After 45 min, nonadherent cells are removed and tested for purity by flow cytometry. CD4 and surface Ig-depleted cells should be >90% TCR-ab, $CD8^+$, whereas CD8 and surface Ig-depleted cells should be >95% TCR-ab, $CD4^+$. Finally, to enrich for mature adult thymocytes, cells are suspended at $10^8$/mL in 10% anti-HSA and 10% low tox rabbit complement (Cedarlane, Ontario, Canada), incubated for 45 min at 37° C., and remaining viable cells isolated over FICOLL™-Hypaque (PHARMACIA™, Piscataway, N.J.). This procedure should yield between 90 and 95% $CD3^{hi}$ cells that are either $CD4^+8^-$ or $CD4^-8^+$.

To analyze the proliferative response of the above-described primary cell cultures, in vitro proliferation assays are set up in round bottom or flat bottom 96-well plates using $0.5-1.5\times10^5$ cells/well. For stimulation, T-cells are incubated with suboptimal concentrations (0.25-0.5 micrograms per milliliter) of Con A (SIGMA™, St. Louis, Mo.), PHA (0.25-0.5%; Difco, Detroit, Mich.), immobilized anti-CD3, or immobilized anti-TCR-ab. Anti-CD3 and anti-TCR-ab are immobilized for >2 hours at 37° C. before the addition of effector cells. Incubations are done in the presence and absence of fixed CV-1/EBNA cells transfected with IL17RLP, muteins thereof, a control vector, or a control antigen such as rCD40L (Armitage, et al., *Nature* 357:80 (1992)); Spriggs, et al., *J. Exp. Med.* 176:1543 (1992)). Surface expression of CD40L is monitored by flow cytometry using a human CD40-Fc fusion protein. Cell cultures are pulsed overnight with [³H]-thymidine (1 microcurie per well) for the last 18 hours of a 3 day culture. Labeled cultures are then harvested on a 96-well Inotech harvester and radioactive counts detected using a scintillation counter.

Like other cytokine receptors, IL17RLP exhibits activity on leukocytes including for example monocytes, lymphocytes and neutrophils. For this reason IL17RLP is active in directing the proliferation and differentiation of these cell types. Such activity is useful for immune enhancement or suppression, myeloprotection, stem cell mobilization, acute and chronic inflammatory control and treatment of leukemia. Assays for measuring such activity are well known in the art (Peters, et al., *Immun. Today* 17:273 (1996); Young, et al., *J. Exp. Med.* 182:1111 (1995); Caux, et al., *Nature* 390:258 (1992); and Santiago-Schwarz, et al., *Adv. Exp. Med. Biol.* 378:7 (1995).

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98%, 99% or 100% identical to the nucleic acid sequence of the deposited cDNA or the nucleic acid sequence shown in FIGS. 1A, 1B, and 1C (SEQ ID NO:1) will encode a polypeptide "having IL17RLP protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having IL17RLP protein activity. This is because the skilled artisan is fully aware of amino acid substitutions that are either less likely or not likely to significantly effect protein function (e.g., replacing one aliphatic amino acid with a second aliphatic amino acid), as further described below.

In specific embodiments, antagonists according to the present invention are nucleic acids corresponding to the sequences contained in IL17RLP, or the complementary strand thereof, and/or to nucleotide sequences contained in the deposited clone HAPOR40. In one embodiment, antisense sequence is generated internally by the organism, in another embodiment, the antisense sequence is separately administered (see, for example, O'Connor, J., Neurochem. 56:560 (1991), and Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1300 (1991). The methods are based on binding of a polynucleotide to a complementary DNA or RNA.

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the IL17RLP antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the IL17RLP antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding IL17RLP, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., *Nature* 296:39-42 (1982)), etc.

The antisense nucleic acids of the invention comprise a sequence complementary to at least a portion of an RNA transcript of aN IL17RLP gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded IL17RLP antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a IL17RLP RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of the IL17RLP shown in FIGS. 1A, 1B, and 1C could be used in an antisense approach to inhibit translation of endogenous IL17RLP mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of IL17RLP mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553-6556 (1989); Lemaitre et al., Proc. Natl. Acad. Sci. 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958-976 (1988)) or intercalating agents. (See, e.g., Zon, Pharm. Res. 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res. 15:6625-6641 (1987)). The oligonucleotide is a 2-0-methylribonucleotide (Inoue et al., Nucl. Acids Res. 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448-7451 (1988)), etc.

While antisense nucleotides complementary to the IL17RLP coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222-1225 (1990). While ribozymes that cleave mRNA at site specific recognition sequences can be used to destroy IL17RLP mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of IL17RLP (FIGS. 1A, 1B, and 1C (SEQ ID NO:1)). Preferably, the ribozyme is engineered so that the cleavage recognition site is located near the 5' end of the IL17RLP mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express IL17RLP in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous IL17RLP messages and inhibit translation. Since ribozymes unlike antisense molecules, are catalytic, a lower intracellular concentration is required for efficiency.

Endogenous gene expression can also be reduced by inactivating or "knocking out" the IL17RLP gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of IL17RLP (e.g., fragments of the IL17RLP shown in FIGS. 1A, 1B, and 1C (SEQ ID NO:2) that include the ligand binding domain from the extracellular region of the full length receptor). Such soluble forms of the IL17RLP, which may be naturally occurring or synthetic, antagonize IL17RLP-mediated signaling by competing with the cell surface bound forms of the receptor for binding to IL-20 or IL-20-like ligands. Antagonists of the present invention also include antibodies specific for IL17RLP ligands and IL17RLP-Fc fusion proteins.

The present invention also relates to vectors which include the isolated DNA molecules of the present invention, host cells which are genetically engineered with the recombinant vectors, and the production of IL17RLP polypeptides or fragments thereof by recombinant or synthetic techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC™ Accession No. 201178)); insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Vectors preferred for use in bacteria include pHE4-5 (ATCC™ Accession No. 209311; and variations thereof), pQE70, pQE60 and pQE-9 (QIAGEN, Inc., supra); pBS vectors, Phagescript vectors, Bluescript vectors, pNH8A, pNH16a, pNH18A, pNH46A (STRATAGENE™); and ptrc99a, pKK223-3, pKK233-3, pDR540, pRIT5 (PHARMACIA™). Preferred expression vectors for use in yeast systems include, but are not limited to, pYES2, pYD1, pTEF1/Zeo, pYES2/GS, pPICZ, pGAPZ, pGAPZalpha, pPIC9, pPIC3.5, pHIL-D2, pPIC3.5K, pPIC9K, and PAO815 (all available from Invitrogen, Carlsbad, Calif.). Among preferred eukaryotic vectors are pWLNEO, pSV2CAT, pOG44, pXT1, and pSG (STRATAGENE™); and pSVK3, pBPV, pMSG and pSVL (PHARMACIA™). Other suitable vectors will be readily apparent to the skilled artisan.

In one embodiment, the yeast Pichia pastoris is used to express IL17RLP protein in a eukaryotic system. Pichia pastoris is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111-21 (1985); Koutz, P. J, et al., Yeast 5:167-77 (1989); Tschopp, J. F., et al, Nucl. Acids Res. 15:3859-76 (1987). Thus, a heterologous coding sequence, such as, for example, an IL17RLP polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding an IL17RLP polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of an IL17RLP protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In one embodiment, high-level expression of a heterologous coding sequence, such as, for example, an IL17RLP polynucleotide of the present invention, may be achieved by cloning the heterologous polynucleotide of the invention into an expression vector such as, for example, pGAPZ or pGAPZalpha, and growing the yeast culture in the absence of methanol.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals (for example, Davis, et al., Basic Methods In Molecular Biology (1986)).

The polypeptide (e.g., the mature or the extracellular domain of IL17RLP of the invention) may be expressed in a modified form, such as a fusion protein, and may include not only secretion signals, but also additional heterologous functional or non-functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-0 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5 (Bennett, D., et al., *J. Molecular Recognition* 8:52-58 (1995); Johanson, K., et al., *J. Biol. Chem.* 270:9459-9471 (1995)).

The IL17RLP protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., IL17RLP coding sequence), and/or to include genetic material (e.g., heterologous polynucleotide sequences) that is operably associated with IL17RLP polynucleotides of the invention, and which activates, alters, and/or amplifies endogenous IL17RLP polynucleotides. For example, techniques known in the art may be used to operably associate heterologous control regions (e.g., promoter and/or enhancer) and endogenous IL17RLP polynucleotide sequences via homologous recombination (see, e.g., U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

Polypeptides and Fragments

The invention further provides an isolated IL17RLP polypeptide comprising, or alternatively consisting of, the amino acid sequence encoded by the deposited cDNA, or the amino acid sequence in SEQ ID NO:2, or a peptide or polypeptide comprising, or alternatively consisting of, a portion of the above polypeptides.

To improve or alter the characteristics of IL17RLP polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron and colleagues (*J. Biol. Chem.*, 268:2984-2988 (1993)) reported modified KGF proteins that had heparin binding activity even if 3, 8, or 27 N-terminal amino acid residues were missing. In the present case, since the protein of the invention is a member of the interleukin (IL)-17 receptor polypeptide family, deletions of N-terminal amino acids up to the cysteine at position 5 of SEQ ID NO:2 may retain some biological activity such as ligand binding or modulation of target cell activities. Polypeptides having further N-terminal deletions including the cysteine residue at position 5 in SEQ ID NO:2 would not be expected to retain such biological activities because it is known that this residue in the murine IL-17 receptor polypeptide is likely required for forming a disulfide bridge to provide structural stability which is needed for ligand binding and the initiation of the appropriate signal transduction pathways.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete, mature or extracellular domain of the protein generally will be retained when less than the majority of the residues of the complete, mature or extracellular domain of the protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the IL17RLP shown in SEQ ID NO:2, up to the cysteine residue at position number 5, and polynucleotides encoding such polypeptides. In particular, the present invention provides polypeptides comprising, or alternatively consisting of, the amino acid sequence of residues $n^1$-407 of SEQ ID NO:2, where $n^1$ is an integer in the range of −19 to 5, and 5 is the position of the first residue from the N-terminus of the complete IL17RLP polypeptide (shown in SEQ ID NO:2) believed to be required for ligand binding activity of the IL17RLP protein. More in particular, the invention provides polynucleotides encoding polypeptides comprising, or alternatively consisting of, a member of the group consisting of the amino acid sequence of residues of −18-407, −17-407, −16-407, −15-407, −14-407, −13-407, −12-407, −11-407, −10-407, −9-407, −8-407, −7-407, −6-407, −5-407, −4-407, −3-407, −2-407, −1-407, 1-407, 2-407, 3-407, 4-407, and 5-407 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98%, 99% or 100% identical to the polynucleotide sequence encoding the IL17RLP polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, 99% or 100% identical to the amino acid sequence described above, and polynucleotides that encode such polypeptides.

Similarly, many examples of biologically functional C-terminal deletion muteins are known. For instance, Interferon gamma shows up to ten times higher activities by deleting 8-10 amino acid residues from the carboxy terminus of the protein (Dobeli, et al, *J. Biotechnology* 7:199-216 (1988)). In the present case, since the protein of the invention is a member of the interleukin (IL)-17 receptor polypeptide family, deletions of C-terminal amino acids up to the cysteine at position 340 of SEQ ID NO:2 may retain some biological activity such as ligand-binding. Polypeptides having further C-terminal deletions including the cysteine residue at position 340 of SEQ ID NO:2 would not be expected to retain such biological activities because it is known that this residue in the murine IL-17 receptor polypeptide is likely required for forming a disulfide bridge to provide structural stability which is needed for receptor binding and signal transduction.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete, mature or extracellular domain of the protein generally will be retained when less than the majority of the residues of complete, mature or extracellular domain of the protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the IL17RLP shown in SEQ ID NO:2, up to the cysteine residue at position 340 of SEQ ID NO:2, and polynucleotides encoding such polypeptides. In particular, the present invention provides polypeptides comprising, or alternatively consisting of, the amino acid sequence of residues-19-$m^1$ of the amino acid sequence in SEQ ID NO:2, where $m^1$ is any integer in the range of 340 to 407, and residue 340 is the position of the first residue from the C-terminus of the complete IL17RLP polypeptide (shown in SEQ ID NO:2) believed to be required for the IL17RLP protein to transfer its extracellular signal to the interior of the cell. More in particular, the invention provides polynucleotides encoding polypeptides comprising, or alternatively consisting of, a member selected from the group consisting of the amino acid sequence of residues −19-340, −19-341, −19-342, −19-343, −19-344, −19-345, −19-346, −19-347, −19-348, −19-349, −19-350, −19-351, −19-352, −19-353, −19-354, −19-355, −19-356, −19-357, −19-358, −19-359, −19-360, −19-361, −19-362, −19-363, −19-364, −19-365, −19-366, −19-367, −19-368, −19-369, −19-370, −19-371, −19-372, −19-373, −19-374, =19-375, −19-376, −19-377, −19-378, −19-379, −19-380, −19-381, −19-382, −19-383, −19-384, −19-385, −19-386, −19-387, −19-388, −19-389, −19-390, −19-391, −19-392, −19-393, −19-394, −19-395, −19-396, −19-397, −19-398, −19-399, −19-400, −19-401, −19-402, −19-403, −19-404, −19-405, −19-406, and −19-407 of SEQ ID NO:2. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98%, 99% or 100% identical to the polynucleotide sequence encoding the IL17RLP polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, 99% or 100% identical to the amino acid sequence described above, and polynucleotides that encode such polypeptides.

The invention also provides polypeptides having one or more amino acids deleted from both the amino and the carboxyl termini, which may be described generally as comprising, or alternatively consisting of, residues $n^1$-$m^1$ of SEQ ID NO:2, where $n^1$ and $m^1$ are integers as described above.

Also included are a nucleotide sequence encoding a polypeptide comprising, or alternatively consisting of, a portion of the complete IL17RLP amino acid sequence encoded by the cDNA clone contained in ATCC™ Deposit No. 209198, where this portion excludes from 1 to about 23 amino acids from the amino terminus of the complete amino acid sequence encoded by the cDNA clone contained in ATCC™ Deposit No. 209198, or from 1 to about 67 amino acids from the carboxy terminus, or any combination of the above amino terminal and carboxy terminal deletions, of the complete amino acid sequence encoded by the cDNA clone contained in ATCC™ Deposit No. 209198. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98%, 99% or 100% identical to the polynucleotide sequence encoding the IL17RLP polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, 99% or 100% identical to the amino acid sequence described above, and polynucleotides that encode such polypeptides.

As mentioned above, even if deletion of one or more amino acids from the N-terminus of a protein results in modification of loss of one or more biological functions of the protein, other biological activities may still be retained. Thus, the ability of the shortened IL17RLP mutein to induce and/or bind to antibodies which recognize the complete or mature of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art. It is not unlikely that a IL17RLP mutein with a large number of deleted N-terminal amino acid residues may retain some biological or immungenic activities. In fact, peptides composed of as few as six IL17RLP amino acid residues may often evoke an immune response.

Accordingly, the present invention further provides polypeptides having one or more residues deleted from the amino terminus of the IL17RLP amino acid sequence shown in SEQ ID NO:2, up to the aspartic acid residue at position number 421 and polynucleotides encoding such polypeptides. In particular, the present invention provides polypeptides comprising, or alternatively consisting of, the amino acid sequence of residues $n^2$-426 of FIGS. 1A, 1B, and 1C (SEQ ID NO:2), where $n^2$ is an integer in the range of 2 to 421, and 422 is the position of the first residue from the N-terminus of the complete IL17RLP polypeptide believed to be required for at least immunogenic activity of the IL17RLP protein. More in particular, the invention provides polynucleotides encoding polypeptides comprising, or alternatively consisting of, a member selected from the group consisting of the amino acid sequence of residues of S-2 to L-426; L-3 to L-426; V-4 to L-426; L-5 to L-426; L-6 to L-426; S-7 to L-426; L-8 to L-426; A-9 to L-426; A-10 to L-426; L-11 to L-426; C-12 to L-426; R-13 to L-426; S-14 to L-426; A-15 to L-426; V-16 to L-426; P-17 to L-426; R-18 to L-426; E-19 to L-426; P-20 to L-426; T-21 to L-426; V-22 to L-426; Q-23 to L-426; C-24 to L-426; G-25 to L-426; S-26 to L-426; E-27 to L-426; T-28 to L-426; G-29 to L-426; P-30 to L-426; S-31 to L-426; P-32 to L-426; E-33 to L-426; W-34 to L-426; M-35 to L-426; L-36 to L-426; Q-37 to L-426; H-38 to L-426; D-39 to L-426; L-40 to L-426; I-41 to L-426; P-42 to L-426; G-43 to L-426; D-44 to L-426; L-45 to L-426; R-46 to L-426; D-47 to L-426; L-48 to L-426; R-49 to L-426; V-50 to L-426; E-51 to L-426; P-52 to L-426; V-53 to L-426; T-54 to L-426; T-55 to L-426; S-56 to L-426; V-57 to L-426; A-58 to L-426; T-59 to L-426; G-60 to L-426; D-61 to L-426; Y-62 to L-426; S-63 to L-426; I-64 to L-426; L-65 to L-426; M-66 to L-426; N-67 to L-426; V-68 to L-426; S-69 to L-426; W-70 to L-426; V-71 to L-426; L-72 to L-426; R-73 to L-426; A-74 to L-426; D-75 to L-426; A-76 to L-426; S-77 to L-426; I-78 to L-426; R-79 to L-426; L-80 to L-426; L-81 to L-426; K-82 to L-426; A-83 to L-426; T-84 to L-426; K-85 to L-426; I-86 to L-426; C-87 to L-426; V-88 to L-426; T-89 to L-426; G-90 to L-426; K-91 to L-426; S-92 to L-426; N-93 to L-426; F-94 to L-426; Q-95 to L-426; S-96 to L-426; Y-97 to L-426; S-98 to L-426; C-99 to L-426; V-100 to L-426; R-101 to L-426; C-102 to L-426; N-103 to L-426; Y-104 to L-426; T-105 to L-426; E-106 to L-426; A-107 to L-426; F-108 to L-426; Q-109 to L-426; T-110 to L-426; Q-111 to L-426; T-112 to L-426; R-113 to L-426; P-114 to L-426; S-115 to L-426; G-116 to L-426; G-117 to L-426; K-118 to L-426; W-119 to L-426; T-120 to L-426; F-121 to L-426; S-122 to L-426; Y-123 to L-426; I-124 to L-426; G-125 to L-426; F-126 to L-426; P-127 to L-426; V-128 to L-426; E-129 to L-426; L-130 to L-426; N-131 to L-426; T-132 to L-426; V-133 to L-426; Y-134 to L-426; F-135 to L-426; I-136 to L-426; G-137 to L-426; A-138 to L-426; H-139 to L-426; N-140 to L-426; I-141 to L-426; P-142 to L-426; N-143 to L-426; N-144 to L-426; A-145 to L-426; N-145 to L-426; M-146 to L-426; N-147 to L-426; E-148 to L-426; D-149 to L-426; G-150 to L-426; P-151 to L-426; S-152 to L-426; M-153 to L-426; S-154 to L-426; V-155 to L-426; N-156 to L-426; F-157 to L-426; T-158 to L-426; S-159 to L-426; P-160 to L-426; G-161 to L-426; C-162 to L-426; L-163 to L-426; D-164 to L-426; H-165 to L-426; I-166 to L-426; M-167 to L-426; K-168 to L-426; Y-169 to L-426; K-170 to L-426; K-171 to L-426; K-172 to L-426; C-173 to L-426; V-174 to L-426; K-175 to L-426; A-176 to L-426; G-177 to L-426; S-178 to L-426; L-179 to L-426; W-180 to L-426; D-181 to L-426; P-182 to L-426; N-183 to L-426; I-184 to L-426; T-185 to L-426; A-186 to L-426; C-187 to L-426; K-188 to L-426; K-189 to L-426; N-190 to L-426; E-191 to L-426; E-192 to L-426; T-193 to L-426; V-194 to L-426; E-195 to L-426; V-196 to L-426; N-197 to L-426; F-198 to L-426; T-199 to L-426; T-200 to L-426; T-201 to L-426; P-202 to L-426; L-203 to L-426; G-204 to L-426; N-205 to L-426; R-206 to L-426; Y-207 to L-426; M-208 to L-426; A-209 to L-426; L-210 to L-426; I-211 to L-426; Q-212 to L-426; H-213 to L-426; S-214 to L-426; T-215 to L-426; I-216 to L-426; I-217 to L-426; G-218 to L-426; F-219 to L-426; S-220 to L-426; Q-221 to L-426; V-222 to L-426; F-223 to L-426; E-224 to L-426; P-225 to L-426; H-226 to L-426; Q-227 to L-426; K-228 to L-426; K-229 to L-426; Q-230 to L-426; T-231 to L-426; R-232 to L-426; A-233 to L-426; S-234 to L-426; V-235 to L-426; V-236 to L-426; I-237 to L-426; P-238 to L-426; V-239 to L-426; T-240 to L-426; G-241 to L-426; D-242 to L-426; S-243 to L-426; E-244 to L-426; G-245 to L-426; A-246 to L-426; T-247 to L-426; V-248 to L-426; Q-249 to L-426; L-250 to L-426; T-251 to L-426; P-252 to L-426; Y-253 to L-426; F-254 to L-426; P-255 to L-426; T-256 to L-426; C-257 to L-426; G-258 to L-426; S-259 to L-426; D-260 to L-426; C-261 to L-426; I-262 to L-426; R-263 to L-426; H-264 to L-426; K-265 to L-426; G-266 to L-426; T-267 to L-426; V-268 to L-426; V-269 to L-426; L-270 to L-426; C-271 to L-426; P-272 to L-426; Q-273 to L-426; T-274 to L-426; G-275 to L-426; V-276 to L-426; P-277 to L-426; F-278 to L-426; P-279 to L-426; L-280 to L-426; D-281 to L-426; N-282 to L-426; N-283 to L-426; K-284 to L-426; S-285 to L-426; K-286 to L-426; P-287 to L-426; G-288 to L-426; G-289 to L-426; W-290 to L-426; L-291 to L-426; P-292 to L-426; L-293 to L-426; L-294 to L-426; L-295 to L-426; L-296 to L-426; S-297 to L-426; L-298 to L-426; L-299 to L-426; V-300 to L-426; A-301 to L-426; T-302 to L-426; W-303 to L-426; V-304 to L-426; L-305 to L-426; V-306 to L-426; A-307 to L-426; G-308 to L-426; I-309 to L-426; Y-310 to L-426; L-311 to L-426; M-312 to L-426; W-313 to L-426; R-314 to L-426; H-315 to L-426; E-316 to L-426; R-317 to L-426; I-318 to L-426; K-319 to L-426; K-320 to L-426; T-321 to L-426; S-322 to L-426; F-323 to L-426; S-324 to L-426; T-325 to L-426; T-326 to L-426; T-327 to L-426; L-328 to L-426; L-329 to L-426; P-330 to L-426; P-331 to L-426; I-332 to L-426; K-333 to L-426; V-334 to L-426; L-335 to L-426; V-336 to L-426; V-337 to L-426; Y-338 to L-426; P-339 to L-426; S-340 to L-426; E-341 to L-426; I-342 to L-426; C-343 to L-426; F-344 to L-426; H-345 to L-426; H-346 to L-426; T-347 to L-426; I-348 to L-426; C-349 to L-426; Y-350 to L-426; F-351 to L-426; T-352 to L-426; E-353 to L-426; F-354 to L-426; L-355 to L-426; Q-356 to L-426; N-357 to L-426; H-358 to L-426; C-359 to L-426; R-360 to L-426; S-361 to L-426; E-362 to L-426; V-363 to L-426; I-364 to L-426; L-365 to L-426; E-366 to L-426; K-367 to L-426; W-368 to L-426; Q-369 to L-426; K-370 to L-426; K-371 to L-426; K-372 to L-426; I-373 to L-426; A-374 to L-426; E-375 to L-426; M-376 to L-426; G-377 to L-426; P-378 to L-426; V-379 to L-426; Q-380 to L-426; W-381 to L-426; F-382 to L-426; A-383 to L-426; T-384 to L-426; Q-385 to L-426; K-386 to L-426; K-387 to L-426; A-388 to L-426; A-389 to L-426; D-390 to L-426; K-391 to L-426; V-392 to L-426; V-393 to L-426; F-394 to L-426; L-395 to L-426; L-396 to L-426; S-397 to L-426; N-398 to L-426; D-399 to L-426; V-400 to L-426; N-401 to L-426; S-402 to L-426; V-403 to L-426; C-404 to L-426; D-405 to L-426; G-406 to L-426; T-407 to L-426; C-408 to L-426; G-409 to L-426; K-410 to L-426; S-411 to L-426; E-412 to L-426; G-413 to L-426; S-414 to L-426; P-415 to L-426; S-416 to L-426; E-417 to L-426; N-418 to L-426; S-419 to L-426; Q-420 to L-426; and D-421 to L-426 of the IL17RLP amino acid sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 426 from the N-terminus to the C-terminus, while the amino acid residues in SEQ ID NO:2 are numbered consecutively from −19 through 407 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98%, 99% or 100% identical to the polynucleotide sequence encoding the IL17RLP polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, 99% or 100% identical to the amino acid sequence described above, and polynucleotides that encode such polypeptides.

Also as mentioned above, even if deletion of one or more amino acids from the C-terminus of a protein results in modification of loss of one or more biological functions of the protein, other biological activities may still be retained. Thus, the ability of the shortened IL17RLP mutein to induce and/or bind to antibodies which recognize the complete or mature of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art. It is not unlikely that a IL17RLP mutein with a large number of deleted C-terminal amino acid residues may retain some biological or immungenic activities. In fact, peptides composed of as few as six IL17RLP amino acid residues may often evoke an immune response.

Accordingly, the present invention further provides polypeptides having one or more residues deleted from the carboxy terminus of the amino acid sequence of the IL17RLP shown in SEQ ID NO:2, up to the leucine residue at position number 6, and polynucleotides encoding such polypeptides. In particular, the present invention provides polypeptides comprising, or alternatively consisting of, the amino acid sequence of residues 1-m$^2$ of SEQ ID NO:2, where m$^2$ is an integer in the range of 6 to 426, and 6 is the position of the first residue from the C-terminus of the complete IL17RLP polypeptide believed to be required for at least immunogenic activity of the IL17RLP protein. More in particular, the invention provides polynucleotides encoding polypeptides comprising, or alternatively consisting of, a member selected from the group consisting of the amino acid sequence of residues M-1 to C-425; M-1 to P-424; M-1 to S-423; M-1 to S-422; M-1 to D-421; M-1 to Q-420; M-1 to S-419; M-1 to N-418; M-1 to E-417; M-1 to S-416; M-1 to P-415; M-1 to S-414; M-1 to G-413; M-1 to E-412; M-1 to S-411; M-1 to K-410; M-1 to G-409; M-1 to C-408; M-1 to T-407; M-1 to G-406; M-1 to D-405; M-1 to C-404; M-1 to V-403; M-1 to S-402; M-1 to N-401; M-1 to V-400; M-1 to D-399; M-1 to N-398; M-1 to S-397; M-1 to L-396; M-1 to L-395; M-1 to F-394; M-1 to V-393; M-1 to V-392; M-1 to K-391; M-1 to D-390; M-1 to A-389; M-1 to A-388; M-1 to K-387; M-1 to K-386; M-1 to Q-385; M-1 to T-384; M-1 to A-383; M-1 to L-382; M-1 to W-381; M-1 to Q-380; M-1 to V-379; M-1 to P-378; M-1 to G-377; M-1 to M-376; M-1 to E-375; M-1 to A-374; M-1 to I-373; M-1 to K-372; M-1 to K-371; M-1 to K-370; M-1 to Q-369; M-1 to W-368; M-1 to K-367; M-1 to E-366; M-1 to L-365; M-1 to I-364; M-1 to V-363; M-1 to E-362; M-1 to S-361; M-1 to R-360; M-1 to C-359; M-1 to H-358; M-1 to N-357; M-1 to Q-356; M-1 to L-355; M-1 to F-354; M-1 to E-353; M-1 to T-352; M-1 to F-351; M-1 to Y-350; M-1 to C-349; M-1 to I-348; M-1 to T-347; M-1 to H-346; M-1 to H-345; M-1 to F-344; M-1 to C-343; M-1 to I-342; M-1 to E-341; M-1 to S-340; M-1 to P-339; M-1 to Y-338; M-1 to V-337; M-1 to V-336; M-1 to L-335; M-1 to V-334; M-1 to K-333; M-1 to I-332; M-1 to P-331; M-1 to P-330; M-1 to L-329; M-1 to L-328; M-1 to T-327; M-1 to T-326; M-1 to T-325; M-1 to S-324; M-1 to F-323; M-1 to S-322; M-1 to T-321; M-1 to K-320; M-1 to K-319; M-1 to I-318; M-1 to R-317; M-1 to E-316; M-1 to H-315; M-1 to R-314; M-1 to W-313; M-1 to M-312; M-1 to L-311; M-1 to Y-310; M-1 to I-309; M-1 to G-308; M-1 to A-307; M-1 to V-306; M-1 to L-305; M-1 to V-304; M-1 to W-303; M-1 to T-302; M-1 to A-301; M-1 to V-300; M-1 to L-299; M-1 to L-298; M-1 to S-297; M-1 to L-296; M-1 to L-295; M-1 to L-294; M-1 to L-293; M-1 to P-292; M-1 to L-291; M-1 to W-290; M-1 to G-289; M-1 to G-288; M-1 to P-287; M-1 to K-286; M-1 to S-285; M-1 to K-284; M-1 to N-283; M-1 to N-282; M-1 to D-281; M-1 to L-280; M-1 to P-279; M-1 to F-278; M-1 to P-277; M-1 to V-276; M-1 to G-275; M-1 to T-274; M-1 to Q-273; M-1 to P-272; M-1 to C-271; M-1 to L-270; M-1 to V-269; M-1 to V-268; M-1 to T-267; M-1 to G-266; M-1 to K-265; M-1 to H-264; M-1 to R-263; M-1 to I-262; M-1 to C-261; M-1 to D-260; M-1 to S-259; M-1 to G-258; M-1 to C-257; M-1 to T-256; M-1 to P-255; M-1 to F-254; M-1 to Y-253; M-1 to P-252; M-1 to T-251; M-1 to L-250; M-1 to Q-249; M-1 to V-248; M-1 to T-247; M-1 to A-246; M-1 to G-245; M-1 to E-244; M-1 to S-243; M-1 to D-242; M-1 to G-241; M-1 to T-240; M-1 to V-239; M-1 to P-238; M-1 to I-237; M-1 to V-236; M-1 to V-235; M-1 to S-234; M-1 to A-233; M-1 to R-232; M-1 to T-231; M-1 to Q-230; M-1 to K-229; M-1 to K-228; M-1 to Q-227; M-1 to H-226; M-1 to P-225; M-1 to E-224; M-1 to F-223; M-1 to V-222; M-1 to Q-221; M-1 to S-220; M-1 to F-219; M-1 to G-218; M-1 to I-217; M-1 to I-216; M-1 to T-215; M-1 to S-214; M-1 to H-213; M-1 to Q-212; M-1 to I-211; M-1 to L-210; M-1 to A-209; M-1 to M-208; M-1 to Y-207; M-1 to R-206; M-1 to N-205; M-1 to G-204; M-1 to L-203; M-1 to P-202; M-1 to T-201; M-1 to T-200; M-1 to T-199; M-1 to F-198; M-1 to N-197; M-1 to V-196; M-1 to E-195; M-1 to V-194; M-1 to T-193; M-1 to E-192; M-1 to E-191; M-1 to N-190; M-1 to K-189; M-1 to K-188; M-1 to C-187; M-1 to A-186; M-1 to T-185; M-1 to T-184; M-1 to N-183; M-1 to P-182; M-1 to D-181; M-1 to W-180; M-1 to L-179; M-1 to S-178; M-1 to G-177; M-1 to A-176; M-1 to K-175; M-1 to V-174; M-1 to C-173; M-1 to K-172; M-1 to K-171; M-1 to K-170; M-1 to Y-169; M-1 to K-168; M-1 to M-167; M-1 to I-166; M-1 to H-165; M-1 to D-164; M-1 to L-163; M-1 to C-162; M-1 to G-161; M-1 to P-160; M-1 to S-159; M-1 to T-158; M-1 to F-157; M-1 to N-156; M-1 to V-155; M-1 to S-154; M-1 to M-153; M-1 to S-152; M-1 to P-151; M-1 to G-150; M-1 to D-149; M-1 to E-148; M-1 to N-147; M-1 to M-146; M-1 to N-145; M-1 to A-144; M-1 to N-143; M-1 to P-142; M-1 to I-141; M-1 to N-140; M-1 to H-139; M-1 to A-138; M-1 to G-137; M-1 to I-136; M-1 to F-135; M-1 to Y-134; M-1 to V-133; M-1 to T-132; M-1 to N-131; M-1 to L-130; M-1 to E-129; M-1 to V-128; M-1 to P-127; M-1 to F-126; M-1 to G-125; M-1 to I-124; M-1 to Y-123; M-1 to S-122; M-1 to F-121; M-1 to T-120; M-1 to W-119; M-1 to K-118; M-1 to G-117; M-1 to G-116; M-1 to S-115; M-1 to P-114; M-1 to R-113; M-1 to T-112; M-1 to Q-111; M-1 to T-110; M-1 to Q-109; M-1 to F-108; M-1 to A-107; M-1 to E-106; M-1 to T-105; M-1 to Y-104; M-1 to N-103; M-1 to C-102; M-1 to R-101; M-1 to V-100; M-1 to C-99; M-1 to S-98; M-1 to Y-97; M-1 to S-96; M-1 to Q-95; M-1 to F-94; M-1 to N-93; M-1 to S-92; M-1 to K-91; M-1 to G-90; M-1 to T-89; M-1 to V-88; M-1 to C-87; M-1 to I-86; M-1 to K-85; M-1 to T-84; M-1 to A-83; M-1 to K-82; M-1 to L-81; M-1 to L-80; M-1 to R-79; M-1 to I-78; M-1 to S-77; M-1 to A-76; M-1 to D-75; M-1 to A-74; M-1 to R-73; M-1 to L-72; M-1 to V-71; M-1 to W-70; M-1 to S-69; M-1 to V-68; M-1 to N-67; M-1 to M-66; M-1 to L-65; M-1 to I-64; M-1 to S-63; M-1 to Y-62; M-1 to D-61; M-1 to G-60; M-1 to T-59; M-1 to A-58; M-1 to V-57; M-1 to S-56; M-1 to T-55; M-1 to T-54; M-1 to V-53; M-1 to P-52; M-1 to E-51; M-1 to V-50; M-1 to R-49; M-1 to L-48; M-1 to D-47; M-1 to R-46; M-1 to L-45; M-1 to D-44; M-1 to G-43; M-1 to P-42; M-1 to I-41; M-1 to L-40; M-1 to D-39; M-1 to H-38; M-1 to Q-37; M-1 to L-36; M-1 to M-35; M-1 to W-34; M-1 to E-33; M-1 to P-32; M-1 to S-31; M-1 to P-30; M-1 to G-29; M-1 to T-28; M-1 to E-27; M-1 to S-26; M-1 to G-25; M-1 to C-24; M-1 to Q-23; M-1 to V-22; M-1 to T-21; M-1 to P-20; M-1 to E-19; M-1 to R-18; M-1 to P-17; M-1 to V-16; M-1 to A-15; M-1 to S-14; M-1 to R-13; M-1 to C-12; M-1 to L-11; M-1 to A-10; M-1 to A-9; M-1 to L-8; M-1 to S-7; and M-1 to L-6 of the sequence of the IL17RLP sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 426 from the N-terminus to the C-terminus, while the amino acid residues in SEQ ID NO:2 are numbered consecutively from −19 through 407 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98%, 99% or 100% identical to the polynucleotide sequence encoding the IL17RLP polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, 99% or 100% identical to the amino acid sequence described above, and polynucleotides that encode such polypeptides.

The invention also provides polypeptides having one or more amino acids deleted from both the amino and the carboxyl termini of an IL17RLP polypeptide, which may be described generally as comprising, or alternatively consisting of, residues $n^2$-$m^2$ of FIGS. 1A, 1B, and 1C (SEQ ID NO:2), where $n^2$ and $m^2$ are integers as described above.

Also as mentioned above, even if deletion of one or more amino acids from the N-terminus of a protein results in modification of loss of one or more biological functions of the protein, other biological activities may still be retained. Thus, the ability of the shortened extracellular domain of the IL17RLP mutein to induce and/or bind to antibodies which recognize the extracellular domain of the IL17RLP protein generally will be retained when less than the majority of the residues of the extracellular domain of the IL17RLP protein are removed from the N-terminus. Whether a particular polypeptide lacking N-terminal residues of an extracellular domain of the IL17RLP protein retains such immunologic activities can readily be determined by routine methods described herein and otherwise known in the art. It is not unlikely that a IL17RLP mutein with a large number of deleted N-terminal amino acid residues may retain some biological or immunogenic activities. In fact, peptides composed of as few as six amino acid residues of the extracellular domain of the IL17RLP protein may often evoke an immune response.

Accordingly, the present invention further provides polypeptides having one or more residues deleted from the amino terminus of the extracellular domain of the IL17RLP amino acid sequence shown in SEQ ID NO:2, up to the aspartic acid residue at position number 421 and polynucleotides encoding such polypeptides. In particular, the present invention provides polypeptides comprising, or alternatively consisting of, the amino acid sequence of residues $n^3$-290 of FIGS. 1A, 1B, and 1C (SEQ ID NO:2), where $n^3$ is an integer in the range of 15 to 285, and 286 is the position of the first residue from the N-terminus of the extracellular domain of the IL17RLP polypeptide believed to be required for at least immunogenic activity of the IL17RLP protein. More in particular, the invention provides polynucleotides encoding polypeptides comprising, or alternatively consisting of, a member selected from the group consisting of the amino acid sequence of residues of A-15 to W-290; V-16 to W-290; P-17 to W-290; R-18 to W-290; E-19 to W-290; P-20 to W-290; T-21 to W-290; V-22 to W-290; Q-23 to W-290; C-24 to W-290; G-25 to W-290; S-26 to W-290; E-27 to W-290; T-28 to W-290; G-29 to W-290; P-30 to W-290; S-31 to W-290; P-32 to W-290; E-33 to W-290; W-34 to W-290; M-35 to W-290; L-36 to W-290; Q-37 to W-290; H-38 to W-290; D-39 to W-290; L-40 to W-290; I-41 to W-290; P-42 to W-290; G-43 to W-290; D-44 to W-290; L-45 to W-290; R-46 to W-290; D-47 to W-290; L-48 to W-290; R-49 to W-290; V-50 to W-290; E-51 to W-290; P-52 to W-290; V-53 to W-290; T-54 to W-290; T-55 to W-290; S-56 to W-290; V-57 to W-290; A-58 to W-290; T-59 to W-290; G-60 to W-290; D-61 to W-290; Y-62 to W-290; S-63 to W-290; I-64 to W-290; L-65 to W-290; M-66 to W-290; N-67 to W-290; V-68 to W-290; S-69 to W-290; W-70 to W-290; V-71 to W-290; L-72 to W-290; R-73 to W-290; A-74 to W-290; D-75 to W-290; A-76 to W-290; S-77 to W-290; I-78 to W-290; R-79 to W-290; L-80 to W-290; L-81 to W-290; K-82 to W-290; A-83 to W-290; T-84 to W-290; K-85 to W-290; I-86 to W-290; C-87 to W-290; V-88 to W-290; T-89 to W-290; G-90 to W-290; K-91 to W-290; S-92 to W-290; N-93 to W-290; F-94 to W-290; Q-95 to W-290; S-96 to W-290; Y-97 to W-290; S-98 to W-290; C-99 to W-290; V-100 to W-290; R-101 to W-290; C-102 to W-290; N-103 to W-290; Y-104 to W-290; T-105 to W-290; E-106 to W-290; A-107 to W-290; F-108 to W-290; Q-109 to W-290; T-110 to W-290; Q-111 to W-290; T-112 to W-290; R-113 to W-290; P-114 to W-290; S-115 to W-290; G-116 to W-290; G-117 to W-290; K-118 to W-290; W-119 to W-290; T-120 to W-290; F-121 to W-290; S-122 to W-290; Y-123 to W-290; I-124 to W-290; G-125 to W-290; F-126 to W-290; P-127 to W-290; V-128 to W-290; E-129 to W-290; L-130 to W-290; N-131 to W-290; T-132 to W-290; V-133 to W-290; Y-134 to W-290; F-135 to W-290; I-136 to W-290; G-137 to W-290; A-138 to W-290; H-139 to W-290; N-140 to W-290; I-141 to W-290; P-142 to W-290; N-143 to W-290; A-144 to W-290; N-145 to W-290; M-146 to W-290; N-147 to W-290; E-148 to W-290; D-149 to W-290; G-150 to W-290; P-151 to W-290; S-152 to W-290; M-153 to W-290; S-154 to W-290; V-155 to W-290; N-156 to W-290; F-157 to W-290; T-158 to W-290; S-159 to W-290; P-160 to W-290; G-161 to W-290; C-162 to W-290; L-163 to W-290; D-164 to W-290; H-165 to W-290; I-166 to W-290; M-167 to W-290; K-168 to W-290; Y-169 to W-290; K-170 to W-290; K-171 to W-290; K-172 to W-290; C-173 to W-290; V-174 to W-290; K-175 to W-290; A-176 to W-290; G-177 to W-290; S-178 to W-290; L-179 to W-290; W-180 to W-290; D-181 to W-290; P-182 to W-290; N-183 to W-290; I-184 to W-290; T-185 to W-290; A-186 to W-290; C-187 to W-290; K-188 to W-290; K-189 to W-290; N-190 to W-290; E-191 to W-290; E-192 to W-290; T-193 to W-290; V-194 to W-290; E-195 to W-290; V-196 to W-290; N-197 to W-290; F-198 to W-290; T-199 to W-290; T-200 to W-290; T-201 to W-290; P-202 to W-290; L-203 to W-290; G-204 to W-290; N-205 to W-290; R-206 to W-290; Y-207 to W-290; M-208 to W-290; A-209 to W-290; L-210 to W-290; I-211 to W-290; Q-212 to W-290; H-213 to W-290; S-214 to W-290; T-215 to W-290; I-216 to W-290; I-217 to W-290; G-218 to W-290; F-219 to W-290; S-220 to W-290; Q-221 to W-290; V-222 to W-290; F-223 to W-290; E-224 to W-290; P-225 to W-290; H-226 to W-290; Q-227 to W-290; K-228 to W-290; K-229 to W-290; Q-230 to W-290; T-231 to W-290; R-232 to W-290; A-233 to W-290; S-234 to W-290; V-235 to W-290; V-236 to W-290; I-237 to W-290; P-238 to W-290; V-239 to W-290; T-240 to W-290; G-241 to W-290; D-242 to W-290; S-243 to W-290; E-244 to W-290; G-245 to W-290; A-246 to W-290; T-247 to W-290; V-248 to W-290; Q-249 to W-290; L-250 to W-290; T-251 to W-290; P-252 to W-290; Y-253 to W-290; F-254 to W-290; P-255 to W-290; T-256 to W-290; C-257 to W-290; G-258 to W-290; S-259 to W-290; D-260 to W-290; C-261 to W-290; I-262 to W-290; R-263 to W-290; H-264 to W-290; K-265 to W-290; G-266 to W-290; T-267 to W-290; V-268 to W-290; V-269 to W-290; L-270 to W-290; C-271 to W-290; P-272 to W-290; Q-273 to W-290; T-274 to W-290; G-275 to W-290; V-276 to W-290; P-277 to W-290; F-278 to W-290; P-279 to W-290; L-280 to W-290; D-281 to W-290; N-282 to W-290; N-283 to W-290; K-284 to W-290; and S-285 to W-290 of the IL17RLP amino acid sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 426 from the N-terminus to the C-terminus, while the amino acid residues in SEQ ID NO:2 are numbered consecutively from −19 through 407 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98%, 99% or 100% identical to the polynucleotide sequence encoding the IL17RLP polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, 99% or 100% identical to the amino acid sequence described above, and polynucleotides that encode such polypeptides.

Also as mentioned above, even if deletion of one or more amino acids from the C-terminus of the extracellular domain of an IL17RLP protein results in modification of loss of one or more biological functions of the protein, other biological activities may still be retained. Thus, the ability of the shortened extracellular domain of an IL17RLP mutein to induce and/or bind to antibodies which recognize the extracellular domain of an IL17RLP protein generally will be retained when less than the majority of the residues of the extracellular domain of an IL17RLP protein are removed from the C-terminus. Whether a particular polypeptide lacking C-terminal residues of a extracellular domain of an IL17RLP protein retains such immunologic activities can readily be determined by routine methods described herein and otherwise known in the art. It is not unlikely that an extracellular domain of an IL17RLP mutein with a large number of deleted C-terminal amino acid residues may retain some biological or immungenic activities. In fact, peptides composed of as few as six extracellular IL17RLP amino acid residues may often evoke an immune response.

Accordingly, the present invention further provides polypeptides having one or more residues deleted from the carboxy terminus of the amino acid sequence of the extracellular domain of the IL17RLP shown in SEQ ID NO:2, up to the leucine residue at position number 6, and polynucleotides encoding such polypeptides. In particular, the present invention provides polypeptides comprising, or alternatively consisting of, the amino acid sequence of residues 15-$m^3$ of SEQ ID NO:2, where $m^3$ is an integer in the range of 20 to 290, and 20 is the position of the first residue from the C-terminus of the extracellular domain IL17RLP polypeptide believed to be required for at least immunogenic activity of the IL17RLP protein. More in particular, the invention provides polynucleotides encoding polypeptides comprising, or alternatively consisting of, a member selected from the group consisting of the amino acid sequence of residues A-15 to W-290; A-15 to G-289; A-15 to G-288; A-15 to P-287; A-15 to K-286; A-15 to S-285; A-15 to K-284; A-15 to N-283; A-15 to N-282; A-15 to D-281; A-15 to L-280; A-15 to P-279; A-15 to F-278; A-15 to P-277; A-15 to V-276; A-15 to G-275; A-15 to T-274; A-15 to Q-273; A-15 to P-272; A-15 to C-271; A-15 to L-270; A-15 to V-269; A-15 to V-268; A-15 to T-267; A-15 to G-266; A-15 to K-265; A-15 to H-264; A-15 to R-263; A-15 to I-262; A-15 to C-261; A-15 to D-260; A-15 to S-259; A-15 to G-258; A-15 to C-257; A-15 to T-256; A-15 to P-255; A-15 to F-254; A-15 to Y-253; A-15 to P-252; A-15 to T-251; A-15 to L-250; A-15 to Q-249; A-15 to V-248; A-15 to T-247; A-15 to A-246; A-15 to G-245; A-15 to E-244; A-15 to S-243; A-15 to D-242; A-15 to G-241; A-15 to T-240; A-15 to V-239; A-15 to P-238; A-15 to I-237; A-15 to V-236; A-15 to V-235; A-15 to S-234; A-15 to A-233; A-15 to R-232; A-15 to T-231; A-15 to Q-230; A-15 to K-229; A-15 to K-228; A-15 to Q-227; A-15 to H-226; A-15 to P-225; A-15 to E-224; A-15 to F-223; A-15 to V-222; A-15 to Q-221; A-15 to S-220; A-15 to F-219; A-15 to G-218; A-15 to I-217; A-15 to I-216; A-15 to T-215; A-15 to S-214; A-15 to H-213; A-15 to Q-212; A-15 to I-211; A-15 to L-210; A-15 to A-209; A-15 to M-208; A-15 to Y-207; A-15 to R-206; A-15 to N-205; A-15 to G-204; A-15 to L-203; A-15 to P-202; A-15 to T-201; A-15 to T-200; A-15 to T-199; A-15 to F-198; A-15 to N-197; A-15 to V-196; A-15 to E-195; A-15 to V-194; A-15 to T-193; A-15 to E-192; A-15 to E-191; A-15 to N-190; A-15 to K-189; A-15 to K-188; A-15 to C-187; A-15 to A-186; A-15 to T-185; A-15 to I-184; A-15 to N-183; A-15 to P-182; A-15 to D-181; A-15 to W-180; A-15 to L-179; A-15 to S-178; A-15 to G-177; A-15 to A-176; A-15 to K-175; A-15 to V-174; A-15 to C-173; A-15 to K-172; A-15 to K-171; A-15 to K-170; A-15 to Y-169; A-15 to K-168; A-15 to A-1567; A-15 to I-166; A-15 to H-165; A-15 to D-164; A-15 to L-163; A-15 to C-162; A-15 to G-161; A-15 to P-160; A-15 to S-159; A-15 to T-158; A-15 to F-157; A-15 to N-156; A-15 to V-155; A-15 to S-154; A-15 to A-1553; A-15 to S-152; A-15 to P-151; A-15 to G-150; A-15 to D-149; A-15 to E-148; A-15 to N-147; A-15 to A-1546; A-15 to N-145; A-15 to A-144; A-15 to N-143; A-15 to P-142; A-15 to I-141; A-15 to N-140; A-15 to H-139; A-15 to A-138; A-15 to G-137; A-15 to I-136; A-15 to F-135; A-15 to Y-134; A-15 to V-133; A-15 to T-132; A-15 to N-131; A-15 to L-130; A-15 to E-129; A-15 to V-128; A-15 to P-127; A-15 to F-126; A-15 to G-125; A-15 to I-124; A-15 to Y-123; A-15 to S-122; A-15 to F-121; A-15 to T-120; A-15 to W-119; A-15 to K-118; A-15 to G-117; A-15 to G-116; A-15 to S-115; A-15 to P-114; A-15 to R-113; A-15 to T-112; A-15 to Q-111; A-15 to T-110; A-15 to Q-109; A-15 to F-108; A-15 to A-107; A-15 to E-106; A-15 to T-105; A-15 to Y-104; A-15 to N-103; A-15 to C-102; A-15 to R-101; A-15 to V-100; A-15 to C-99; A-15 to S-98; A-15 to Y-97; A-15 to S-96; A-15 to Q-95; A-15 to F-94; A-15 to N-93; A-15 to S-92; A-15 to K-91; A-15 to G-90; A-15 to T-89; A-15 to V-88; A-15 to C-87; A-15 to I-86; A-15 to K-85; A-15 to T-84; A-15 to A-83; A-15 to K-82; A-15 to L-81; A-15 to L-80; A-15 to R-79; A-15 to I-78; A-15 to S-77; A-15 to A-76; A-15 to D-75; A-15 to A-74; A-15 to R-73; A-15 to L-72; A-15 to V-71; A-15 to W-70; A-15 to S-69; A-15 to V-68; A-15 to N-67; A-15 to M-66; A-15 to L-65; A-15 to I-64; A-15 to S-63; A-15 to Y-62; A-15 to D-61; A-15 to G-60; A-15 to T-59; A-15 to A-58; A-15 to V-57; A-15 to S-56; A-15 to T-55; A-15 to T-54; A-15 to V-53; A-15 to P-52; A-15 to E-51; A-15 to V-50; A-15 to R-49; A-15 to L-48; A-15 to D-47; A-15 to R-46; A-15 to L-45; A-15 to D-44; A-15 to G-43; A-15 to P-42; A-15 to I-41; A-15 to L-40; A-15 to D-39; A-15 to H-38; A-15 to Q-37; A-15 to L-36; A-15 to M-35; A-15 to W-34; A-15 to E-33; A-15 to P-32; A-15 to S-31; A-15 to P-30; A-15 to G-29; A-15 to T-28; A-15 to E-27; A-15 to S-26; A-15 to G-25; A-15 to C-24; A-15 to Q-23; A-15 to V-22; A-15 to T-21; and A-15 to P-20 of the sequence of the IL17RLP sequence shown in FIGS. 1A, 1B, and 1C (which is identical to the sequence shown as SEQ ID NO:2, with the exception that the amino acid residues in FIGS. 1A, 1B, and 1C are numbered consecutively from 1 through 426 from the N-terminus to the C-terminus, while the amino acid residues in SEQ ID NO:2 are numbered consecutively from −19 through 407 to reflect the position of the predicted signal peptide). Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98%, 99% or 100% identical to the polynucleotide sequence encoding the IL17RLP polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, 99% or 100% identical to the amino acid sequence described above, and polynucleotides that encode such polypeptides.

The invention also provides polypeptides having one or more amino acids deleted from both the amino and the carboxyl termini of an extracellular domain of the IL17RLP polypeptide, which may be described generally as comprising, or alternatively consisting of, residues $n^3$-$m^3$ of FIGS. 1A, 1B, and 1C (SEQ ID NO:2), where $n^3$ and $m^3$ are integers as described above.

One specific embodiment of the present invention includes polypeptide fragments of the amino acid sequence set forth in SEQ ID NO:2 which may be used, for example, to generate monoclonal antibodies as described herein below. Particular examples of such polypeptides include polypeptides comprising, or alternatively consisting of, the amino acid sequences PREPTVQCGSETGPSPE (SEQ ID NO:14) (i.e., amino acid positions Pro-17 to Glu-33 of SEQ ID NO:2); LDHIMKYKKK (SEQ ID NO:15) (i.e., amino acid positions Leu-163 to Lys-173 of SEQ ID NO:2); and KKNEETVEVN (SEQ ID NO:16) (i.e., amino acid positions Lys-188 to Asn-197 of SEQ ID NO:2).

In addition to terminal deletion forms of the protein discussed above, it also will be recognized by one of ordinary skill in the art that some amino acid sequences of the IL17RLP polypeptide can be varied without significant effect of the structure or function of the protein. If such differences in sequence are contemplated, it should be remembered that there will be critical areas on the protein which determine activity.

Thus, the invention further includes variations of the IL17RLP polypeptide which show substantial IL17RLP polypeptide activity or which include regions of IL17RLP protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided wherein the authors indicate that there are two main approaches for studying the tolerance of an amino acid sequence to change (Bowie, J. U., et al., *Science* 247:1306-1310 (1990)). The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described by Bowie and coworkers (supra) and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the extracellular domain of the polypeptide is fused with another compound, such as a compound to increase the half-life of the polypeptide (for example, polyethylene glycol), or (v) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein.

Thus, the IL17RLP of the present invention may include one or more amino acid substitutions, deletions or additions, either from natural mutations or human manipulation. As indicated, changes are preferably of a minor nature, such as conservative amino acid substitutions that do not significantly affect the folding or activity of the protein (see Table II).

TABLE II

| Conservative Amino Acid Substitutions. | |
|---|---|
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |
| Small | Alanine |
|  | Serine |
|  | Threonine |
|  | Methionine |
|  | Glycine |

For example, site directed changes at the amino acid level of IL17RLP can be made by replacing a particular amino acid with a conservative amino acid. Preferred conservative mutations include: M1 replaced with A, G, I, L, S, T, or V; S2 replaced with A, G, I, L, T, M, or V; L3 replaced with A, G, I, S, T, M, or V; V4 replaced with A, G, I, L, S, T, or M; L5 replaced with A, G, I, S, T, M, or V; L6 replaced with A, G, I, S, T, M, or V; S7 replaced with A, G, I, L, T, M, or V; L8 replaced with A, G, I, S, T, M, or V; A9 replaced with G, I, L, S, T, M, or V; A10 replaced with G, I, L, S, T, M, or V; L11 replaced with A, G, I, S, T, M, or V; R13 replaced with H, or K; S14 replaced with A, G, I, L, T, M, or V; A15 replaced with G, I, L, S, T, M, or V; V16 replaced with A, G, I, L, S, T, or M; R18 replaced with H, or K; E19 replaced with D; T21 replaced with A, G, I, L, S, M, or V; V22 replaced with A, G, I, L, S, T, or M; Q23 replaced with N; G25 replaced with A, I, L, S, T, M, or V; S26 replaced with A, G, I, L, T, M, or V; E27 replaced with D; T28 replaced with A, G, I, L, S, M, or V; G29 replaced with A, I, L, S, T, M, or V; S31 replaced with A, G, I, L, T, M, or V; E33 replaced with D; W34 replaced with F, or Y; M35 replaced with A, G, I, L, S, T, or V; L36 replaced with A, G, I, S, T, M, or V; Q37 replaced with N; H38 replaced with K, or R; D39 replaced with E; L40 replaced with A, G, I, S, T, M, or V; I41 replaced with A, G, L, S, T, M, or V; G43 replaced with A, I, L, S, T, M, or V; D44 replaced with E; L45 replaced with A, G, I, S, T, M, or V; R46 replaced with H, or K; D47 replaced with E; L48 replaced with A, G, I, S, T, M, or V; R49 replaced with H, or K; V50 replaced with A, G, I, L, S, T, or M; E51 replaced with D; V53 replaced with A, G, I, L, S, T, or M; T54 replaced with A, G, I, L, S, M, or V; T55 replaced with A, G, I, L, S, M, or V; S56 replaced with A, G, I, L, T, M, or V; V57 replaced with A, G, I, L, S, T, or M; A58 replaced with G, I, L, S, T, M, or V; T59 replaced with A, G, I, L, S, M, or V; G60 replaced with A, I, L, S, T, M, or V; D61 replaced with E; Y62 replaced with F, or W; S63 replaced with A, G, I, L, T, M, or V; I64 replaced with A, G, L, S, T, M, or V; L65 replaced with A, G, I, S, T, M, or V; M66 replaced with A, G, I, L, S, T, or V; N67 replaced with Q; V68 replaced with A, G, I, L, S, T, or M; S69 replaced with A, G, I, L, T, M, or V; W70 replaced with F, or Y; V71 replaced with A, G, I, L, S, T, or M; L72 replaced with A, G, I, S, T, M, or V; R73 replaced with H, or K; A74 replaced with G, I, L, S, T, M, or V; D75 replaced with E; A76 replaced with G, I, L, S, T, M, or V; S77 replaced with A, G, I, L, T, M, or V; I78 replaced with A, G, L, S, T, M, or V; R79 replaced with H, or K; L80 replaced with A, G, I, S, T, M, or V; L81 replaced with A, G, I, S, T, M, or V; K82 replaced with H, or R; A83 replaced with G, I, L, S, T, M, or V; T84 replaced with A, G, I, L, S, M, or V; K85 replaced with H, or R; I86 replaced with A, G, L, S, T, M, or V; V88 replaced with A, G, I, L, S, T, or M; T89 replaced with A, G, I, L, S, M, or V; G90 replaced with A, I, L, S, T, M, or V; K91 replaced with H, or R; S92 replaced with A, G, I, L, T, M, or V; N93 replaced with Q; F94 replaced with W, or Y; Q95 replaced with N; S96 replaced with A, G, I, L, T, M, or V; Y97 replaced with F, or W; S98 replaced with A, G, I, L, T, M, or V; V100 replaced with A, G, I, L, S, T, or M; R101 replaced with H, or K; N103 replaced with Q; Y104 replaced with F, or W; T105 replaced with A, G, I, L, S, M, or V; E106 replaced with D; A107 replaced with G, I, L, S, T, M, or V; F108 replaced with W, or Y; Q109 replaced with N; T110 replaced with A, G, I, L, S, M, or V; Q111 replaced with N; T112 replaced with A, G, I, L, S, M, or V; R113 replaced with H, or K; S115 replaced with A, G, I, L, T, M, or V; G116 replaced with A, I, L, S, T, M, or V; G117 replaced with A, I, L, S, T, M, or V; K118 replaced with H, or R; W119 replaced with F, or Y; T120 replaced with A, G, I, L, S, M, or V; F121 replaced with W, or Y; S122 replaced with A, G, I, L, T, M, or V; Y123 replaced with F, or W; I124 replaced with A, G, L, S, T, M, or V; G125 replaced with A, I, L, S, T, M, or V; F126 replaced with W, or Y; V128 replaced with A, G, I, L, S, T, or M; E129 replaced with D; L130 replaced with A, G, I, S, T, M, or V; N131 replaced with Q; T132 replaced with A, G, I, L, S, M, or V; V133 replaced with A, G, I, L, S, T, or M; Y134 replaced with F, or W; F135 replaced with W, or Y; I136 replaced with A, G, L, S, T, M, or V; G137 replaced with A, I, L, S, T, M, or V; A138 replaced with G, I, L, S, T, M, or V; H139 replaced with K, or R; N140 replaced with Q; I141 replaced with A, G, L, S, T, M, or V; N143 replaced with Q; A144 replaced with G, I, L, S, T, M, or V; N145 replaced with Q; M146 replaced with A, G, I, L, S, T, or V; N147 replaced with Q; E148 replaced with D; D149 replaced with E; G150 replaced with A, I, L, S, T, M, or V; S152 replaced with A, G, I, L, T, M, or V; M153 replaced with A, G, I, L, S, T, or V; S154 replaced with A, G, I, L, T, M, or V; V155 replaced with A, G, I, L, S, T, or M; N156 replaced with Q; F157 replaced with W, or Y; T158 replaced with A, G, I, L, S, M, or V; S159 replaced with A, G, I, L, T, M, or V; G161 replaced with A, I, L, S, T, M, or V; L163 replaced with A, G, S, T, M, or V; D164 replaced with E; H165 replaced with K, or R; I166 replaced with A, G, L, S, T, M, or V; M167 replaced with A, G, I, L, S, T, or V; K168 replaced with H, or R; Y169 replaced with F, or W; K170 replaced with H, or R; K171 replaced with H, or R; K172 replaced with H, or R; V174 replaced with A, G, I, L, S, T, or M; K175 replaced with H, or R; A176 replaced with G, I, L, S, T, M, or V; G177 replaced with A, I, L, S, T, M, or V; S178 replaced with A, G, I, L, T, M, or V; L179 replaced with A, G, I, S, T, M, or V; W180 replaced with F, or Y; D181 replaced with E; N183 replaced with Q; I184 replaced with A, G, L, S, T, M, or V; T185 replaced with A, G, I, L, S, M, or V; A186 replaced with G, I, L, S, T, M, or V; K188 replaced with H, or R; K189 replaced with H, or R; N190 replaced with Q; E191 replaced with D; E192 replaced with D; T193 replaced with A, G, I, L, S, M, or V; V194 replaced with A, G, I, L, S, T, or M; E195 replaced with D; V196 replaced with A, G, I, L, S, T, or M;

N197 replaced with Q; F198 replaced with W, or Y; T199 replaced with A, G, I, L, S, M, or V; T200 replaced with A, G, I, L, S, M, or V; T201 replaced with A, G, I, L, S, M, or V; L203 replaced with A, G, I, S, T, M, or V; G204 replaced with A, I, L, S, T, M, or V; N$_{205}$ replaced with Q; R206 replaced with H, or K; Y207 replaced with F, or W; M208 replaced with A, G, I, L, S, T, or V; A209 replaced with G, I, L, S, T, M, or V; L210 replaced with A, G, I, S, T, M, or V; I211 replaced with A, G, L, S, T, M, or V; Q212 replaced with N; H213 replaced with K, or R; S214 replaced with A, G, I, L, T, M, or V; T215 replaced with A, G, I, L, S, M, or V; I216 replaced with A, G, L, S, T, M, or V; I217 replaced with A, G, L, S, T, M, or V; G218 replaced with A, I, L, S, T, M, or V; F219 replaced with W, or Y; S220 replaced with A, G, I, L, T, M, or V; Q221 replaced with N; V222 replaced with A, G, I, L, S, T, or M; F223 replaced with W, or Y; E224 replaced with D; H226 replaced with K, or R; Q227 replaced with N; K228 replaced with H, or R; K229 replaced with H, or R; Q230 replaced with N; T231 replaced with A, G, I, L, S, M, or V; R232 replaced with H, or K; A233 replaced with G, I, L, S, T, M, or V; S234 replaced with A, G, I, L, T, M, or V; V235 replaced with A, G, I, L, S, T, or M; V236 replaced with A, G, I, L, S, T, or M; I237 replaced with A, G, L, S, T, M, or V; V239 replaced with A, G, I, L, S, T, or M; T240 replaced with A, G, I, L, S, M, or V; G241 replaced with A, I, L, S, T, M, or V; D242 replaced with E; S243 replaced with A, G, I, L, T, M, or V; E244 replaced with D; G245 replaced with A, I, L, S, T, M, or V; A246 replaced with G, I, L, S, T, M, or V; T247 replaced with A, G, I, L, S, M, or V; V248 replaced with A, G, I, L, S, T, or M; Q249 replaced with N; L250 replaced with A, G, I, S, T, M, or V; T251 replaced with A, G, I, L, S, M, or V; Y253 replaced with F, or W; F254 replaced with W, or Y; T256 replaced with A, G, I, L, S, M, or V; G258 replaced with A, I, L, S, T, M, or V; S259 replaced with A, G, I, L, T, M, or V; D260 replaced with E; I262 replaced with A, G, L, S, T, M, or V; R263 replaced with H, or K; H264 replaced with K, or R; K265 replaced with H, or R; G266 replaced with A, I, L, S, T, M, or V; T267 replaced with A, G, I, L, S, M, or V; V268 replaced with A, G, I, L, S, T, or M; V269 replaced with A, G, I, L, S, T, or M; L270 replaced with A, G, I, S, T, M, or V; Q273 replaced with N; T274 replaced with A, G, L, S, M, or V; G275 replaced with A, I, L, S, T, M, or V; V276 replaced with A, G, I, L, S, T, or M; F278 replaced with W, or Y; L280 replaced with A, G, I, S, T, M, or V; D281 replaced with E; N282 replaced with Q; N283 replaced with Q; K284 replaced with H, or R; S285 replaced with A, G, I, L, T, M, or V; K286 replaced with H, or R; G288 replaced with A, I, L, S, T, M, or V; G289 replaced with A, I, L, S, T, M, or V; W290 replaced with F, or Y; L291 replaced with A, G, I, S, T, M, or V; L293 replaced with A, G, I, S, T, M, or V; L294 replaced with A, G, I, S, T, M, or V; L295 replaced with A, G, I, S, T, M, or V; L296 replaced with A, G, I, S, T, M, or V; S297 replaced with A, G, I, L, T, M, or V; L298 replaced with A, G, I, S, T, M, or V; L299 replaced with A, G, I, S, T, M, or V; V300 replaced with A, G, I, L, S, T, or M; A301 replaced with G, I, L, S, T, M, or V; T302 replaced with A, G, I, L, S, M, or V; W303 replaced with F, or Y; V304 replaced with A, G, I, L, S, T, or M; L305 replaced with A, G, I, S, T, M, or V; V306 replaced with A, G, L, S, T, or M; A307 replaced with G, I, L, S, T, M, or V; G308 replaced with A, I, L, S, T, M, or V; I309 replaced with A, G, L, S, T, M, or V; Y310 replaced with F, or W; L311 replaced with A, G, I, S, T, M, or V; M312 replaced with A, G, I, L, S, T, or V; W313 replaced with F, or Y; R314 replaced with H, or K; H315 replaced with K, or R; E316 replaced with D; R317 replaced with H, or K; I318 replaced with A, G, L, S, T, M, or V; K319 replaced with H, or R; K320 replaced with H, or R; T321 replaced with A, G, I, L, S, M, or V; S322 replaced with A, G, I, L, T, M, or V; F323 replaced with W, or Y; S324 replaced with A, G, I, L, T, M, or V; T325 replaced with A, G, I, L, S, M, or V; T326 replaced with A, G, I, L, S, M, or V; T327 replaced with A, G, I, L, S, M, or V; L328 replaced with A, G, I, S, T, M, or V; L329 replaced with A, G, I, S, T, M, or V; I332 replaced with A, G, L, S, T, M, or V; K333 replaced with H, or R; V334 replaced with A, G, I, L, S, T, or M; L335 replaced with A, G, I, S, T, M, or V; V336 replaced with A, G, I, L, S, T, or M; V337 replaced with A, G, I, L, S, T, or M; Y338 replaced with F, or W; S340 replaced with A, G, I, L, T, M, or V; E341 replaced with D; I342 replaced with A, G, L, S, T, M, or V; F344 replaced with W, or Y; H345 replaced with K, or R; H346 replaced with K, or R; T347 replaced with A, G, I, L, S, M, or V; I348 replaced with A, G, L, S, T, M, or V; Y350 replaced with F, or W; F351 replaced with W, or Y; T352 replaced with A, G, I, L, S, M, or V; E353 replaced with D; F354 replaced with W, or Y; L355 replaced with A, G, I, S, T, M, or V; Q356 replaced with N; N357 replaced with Q; H358 replaced with K, or R; R360 replaced with H, or K; S361 replaced with A, G, I, L, T, M, or V; E362 replaced with D; V363 replaced with A, G, I, L, S, T, or M; I364 replaced with A, G, L, S, T, M, or V; L365 replaced with A, G, I, S, T, M, or V; E366 replaced with D; K367 replaced with H, or R; W368 replaced with F, or Y; Q369 replaced with N; K370 replaced with H, or R; K371 replaced with H, or R; K372 replaced with H, or R; I373 replaced with A, G, L, S, T, M, or V; A374 replaced with G, I, L, S, T, M, or V; E375 replaced with D; M376 replaced with A, G, I, L, S, T, or V; G377 replaced with A, I, L, S, T, M, or V; V379 replaced with A, G, I, L, S, T, or M; Q380 replaced with N; W381 replaced with F, or Y; L382 replaced with A, G, I, S, T, M, or V; A383 replaced with G, I, L, S, T, M, or V; T384 replaced with A, G, I, L, S, M, or V; Q385 replaced with N; K386 replaced with H, or R; K387 replaced with H, or R; A388 replaced with G, I, L, S, T, M, or V; A389 replaced with G, I, L, S, T, M, or V; D390 replaced with E; K391 replaced with H, or R; V392 replaced with A, G, I, L, S, T, or M; V393 replaced with A, G, I, L, S, T, or M; F394 replaced with W, or Y; L395 replaced with A, G, I, S, T, M, or V; L396 replaced with A, G, I, S, T, M, or V; S397 replaced with A, G, I, L, T, M, or V; N398 replaced with Q; D399 replaced with E; V400 replaced with A, G, I, L, S, T, or M; N401 replaced with Q; S402 replaced with A, G, I, L, T, M, or V; V403 replaced with A, G, I, L, S, T, or M; D405 replaced with E; G406 replaced with A, I, L, S, T, M, or V; T407 replaced with A, G, I, L, S, M, or V; G409 replaced with A, I, L, S, T, M, or V; K410 replaced with H, or R; S411 replaced with A, G, I, L, T, M, or V; E412 replaced with D; G413 replaced with A, I, L, S, T, M, or V; S414 replaced with A, G, I, L, T, M, or V; S416 replaced with A, G, I, L, T, M, or V; E417 replaced with D; N418 replaced with Q; S419 replaced with A, G, I, L, T, M, or V; Q420 replaced with N; D421 replaced with E; S422 replaced with A, G, I, L, T, M, or V; S423 replaced with A, G, I, L, T, M, or V; and L426 replaced with A, G, I, S, T, M, or V in the amino acid sequence shown in SEQ ID NO:2.

The resulting constructs can be routinely screened for activities or functions described throughout the specification and known in the art. Preferably, the resulting constructs have an increased and/or a decreased IL17RLP activity or function, while the remaining IL17RLP activities or functions are maintained. More preferably, the resulting constructs have more than one increased and/or decreased IL17RLP activity or function, while the remaining IL17RLP activities or functions are maintained.

Besides conservative amino acid substitution, variants of IL17RLP include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, IL17RLP polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331-340 (1967); Robbins et al., Diabetes 36: 838-845 (1987); Cleland et al., Crit. Rev. Therapeutic Drug Carrier Systems 10:307-377 (1993).)

For example, preferred non-conservative substitutions of HA 7RLP include: M1 replaced with D, E, H, K, R, N, Q, F, W, Y, P, or C; S2 replaced with D, E, H, K, R, N, Q, F, W, Y, P, or C; L3 replaced with D, E, H, K, R, N, Q, F, W, Y, P, or C; V4 replaced with D, E, H, K, R, N, Q, F, W, Y, P, or C; L5 replaced with D, E, H, K, R, N, Q, F, W, Y, P, or C; L6 replaced with D, E, H, K, R, N, Q, F, W, Y, P, or C; S7 replaced with D, E, H, K, R, N, Q, F, W, Y, P, or C; L8 replaced with D, E, H, K, R, N, Q, F, W, Y, P, or C; A9 replaced with D, E, H, K, R, N, Q, F, W, Y, P, or C; A10 replaced with D, E, H, K, R, N, Q, F, W, Y, P, or C; L11 replaced with D, E, H, K, R, N, Q, F, W, Y, P, or C; C12 replaced with D, E, H, K, R, A, G, I, L, S, T, M, V, N, Q, F, W, Y, or P; R13 replaced with D, E, A, G, I, L, S, T, M, V, N, Q, F, W, Y, P, or C; S14 replaced with D, E, H, K, R, N, Q, F, W, Y, P, or C; A15 replaced with D, E, H, K, R, N, Q, F, W, Y, P, or C; V16 replaced with D, E, H, K, R, N, Q, F, W, Y, P, or C; P17 replaced with D, E, H, K, R, A, G, I, L, S, T, M, V, N, Q, F, W, Y, or C; R18 replaced with D, E, A, G, I, L, S, T, M, V, N, Q, F, W, Y, P, or C; E19 replaced with H, K, R, A, G, I, L, S, T, M, V, N, Q, F, W, Y, P, or C; P20 replaced with D, E, H, K, R, A, G, I, L, S, T, M, V, N, Q, F, W, Y, or C; T21 replaced with D, E, H, K, R, N, Q, F, W, Y, P, or C; V22 replaced with D, E, H, K, R, N, Q, F, W, Y, P, or C; Q23 replaced with D, E, H, K, R, A, G, I, L, S, T, M, V, F, W, Y, P, or C; C24 replaced with D, E, H, K, R, A, G, I, L, S, T, M, V, N, Q, F, W, Y, or P; G25 replaced with D, E, H, K, R, N, Q, F, W, Y, P, or C; S26 replaced with D, E, H, K, R, N, Q, F, W, Y, P, or C; E27 replaced with H, K, R, A, G, I, L, S, T, M, V, N, Q, F, W, Y, or C; T28 replaced with D, E, H, K, R, N, Q, F, W, Y, P, or C; G29 replaced with D, E, H, K, R, N, Q, F, W, Y, P, or C; P30 replaced with D, E, H, K, R, A, G, I, L, S, T, M, V, N, Q, F, W, Y, or C; S31 replaced with D, E, H, K, R, N, Q, F, W, Y, P, or C; P32 replaced with D, E, H, K, R, A, G, I, L, S, T, M, V, N, Q, F, W, Y, or C; E33 replaced with H, K, R, A, G, I, L, S, T, M, V, N, Q, F, W, Y, P, or C; W34 replaced with D, E, H, K, R, N, Q, A, G, I, L, S, T, M, V, P, or C; M35 replaced with D, E, H, K, R, N, Q, F, W, Y, P, or C; L36 replaced with D, E, H, K, R, N, Q, F, W, Y, P, or C; Q37 replaced with D, E, H, K, R, A, G, I, L, S, T, M, V, F, W, Y, P, or C; H38 replaced with D, E, A, G, I, L, S, T, M, V, N, Q, F, W, Y, P, or C; D39 replaced with H, K, R, A, G, I, L, S, T, M, V, N, Q, F, W, Y, P, or C; L40 replaced with D, E, H, K, R, N, Q, F, W, Y, P, or C; I41 replaced with D, E, H, K, R, N, Q, F, W, Y, P, or C; P42 replaced with D, E, H, K, R, A, G, I, L, S, T, M, V, N, Q, F, W, Y, or C; G43 replaced with D, E, H, K, R, N, Q, F, W, Y, P, or C; D44 replaced with H, K, R, A, G, I, L, S, T, M, V, N, Q, F, W, Y, P, or C; L45 replaced with D, E, H, K, R, N, Q, F, W, Y, P, or C; R46 replaced with D, E, A, G, I, L, S, T, M, V, N, Q, F, W, Y, P, or C; D47 replaced with H, K, R, A, G, I, L, S, T, M, V, N, Q, F, W, Y, P, or C; L48 replaced with D, E, H, K, R, N, Q, F, W, Y, P, or C; R49 replaced with D, E, A, G, I, L, S, T, M, V, N, Q, F, W, Y, P, or C; V50 replaced with D, E, H, K, R, N, Q, F, W, Y, P, or C; E51 replaced with H, K, R, A, G, I, L, S, T, M, V, N, Q, F, W, Y, P, or C; P52 replaced with D, E, H, K, R, A, G, I, L, S, T, M, V, N, Q, F, W, Y, or C; V53 replaced with D, E, H, K, R, N, Q, F, W, Y, P, or C; T54 replaced with D, E, H, K, R, N, Q, F, W, Y, P, or C; T55 replaced with D, E, H, K, R, N, Q, F, W, Y, P, or C; S56 replaced with D, E, H, K, R, N, Q, F, W, Y, P, or C; V57 replaced with D, E, H, K, R, N, Q, F, W, Y, P, or C; A58 replaced with D, E, H, K, R, N, Q, F, W, Y, P, or C; T59 replaced with D, E, H, K, R, N, Q, F, W, Y, P, or C; G60 replaced with D, E, H, K, R, N, Q, F, W, Y, P, or C; D61 replaced with H, K, R, A, G, I, L, S, T, M, V, N, Q, F, W, Y, P, or C; Y62 replaced with D, E, H, K, R, N, Q, A, G, I, L, S, T, M, V, P, or C; S63 replaced with D, E, H, K, R, N, Q, F, W, Y, P, or C; I64 replaced with D, E, H, K, R, N, Q, F, W, Y, P, or C; L65 replaced with D, E, H, K, R, N, Q, F, W, Y, P, or C; M66 replaced with D, E, H, K, R, N, Q, F, W, Y, P, or C; N67 replaced with D, E, H, K, R, A, G, I, L, S, T, M, V, F, W, Y, P, or C; V68 replaced with D, E, H, K, R, N, Q, F, W, Y, P, or C; S69 replaced with D, E, H, K, R, N, Q, F, W, Y, P, or C; W70 replaced with D, E, H, K, R, N, Q, A, G, I, L, S, T, M, V, P, or C; V71 replaced with D, E, H, K, R, N, Q, F, W, Y, P, or C; L72 replaced with D, E, H, K, R, N, Q, F, W, Y, P, or C; R73 replaced with D, E, A, G, I, L, S, T, M, V, N, Q, F, W, Y, P, or C; A74 replaced with D, E, H, K, R, N, Q, F, W, Y, P, or C; D75 replaced with H, K, R, A, G, I, L, S, T, M, V, N, Q, F, W, Y, P, or C; A76 replaced with D, E, H, K, R, N, Q, F, W, Y, P, or C; S77 replaced with D, E, H, K, R, N, Q, F, W, Y, P, or C; I78 replaced with D, E, H, K, R, N, Q, F, W, Y, P, or C; R79 replaced with D, E, A, G, I, L, S, T, M, V, N, Q, F, W, Y, P, or C; L80 replaced with D, E, H, K, R, N, Q, F, W, Y, P, or C; L81 replaced with D, E, H, K, R, N, Q, F, W, Y, P, or C; K82 replaced with D, E, A, G, I, L, S, T, M, V, N, Q, F, W, Y, P, or C; A83 replaced with D, E, H, K, R, N, Q, F, W, Y, P, or C; T84 replaced with D, E, H, K, R, N, Q, F, W, Y, P, or C; K85 replaced with D, E, A, G, I, L, S, T, M, V, N, Q, F, W, Y, P, or C; I86 replaced with D, E, H, K, R, N, Q, F, W, Y, P, or C; C87 replaced with D, E, H, K, R, A, G, I, L, S, T, M, V, N, Q, F, W, Y, or P; V88 replaced with D, E, H, K, R, N, Q, F, W, Y, P, or C; T89 replaced with D, E, H, K, R, N, Q, F, W, Y, P, or C; G90 replaced with D, E, H, K, R, N, Q, F, W, Y, P, or C; K91 replaced with D, E, A, G, I, L, S, T, M, V, N, Q, F, W, Y, P, or C; S92 replaced with D, E, H, K, R, N, Q, F, W, Y, P, or C; N93 replaced with D, E, H, K, R, A, G, I, L, S, T, M, V, F, W, Y, P, or C; F94 replaced with D, E, H, K, R, N, Q, A, G, I, L, S, T, M, V, P, or C; Q95 replaced with D, E, H, K, R, A, G, I, L, S, T, M, V, F, W, Y, P, or C; S96 replaced with D, E, H, K, R, N, Q, F, W, Y, P, or C; Y97 replaced with D, E, H, K, R, N, Q, A, G, I, L, S, T, M, V, P, or C; S98 replaced with D, E, H, K, R, N, Q, F, W, Y, P, or C; C99 replaced with D, E, H, K, R, A, G, I, L, S, T, M, V, N, Q, F, W, Y, or P; V100 replaced with D, E, H, K, R, N, Q, F, W, Y, P, or C; R101 replaced with D, E, A, G, I, L, S, T, M, V, N, Q, F, W, Y, P, or C; C102 replaced with D, E, H, K, R, A, G, I, L, S, T, M, V, N, Q, F, W, Y, or P; N103 replaced with D, E, H, K, R, A, G, I, L, S, T, M, V, F, W, Y, P, or C; Y104 replaced with D, E, H, K, R, N, Q, A, G, I, L, S, T, M, V, P, or C; T105 replaced with D, E, H, K, R, N, Q, F, W, Y, P, or C; E106 replaced with H, K, R, A, G, I, L, S, T, M, V, N, Q, F, W, Y, P, or C; A107 replaced with D, E, H, K, R, N, Q, F, W, Y, P, or C; F108 replaced with D, E, H, K, R, N, Q, A, G, I, L, S, T, M, V, P, or C; Q109 replaced with D, E, H, K, R, A, G, I, L, S, T, M, V, F, W, Y, P, or C; T110 replaced with D, E, H, K, R, N, Q, F, W, Y, P, or C; Q111 replaced with D, E, H, K, R, A, G, I, L, S, T, M, V, F, W, Y, P, or C; T112 replaced with D, E, H, K, R, N, Q, F, W, Y, P, or C; R113 replaced with D, E, A, G, I, L, S, T, M, V, N, Q, F, W, Y, P, or C; P114 replaced with D, E, H, K, R, A, G, I, L, S, T, M, V, N, Q, F, W, Y, or C; S115 replaced with D, E, H, K, R, N, Q, F, W, Y, P, or C; G116 replaced with D, E, H, K, R, N, Q, F, W, Y, P, or C; G117 replaced with D, E, H, K, R, N, Q, F, W, Y, P, or C; K118 replaced with D, E, A, G, I, L, S, T, M, V, N, Q, F, W, Y, P, or C; W119 replaced with D, E, H, K, R, N, Q, A, G, I, L, S, T, M, V, P, or C; T120 replaced with D, E, H, K, R, N, Q, F, W, Y, P, or C; F121 replaced with D, E, H, K, R, N, Q, A, G, I, L, S, T, M, V, P, or C; S122 replaced with D, E, H, K, R, N, Q, F, W, Y, P, or C; Y123 replaced with D, E, H, K, R, N, Q, A, G, I, L, S, T, M, V, P, or C; I124 replaced with D, E, H, K, R, N, Q, F, W, Y, P, or C; G125 replaced with D, E, H, K, R, N, Q, F, W, Y, P, or C; F126 replaced with D, E, H, K, R, N, Q, A, G, I, L, S, T, M, V, P, or C; P127 replaced with D, E, H, K, R, A, G, I, L, S, T, M, V, N, Q, F, W, Y, or C; V128 replaced with D, E, H, K, R, N, Q, F, W, Y, P, or C; E129 replaced with H, K, R, A, G, I, L, S, T, M, V, N, Q, F, W, Y, P, or C; L130 replaced with D, E, H, K, R, N, Q, F, W, Y, P, or C; N131 replaced with D, E, H, K, R, A, G, I, L, S, T, M, V, F, W, Y, P, or C; T132 replaced with D, E, H, K, R, N, Q, F, W, Y, P, or C; V133 replaced with D, E, H, K, R, N, Q, F, W, Y, P, or C; Y134 replaced with D, E, H, K, R, N, Q, A, G, I, L, S, T, M, V, P, or C; F135 replaced with D, E, H, K, R, N, Q, A, G, I, L, S, T, M, V, P, or C; I136 replaced with D, E, H, K, R, N, Q, F, W, Y, P, or C; G137 replaced with D, E, H, K, R, N, Q, F, W, Y, P, or C; A138 replaced with D, E, H, K, R, N, Q, F, W, Y, P, or C; H139 replaced with D, E, A, G, I, L, S, T, M, V, N, Q, F, W, Y, P, or C; N140 replaced with D, E, H, K, R, A, G, I, L, S, T, M, V, F, W, Y, P, or C; I141 replaced with D, E, H, K, R, N, Q, F, W, Y, P, or C; P142 replaced with D, E, H, K, R, A, G, I, L, S, T, M, V, N, Q, F, W, Y, or C; N143 replaced with D, E, H, K, R, A, G, I, L, S, T, M, V, F, W, Y, P, or C; A144 replaced with D, E, H, K, R, N, Q, F, W, Y, P, or C; N145 replaced with D, E, H, K, R, A, G, I, L, S, T, M, V, F, W, Y, P, or C; M146 replaced with D, E, H, K, R, N, Q, F, W, Y, P, or C; N147 replaced with D, E, H, K, R, A, G, I, L, S, T, M, V, F, W, Y, P, or C; E148 replaced with H, K, R, A, G, I, L, S, T, M, V, N, Q, F, W, Y, P, or C; D149 replaced with H, K, R, A, G, I, L, S, T, M, V, N, Q, F, W, Y, P, or C; G150 replaced with D, E, H, K, R, N, Q, F, W, Y, P, or C; P151 replaced with D, E, H, K, R, A, G, I, L, S, T, M, V, N, Q, F, W, Y, or C; 5152 replaced with D, E, H, K, R, N, Q, F, W, Y, P, or C; M153 replaced with D, E, H, K, R, N, Q, F, W, Y, P, or C; S154 replaced with D, E, H, K, R, N, Q, F, W, Y, P, or C; V155 replaced with D, E, H, K, R, N, Q, F, W, Y, P, or C; N156 replaced with D, E, H, K, R, A, G, I, L, S, T, M, V, F, W, Y, P, or C; F157 replaced with D, E, H, K, R, N, Q, A, G, I, L, S, T, M, V, P, or C; T158 replaced with D, E, H, K, R, N, Q, F, W, Y, P, or C; 5159 replaced with D, E, H, K, R, N, Q, F, W, Y, P, or C; P160 replaced with D, E, H, K, R, A, G, I, L, S, T, M, V, N, Q, F, W, Y, or C; G161 replaced with D, E, H, K, R, N, Q, F, W, Y, P, or C; C162 replaced with D, E, H, K, R, A, G, I, L, S, T, M, V, N, Q, F, W, Y, or P; L163 replaced with D, E, H, K, R, N, Q, F, W, Y, P, or C; D164 replaced with H, K, R, A, G, I, L, S, T, M, V, N, Q, F, W, Y, P, or C; H165 replaced with D, E, A, G, I, L, S, T, M, V, N, Q, F, W, Y, P, or C; I166 replaced with D, E, H, K, R, N, Q, F, W, Y, P, or C; M167 replaced with D, E, H, K, R, N, Q, F, W, Y, P, or C; K168 replaced with D, E, A, G, I, L, S, T, M, V, N, Q, F, W, Y, P, or C; Y169 replaced with D, E, H, K, R, N, Q, A, G, I, L, S, T, M, V, P, or C; K170 replaced with D, E, A, G, I, L, S, T, M, V, N, Q, F, W, Y, P, or C; K171 replaced with D, E, A, G, I, L, S, T, M, V, N, Q, F, W, Y, P, or C; K172 replaced with D, E, A, G, I, L, S, T, M, V, N, Q, F, W, Y, P, or C; C173 replaced with D, E, H, K, R, A, G, I, L, S, T, M, V, N, Q, F, W, Y, or P; V174 replaced with D, E, H, K, R, N, Q, F, W, Y, P, or C; K175 replaced with D, E, A, G, I, L, S, T, M, V, N, Q, F, W, Y, P, or C; A176 replaced with D, E, H, K, R, N, Q, F, W, Y, P, or C; G177 replaced with D, E, H, K, R, N, Q, F, W, Y, P, or C; S178 replaced with D, E, H, K, R, N, Q, F, W, Y, P, or C; L179 replaced with D, E, H, K, R, N, Q, F, W, Y, P, or C; W180 replaced with D, E, H, K, R, N, Q, A, G, I, L, S, T, M, V, P, or C; D181 replaced with H, K, R, A, G, I, L, S, T, M, V, N, Q, F, W, Y, P, or C; P182 replaced with D, E, H, K, R, A, G, I, L, S, T, M, V, N, Q, F, W, Y, or C; N183 replaced with D, E, H, K, R, A, G, I, L, S, T, M, V, F, W, Y, P, or C; I184 replaced with D, E, H, K, R, N, Q, F, W, Y, P, or C; T185 replaced with D, E, H, K, R, N, Q, F, W, Y, P, or C; A186 replaced with D, E, H, K, R, N, Q, F, W, Y, P, or C; C187 replaced with D, E, H, K, R, A, G, I, L, S, T, M, V, N, Q, F, W, Y, or P; K188 replaced with D, E, A, G, I, L, S, T, M, V, N, Q, F, W, Y, P, or C; K189 replaced with D, E, A, G, I, L, S, T, M, V, N, Q, F, W, Y, P, or C; N190 replaced with D, E, H, K, R, A, G, I, L, S, T, M, V, F, W, Y, P, or C; E191 replaced with H, K, R, A, G, I, L, S, T, M, V, N, Q, F, W, Y, P, or C; E192 replaced with H, K, R, A, G, I, L, S, T, M, V, N, Q, F, W, Y, P, or C; T193 replaced with D, E, H, K, R, N, Q, F, W, Y, P, or C; V194 replaced with D, E, H, K, R, N, Q, F, W, Y, P, or C; E195 replaced with H, K, R, A, G, I, L, S, T, M, V, N, Q, F, W, Y, P, or C; V196 replaced with D, E, H, K, R, N, Q, F, W, Y, P, or C; N197 replaced with D, E, H, K, R, A, G, I, L, S, T, M, V, F, W, Y, P, or C; F198 replaced with D, E, H, K, R, N, Q, A, G, I, L, S, T, M, V, P, or C; T199 replaced with D, E, H, K, R, N, Q, F, W, Y, P, or C; T200 replaced with D, E, H, K, R, N, Q, F, W, Y, P, or C; T201 replaced with D, E, H, K, R, N, Q, F, W, Y, P, or C; P202 replaced with D, E, H, K, R, A, G, I, L, S, T, M, V, N, Q, F, W, Y, or C; L203 replaced with D, E, H, K, R, N, Q, F, W, Y, P, or C; G204 replaced with D, E, H, K, R, N, Q, F, W, Y, P, or C; $N_2O_5$ replaced with D, E, H, K, R, A, G, I, L, S, T, M, V, F, W, Y, P, or C; R206 replaced with D, E, A, G, I, L, S, T, M, V, N, Q, F, W, Y, P, or C; Y207 replaced with D, E, H, K, R, N, Q, A, G, I, L, S, T, M, V, P, or C; M208 replaced with D, E, H, K, R, N, Q, F, W, Y, P, or C; A209 replaced with D, E, H, K, R, N, Q, F, W, Y, P, or C; L210 replaced with D, E, H, K, R, N, Q, F, W, Y, P, or C; I211 replaced with D, E, H, K, R, N, Q, F, W, Y, P, or C; Q212 replaced with D, E, H, K, R, A, G, I, L, S, T, M, V, F, W, Y, P, or C; H213 replaced with D, E, A, G, I, L, S, T, M, V, N, Q, F, W, Y, P, or C; S214 replaced with D, E, H, K, R, N, Q, F, W, Y, P, or C; T215 replaced with D, E, H, K, R, N, Q, F, W, Y, P, or C; 1216 replaced with D, E, H, K, R, N, Q, F, W, Y, P, or C; I217 replaced with D, E, H, K, R, N, Q, F, W, Y, P, or C; G218 replaced with D, E, H, K, R, N, Q, F, W, Y, P, or C; F219 replaced with D, E, H, K, R, N, Q, A, G, I, L, S, T, M, V, P, or C; 5220 replaced with D, E, H, K, R, N, Q, F, W, Y, P, or C; Q221 replaced with D, E, H, K, R, A, G, I, L, S, T, M, V, F, W, Y, P, or C; V222 replaced with D, E, H, K, R, N, Q, F, W, Y, P, or C; F223 replaced with D, E, H, K, R, N, Q, A, G, I, L, S, T, M, V, P, or C; E224 replaced with H, K, R, A, G, I, L, S, T, M, V, N, Q, F, W, Y, P, or C; P225 replaced with D, E, H, K, R, A, G, I, L, S, T, M, V, N, Q, F, W, Y, or C; H226 replaced with D, E, A, G, I, L, S, T, M, V, N, Q, F, W, Y, P, or C; Q227 replaced with D, E, H, K, R, A, G, I, L, S, T, M, V, F, W, Y, P, or C; K228 replaced with D, E, A, G, I, L, S, T, M, V, N, Q, F, W, Y, P, or C; K229 replaced with D, E, A, G, I, L, S, T, M, V, N, Q, F, W, Y, P, or C; Q230 replaced with D, E, H, K, R, A, G, I, L, S, T, M, V, F, W, Y, P, or C; T231 replaced with D, E, H, K, R, N, Q, F, W, Y, P, or C; R232 replaced with D, E, A, G, I, L, S, T, M, V, N, Q, F, W, Y, P, or C; A233 replaced with D, E, H, K, R, N, Q, F, W, Y, P, or C; S234 replaced with D, E, H, K, R, N, Q, F, W, Y, P, or C; V235 replaced with D, E, H, K, R, N, Q, F, W, Y, P, or C; V236 replaced with D, E, H, K, R, N, Q, F, W, Y, P, or C; 1237 replaced with D, E, H, K, R, N, Q, F, W, Y, P, or C; P238 replaced with D, E, H, K, R, A, G, I, L, S, T, M, V, N, Q, F, W, Y, or C; V239 replaced with D, E, H, K, R, N, Q, F, W, Y, P, or C; T240 replaced with D, E, H, K, R, N, Q, F, W, Y, P, or C; G241 replaced with D, E, H, K, R, N, Q, F, W, Y, P, or C; D242 replaced with H, K, R, A, G, I, L, S, T, M, V, N, Q, F, W, Y, P, or C; S243 replaced with D, E, H, K, R, N, Q, F, W, Y, P, or C; E244 replaced with H, K, R, A, G, I, L, S, T, M, V, N, Q, F, W, Y, P, or C; G245 replaced with D, E, H, K, R, N, Q, F, W, Y, P, or C; A246 replaced with D, E, H, K, R, N, Q, F, W, Y, P, or C; T247 replaced with D, E, H, K, R, N, Q, F, W, Y, P, or C; V248 replaced with D, E, H, K, R, N, Q, F, W, Y, P, or C; Q249 replaced with D, E, H, K, R, A, G, I, L, S, T, M, V, F, W, Y, P, or C; L250 replaced with D, E, H, K, R, N, Q, F, W, Y, P, or C; T251 replaced with D, E, H, K, R, N, Q, F, W, Y, P, or C; P252 replaced with D, E, H, K, R, A, G, I, L, S, T, M, V, N, Q, F, W, Y, or C; Y253 replaced with D, E, H, K, R, N, Q, A, G, I, L, S, T, M, V, P, or C; F254 replaced with D, E, H, K, R, N, Q, A, G, I, L, S, T, M, V, P, or C; P255 replaced with D, E, H, K, R, A, G, I, L, S, T, M, V, N, Q, F, W, Y, or C; T256 replaced with D, E, H, K, R, N, Q, F, W, Y, P, or C; C257 replaced with D, E, H, K, R, A, G, I, L, S, T, M, V, N, Q, F, W, Y, or P; G258 replaced with D, E, H, K, R, N, Q, F, W, Y, P, or C; S259 replaced with D, E, H, K, R, N, Q, F, W, Y, P, or C; D260 replaced with H, K, R, A, G, I, L, S, T, M, V, N, Q, F, W, Y, P, or C; C261 replaced with D, E, H, K, R, A, G, I, L, S, T, M, V, N, Q, F, W, Y, or P; 1262 replaced with D, E, H, K, R, N, Q, F, W, Y, P, or C; R263 replaced with D, E, A, G, I, L, S, T, M, V, N, Q, F, W, Y, P, or C; H264 replaced with D, E, A, G, I, L, S, T, M, V, N, Q, F, W, Y, P, or C; K265 replaced with D, E, A, G, I, L, S, T, M, V, N, Q, F, W, Y, P, or C; G266 replaced with D, E, H, K, R, N, Q, F, W, Y, P, or C; T267 replaced with D, E, H, K, R, N, Q, F, W, Y, P, or C; V268 replaced with D, E, H, K, R, N, Q, F, W, Y, P, or C; V269 replaced with D, E, H, K, R, N, Q, F, W, Y, P, or C; L270 replaced with D, E, H, K, R, N, Q, F, W, Y, P, or C; C271 replaced with D, E, H, K, R, A, G, I, L, S, T, M, V, N, Q, F, W, Y, or P; P272 replaced with D, E, H, K, R, A, G, I, L, S, T, M, V, N, Q, F, W, Y, or C; Q273 replaced with D, E, H, K, R, A, G, I, L, S, T, M, V, F, W, Y, P, or C; T274 replaced with D, E, H, K, R, N, Q, F, W, Y, P, or C; G275 replaced with D, E, H, K, R, N, Q, F, W, Y, P, or C; V276 replaced with D, E, H, K, R, N, Q, F, W, Y, P, or C; P277 replaced with D, E, H, K, R, A, G, I, L, S, T, M, V, N, Q, F, W, Y, or C; F278 replaced with D, E, H, K, R, N, Q, A, G, I, L, S, T, M, V, P, or C; P279 replaced with D, E, H, K, R, A, G, I, L, S, T, M, V, N, Q, F, W, Y, or C; L280 replaced with D, E, H, K, R, N, Q, F, W, Y, P, or C; D281 replaced with H, K, R, A, G, I, L, S, T, M, V, N, Q, F, W, Y, P, or C; N282 replaced with D, E, H, K, R, A, G, I, L, S, T, M, V, F, W, Y, P, or C; N283 replaced with D, E, H, K, R, A, G, I, L, S, T, M, V, F, W, Y, P, or C; K284 replaced with D, E, A, G, I, L, S, T, M, V, N, Q, F, W, Y, P, or C; 5285 replaced with D, E, H, K, R, N, Q, F, W, Y, P, or C; K286 replaced with D, E, A, G, I, L, S, T, M, V, N, Q, F, W, Y, P, or C; P287 replaced with D, E, H, K, R, A, G, I, L, S, T, M, V, N, Q, F, W, Y, or C; G288 replaced with D, E, H, K, R, N, Q, F, W, Y, P, or C; G289 replaced with D, E, H, K, R, N, Q, F, W, Y, P, or C; W290 replaced with D, E, H, K, R, N, Q, A, G, I, L, S, T, M, V, P, or C; L291 replaced with D, E, H, K, R, N, Q, F, W, Y, P, or C; P292 replaced with D, E, H, K, R, A, G, I, L, S, T, M, V, N, Q, F, W, Y, or C; L293 replaced with D, E, H, K, R, N, Q, F, W, Y, P, or C; L294 replaced with D, E, H, K, R, N, Q, F, W, Y, P, or C; L295 replaced with D, E, H, K, R, N, Q, F, W, Y, P, or C; L296 replaced with D, E, H, K, R, N, Q, F, W, Y, P, or C; S297 replaced with D, E, H, K, R, N, Q, F, W, Y, P, or C; L298 replaced with D, E, H, K, R, N, Q, F, W, Y, P, or C; L299 replaced with D, E, H, K, R, N, Q, F, W, Y, P, or C; V300 replaced with D, E, H, K, R, N, Q, F, W, Y, P, or C; A301 replaced with D, E, H, K, R, N, Q, F, W, Y, P, or C; T302 replaced with D, E, H, K, R, N, Q, F, W, Y, P, or C; W303 replaced with D, E, H, K, R, N, Q, A, G, I, L, S, T, M, V, P, or C; V304 replaced with D, E, H, K, R, N, Q, F, W, Y, P, or C; L305 replaced with D, E, H, K, R, N, Q, F, W, Y, P, or C; V306 replaced with D, E, H, K, R, N, Q, F, W, Y, P, or C; A307 replaced with D, E, H, K, R, N, Q, F, W, Y, P, or C; G308 replaced with D, E, H, K, R, N, Q, F, W, Y, P, or C; 1309 replaced with D, E, H, K, R, N, Q, F, W, Y, P, or C; Y310 replaced with D, E, H, K, R, N, Q, A, G, I, L, S, T, M, V, P, or C; L311 replaced with D, E, H, K, R, N, Q, F, W, Y, P, or C; M312 replaced with D, E, H, K, R, N, Q, F, W, Y, P, or C; W313 replaced with D, E, H, K, R, N, Q, A, G, I, L, S, T, M, V, P, or C; R314 replaced with D, E, A, G, I, L, S, T, M, V, N, Q, F, W, Y, P, or C; H315 replaced with D, E, A, G, I, L, S, T, M, V, N, Q, F, W, Y, P, or C; E316 replaced with H, K, R, A, G, I, L, S, T, M, V, N, Q, F, W, Y, P, or C; R317 replaced with D, E, A, G, I, L, S, T, M, V, N, Q, F, W, Y, P, or C; 1318 replaced with D, E, H, K, R, N, Q, F, W, Y, P, or C; K319 replaced with D, E, A, G, I, L, S, T, M, V, N, Q, F, W, Y, P, or C; K320 replaced with D, E, A, G, I, L, S, T, M, V, N, Q, F, W, Y, P, or C; T321 replaced with D, E, H, K, R, N, Q, F, W, Y, P, or C; S322 replaced with D, E, H, K, R, N, Q, F, W, Y, P, or C; F323 replaced with D, E, H, K, R, N, Q, A, G, I, L, S, T, M, V, P, or C; S324 replaced with D, E, H, K, R, N, Q, F, W, Y, P, or C; T325 replaced with D, E, H, K, R, N, Q, F, W, Y, P, or C; T326 replaced with D, E, H, K, R, N, Q, F, W, Y, P, or C; T327 replaced with D, E, H, K, R, N, Q, F, W, Y, P, or C; L328 replaced with D, E, H, K, R, N, Q, F, W, Y, P, or C; L329 replaced with D, E, H, K, R, N, Q, F, W, Y, P, or C; P330 replaced with D, E, H, K, R, A, G, I, L, S, T, M, V, N, Q, F, W, Y, or C; P331 replaced with D, E, H, K, R, A, G, I, L, S, T, M, V, N, Q, F, W, Y, or C; 1332 replaced with D, E, H, K, R, N, Q, F, W, Y, P, or C; K333 replaced with D, E, A, G, I, L, S, T, M, V, N, Q, F, W, Y, or C; V334 replaced with D, E, H, K, R, N, Q, F, W, Y, P, or C; L335 replaced with D, E, H, K, R, N, Q, F, W, Y, P, or C; V336 replaced with D, E, H, K, R, N, Q, F, W, Y, P, or C; V337 replaced with D, E, H, K, R, N, Q, F, W, Y, P, or C; Y338 replaced with D, E, H, K, R, N, Q, A, G, I, L, S, T, M, V, P, or C; P339 replaced with D, E, H, K, R, A, G, I, L, S, T, M, V, N, Q, F, W, Y, or C; S340 replaced with D, E, H, K, R, N, Q, F, W, Y, P, or C; E341 replaced with H, K, R, A, G, I, L, S, T, M, V, N, Q, F, W, Y, P, or C; I342 replaced with D, E, H, K, R, N, Q, F, W, Y, P, or C; C343 replaced with D, E, H, K, R, A, G, I, L, S, T, M, V, N, Q, F, W, Y, or P; F344 replaced with D, E, H, K, R, N, Q, A, G, I, L, S, T, M, V, P, or C; H345 replaced with D, E, A, G, I, L, S, T, M, V, N, Q, F, W, Y, P, or C; H346 replaced with D, E, A, G, I, L, S, T, M, V, N, Q, F, W, Y, P, or C; T347 replaced with D, E, H, K, R, N, Q, F, W, Y, P, or C; I348 replaced with D, E, H, K, R, N, Q, F, W, Y, P, or C; C349 replaced with D, E, H, K, R, A, G, I, L, S, T, M, V, N, Q, F, W, Y, or P; Y350 replaced with D, E, H, K, R, N, Q, A, G, I, L, S, T, M, V, P, or C; F351 replaced with D, E, H, K, R, N, Q, A, G, I, L, S, T, M, V, P, or C; T352 replaced with D, E, H, K, R, N, Q, F, W, Y, P, or C; E353 replaced with H, K, R, A, G, I, L, S, T, M, V, N, Q, F, W, Y, P, or C; F354 replaced with D, E, H, K, R, N, Q, A, G, I, L, S, T, M, V, P, or C; L355 replaced with D, E, H, K, R, N, Q, F, W, Y, P, or C; Q356 replaced with D, E, H, K, R, A, G, I, L, S, T, M, V, F, W, Y, P, or C; N357 replaced with D, E, H, K, R, A, G, I, L, S, T, M, V, F, W, Y, P, or C; H358 replaced with D, E, A, G, I, L, S, T, M, V, N, Q, F, W, Y, P, or C; C359 replaced with D, E, H, K, R, A, G, I, L, S, T, M, V, N, Q, F, W, Y, or P; R360 replaced with D, E, A, G, I, L, S, T, M, V, N, Q, F, W, Y, P, or C; 5361 replaced with D, E, H, K, R, N, Q, F, W, Y, P, or C; E362 replaced with H, K, R, A, G, I, L, S, T, M, V, N, Q, F, W, Y, P, or C; V363 replaced with D, E, H, K, R, N, Q, F, W, Y, P, or C; I364 replaced with D, E, H, K, R, N, Q, F, W, Y, P, or C; L365 replaced with D, E, H, K, R, N, Q, F, W, Y, P, or C; E366 replaced with H, K, R, A, G, I, L, S, T, M, V, N, Q, F, W, Y, P, or C; K367 replaced with D, E, A, G, I, L, S, T, M, V, N, Q, F, W, Y, P, or C; W368 replaced with D, E, H, K, R, N, Q, A, G, I, L, S, T, M, V, P, or C; Q369 replaced with D, E, H, K, R, A, G, I, L, S, T, M, V, F, W, Y, P, or C; K370 replaced with D, E, A, G, I, L, S, T, M, V, N, Q, F, W, Y, P, or C; K371 replaced with D, E, A, G, I, L, S, T, M, V, N, Q, F, W, Y, P, or C; K372 replaced with D, E, A, G, I, L, S, T, M, V, N, Q, F, W, Y, P, or C; I373 replaced with D, E, H, K, R, N, Q, F, W, Y, P, or C; A374 replaced with D, E, H, K, R, N, Q, F, W, Y, P, or C; E375 replaced with H, K, R, A, G, I, L, S, T, M, V, N, Q, F, W, Y, P, or C; M376 replaced with D, E, H, K, R, N, Q, F, W, Y, P, or C; G377 replaced with D, E, H, K, R, N, Q, F, W, Y, P, or C; P378 replaced with D, E, H, K, R, A, G, I, L, S, T, M, V, N, Q, F, W, Y, or C; V379 replaced with D, E, H, K, R, N, Q, F, W, Y, P, or C; Q380 replaced with D, E, H, K, R, A, G, I, L, S, T, M, V, F, W, Y, P, or C; W381 replaced with D, E, H, K, R, N, Q, A, G, I, L, S, T, M, V, P, or C; L382 replaced with D, E, H, K, R, N, Q, F, W, Y, P, or C; A383 replaced with D, E, H, K, R, N, Q, F, W, Y, P, or C; T384 replaced with D, E, H, K, R, N, Q, F, W, Y, P, or C; Q385 replaced with D, E, H, K, R, A, G, I, L, S, T, M, V, F, W, Y, P, or C; K386 replaced with D, E, A, G, I, L, S, T, M, V, N, Q, F, W, Y, P, or C; K387 replaced with D, E, A, G, I, L, S, T, M, V, N, Q, F, W, Y, P, or C; A388 replaced with D, E, H, K, R, N, Q, F, W, Y, P, or C; A389 replaced with D, E, H, K, R, N, Q, F, W, Y, P, or C; D390 replaced with H, K, R, A, G, I, L, S, T, M, V, N, Q, F, W, Y, P, or C; K391 replaced with D, E, A, G, I, L, S, T, M, V, N, Q, F, W, Y, P, or C; V392 replaced with D, E, H, K, R, N, Q, F, W, Y, P, or C; V393 replaced with D, E, H, K, R, N, Q, F, W, Y, P, or C; F394 replaced with D, E, H, K, R, N, Q, A, G, I, L, S, T, M, V, P, or C; L395 replaced with D, E, H, K, R, N, Q, F, W, Y, P, or C; L396 replaced with D, E, H, K, R, N, Q, F, W, Y, P, or C; S397 replaced with D, E, H, K, R, N, Q, F, W, Y, P, or C; N398 replaced with D, E, H, K, R, A, G, I, L, S, T, M, V, F, W, Y, P, or C; D399 replaced with H, K, R, A, G, I, L, S, T, M, V, N, Q, F, W, Y, P, or C; V400 replaced with D, E, H, K, R, N, Q, F, W, Y, P, or C; N401 replaced with D, E, H, K, R, A, G, I, L, S, T, M, V, F, W, Y, P, or C; S402 replaced with D, E, H, K, R, N, Q, F, W, Y, P, or C; V403 replaced with D, E, H, K, R, N, Q, F, W, Y, P, or C; C404 replaced with D, E, H, K, R, A, G, I, L, S, T, M, V, N, Q, F, W, Y, or P; D405 replaced with H, K, R, A, G, I, L, S, T, M, V, N, Q, F, W, Y, P, or C; G406 replaced with D, E, H, K, R, N, Q, F, W, Y, P, or C; T407 replaced with D, E, H, K, R, N, Q, F, W, Y, P, or C; C408 replaced with D, E, H, K, R, A, G, I, L, S, T, M, V, N, Q, F, W, Y, or P; G409 replaced with D, E, H, K, R, N, Q, F, W, Y, P, or C; K410 replaced with D, E, A, G, I, L, S, T, M, V, N, Q, F, W, Y, P, or C; S411 replaced with D, E, H, K, R, N, Q, F, W, Y, P, or C; E412 replaced with H, K, R, A, G, I, L, S, T, M, V, N, Q, F, W, Y, P, or C; G413 replaced with D, E, H, K, R, N, Q, F, W, Y, P, or C; S414 replaced with D, E, H, K, R, N, Q, F, W, Y, P, or C; P415 replaced with D, E, H, K, R, A, G, I, L, S, T, M, V, N, Q, F, W, Y, or C; S416 replaced with D, E, H, K, R, N, Q, F, W, Y, P, or C; E417 replaced with H, K, R, A, G, I, L, S, T, M, V, N, Q, F, W, Y, P, or C; N418 replaced with D, E, H, K, R, A, G, I, L, S, T, M, V, F, W, Y, P, or C; S419 replaced with D, E, H, K, R, N, Q, F, W, Y, P, or C; Q420 replaced with D, E, H, K, R, A, G, I, L, S, T, M, V, F, W, Y, P, or C; D421 replaced with H, K, R, A, G, I, L, S, T, M, V, N, Q, F, W, Y, P, or C; S422 replaced with D, E, H, K, R, N, Q, F, W, Y, P, or C; S423 replaced with D, E, H, K, R, N, Q, F, W, Y, P, or C; P424 replaced with D, E, H, K, R, A, G, I, L, S, T, M, V, N, Q, F, W, Y, or C; C425 replaced with D, E, H, K, R, A, G, I, L, S, T, M, V, N, Q, F, W, Y, or P; and L426 replaced with D, E, H, K, R, N, Q, F, W, Y, P, or C in the amino acid sequence shown in SEQ ID NO:2.

The resulting constructs can be routinely screened for activities or functions described throughout the specification and known in the art. Preferably, the resulting constructs have an increased and/or decreased IL17RLP activity or function, while the remaining IL17RLP activities or functions are maintained. More preferably, the resulting constructs have more than one increased and/or decreased IL17RLP activity or function, while the remaining IL17RLP activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, or proprotein form of IL17RLP protein, as well as the N- and C-terminal deletion mutants, having the general formula n-m, listed above (e.g., $n^1$-$m^1$, $n^1$-$m^2$, $n^1$-$m^3$, $n^2$-$m^1$, $n^2$-$m^2$, $n^2$-$m^3$, $n^3$-$m^1$, $n^3$-$m^2$, and/or $n^3$-$m^3$).

Embodiments of the invention are directed to polypeptides which comprise the amino acid sequence of an IL17RLP polypeptide described herein, but having an amino acid sequence which contains at least one conservative amino acid substitution, but not more than 50 conservative amino acid substitutions, even more preferably, not more than 40 conservative amino acid substitutions, still more preferably, not more than 30 conservative amino acid substitutions, and still more even more preferably, not more than 20 conservative amino acid substitutions, when compared with the follistatin-3 polynucleotide sequence described herein. Of course, in order of ever-increasing preference, it is highly preferable for a peptide or polypeptide to have an amino acid sequence which comprises the amino acid sequence of an IL17RLP polypeptide, which contains at least one, but not more than 20, 10, 9, 8, 7, 6, 5, 4, 3, 2 or 1 conservative amino acid substitutions.

In further specific embodiments, the number of substitutions, additions or deletions in the amino acid sequence of FIGS. 1A, 1B, and 1C (SEQ ID NO:2), a polypeptide sequence encoded by the deposited clones, and/or any of the polypeptide fragments described herein is 150, 100, 75, 70, 60, 50, 40, 35, 30, 25, 20, 15, 10, 9, 8, 7, 6, 5, 4, 3, 2, 1 or 250-150, 200-50, 150-50, 100-50, 50-20, 30-20, 20-15, 20-10, 15-10, 10-1, 5-10, 1-5, 1-3 or 1-2.

To improve or alter the characteristics of IL17RLP polypeptides, protein engineering may be employed. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Thus, the invention also encompasses IL17RLP derivatives and analogs that have one or more amino acid residues deleted, added, or substituted to generate IL17RLP polypeptides that are better suited for expression, scale up, etc., in the host cells chosen. For example, cysteine residues can be deleted or substituted with another amino acid residue in order to eliminate disulfide bridges, PKC phosphorylation sites, CK2 phosphorylation sites, cAMP- and cGMP-dependent protein kinase phosphorylation sites, myristolation, and/or N-linked glycosylation sites can be altered or eliminated to achieve an altered function or expression pattern of the polypeptide (for example, a mutated N-linked glycosylation site may alter the expression of a homogeneous product that is more easily recovered and purified from yeast hosts which are known to hyperglycosylate N-linked sites). To this end, a variety of amino acid substitutions at one or both of the first or third amino acid positions on any one or more of the disulfide bridge cysteines, PKC phosphorylation sites, CK2 phosphorylation sites, cAMP- and cGMP-dependent protein kinase phosphorylation sites, myristolation, and/or glycosylation recognition sequences in the IL17RLP polypeptides of the invention, and/or an amino acid deletion at the second position of any one or more such recognition sequences will alter function or expression or prevent glycosylation of the IL17RLP polypeptide at the modified tripeptide sequence (see, e.g., Miyajima, A., et al., *EMBO J.* 5(6):1193-1197 (1986)).

Amino acids in the IL17RLP protein of the present invention that are essential for function can be identified by methods known in the art, such as site-directed mutagenesis or alanine-scanning mutagenesis (Cunningham and Wells, *Science* 244:1081-1085 (1989)). The latter procedure introduces single alanine mutations at every residue in the molecule. The resulting mutant molecules are then tested for biological activity such as receptor binding or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard, et al., *Clin. Exp. Immunol.* 2:331-340 (1967); Robbins, et al., *Diabetes* 36:838-845 (1987); Cleland, et al., *Crit. Rev. Therapeutic Drug Carrier Systems* 10:307-377 (1993)).

Replacement of amino acids can also change the selectivity of the binding of a ligand to cell surface receptors (for example, Ostade, et al., *Nature* 361:266-268 (1993)) describes certain mutations resulting in selective binding of TNF-alpha to only one of the two known types of TNF receptors. Sites that are critical for ligand-receptor binding can also be determined by structural analysis such as crystallization, nuclear magnetic resonance or photoaffinity labeling (Smith, et al., *J. Mol. Biol.* 224:899-904 (1992); de Vos, et al. *Science* 255:306-312 (1992)).

Since IL17RLP is a homologue of the murine IL-17 receptor protein, to modulate rather than completely eliminate biological activities of IL17RLP preferably mutations are made in sequences encoding amino acids in the IL17RLP conserved extracellular domain, i.e., in positions I-271 of SEQ ID NO:2, more preferably in residues within this region which are not conserved in the murine IL-17 receptor protein. Also forming part of the present invention are isolated polynucleotides comprising nucleic acid sequences which encode the above IL17RLP mutants.

Amino acid regions of the IL17RLP sequence shown in SEQ ID NO:2 which are highly conserved when compared to the murine IL-17R polypeptide sequence shown as SEQ ID NO:3 (see FIG. 2) are attractive regions for targeted mutagenesis of the IL17RLP polypeptides of the invention. In fact, a number of conserved regions or domains have been set forth in FIGS. 1A, 1B, and 1C (labeled as Domains I-VIII). These domains are as follows: Domain I (i.e., Val-49 through Leu-62 of SEQ ID NO:2 (Val-68 through Leu-81 of FIGS. 1A, 1B, and 1C)); Domain II (Cys-154 through Thr-166 of SEQ ID NO:2 (i.e., Cys-173 through Thr-185 of FIGS. 1A, 1B, and 1C)); Domain III (Gln-202 through Gln-208 of SEQ ID NO:2 (i.e., Gln-221 through Gln-227 of FIGS. 1A, 1B, and 1C)); Domain IV (Asp-241 through Val-249 of SEQ ID NO:2 (i.e., Asp-260 through Val-268 of FIGS. 1A, 1B, and 1C)); Domain V (Thr-255 through Leu-261 of SEQ ID NO:2 (i.e., Thr-274 through Leu-280 of FIGS. 1A, 1B, and 1C)); Domain VI (Leu-310 through Tyr-319 of SEQ ID NO:2 (i.e., Leu-329 through Tyr-338 of FIGS. 1A, 1B, and 1C)); Domain VII (Cys-340 through Leu-346 of SEQ ID NO:2 (i.e., Cys-359 through Leu-365 of FIGS. 1A, 1B, and 1C)); and Domain VIII (Ile-354 through Gly-358 of SEQ ID NO:2 (i.e., Ile-373 through Gly-377 of FIGS. 1A, 1B, and 1C)).

In another embodiment of the invention, seven cysteine residues of IL17RLP are conserved with respect to the murine IL-17R polypeptide sequence shown in SEQ ID NO:3. Cysteine residues tend to play an important role in the structural conformation, and thus, the function of a polypeptide. As such, the seven conserved cysteine residues are also attractive residues for targeted mutagenesis of the IL17RLP polypeptides of the invention. The seven highly conserved cysteine residues of the IL17RLP shown in SEQ ID NO:2 of the present invention are as follows: Cys-5, Cys-80, Cys-143, Cys-154, Cys-238, Cys-242, and Cys-340 of SEQ ID NO:2 (which correspond exactly to Cys-24, Cys-99, Cys-162, Cys-173, Cys-257, Cys-261, and Cys-359 of FIGS. 1A, 1B, and 1C).

Thus, a polynucleotide encoding a polypeptide comprising, or alternatively consisting of, a member selected from the group consisting of amino acid residues Cys-5 to Cys-340, Cys-80 to Cys-340, Cys-143 to Cys-340, Cys-154 to Cys-340, Cys-238 to Cys-340, Cys-242 to Cys-340, Cys-5 to Cys-242, Cys-80 to Cys-242, Cys-143 to Cys-242, Cys-154 to Cys-242, Cys-238 to Cys-242, Cys-5 to Cys-238, Cys-80 to Cys-238, Cys-143 to Cys-238, Cys-154 to Cys-238, Cys-5 to Cys-154, Cys-80 to Cys-154, Cys-143 to Cys-154, Cys-5 to Cys-143, Cys-80 to Cys-143, and Cys-5 to Cys-80 of the IL17RLP amino acid sequence shown as SEQ ID NO:2 is a preferred polynucleotide fragment of the present invention. Polypeptides encoded by these polynucleotides are also encompassed by the invention. The present invention is also directed to nucleic acid molecules comprising, or alternatively, consisting of, a polynucleotide sequence at least 80%, 85%, 90%, 92%, 95%, 96%, 97%, 98%, 99% or 100% identical to the polynucleotide sequence encoding the IL17RLP polypeptides described above. The present invention also encompasses the above polynucleotide sequences fused to a heterologous polynucleotide sequence. Polypeptides encoded by these nucleic acids and/or polynucleotide sequences are also encompassed by the invention, as are polypeptides comprising, or alternatively consisting of, an amino acid sequence at least 80%, 85%, 90%, 92%, 95%, 96%, 97%, 98%, 99% or 100% identical to the amino acid sequence described above, and polynucleotides that encode such polypeptides.

The polypeptides of the present invention are preferably provided in an isolated form, and preferably are substantially purified. A recombinantly produced version of the IL17RLP polypeptide can be substantially purified by the one-step method described by Smith and Johnson (*Gene* 67:31-40 (1988)). Polypeptides of the invention also can be purified from natural or recombinant sources using anti-IL17RLP antibodies of the invention in methods which are well known in the art of protein purification.

The invention further provides an isolated IL17RLP polypeptide comprising, or alternatively consisting of, an amino acid sequence selected from the group consisting of: (a) the amino acid sequence of the full-length IL17RLP polypeptide having the complete amino acid sequence shown in SEQ ID NO:2 (i.e., positions −19 to 407 of SEQ ID NO:2); (b) the amino acid sequence of the full-length IL17RLP polypeptide having the complete amino acid sequence shown in SEQ ID NO:2 excepting the N-terminal methionine (i.e., positions −18 to 407 of SEQ ID NO:2); (c) the amino acid sequence of the mature IL17RLP polypeptide having the complete amino acid sequence shown in SEQ ID NO:2 (i.e., positions 1 to 407 of SEQ ID NO:2); (d) the amino acid sequence of the predicted extracellular domain of the IL17RLP polypeptide having the complete amino acid sequence shown in SEQ ID NO:2 (i.e., positions 1 to 271 of SEQ ID NO:2); (e) the amino acid sequence of a soluble IL17RLP polypeptide having the predicted extracellular and intracellular domains, but lacking the predicted transmembrane domain; (f) the complete amino acid sequence encoded by the human cDNA contained in the ATCC™ Deposit No. 209198; (g) the complete amino acid sequence excepting the N-terminal methionine encoded by the human cDNA contained in the ATCC™ Deposit No. 209198; (h) the complete amino acid sequence of the mature IL17RLP encoded by the human cDNA contained in the ATCC™ Deposit No. 209198, and; (i) the complete amino acid sequence of the extracellular domain of the IL17RLP encoded by the human cDNA contained in the ATCC™ Deposit No. 209198. The polypeptides of the present invention also include polypeptides having an amino acid sequence at least 80% identical, more preferably at least 90% identical, and still more preferably 95%, 96%, 97%, 98%, 99%, or 100% identical to those described in (a), (b), (c), (d), (e), (f), (g), (h) or (i) above, as well as polypeptides having an amino acid sequence with at least 90% similarity, and more preferably at least 95% similarity, to those above.

Further polypeptides of the present invention include polypeptides which have at least 90% similarity, more preferably at least 95% similarity, and still more preferably at least 96%, 97%, 98%, 99% or 100% similarity to those described above. The polypeptides of the invention also comprise those which are at least 80% identical, more preferably at least 90% or 95% identical, still more preferably at least 96%, 97%, 98%, 99% or 100% identical to the polypeptide encoded by the deposited cDNA or to the polypeptide of SEQ ID NO:2, and also include portions of such polypeptides with at least 25 amino acids, at least 30 amino acids, at least 35 amino acids, at least 40 amino acids, at least 45 amino acids, and more preferably at least 50 amino acids, at least 55 amino acids, at least 60 amino acids, at least 65 amino acids, at least 70 amino acids, at least 75 amino acids, at least 80 amino acids, at least 85 amino acids, at least 90 amino acids, at least 95 amino acids, and at least 100 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482-489, 1981) to find the best segment of similarity between two sequences.

By a polypeptide having an amino acid sequence at least, for example, 95% "identical" to a reference amino acid sequence of a IL17RLP polypeptide is intended that the amino acid sequence of the polypeptide is identical to the reference sequence except that the polypeptide sequence may include up to five amino acid alterations per each 100 amino acids of the reference amino acid of the IL17RLP polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98%, 99% or 100% identical to, for instance, the amino acid sequence shown in FIGS. 1A, 1B, and 1C (SEQ ID NO:2), the amino acid sequence encoded by deposited cDNA clone HAPOR40, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The present application is also directed to proteins containing polypeptides at least 80%, 85%, 90%, 92%, 95%, 96%, 97%, 98%, 99% or 100% identical to the IL17RLP polypeptide sequence set forth herein as $n^1$-$m^1$, $n^2$-$m^2$, and/or $n^3$-$m^3$. In preferred embodiments, the application is directed to proteins comprising, or alternatively consisting of, polypeptides at least 80%, 85%, 90%, 92%, 95%, 96%, 97%, 98%, 99% or 100% identical to polypeptides having the amino acid sequence of the specific IL17RLP N- and C-terminal deletions recited herein. Polynucleotides encoding these polypeptides are also encompassed by the invention. The present invention also encompasses the above polypeptide sequences fused to a heterologous polypeptide sequence. Polynucleotides encoding these amino acid sequences are also encompassed by the invention.

The invention also encompasses fusion proteins in which the full-length IL17RLP polypeptide or fragment, variant, derivative, or analog thereof is fused or joined to an unrelated protein. These fusion proteins can be routinely designed on the basis of the IL17RLP nucleotide and polypeptide sequences disclosed herein. For example, as one of skill in the art will appreciate, IL17RLP polypeptides and fragments (including epitope-bearing fragments) thereof described herein can be combined with parts of the constant domain of immunoglobulins (IgG), resulting in chimeric (fusion) polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84-86 (1988)). Fusion proteins that have a disulfide-linked dimeric structure due to the IgG part can also be more efficient in binding and neutralizing other molecules than the monomeric IL17RLP polypeptide or polypeptide fragments alone (Fountoulakis, et al., *J. Biochem.* 270:3958-3964 (1995)). Examples of IL17RLP fusion proteins that are encompassed by the invention include, but are not limited to, fusion of the IL17RLP polypeptide sequences to any amino acid sequence that allows the fusion proteins to be displayed on the cell surface (e.g. the IgG Fc domain); or fusions to an enzyme, fluorescent protein, or luminescent protein which provides a marker function.

As described in detail below, the polypeptides of the present invention can also be used to raise polyclonal and monoclonal antibodies, which are useful in assays for detecting IL17RLP protein expression as described below or as agonists and antagonists capable of enhancing or inhibiting IL17RLP protein function. Further, such polypeptides can be used in the yeast two-hybrid system to "capture" IL17RLP protein binding proteins which are also candidate agonists and antagonists according to the present invention. The yeast two hybrid system is described by Fields and Song (Nature 340:245-246 (1989)).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes (see, for instance, Geysen, et al., *Proc. Natl. Acad. Sci. USA* 81:3998-4002 (1983)).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, for instance, Sutcliffe, J. G., et al., *Science* 219:660-666 (1983)). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention (see, for instance, Wilson, et al., *Cell* 37:767-778 (1984)).

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate IL17RLP-specific antibodies include: a polypeptide comprising, or alternatively consisting of, amino acid residues from about Ser-14 to about Val-22 in SEQ ID NO:2, a polypeptide comprising, or alternatively consisting of, amino acid residues from about Cys-24 to about Pro-32 in SEQ ID NO:2, a polypeptide comprising, or alternatively consisting of, amino acid residues from about Ile-41 to about Arg-49 in SEQ ID NO:2, a polypeptide comprising, or alternatively consisting of, amino acid residues from about Thr-89 to about Val-97 in SEQ ID NO:2, a polypeptide comprising, or alternatively consisting of, amino acid residues from about Thr-110 to about Lys-118 in SEQ ID NO:2, a polypeptide comprising, or alternatively consisting of, amino acid residues from about Ala-144 to about Ser-152 in SEQ ID NO:2, a polypeptide comprising, or alternatively consisting of, amino acid residues from about Thr-240 to about Val-248 in SEQ ID NO:2, a polypeptide comprising, or alternatively consisting of, amino acid residues from about Gly-258 to about Thr-267 in SEQ ID NO:2, a polypeptide comprising, or alternatively consisting of, amino acid residues from about Leu-280 to about Gly-288 in SEQ ID NO:2, a polypeptide comprising, or alternatively consisting of, amino acid residues from about Cys-404 to about Glu-412 in SEQ ID NO:2, a polypeptide comprising, or alternatively consisting of, amino acid residues from about Pro-415 to about Ser-423 in SEQ ID NO:2, a polypeptide comprising, or alternatively consisting of, amino acid residues from about Gly-409 to about Glu-417 in SEQ ID NO:2, and a polypeptide comprising, or alternatively consisting of, amino acid residues from about Cys-404 to about Leu-426 in FIGS. 1A, 1B, and 1C (which is identical to the sequence shown in SEQ ID NO:2 with the exception of the numbering scheme as detailed above). These polypeptide fragments have been determined to bear antigenic epitopes of the IL17RLP protein by the analysis of the Jameson-Wolf antigenic index, as shown in FIG. 3, above.

The epitope-bearing peptides and polypeptides of the invention may be produced by any conventional means (see, for example, Houghten, R. A., et al., *Proc. Natl. Acad. Sci. USA* 82:5131-5135 (1985); and U.S. Pat. No. 4,631,211 to Houghten, et al., (1986)).

Epitope-bearing peptides and polypeptides of the invention are used to induce antibodies according to methods well known in the art (see, for instance, Sutcliffe, et al., supra; Wilson, et al., supra; Chow, M, et al., *Proc. Natl. Acad. Sci. USA* 82:910-914; and Bittle, F. J., et al., *J. Gen. Virol.* 66:2347-2354 (1985)). Immunogenic epitope-bearing peptides of the invention, i.e., those parts of a protein that elicit an antibody response when the whole protein is the immunogen, are identified according to methods known in the art (see, for instance, Geysen, et al., supra). Further still, U.S. Pat. No. 5,194,392, issued to Geysen, describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092, issued to Geysen, describes a method of detecting or determining a sequence of monomers which is a topographical equivalent of a ligand which is complementary to the ligand binding site of a particular receptor of interest. Similarly, U.S. Pat. No. 5,480,971, issued to Houghten and colleagues, on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

As one of skill in the art will appreciate, IL17RLP polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EP A 394,827; Traunecker, et al., *Nature* 331:84-86 (1988)). Fusion proteins that have a disulfide-linked dimeric structure due to the IgG part can also be more efficient in binding and neutralizing other molecules than the monomeric IL17RLP protein or protein fragment alone (Fountoulakis, et al., *J. Biochem.* 270:3958-3964 (1995)).

The techniques of gene-shuffling, motif-shuffling, exon-shuffling, and/or codon-shuffling (collectively referred to as "DNA shuffling") may be employed to modulate the activities of IL17RLP thereby effectively generating agonists and antagonists of IL17RLP. See generally, U.S. Pat. Nos. 5,605,793, 5,811,238, 5,830,721, 5,834,252, and 5,837,458, and Patten, P. A., et al., *Curr. Opinion Biotechnol.* 8:724-33 (1997); Harayama, S. *Trends Biotechnol.* 16(2):76-82 (1998); Hansson, L. O., et al., *J. Mol. Biol.* 287:265-76 (1999); and Lorenzo, M. M. and Blasco, R. *Biotechniques* 24(2):308-13 (1998) (each of these patents and publications are hereby incorporated by reference). In one embodiment, alteration of IL17RLP polynucleotides and corresponding polypeptides may be achieved by DNA shuffling. DNA shuffling involves the assembly of two or more DNA segments into a desired IL17RLP molecule by homologous, or site-specific, recombination. In another embodiment, IL17RLP polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of IL17RLP may be recombined with one or more components, motifs, sections, parts, domains, fragments, etc. of one or more heterologous molecules. In preferred embodiments, the heterologous molecule is the IL-17 receptor.

In further preferred embodiments, IL17RLP polynucleotides of the invention are fused to a polynucleotide encoding a "FLAG" polypeptide. Thus, an IL17RLP-FLAG fusion protein is encompassed by the present invention. The FLAG antigenic polypeptide may be fused to an IL17RLP polypeptide of the invention at either or both the amino or the carboxy terminus. In preferred embodiments, an IL17RLP-FLAG fusion protein is expressed from a pFLAG-CMV-5a or a pFLAG-CMV-1 expression vector (available from SIGMA™, St. Louis, Mo., USA). See, Andersson, S., et al., *J. Biol. Chem.* 264:8222-29 (1989); Thomsen, D. R., et al., *Proc. Natl. Acad. Sci. USA,* 81:659-63 (1984); and Kozak, M., *Nature* 308:241 (1984) (each of which is hereby incorporated by reference). In further preferred embodiments, an IL17RLP-FLAG fusion protein is detectable by anti-FLAG monoclonal antibodies (also available from SIGMA™).

The functional activity of IL17RLP polypeptides, and fragments, variants derivatives, and analogs thereof, can be assayed by various methods.

For example, in one embodiment where one is assaying for the ability to bind or compete with full-length IL17RLP polypeptide for binding to an anti-IL17RLP antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where an IL17RLP ligand is identified (e.g. IL-20), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, *Microbiol. Rev.* 59:94-123. In another embodiment, physiological correlates of IL17RLP binding to its substrates (signal transduction) can be assayed.

In addition, assays described herein (see Examples 5-8 and otherwise known in the art may routinely be applied to measure the ability of IL17RLP polypeptides and fragments, variants derivatives and analogs thereof to elicit IL17RLP related biological activity (e.g., to act as an attractant for neutrophils in vitro or in vivo).

Other methods will be known to the skilled artisan and are within the scope of the invention.

The invention further provides for the proteins containing, or alternatively comprising, or alternatively consisting of, polypeptide sequences encoded by the polynucleotides of the invention.

The IL17RLP proteins, or fragments thereof, of the invention may be in monomers or multimers (i.e., dimers, trimers, tetramers, and higher multimers). Accordingly, the present invention relates to monomers and multimers of the IL17RLP proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only IL17RLP proteins of the invention (including IL17RLP fragments, variants, and fusion proteins, as described herein). These homomers may contain IL17RLP proteins having identical or different polypeptide sequences. In a specific embodiment, a homomer of the invention is a multimer containing only IL17RLP proteins having an identical polypeptide sequence. In another specific embodiment, a homomer of the invention is a multimer containing IL17RLP proteins having different polypeptide sequences. In specific embodiments, the multimer of the invention is a homodimer (e.g., containing IL17RLP proteins having identical or different polypeptide sequences) or a homotrimer (e.g., containing IL17RLP proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the IL17RLP gene) in addition to the IL17RLP proteins of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the IL17RLP proteins of the invention. Such covalent associations may involve one or more amino acid residues contained in the polypeptide sequence of the polypeptide sequence recited in SEQ ID NO:2 and contained in the polypeptide encoded by the cDNA clone contained in ATCC™ Deposit No. 209198. In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in an IL17RLP fusion protein. In one example, covalent associations are between the heterologous sequence contained in a fusion protein of the invention (see, e.g., U.S. Pat. No. 5,478,925). In a specific example, the covalent associations are between the heterologous sequence contained in an IL17RLP-Fc fusion protein of the invention (as described herein).

In another embodiment, the IL17RLP polypeptides of the present invention and the epitope-bearing fragments thereof are fused with a heterologous antigen (e.g., polypeptide, carbohydrate, phospholipid, or nucleic acid).

In specific embodiments, the heterologous antigen is an immunogen. In a more specific embodiment, the heterologous antigen is the gp120 protein of HIV, or a fragment thereof. Polynucleotides encoding these polypeptides are also encompassed by the invention.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In addition, proteins of the invention can be chemically synthesized using techniques known in the art (e.g., see Creighton, 1983, Proteins: Structures and Molecular Principles, W.H. Freeman & Co., N.Y., and Hunkapiller, M., et al., Nature 310:105-111 (1984)). For example, a peptide corresponding to a fragment of the IL17RLP polypeptides of the invention can be synthesized by use of a peptide synthesizer. Furthermore, if desired, nonclassical amino acids or chemical amino acid analogs can be introduced as a substitution or addition into the IL17RLP polypeptide sequence. Non-classical amino acids include, but are not limited to, to the D-isomers of the common amino acids, 2,4-diaminobutyric acid, α-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention additionally, encompasses IL17RLP polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH$_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of IL17RLP which may provide additional advantages such as increased solubility, stability and circulating time of the polypeptide, or decreased immunogenicity (see U.S. Pat. No. 4,179,337). The chemical moieties for deriviti- zation may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10:638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado of al., *Crit. Rev. Thera. Drug Carrier Sys.* 9:249-304 (1992).

The proteins of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., *Proc. Natl. Acad. Sci.*, USA 82:6148-6152 (1985)), blastocysts or embryos; gene targeting in embryonic stem cells (Thompson et al., *Cell* 56:313-321 (1989)); electroporation of cells or embryos (Lo, Mol. Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103-106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of IL17RLP polypeptides, studying conditions and/or disorders associated with aberrant IL17RLP expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$M, $10^{-2}$M, $5\times10^{-3}$M, $10^{-3}$M, $5\times10^{-4}$M, $10^{-4}$M, $5\times10^{-5}$M, $10^{-5}$M, $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

The invention also provides antibodies that competitively inhibit the binding of a monoclonal antibody to a polypeptide of the invention, preferably the polypeptide of SEQ ID NO:2. Competitive inhibition can be determined by any method known in the art, for example, using the competitive binding assays described herein. In preferred embodiments, the antibody competitively inhibits the binding of a monoclonal antibody of the invention by at least 90%, at least 80%, at least 70%, at least 60%, or at least 50% to the polypeptide of SEQ ID NO:2.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex. Also included are receptor-specific antibodies that do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6): 1981-1988 (1998); Chen, et al., Cancer Res. 58(16):3668-3678 (1998); Harrop et al., J. Immunol. 161(4):1786-1794 (1998); Zhu et al., Cancer Res. 58(15):3209-3214 (1998); Yoon, et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272 (17):11295-11301 (1997); Taryman et al., Neuron 14(4):755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well-known in the art and are discussed in detail in Example 10. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC™. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment, diagnosis, and/or detection of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as ABGENIX™, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The term "bind(ing) of a polypeptide of the invention to a ligand" includes, but is not limited to, the binding of a ligand polypeptide of the present invention to a receptor, the binding of a receptor polypeptide of the present invention to a ligand; the binding of an antibody of the present invention to an antigen or epitope; the binding of an antigen or epitope of the present invention to an antibody; the binding of an antibody of the present invention to an anti-idiotypic antibody; the binding of an anti-idiotypic antibody of the present invention to a ligand; the biding of an anti-idiotypic antibody of the present invention to a receptor; the binding of an anti-anti-idiotypic antibody of the present invention to a ligand, receptor or antibody, etc.

As another example, antibodies which bind to and competitively activate the polypeptide of the invention or its ligand can be used to generate anti-idiotypic antibodies that mimic the polypeptide binding domain and/or activation domain and, as a consequence, bind to and activate the polypeptide and/or its ligand. Such activating anti-idiotypes or Fab fragments of such anti-idiotypes can be used in therapeutic regimens to activate polypeptide ligand. For example, such anti-idiotypic antibodies can be used to bind a polypeptide of the invention to thereby activate its biological activity and/or bind a ligand/receptor of the polypeptide of the invention to thereby activate its biological activity.

Polynucleotides Encoding Antibodies.

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2 or SEQ ID NO:18.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions. In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, Proc. Natl. Acad. Sci. 81:851-855; Neuberger et al., 1984, Nature 312: 604-608; Takeda et al., 1985, Nature 314:452-454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334: 544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-215); and hygro, which confers resistance to hygromycin (Santerre et al., 1984, Gene 30:147). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention (e.g., those comprising an immunogenic or antigenic epitope) fused or conjugated to heterologous polypeptide sequences (e.g., antibody domains other than the variable regions). For example, the polypeptides of the present invention may be fused or conjugated to an antibody Fc region, or portion thereof. For example, polypeptides of the present invention (including fragments or variants thereof), may be fused with the constant domain of immunoglobulins (IgA, IgE, IgG, IgM), or portions thereof (CH1, CH2, CH3, or any combination thereof and portions thereof, resulting in chimeric polypeptides. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341 (1992) (said references incorporated by reference in their entireties). By way of another non-limiting example, polypeptides and/or antibodies of the present invention (including fragments or variants thereof) may be fused with albumin (including but not limited to recombinant human serum albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)). In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. In another preferred embodiment, polypeptides and/or antibodies of the present invention (including fragments or variants thereof) are fused with polypeptide fragments comprising, or alternatively consisting of, amino acid residues 1-z of human serum albumin, where z is an integer from 369 to 419, as described in U.S. Pat. No. 5,766,883 herein incorporated by reference in its entirety. Polypeptides and/or antibodies of the present invention (including fragments or variants thereof) may be fused to either the N- or C-terminal end of the heterologous protein (e.g., immunoglobulin Fc polypeptide or human serum albumin polypeptide). Polynucleotides encoding fusion proteins of the invention are also encompassed by the invention.

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (See, e.g., EP 394,827; Traunecker et al., Nature 331:84-86 (1988)). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232, 262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52-58 (1995); K. Johanson et al., J. Biol. Chem. 270:9459-9471 (1995) 0.

Moreover, the polypeptides of the invention (e.g., antibodies or fragments thereof) can be fused to marker sequences, such as a peptide to facilitates their purification. In a further embodiment, nucleic acids encoding the polypeptides of the invention (including, but not limited to nucleic acids encoding immunogenic and/or antigenic epitopes) can also be recombined with a gene of interest as an epitope tag (e.g., the hemagglutinin tag ("HA") or flag tag) to aid in detection and purification of the expressed polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment, diagnosis, detection, and/or prevention regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$TC.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al.

(eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as REM buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treatment, diagnosis, detection, and/or prevention of one or more of the described disorders. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein). The antibodies of the invention can be used to treat, diagnose, detect, prevent, and/or inhibit diseases and disorders associated with aberrant expression and/or activity of a polypeptide of the invention, including, for example, but not limited to, osteoporosis, disorders in cartilage production and/or maintenance, arthritis (e.g., rheumatoid arthritis, and osteoarthritis); regeneration of dentin or bone lost due to periodontal disease; neurodegenerative diseases; and autoimmune diseases and/or disorders (e.g., systemic erythromatosus lupus). The treatment, diagnosis, detection, and/or prevention of diseases and disorders associated with aberrant expression and/or activity of a polypeptide of the invention includes, but is not limited to, alleviating symptoms associated with those diseases and disorders. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, diagnose, detect, prevent, and/or inhibit a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932-8935; Zijlstra et al., 1989, Nature 342:435-438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, DUPONT™), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, viral vectors that contains nucleic acid sequences encoding an antibody of the invention are used. For example, a retroviral vector can be used (see Miller et al., 1993, Meth. Enzymol. 217:581-599). These retroviral vectors have been deleted of retroviral sequences that are not necessary for packaging of the viral genome and integration into host cell DNA. The nucleic acid sequences encoding the antibody to be used in gene therapy are then cloned into one or more vectors, that facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang, et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598, dated Apr. 28, 1994; Stemple and Anderson, 1992, Cell 71:973-985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, diagnosis, detection, prevention, inhibition, and/or prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (1990, Science 249:1527-1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, DUPONT™), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, diagnosis, detection, inhibition, and/or prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

Antibodies of the present invention may be radiolabeled to be employed in radioimmunotherapy. Antibodies may be used as targeting and pretargeting molecules. Such molecules of the present invention may be radiolabeled by methods well known to those of ordinary skill in the art, which include, but are not limited to, radiolabeled chelation of the antibody and antibody phage libraries for targeting radioimmunotherapeutics. See e.g., DeNardo, et al., *Clin. Cancer Res.* 5(10S): 3213s-3218s (1999); Quadri, et al., *Q. J. Nucl. Med.* 42:250-261 (1998); the contents of each of which are incorporated by reference in its entirety.

For chelation, different chemical linkages can be inserted between the antibody and the radiolabeled chelate. Radiolabeled monoclonal antibodies reactive with a target antigen can selectively deliver cytotoxic or diagnostic isotopes to malignant cells in vivo. The construction of pretargeting molecules can be provided using the diversity and malleability of antibody genes. Diverse arrays of single chain antibody fragments (i.e., scFvs) can be obtained that are reactive with a target antigen by selection from human naive phage antibody libraries. ScFvs can also be cloned directly from hybridoma for construction of phage libraries that facilitate subsequent manipulation: e.g., affinity maturation and modification of specificity. ScFvs affinity selected from these sources to their specific antigen targets have demonstrated a wide spectrum of binding characteristics. Antibody heavy (V(H)) and light (V(L)) genes from selected ScFvs may be cloned as cassettes into diabody molecules. This application is discussed further, below, in the method for specific destruction of cells by administering polypeptides of the invention in association with toxins or cytotoxic prodrugs.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, M., et al., J. Cell. Biol. 101:976-985 (1985); Jalkanen, M., et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{63}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (SIGMA™, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Immune System-Related Disorders
Diagnosis

The present inventors have discovered that IL17RLP is expressed in adult pulmonary tissue. For a number of immune system-related disorders, substantially altered (increased or decreased) levels of IL17RLP gene expression can be detected in immune system tissue or other cells or bodily fluids (e.g., sera, plasma, urine, synovial fluid or spinal fluid) taken from an individual having such a disorder, relative to a "standard" IL17RLP gene expression level, that is, the IL17RLP expression level in immune system tissues or bodily fluids from an individual not having the immune system disorder. Thus, the invention provides a diagnostic method useful during diagnosis of an immune system disorder, which involves measuring the expression level of the gene encoding the IL17RLP protein in immune system tissue or other cells or body fluid from an individual and comparing the measured gene expression level with a standard IL17RLP gene expression level, whereby an increase or decrease in the gene expression level compared to the standard is indicative of an immune system disorder.

In particular, it is believed that certain tissues in mammals with cancer of the immune system express significantly enhanced levels of the IL17RLP protein and mRNA encoding the IL17RLP protein when compared to a corresponding "standard" level. Further, it is believed that enhanced levels of the IL17RLP protein can be detected in certain body fluids (e.g., sera, plasma, urine, and spinal fluid) from mammals with such a cancer when compared to sera from mammals of the same species not having the cancer.

Thus, the invention provides a diagnostic method useful during diagnosis of an immune system disorder, including cancers of this system, which involves measuring the expression level of the gene encoding the IL17RLP protein in immune system tissue or other cells or body fluid from an individual and comparing the measured gene expression level with a standard IL17RLP gene expression level, whereby an increase or decrease in the gene expression level compared to the standard is indicative of an immune system disorder.

Where a diagnosis of a disorder in the immune system including diagnosis of a tumor, has already been made according to conventional methods, the present invention is useful as a prognostic indicator, whereby patients exhibiting enhanced IL17RLP gene expression will experience a worse clinical outcome relative to patients expressing the gene at a level nearer the standard level.

By "assaying the expression level of the gene encoding the IL17RLP protein" is intended qualitatively or quantitatively measuring or estimating the level of the IL17RLP protein or the level of the mRNA encoding the IL17RLP protein in a first biological sample either directly (e.g., by determining or estimating absolute protein level or mRNA level) or relatively (e.g., by comparing to the IL17RLP protein level or mRNA level in a second biological sample). Preferably, the IL17RLP protein level or mRNA level in the first biological sample is measured or estimated and compared to a standard IL17RLP protein level or mRNA level, the standard being taken from a second biological sample obtained from an individual not having the disorder or being determined by averaging levels from a population of individuals not having a disorder of the immune system. As will be appreciated in the art, once a standard IL17RLP protein level or mRNA level is known, it can be used repeatedly as a standard for comparison.

By "biological sample" is intended any biological sample obtained from an individual, body fluid, cell line, tissue culture, or other source which contains IL17RLP protein or mRNA. As indicated, biological samples include body fluids (such as sera, plasma, urine, synovial fluid and spinal fluid) which contain free extracellular domains of IL17RLP protein, immune system tissue, and other tissue sources found to express complete, mature or extracellular domain of the IL17RLP. Methods for obtaining tissue biopsies and body fluids from mammals are well known in the art. Where the biological sample is to include mRNA, a tissue biopsy is the preferred source.

The present invention is useful for treatment, diagnosis, detection, and/or prevention of various immune system-related disorders in mammals, preferably humans. Such disorders include tumors, cancers, interstitial lung disease (such as Langerhans cell granulomatosis), and any disregulation of immune cell function including, but not limited to, autoimmunity, arthritis, leukemias, lymphomas, immunosuppression, immunity, humoral immunity, inflammatory bowel disease, myelo suppression, and the like.

Total cellular RNA can be isolated from a biological sample using any suitable technique such as the single-step guanidinium-thiocyanate-phenol-chloroform method described by Chomczynski and Sacchi (*Anal. Biochem.* 162: 156-159 (1987)). Levels of mRNA encoding the IL17RLP protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Assaying IL17RLP protein levels in a biological sample can occur using antibody-based techniques. For example, IL17RLP protein expression in tissues can be studied with classical immunohistological methods (Jalkanen, M., et al., *J. Cell Biol.* 101:976-985 (1985); Jalkanen, M., et al., *J. Cell. Biol.* 105:3087-3096 (1987)). Other antibody-based methods useful for detecting IL17RLP protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine ($^{131}$I, $^{125}$I, $^{123}$I, $^{121}$I), carbon ($^{14}$C), sulfur ($^{35}$S), tritium ($^3$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

In addition to assaying IL17RLP protein levels in a biological sample obtained from an individual, IL17RLP protein can also be detected in vivo by imaging. Antibody labels or markers for in vivo imaging of IL17RLP protein include those detectable by X-radiography, NMR or ESR. For X-radiography, suitable labels include radioisotopes such as barium or cesium, which emit detectable radiation but are not overtly harmful to the subject Suitable markers for NMR and ESR include those with a detectable characteristic spin, such as deuterium, which may be incorporated into the antibody by labeling of nutrients for the relevant hybridoma.

Antibody labels or markers for in vivo imaging of IL17RLP polypeptide include those detectable by X-radiography, NMR, MRI, CAT-scans or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma. Where in vivo imaging is used to detect enhanced levels of IL17RLP polypeptide for diagnosis in humans, it may be preferable to use human antibodies or "humanized" chimeric monoclonal antibodies. Such antibodies can be produced using techniques described herein or otherwise known in the art. For example methods for producing chimeric antibodies are known in the art. See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne at al., Nature 312:643 (1984); Neuberger et al., Nature 314:268 (1985).

Additionally, any IL17RLP polypeptide whose presence can be detected, can be administered. For example, IL17RLP polypeptides labeled with a radio-opaque or other appropriate compound can be administered and visualized in vivo, as discussed, above for labeled antibodies. Further such IL17RLP polypeptides can be utilized for in vitro diagnostic procedures.

An IL17RLP polypeptide-specific antibody or antibody fragment which has been labeled with an appropriate detectable imaging moiety, such as a radioisotope (for example, $^{131}$I, $^{112}$In, $^{99m}$Tc, ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain IL17RLP protein. In vivo tumor imaging is described by Burchiel and coworkers (Chapter 13 in Tumor Imaging: The Radiochemical Detection of Cancer, Burchiel, S. W. and Rhodes, B. A., eds., Masson Publishing Inc. (1982)).

Treatment

As noted above, IL17RLP polynucleotides and polypeptides are useful for diagnosis of conditions involving abnormally high or low expression of IL17RLP activities. Given the cells and tissues where IL17RLP is expressed as well as the activities modulated by IL17RLP, it is readily apparent that a substantially altered (increased or decreased) level of expression of IL17RLP in an individual compared to the standard or "normal" level produces pathological conditions related to the bodily system(s) in which IL17RLP is expressed and/or is active.

It will also be appreciated by one of ordinary skill that, since the IL17RLP protein of the invention is a member of the interleukin (IL)-17 receptor family, the extracellular domain of the protein may be released in soluble form from the cells which express the IL17RLP by proteolytic cleavage. Therefore, when IL17RLP soluble extracellular domain is added from an exogenous source to cells, tissues or the body of an individual, the protein will exert its physiological activities on its target cells of that individual. Also, cells expressing this transmembrane protein may be added to cells, tissues or the body of an individual and these added cells will bind to cells expressing IL17RLP, whereby the cells expressing IL17RLP can cause actions (e.g. cell stimulation) on the ligand-bearing target cells.

Therefore, it will be appreciated that conditions caused by a decrease in the standard or normal level of IL17RLP activity in an individual, particularly disorders of the immune system, can be treated, diagnosed, detected, and/or prevented by administration of IL17RLP polypeptide (in the form of a soluble extracellular domain or cells expressing the complete protein). Thus, the invention also provides a method of treatment, diagnosis, detection, and/or prevention of an individual in need of an increased level of IL17RLP activity comprising administering to such an individual a pharmaceutical composition comprising an amount of an isolated IL17RLP polypeptide of the invention, particularly an extracellular domain of the IL17RLP protein of the invention, effective to increase the IL17RLP activity level in such an individual.

Since IL17RLP is a novel homologue of the recently described IL-17 receptor, it will have a wide range of cytokine receptor-like activities. IL17RLP, or agonists of IL17RLP, may be employed to enhance host defenses against resistant chronic and acute infections, for example, mycobacterial infections via the attraction and activation of microbicidal leukocytes. IL17RLP may also be employed to increase T-cell proliferation by the stimulation of IL-2 biosynthesis for the treatment, diagnosis, detection, and/or prevention of T-cell mediated auto-immune diseases and lymphocytic leukemias. IL17RLP may also be employed to regulate hematopoiesis, by regulating the activation and differentiation of various hematopoietic progenitor cells, for example, to release mature leukocytes from the bone marrow following chemotherapy, i.e., in stem cell mobilization. IL17RLP may also be employed to treat, diagnose, detect, and/or prevent sepsis. Soluble IL17RLP extracellular domains may be used as antagonists for IL17RLP activity, and, as such, will be useful therapeutically, as a mechanism to regulate the activity of endogenous IL17RLP. Also, stimulation of IL17RLP strongly induces IL-6 expression. IL-6 is a potent growth factor for myelomas, plasmacytomas, and hybridomas and is involved in the growth of Lennert's Lymphoma T-cells. As a result, IL17RLP agonists and soluble IL17RLP extracellular domains may be used in the treatment, diagnosis, detection, and/or prevention of such cancers, analogous disease states, and others known to those of skill in the art.

IL17RLP polynucleotides or polypeptides, or agonists of IL17RLP, can be used in the treatment, diagnosis, detection, and/or prevention of infectious agents. For example, by increasing the immune response, particularly increasing the proliferation and differentiation of T or B cells, infectious diseases may be treated, diagnosed, detected, and/or prevented. The immune response may be increased by either enhancing an existing immune response, or by initiating a new immune response. Alternatively, IL17RLP polynucleotides or polypeptides, or agonists or antagonists of IL17RLP, may also directly inhibit the infectious agent, without necessarily eliciting an immune response.

Viruses are one example of an infectious agent that can cause disease or symptoms that can be treated, diagnosed, detected, and/or prevented by IL17RLP polynucleotides or polypeptides, or agonists of IL17RLP. Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxyiridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. IL17RLP polynucleotides or polypeptides, or agonists or antagonists of IL17RLP, can be used to treat, prevent, diagnose, and/or detect any of these symptoms or diseases. In specific embodiments, IL17RLP polynucleotides, polypeptides, or agonists are used to treat, prevent, detect, and/or diagnose: meningitis, Dengue, EBV, and/or hepatitis (e.g., hepatitis B). In an additional specific embodiment IL17RLP polynucleotides, polypeptides, or agonists are used to treat patients nonresponsive to one or more other commercially available hepatitis vaccines. In a further specific embodiment, IL17RLP polynucleotides, polypeptides, or agonists are used to treat, prevent, detect, and/or diagnose AIDS. In an additional specific embodiment IL17RLP polynucleotides, polypeptides, agonists, and/or antagonists are used to treat, prevent, detect, and/or diagnose patients with cryptosporidiosis.

Similarly, bacterial or fungal agents that can cause disease or symptoms and that can be treated, diagnosed, detected, and/or prevented by IL17RLP polynucleotides or polypeptides, or agonists or antagonists of IL17RLP, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*, Brucellosis, Candidiasis, *Campylobacter*, Coccidioidomycosis, Cryptococcosis, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), *Erysipelothrix, Helicobacter*, Legionellosis, Leptospirosis, *Listeria* (e.g., *Listeria monocytogenes*), Mycoplasmatales, *Mycobacterium leprae, Vibrio cholerae*, Neisseriaceae (e.g., *Acinetobacter*, Gonorrhea, Menigococcal), *Meisseria meningitidis*, Pasteurellacea Infections (e.g., *Actinobacillus, Heamophilus* (e.g., *Heamophilus influenza* type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), *Chlamydia*, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. IL17RLP polynucleotides or polypeptides, or agonists or antagonists of IL17RLP, can be used to treat, prevent, diagnose, and/or detect any of these symptoms or diseases. In specific embodiments, IL17RLP polynucleotides, polypeptides, or agonists thereof are used to treat, prevent, detect, and/or diagnose: tetanus, Diptheria, botulism, and/or meningitis type B.

Moreover, parasitic agents causing disease or symptoms that can be treated, diagnosed, detected, and/or prevented by IL17RLP polynucleotides or polypeptides, or agonists of IL17RLP, include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. IL17RLP polynucleotides or polypeptides, or agonists or antagonists of IL17RLP, can be used to treat, prevent, diagnose, and/or detect any of these symptoms or diseases. In specific embodiments, IL17RLP polynucleotides, polypeptides, or agonists thereof are used to treat, prevent, detect, and/or diagnose malaria.

In another embodiment, the invention provides a method of delivering compositions containing the polypeptides of the invention (e.g., compositions containing IL17RLP polypeptides or anti-IL17RLP antibodies associated with heterologous polypeptides, heterologous nucleic acids, toxins, or prodrugs) to targeted cells, such as, for example, B or T cells expressing IL17RLP. IL17RLP polypeptides or anti-IL17RLP antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., IL17RLP polypeptides or anti-IL17RLP antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., IL17RLP polypeptides or anti-IL17RLP antibodies) in association with toxins or cytotoxic prodrugs.

In a specific embodiment, the invention provides a method for the specific destruction of cells of T or B cell lineage (e.g., T or B cell related leukemias or lymphomas) by administering IL17RLP polypeptides in association with toxins or cytotoxic prodrugs.

In another specific embodiment, the invention provides a method for the specific destruction of cells of monocytic lineage (e.g., monocytic leukemias or lymphomas) by administering anti-IL17RLP antibodies in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{165}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

An additional condition, disease or symptom that can be treated, prevented, detected, and/or diagnosed by IL17RLP polynucleotides or polypeptides, or agonists of IL17RLP, is osteomyelitis.

An additional condition, disease or symptom that can be treated, prevented, detected, and/or diagnosed by IL17RLP polynucleotides or polypeptides, or agonists of IL17RLP, is endocarditis.

Preferably, treatment, diagnosis, detection, and/or prevention using IL17RLP polynucleotides or polypeptides, or agonists of IL17RLP, could either be by administering an effective amount of IL17RLP polypeptide to the patient, or by removing cells from the patient, supplying the cells with IL17RLP polynucleotide, and returning the engineered cells to the patient (ex vivo therapy). Moreover, as further discussed herein, the IL17RLP polypeptide or polynucleotide can be used as an adjuvant in a vaccine to raise an immune response against infectious disease.

In a specific embodiment, IL17RLP polynucleotides or polypeptides, or agonists thereof (e.g., anti-IL17RLP antibodies) are used to treat, diagnose, detect, and/or prevent a disorder characterized by deficient serum immunoglobulin production, recurrent infections, and/or immune system dysfunction. Moreover, IL17RLP polynucleotides or polypeptides, or agonists thereof (e.g., anti-IL17RLP antibodies) may be used to treat, diagnose, detect, and/or prevent infections of the joints, bones, skin, and/or parotid glands, blood-borne infections (e.g., sepsis, meningitis, septic arthritis, and/or osteomyelitis), autoimmune diseases (e.g., those disclosed herein), inflammatory disorders, and malignancies, and/or any disease or disorder or condition associated with these infections, diseases, disorders and/or malignancies) including, but not limited to, CVID, other primary immune deficiencies, HIV disease, CLL, recurrent bronchitis, sinusitis, otitis media, conjunctivitis, pneumonia, hepatitis, meningitis, herpes zoster (e.g., severe herpes zoster), and/or pheumocystis carnii.

Additional preferred embodiments of the invention include, but are not limited to, the use of IL17RLP polypeptides, IL17RLP polynucleotides, and functional agonists thereof, in the applications that follow below.

As a chemoattractant of neutrophils. In a preferred embodiment, IL17RLP polypeptides, polynucleotides, agonists, and/or antagonists thereof may be used as a chemoattractant of neutrophils in the spinal cord.

As a means of stimulating bone and/or cartilage cell growth. Thus, IL17RLP polypeptides, polynucleotides, agonists, and/or antagonists thereof may be useful, for example, in osteoporosis, cartilage production, osteoarthritis, and/or regeneration of dentin and/or bone lost due to periodontal disease.

As a means of induction of TNF-alpha, IL-1beta, and/or IL-6 expression.

As an agent of regulation and/or maintenance of the growth state and/or cellular activity of cells of the spinal cord. In preferred embodiments, as an agent of regulation and/or maintenance of the growth state and/or cellular activity of glial cells and/or neurons. Thus, IL17RLP polypeptides, polynucleotides, agonists, and/or antagonists thereof may be useful, for example, to treat, diagnose, prevent, and/or detect neurodegenerative diseases including amyotrophic lateral sclerosis (ALS); demyelinating diseases including multiple sclerosis; peripheral neuropathies (e.g., Charcot-Marie Tooth (CMT) disease); sensory neuropathis; neuroallergy; neuroarthropathy; neuroblastoma; olfactory neuroblastoma; neurochorioretinitis; neurochoroiditis; neurocirculatory asthenia (e.g., DaCosta's syndrome; effort syndrome; irritable heart; soldier's heart); neurocristopathy; neurocutaneous melanosis; neurocutaneous syndrome; neurocytolysis; neurocytoma; ganglioneuroma; cataracta neurodermatica; atopic dermatitis; neurodermatitis (e.g., atopic dermatitis; chronic lichen simplex); neurodynia; neuralgia; neuroencephalomyelopathy; neurofibrillary degeneration; Alzheimer's disease; neurofibroma; fibroneuroma; schwannoma; plexiform neurofibroma; storiform neurofibroma; neurofibromatosis (e.g., von Recklinghausen's disease); abortive neurofibromatosis; neurogenic atrophy; neurogenic bladder, neuroglia (e.g., Kolliker's reticulum); neurogliomatosis; neuroleptanalgesia; neuroleptic malignant syndrome; neurolymphomatosis (e.g., neurolymphomatosis gallinarum); neurolymphomatosis gallinarum; neurolysis; rolling disease; neuroma (e.g., acoustic neuroma; amputation neuroma; neuroma cutis; false neuroma; fibrillary neuroma; plexiform neuroma; neuroma telangiectodes; traumatic neuroma; Verneuil's neuroma); neuroma cutis; fibrillary neuroma (e.g., plexiform neurofibroma); neuromalacia; elephantiasis neuromatosa; neuromatosis (e.g., as in neurofibromatosis); neuromimesis; neuromyasthenia (e.g., epidemic neuromyasthenia); neuromyelitis (e.g., myeloneuritis; neuromyelitis optica); neuromyopathy (e.g., carcinomatous neuromyopathy); neuromyositis; neuronitis; neuronopathy (e.g., sensory neuronopathy); neuropapillitis; neuroparalysis (e.g., neuroparalytic keratitis; neuroparalytic ophthalmia); neuropathic albuminuria; neuropathic arthritis (e.g., Charcot's joint; neuropathic arthritis; neuropathic arthropathy; tabetic arthropathy); papilloma neuropathicum; neuropathy (e.g., asymmetric motor neuropathy; brachial plexus neuropathy; diabetic neuropathy; diphtheritic neuropathy; entrapment neuropathy; familial amyloid neuropathy; giant axonal neuropathy; hereditary hypertrophic neuropathy; hereditary sensory radicular, neuropathy; hypertrophic interstitial neuropathy; ischemic optic neuropathy; isoniazid neuropathy; lead neuropathy; leprous neuropathy; motor dapsone neuropathy; onion bulb neuropathy; segmental neuropathy; symmetric distal neuropathy; vitamin B12 neuropathy); neurophonia; neuroplegic; neuropsychologic disorder, neuropsychopathy; neurorelapse; neuroretinitis; neurosarcoidosis; neuroschwannoma (e.g., neurilemoma); neurosis; neurospasm; neurosthenia; neurosyphilis; neurotabes (e.g., Dejerine's peripheral neurotabes); neurothekeoma; alopecia neurotica; lipomatosis neurotics; neurotrauma; neurotrophic atrophy (e.g., neuritic atrophy); neurotrosis; neurovaricosis; and/or other diseases/disorders of the spinal cord.

IL17RLP polypeptides, polynucleotides, agonists, and/or antagonists thereof may be useful, for example, to treat, diagnose, prevent, and/or detect immune and/or autoimmune diseases and disorders and/or conditions associated therewith. Thus, IL17RLP polypeptides, polynucleotides, agonists, and/or antagonists thereof may be useful, for example, to treat, diagnose, prevent, and/or detect immune complex disease; immune complex disorder; immune complex nephritis; immunodeficiency; immune hemolysis (e.g., conditioned hemolysis); immune inflammation; immune thrombocytopenia; immune thrombocytopenic purpura; immunoblastic lymphadenopathy; immunoblastic lymphoma; immunoblastic sarcoma; immunodeficiency (e.g., cellular immunodeficiency with abnormal immunoglobulin synthesis; combined immunodeficiency; common variable immunodeficiency; immunodeficiency with; hypoparathyroidism; phagocytic dysfunction disorders; immunodeficiency; secondary immunodeficiency; severe combined immunodeficiency); immunodeficiency with hypoparathyroidism; immunodeficiency syndrome; immunoproliferative disorders; immunoproliferative small intestinal disease (e.g., Mediterranean lymphoma); chronic discoid lupus erythematosus; discoid lupus erythematosus; disseminated lupus erythematosus; lupus erythematodes; lupus erythematosus; lupus erythematosus profundus; lupus hypertrophicus; lupus livido; lupus lymphaticus; lupus miliaris disseminatus faciei; lupus mutilans; lupus papillomatosus; lupus pernio; lupus psoriasis; lupus sclerosus; lupus sebaceus; lupus serpiginosus; lupus superficialis; systemic lupus erythematosus; lupus tuberculosus; lupus tumidus; lupus verrucosus; lupus vulgaris; lupus vulgaris erythematoides; acute rheumatic arthritis; atrophic arthritis; chlamydial arthritis; chronic absorptive arthritis; chylous arthritis; arthritis deformans; degenerative arthritis; enteropathic arthritis; filarial arthritis; gouty arthritis; hemophilic arthritis; hypertrophic arthritis; Jaccoud's arthritis; juvenile arthritis; Lyme arthritis; arthritis mutilans; neonatal arthritis of foals; neuropathic arthritis; arthritis nodosa; ochronotic arthritis; proliferative arthritis; psoriatic arthritis; rheumatoid arthritis; suppurative arthritis; and/or arthritis uratica.

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response.

Administration to an animal (including, but not limited to, those listed above, and also including transgenic animals) incapable of producing functional endogenous antibody molecules or having an otherwise compromised endogenous immune system, but which is capable of producing human immunoglobulin molecules by means of a reconstituted or partially reconstituted immune system from another animal (see, e.g., published PCT Application Nos. WO98/24893, WO/9634096, WO/9633735, and WO/9110741.

A vaccine adjuvant that enhances immune responsiveness to specific antigen. In a specific embodiment, the vaccine adjuvant is an IL17RLP polypeptide described herein. In another specific embodiment, the vaccine adjuvant is an IL17RLP polynucleotide described herein (i.e., the IL17RLP polynucleotide is a genetic vaccine adjuvant). As discussed herein, IL17RLP polynucleotides may be administered using techniques known in the art, including but not limited to, liposomal delivery, recombinant vector delivery, injection of naked DNA, and gene gun delivery.

An adjuvant to enhance tumor-specific immune responses.

An adjuvant to enhance anti-viral immune responses. Antiviral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of AIDS, meningitis, Dengue, EBV, and hepatitis (e.g., hepatitis B). In another specific embodiment, the compositions of the invention are used as an adjuvant to enhance an immune response to a virus, disease, or symptom selected from the group consisting of HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever. In another specific embodiment, the compositions of the invention are used as an adjuvant to enhance an immune response to the HIV gp120 antigen.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of tetanus, Diphtheria, botulism, and meningitis type B. In another specific embodiment, the compositions of the invention are used as an adjuvant to enhance an immune response to a bacteria or fungus, disease, or symptom selected from the group consisting of: *Vibrio cholerae, Mycobacterium leprae, Salmonella typhi, Salmonella paratyphi, Meisseria meningitidis, Streptococcus pneumoniae*, Group B *streptococcus, Shigella* spp., Enterotoxigenic *Escherichia coli*, Enterohemorrhagic *E. coli, Borrelia burgdorferi*, and *Plasmodium* (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to *Plasmodium* (malaria).

As a stimulator of B cell responsiveness to pathogens.

As an agent that elevates the immune status of an individual prior to their receipt of immunosuppressive therapies.

As an agent to induce higher affinity antibodies.

As an agent to increase serum immunoglobulin concentrations.

As an agent to accelerate recovery of immunocompromised individuals.

As an agent to boost immunoresponsiveness among aged populations.

As an immune system enhancer prior to, during, or after bone marrow transplant and/or other transplants (e.g., allogeneic or xenogeneic organ transplantation). With respect to transplantation, compositions of the invention may be administered prior to, concomitant with, and/or after transplantation. In a specific embodiment, compositions of the invention are administered after transplantation, prior to the beginning of recovery of T-cell populations. In another specific embodiment, compositions of the invention are first administered after transplantation after the beginning of recovery of T cell populations, but prior to full recovery of B cell populations.

As an agent to boost immunoresponsiveness among B cell immunodeficient individuals, such as, for example, an individual who has undergone a partial or complete splenectomy. B cell immunodeficiencies that may be ameliorated, treated, diagnosed, detected, and/or prevented by administering the IL17RLP polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CV1) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymophoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

As an agent to boost immunoresponsiveness among individuals having an acquired loss of B cell function. Conditions resulting in an acquired loss of B cell function that may be ameliorated, treated, diagnosed, detected, and/or prevented by administering the IL17RLP polypeptides or polynucleotides of the invention, or agonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated, treated, diagnosed, detected, and/or prevented by administering the IL17RLP polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

As a regulator of antigen presentation by monocytes, dendritic cells, and/or B-cells. In one embodiment, IL17RLP polypeptides (in soluble, membrane-bound or transmembrane forms) or polynucleotides enhance antigen presentation or antagonize antigen presentation in vitro or in vivo. Moreover, in related embodiments, said enhancement or antagonization of antigen presentation may be useful as an anti-tumor treatment or to modulate the immune system.

As an agent to direct an individual's immune system towards development of a humoral response (i.e. TH2) as opposed to a TH1 cellular response.

As a means to induce tumor proliferation and thus make it more susceptible to anti-neoplastic agents. For example, multiple myeloma is a slowly dividing disease and is thus refractory to virtually all anti-neoplastic regimens. If these cells were forced to proliferate more rapidly their susceptibility profile would likely change.

As a therapy for generation and/or regeneration of lymphoid tissues following surgery, trauma or genetic defect.

As a gene-based therapy for genetically inherited disorders resulting in immuno-incompetence such as observed among SCID patients.

As an antigen for the generation of antibodies to inhibit or enhance IL17RLP mediated responses.

As a means of activating monocytes/macrophages to defend against parasitic diseases that effect monocytes such as *Leshmania*.

As pretreatment of bone marrow samples prior to transplant. Such treatment would increase B cell representation and thus accelerate recover.

As a means of regulating secreted cytokines that are elicited by IL17RLP.

IL17RLP polypeptides or polynucleotides of the invention, or agonists may be used to modulate IgE concentrations in vitro or in vivo.

Additionally, IL17RLP polypeptides or polynucleotides of the invention, or agonists thereof, may be used to treat, prevent, detect, and/or diagnose IgE-mediated allergic reactions. Such allergic reactions include, but are not limited to, asthma, rhinitis, and eczema.

In a specific embodiment, IL17RLP polypeptides or polynucleotides of the invention, or agonists thereof, is administered to treat, prevent, diagnose, and/or ameliorate selective IgA deficiency.

In another specific embodiment, IL17RLP polypeptides or polynucleotides of the invention, or agonists thereof, is administered to treat, prevent, diagnose, and/or ameliorate ataxia-telangiectasia.

In another specific embodiment, IL17RLP polypeptides or polynucleotides of the invention, or agonists thereof, is administered to treat, prevent, diagnose, and/or ameliorate common variable immunodeficiency.

In another specific embodiment, IL17RLP polypeptides or polynucleotides of the invention, or agonists thereof, is administered to treat, prevent, diagnose, and/or ameliorate X-linked agammaglobulinemia.

In another specific embodiment, IL17RLP polypeptides or polynucleotides of the invention, or agonists thereof, is administered to treat, prevent, diagnose, and/or ameliorate severe combined immunodeficiency (SCID).

In another specific embodiment, IL17RLP polypeptides or polynucleotides of the invention, or agonists thereof, is administered to treat, prevent, diagnose, and/or ameliorate Wiskott-Aldrich syndrome.

In another specific embodiment, IL17RLP polypeptides or polynucleotides of the invention, or agonists thereof, is administered to treat, prevent, diagnose, and/or ameliorate X-linked Ig deficiency with hyper IgM.

In another specific embodiment, IL17RLP polypeptides or polynucleotides of the invention, or agonists or antagonists (e.g., anti-IL17RLP antibodies) thereof, is administered to treat, prevent, detect, and/or diagnose chronic myelogenous leukemia, acute myelogenous leukemia, leukemia, hystiocytic leukemia, monocytic leukemia (e.g., acute monocytic leukemia), leukemic reticulosis, Shilling Type monocytic leukemia, and/or other leukemias derived from monocytes and/or monocytic cells and/or tissues.

In another specific embodiment, IL17RLP polypeptides or polynucleotides of the invention, or agonists thereof, is administered to treat, prevent, diagnose, and/or ameliorate monocytic leukemoid reaction, as seen, for example, with tuberculosis.

In another specific embodiment, IL17RLP polypeptides or polynucleotides of the invention, or agonists thereof, is administered to treat, prevent, diagnose, and/or ameliorate monocytic leukocytosis, monocytic leukopenia, monocytopenia, and/or monocytosis.

In a specific embodiment, IL17RLP polynucleotides or polypeptides of the invention, and/or anti-IL17RLP antibodies and/or agonists or antagonists thereof, are used to treat, prevent, detect, and/or diagnose primary B lymphocyte disorders and/or diseases, and/or conditions associated therewith. In one embodiment, such primary B lymphocyte disorders, diseases, and/or conditions are characterized by a complete or partial loss of humoral immunity. Primary B lymphocyte disorders, diseases, and/or conditions associated therewith that are characterized by a complete or partial loss of humoral immunity and that may be prevented, treated, detected and/or diagnosed with compositions of the invention include, but are not limited to, X-Linked Agammaglobulinemia (XLA), severe combined immunodeficiency disease (SCID), and selective IgA deficiency.

In a preferred embodiment, IL17RLP polynucleotides, polypeptides, and/or agonists and/or antagonists thereof are used to treat, prevent, and/or diagnose diseases or disorders affecting or conditions associated with any one or more of the various mucous membranes of the body. Such diseases or disorders include, but are not limited to, for example, mucositis, mucoclasis, mucocolitis, mucocutaneous leishmaniasis (such as, for example, American leishmaniasis, leishmaniasis americana, nasopharyngeal leishmaniasis, and New World leishmaniasis), mucocutaneous lymph node syndrome (for example, Kawasaki disease), mucoenteritis, mucoepidermoid carcinoma, mucoepidermoid tumor, mucoepithelial dysplasia, mucoid adenocarcinoma, mucoid degeneration, myxoid degeneration; myxomatous degeneration; myxomatosis, mucoid medial degeneration (for example, cystic medial necrosis), mucolipidosis (including, for example, mucolipidosis I, mucolipidosis H, mucolipidosis III, and mucolipidosis IV), mucolysis disorders, mucomembranous enteritis, mucoenteritis, mucopolysaccharidosis (such as, for example, type I mucopolysaccharidosis (i.e., Hurler's syndrome), type IS mucopolysaccharidosis (i.e., Scheie's syndrome or type V mucopolysaccharidosis), type II mucopolysaccharidosis (i.e., Hunter's syndrome), type III mucopolysaccharidosis (i.e., Sanfilippo's syndrome), type IV mucopolysaccharidosis (i.e., Morquio's syndrome), type VI mucopolysaccharidosis (i.e., Maroteaux-Lamy syndrome), type VII mucopolysaccharidosis (i.e, mucopolysaccharidosis due to beta-glucuronidase deficiency), and mucosulfatidosis), mucopolysacchariduria, mucopurulent conjunctivitis, mucopus, mucormycosis (i.e., zygomycosis), mucosal disease (i.e., bovine virus diarrhea), mucous colitis (such as, for example, mucocolitis and myxomembranous colitis), and mucoviscidosis (such as, for example, cystic fibrosis, cystic fibrosis of the pancreas, Clarke-Hadfield syndrome, fibrocystic disease of the pancreas, mucoviscidosis, and viscidosis). In a highly preferred embodiment, IL17RLP polynucleotides, polypeptides, and/or agonists and/or antagonists thereof are used to treat, prevent, and/or diagnose mucositis, especially as associated with chemotherapy.

In a preferred embodiment, IL17RLP polynucleotides, polypeptides, and/or agonists and/or antagonists thereof are used to treat, prevent, and/or diagnose diseases or disorders affecting or conditions associated with sinusitis.

All of the above described applications as they may apply to veterinary medicine.

Antagonists of IL17RLP include binding and/or inhibitory antibodies, antisense nucleic acids, ribozymes or soluble forms (e.g., a soluble extracellular domain) of IL17RLP. These would be expected to reverse many of the activities of the ligand described above as well as find clinical or practical application as:

A means of blocking various aspects of immune responses to foreign agents or self. Examples include autoimmune disorders such as lupus, and arthritis, as well as immunoresponsiveness to skin allergies, inflammation, bowel disease, injury and pathogens.

A therapy for preventing the T or B cell proliferation and Ig secretion associated with autoimmune diseases such as idiopathic thrombocytopenic purpura, systemic lupus erythramatosus and MS.

An inhibitor of graft versus host disease or transplant rejection.

A therapy for B cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

A therapy for chronic hypergammaglobulinemeia evident in such diseases as monoclonalgammopathy of undetermined significance (MGUS), Waldenstrom's disease, related idiopathic monoclonalgammopathies, and plasmacytomas.

A therapy for decreasing cellular proliferation of Large B-cell Lymphomas.

A means of decreasing the involvement of B cells and Ig associated with Chronic Myelogenous Leukemia.

An immunosuppressive agent(s).

IL17RLP polypeptides or polynucleotides of the invention, or antagonists may be used to modulate IgE concentrations in vitro or in vivo.

In another embodiment, administration of IL17RLP polypeptides or polynucleotides of the invention, or antagonists thereof, may be used to treat, prevent, and/or diagnose IgE-mediated allergic reactions including, but not limited to, asthma, rhinitis, and eczema.

An inhibitor of signaling pathways involving ERK1, COX2 and Cyclin D2 which have been associated with IL17RLP-induced T or B cell activation.

The above-recited applications have uses in a wide variety of hosts. Such hosts include, but are not limited to, human, murine, rabbit, goat, guinea pig, camel, horse, mouse, rat, hamster, pig, micro-pig, chicken, goat, cow, sheep, dog, cat, non-human primate, and human. In specific embodiments, the host is a mouse, rabbit, goat, guinea pig, chicken, rat, hamster, pig, sheep, dog or cat. In preferred embodiments, the host is a mammal. In most preferred embodiments, the host is a human.

The agonists and antagonists may be employed in a composition with a pharmaceutically acceptable carrier, e.g., as described above.

The antagonists may be employed for instance to inhibit IL17RLP-mediated chemotaxis and activation of macrophages and their precursors, and of neutrophils, basophils, T lymphocytes, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat, prevent, and/or diagnose infectious diseases including silicosis, sarcoidosis, idiopathic pulmonary fibrosis by preventing the recruitment and activation of mononuclear phagocytes. They may also be employed to treat, prevent, and/or diagnose idiopathic hyper-eosinophilic syndrome by preventing eosinophil production and migration. Endotoxic shock may also be treated by the antagonists by preventing the migration of macrophages and their production of the IL17RLP polypeptides of the present invention. The antagonists may also be employed for treating atherosclerosis, by preventing monocyte infiltration in the artery wall. The antagonists may also be employed to treat, prevent, and/or diagnose histamine-mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated. The antagonists may also be employed to treat, prevent, and/or diagnose chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung. Antagonists may also be employed to treat, prevent, and/or diagnose rheumatoid arthritis by preventing the attraction of monocytes into synovial fluid in the joints of patients. Monocyte influx and activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by IL17RLP. The antagonists may also be employed to treat, prevent, and/or diagnose cases of bone marrow failure, for example, aplastic anemia and myelodysplastic syndrome. The antagonists may also be employed to treat, prevent, and/or diagnose asthma and allergy by preventing eosinophil accumulation in the lung. The antagonists may also be employed to treat, prevent, and/or diagnose subepithelial basement membrane fibrosis which is a prominent feature of the asthmatic lung. The antagonists may also be employed to treat, prevent, and/or diagnose lymphomas (e.g., one or more of the extensive, but not limiting, list of lymphomas provided herein).

All of the above described applications as they may apply to veterinary medicine. Moreover, all applications described herein may also apply to veterinary medicine.

Antibodies against IL17RLP may be employed to bind to and inhibit IL17RLP activity to treat, prevent, and/or diagnose ARDS, by preventing infiltration of neutrophils into the lung after injury. The antagonists and antagonists of the instant may be employed in a composition with a pharmaceutically acceptable carrier, e.g., as described hereinafter.

IL17RLP polynucleotides or polypeptides of the invention and/or agonists and/or antagonists thereof, are used to treat, prevent, and/or diagnose diseases and disorders of the pulmonary system (e.g., bronchi such as, for example, sinopulmonary and bronchial infections and conditions associated with such diseases and disorders and other respiratory diseases and disorders. In specific embodiments, such diseases and disorders include, but are not limited to, bronchial adenoma, bronchial asthma, pneumonia (such as, e.g., bronchial pneumonia, bronchopneumonia, and tuberculous bronchopneumonia), chronic obstructive pulmonary disease (COPD), bronchial polyps, bronchiectasia (such as, e.g., bronchiectasia sicca, cylindrical bronchiectasis, and saccular bronchiectasis), bronchiolar adenocarcinoma, bronchiolar carcinoma, bronchiolitis (such as, e.g., exudative bronchiolitis, bronchiolitis fibrosa obliterans, and proliferative bronchiolitis), bronchiolo-alveolar carcinoma, bronchitic asthma, bronchitis (such as, e.g., asthmatic bronchitis, Castellani's bronchitis, chronic bronchitis, croupous bronchitis, fibrinous bronchitis, hemorrhagic bronchitis, infectious avian bronchitis, obliterative bronchitis, plastic bronchitis, pseudomembranous bronchitis, putrid bronchitis, and verminous bronchitis), bronchocentric granulomatosis, bronchoedema, bronchoesophageal fistula, bronchogenic carcinoma, bronchogenic cyst, broncholithiasis, bronchomalacia, bronchomycosis (such as, e.g., bronchopulmonary aspergillosis), bronchopulmonary spirochetosis, hemorrhagic bronchitis, bronchorrhea, bronchospasm, bronchostaxis, bronchostenosis, Biot's respiration, bronchial respiration, Kussmaul respiration, Kussmaul-Kien respiration, respiratory acidosis, respiratory alkalosis, respiratory distress syndrome of the newborn, respiratory insufficiency, respiratory scleroma, respiratory syncytial virus, and the like.

In a specific embodiment, IL17RLP polynucleotides or polypeptides of the invention and/or agonists and/or antagonists thereof, are used to treat, prevent, and/or diagnose chronic obstructive pulmonary disease (COPD).

In another embodiment, IL17RLP polynucleotides or polypeptides of the invention and/or agonists and/or antagonists thereof, are used to treat, prevent, and/or diagnose fibroses and conditions associated with fibroses, such as, for example, but not limited to, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmers' clay pipestem fibrosis.

In another embodiment, IL17RLP polynucleotides or polypeptides of the invention and/or agonists and/or antagonists thereof, are used to treat, prevent, and/or diagnose inner ear infection (such as, for example, otitis media), as well as other infections characterized by infection with *Streptococcus pneumoniae* and other pathogenic organisms.

IL17RLP polynucleotides or polypeptides of the invention and/or agonists and/or antagonists thereof, are used to treat, prevent, and/or diagnose various immune system-related disorders and/or conditions associated with these disorders, in mammals, preferably humans. Many autoimmune disorders result from inappropriate recognition of self as foreign material by immune cells. This inappropriate recognition results in an immune response leading to the destruction of the host tissue. Therefore, the administration of IL17RLP polynucleotides or polypeptides of the invention and/or agonists and/or antagonists thereof that can inhibit an immune response, particularly the proliferation, differentiation, or chemotaxis of T cells, may be an effective therapy in treating and/or preventing autoimmune disorders. Thus, in preferred embodiments, IL17RLP antagonists of the invention (e.g., polypeptide fragments of IL17RLP and anti-IL17RLP antibodies) are used to treat, prevent, and/or diagnose an autoimmune disorder.

Such autoimmune disorders include, but are not limited to, autoimmune diseases such as, for example, autoimmune hemolytic anemia, autoimmune neonatal thrombocytopenia, autoimmunocytopenia, hemolytic anemia, antiphospholipid syndrome, dermatitis, allergic encephalomyelitis, glomerulonephritis, Multiple Sclerosis, Neuritis, Ophthalmia, Polyendocrinopathies, Purpura, Reiter's Disease, Stiff-Man Syndrome, Autoimmune Pulmonary Inflammation, Guillain-Barre Syndrome, insulin dependent diabetes mellitis, and autoimmune inflammatory eye disease.

Additional autoimmune disorders (that are highly probable) that may be treated, prevented, and/or diagnosed with the compositions of the invention include, but are not limited to, autoimmune thyroiditis (i.e., Hashimoto's thyroiditis) (often characterized, e.g., by cell-mediated and humoral thyroid cytotoxicity), systemic lupus erhthematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), Receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), scleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by antispermatozoal antibodies), glomerulonephritis (often characterized, e.g., by glomerular basement membrane antibodies or immune complexes), bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g., by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and 10/1 antibodies to IgE), and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-IL17RLP antibodies and/or a soluble IL17RLP polypeptide of the invention (e.g., an extracellular domain of IL17RLP).

In a specific preferred embodiment, rheumatoid arthritis is treated, prevented, and/or diagnosed using anti-IL17RLP antibodies and/or a soluble IL17RLP polypeptide and/or other antagonist of the invention.

In a specific preferred embodiment, lupus is treated, prevented, and/or diagnosed using anti-IL17RLP antibodies and/or a soluble IL17RLP polypeptide and/or other antagonist of the invention.

In a specific preferred embodiment, nephritis associated with lupus is treated, prevented, and/or diagnosed using anti- IL17RLP antibodies and/or a soluble IL17RLP polypeptide and/or other antagonist of the invention.

In a specific embodiment, IL17RLP polynucleotides or polypeptides, or antagonists thereof (e.g., anti-IL17RLP antibodies) are used to treat or prevent systemic lupus erythramatosus and/or diseases, disorders or conditions associated therewith. Lupus-associated diseases, disorders, or conditions that may be treated or prevented with IL17RLP polynucleotides or polypeptides, or antagonists of the invention, include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleuricy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, the IL17RLP polynucleotides or polypeptides, or antagonists thereof (e.g., anti-IL17RLP antibodies) are used to treat or prevent renal disorders associated with systemic lupus erythramatosus. In a most preferred embodiment, IL17RLP polynucleotides or polypeptides, or antagonists thereof (e.g., anti-IL17RLP antibodies) are used to treat or prevent nephritis associated with systemic lupus erythramatosus.

Similarly, allergic reactions and conditions, such as asthma (particularly allergic asthma) or other respiratory problems, may also be treated by IL17RLP polynucleotides or polypeptides of the invention and/or agonists and/or antagonists thereof. Moreover, these molecules can be used to treat, prevent, and/or diagnose anaphylaxis, hypersensitivity to an antigenic molecule, or blood group incompatibility.

IL17RLP polynucleotides or polypeptides of the invention and/or agonists and/or antagonists thereof, may also be used to treat, prevent, and/or diagnose organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. The administration of IL17RLP polynucleotides or polypeptides of the invention and/or agonists and/or antagonists thereof, that inhibits an immune response, particularly the proliferation, differentiation, or chemotaxis of T-cells, may be an effective therapy in preventing organ rejection or GVHD.

Similarly, IL17RLP polynucleotides or polypeptides of the invention and/or agonists and/or antagonists thereof, may also be used to modulate inflammation. For example, IL17RLP polynucleotides or polypeptides of the invention and/or agonists and/or antagonists thereof, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

In a specific embodiment, anti-IL17RLP antibodies of the invention are used to treat, prevent, modulate, detect, and/or diagnose inflammation.

In a specific embodiment, anti-IL17RLP antibodies of the invention are used to treat, prevent, modulate, detect, and/or diagnose inflamatory disorders.

In another specific embodiment, anti-IL17RLP antibodies of the invention are used to treat, prevent, modulate, detect, and/or diagnose allergy and/or hypersensitivity.

The TNF family ligands are known to be among the most pleiotropic cytokines, inducing a large number of cellular responses, including cytotoxicity, anti-viral activity, immunoregulatory activities, and the transcriptional regulation of several genes (D. V. Goeddel et al., "Tumor Necrosis Factors: Gene Structure and Biological Activities," *Symp. Quant. Biol.* 51:597-609 (1986), Cold Spring Harbor, B. Beutler and A. Cerami, *Annu. Rev. Biochem.* 57:505-518 (1988); L. J. Old, *Sci. Am.* 258:59-75 (1988); W. Fiers, *FEBS Lett.* 285:199-224 (1991)). IL17RLP polypeptides are believed to elicit a potent cellular response including any genotypic, phenotypic, and/or morphologic change to the cell, cell line, tissue, tissue culture or patient. As indicated, such cellular responses include not only normal physiological responses to IL17RLP, but also diseases associated with increased apoptosis or the inhibition of apoptosis. Apoptosis-programmed cell death-is a physiological mechanism involved in the deletion of peripheral B and/or T lymphocytes of the immune system, and its disregulation can lead to a number of different pathogenic processes (J. C. Ameisen, AIDS 8:1197-1213 (1994); P. H. Krammer et al., *Curr. Opin. Immunol.* 6:279-289 (1994)).

Diseases associated with increased cell survival, or the inhibition of apoptosis, include cancers (such as follicular lymphomas, carcinomas with p53 mutations, and hormone-dependent tumors, including, but not limited to, colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. Thus, in preferred embodiments IL17RLP polynucleotides or polypeptides of the invention are used to treat, prevent, and/or diagnose autoimmune diseases and/or inhibit the growth, progression, and/or metastasis of cancers, including, but not limited to, those cancers disclosed herein, such as, for example, lymphocytic leukemias (including, for example, MLL and chronic lymphocytic leukemia (CLL)) and follicular lymphomas. In another embodiment IL17RLP polynucleotides or polypeptides of the invention are used to activate, differentiate or proliferate cancerous cells or tissue (e.g., B cell lineage related cancers (e.g., CLL and MLL), lymphocytic leukemia, or lymphoma) and thereby render the cells more vulnerable to cancer therapy (e.g., chemotherapy or radiation therapy).

Moreover, in other embodiments, IL17RLP polynucleotides or polypeptides of the invention are used to inhibit the growth, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia. Thus, in preferred embodiments IL17RLP polynucleotides or polypeptides of the invention are used to treat, prevent, and/or diagnose the diseases and disorders listed above.

In preferred embodiments, IL17RLP polypeptides of the invention inhibit the growth of human histiocytic lymphoma U-937 cells in a dose-dependent manner. In additional preferred embodiments, IL17RLP polypeptides of the invention inhibit the growth of PC-3 cells, HT-29 cells, HeLa cells, MCF-7 cells, and A293 cells. In highly preferred embodiments, IL17RLP polynucleotides or polypeptides of the invention are used to inhibit growth, progression, and/or metastasis of prostate cancer, colon cancer, cervical carcinoma, and breast carcinoma.

Polynucleotides and/or polypeptides of the invention and/or agonists and/or antagonists thereof are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures). Polynucleotides and/or polypeptides of the invention and/or agonists and/or antagonists thereof are also useful as an adjuvant to enhance immune responsiveness to specific antigen, anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

Formulations

The IL17RLP polypeptide composition will be formulated and dosed in a fashion consistent with good medical practice, taking into account the clinical condition of the individual patient (especially the side effects of treatment with IL17RLP polypeptide alone), the site of delivery of the IL17RLP polypeptide composition, the method of administration, the scheduling of administration, and other factors known to practitioners. The "effective amount" of IL17RLP polypeptide for purposes herein is thus determined by such considerations.

As a general proposition, the total pharmaceutically effective amount of IL17RLP polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the IL17RLP polypeptide is typically administered at a dose rate of about 1 µg/kg/hour to about 50 µg/kg/hour, either by IL-4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Effective dosages of the compositions of the present invention to be administered may be determined through procedures well known to those in the art which address such parameters as biological half-life, bioavailability, and toxicity. Such determination is well within the capability of those skilled in the art, especially in light of the detailed disclosure provided herein.

Bioexposure of an organism to IL17RLP polypeptide during therapy may also play an important role in determining a therapeutically and/or pharmacologically effective dosing regime. Variations of dosing such as repeated administrations of a relatively low dose of IL17RLP polypeptide for a relatively long period of time may have an effect which is therapeutically and/or pharmacologically distinguishable from that achieved with repeated administrations of a relatively high dose of IL17RLP for a relatively short period of time.

Using the equivalent surface area dosage conversion factors supplied by Freireich, E. J., et al. (*Cancer Chemotherapy Reports* 50(4):219-44 (1966)), one of ordinary skill in the art is able to conveniently convert data obtained from the use of IL17RLP in a given experimental system into an accurate estimation of a pharmaceutically effective amount of IL17RLP polypeptide to be administered per dose in another experimental system. Experimental data obtained through the administration of IL17RLP in mice may converted through the conversion factors supplied by Freireich, et al., to accurate estimates of pharmaceutically effective doses of IL17RLP in rat, monkey, dog, and human. The following conversion table (Table III) is a summary of the data provided by Freireich, et al. Table III gives approximate factors for converting doses expressed in terms of mg/kg from one species to an equivalent surface area dose expressed as mg/kg in another species tabulated.

TABLE III

Equivalent Surface Area Dosage Conversion Factors.

| | TO | | | | |
|---|---|---|---|---|---|
| FROM | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 5/3 | 1 | 1/2 |
| Human | 12 | 7 | 3 | 2 | 1 |

Thus, for example, using the conversion factors provided in Table III, a dose of 50 mg/kg in the mouse converts to an appropriate dose of 123 mg/kg in the monkey because (50 mg/kg)×(1/4)=12.5 mg/kg. As an additional example, doses of 0.02, 0.08, 0.8, 2, and 8 mg/kg in the mouse equate to effect doses of 1.667 micrograms/kg, 6.67 micrograms/kg, 66.7 micrograms/kg, 166.7 micrograms/kg, and 0.667 mg/kg, respectively, in the human.

Pharmaceutical compositions containing the IL17RLP of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can be employed as liquid carriers, particularly for injectable solutions. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

The term "parenteral" as used herein refers to modes of administration which include intravenous, intramuscular, intraperitoneal, intrasternal, subcutaneous and intraarticular injection and infusion.

In a preferred embodiment, IL17RLP compositions of the invention (including polypeptides, polynucleotides, and antibodies, and agonists and/or antagonists thereof) are administered subcutaneously.

In another preferred embodiment, IL17RLP compositions of the invention (including polypeptides, polynucleotides, and antibodies, and agonists and/or antagonists thereof) are administered intravenously.

The IL17RLP polypeptide is also suitably administered by sustained-release systems. Suitable examples of sustained-release compositions include semi-permeable polymer matrices in the form of shaped articles, e.g., films, or mirocapsules, suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U., et al, *Biopolymers* 22:547-556 (1983)), poly (2-hydroxyethyl methacrylate; Langer, R., et al, *J. Biomed Mater. Res.* 15:167-277 (1981), and Langer, R., *Chem. Tech* 12:98-105 (1982)), ethylene vinyl acetate (Langer, R., et al, Id) or poly-D-(−)-3-hydroxybutyric acid (EP 133,988). Sustained-release IL17RLP polypeptide compositions also include liposomally entrapped IL17RLP polypeptide. Liposomes containing IL17RLP polypeptide are prepared by methods known in the art (DE 3,218,121; Epstein, et al, *Proc. Natl Acad. Sci.* (USA) 82:3688-3692 (1985); Hwang, et al, *Proc. Natl. Acad Sci* (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324). Ordinarily, the liposomes are of the small (about 200-800 Angstroms) unilamellar type in which the lipid content is greater than about 30 mol. percent cholesterol, the selected proportion being adjusted for the optimal IL17RLP polypeptide therapy.

In another embodiment sustained release compositions of the invention include crystal formulations known in the art.

In yet an additional embodiment, the compositions of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527-1533 (1990)).

For parenteral administration, in one embodiment, the IL17RLP polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the IL17RLP polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The IL17RLP polypeptide is typically formulated in such vehicles at a concentration of about 0.1 mg/ml to 100 mg/ml, preferably 1-10 mg/ml, at a pH of about 3 to 8. It will be understood that the use of certain of the foregoing excipients, carriers, or stabilizers will result in the formation of IL17RLP polypeptide salts.

IL17RLP polypeptide to be used for therapeutic administration must be sterile. Sterility is readily accomplished by filtration through sterile filtration membranes (e.g., 0.2 micron membranes). Therapeutic IL17RLP polypeptide compositions generally are placed into a container having a sterile access port, for example, an intravenous solution bag or vial having a stopper pierceable by a hypodermic injection needle.

IL17RLP polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous IL17RLP polypeptide solution, and the resulting mixture is lyophilized. The infusion solution is prepared by reconstituting the lyophilized IL17RLP polypeptide using bacteriostatic water-for-injection (WFI).

Alternatively, IL17RLP polypeptide is stored in single dose containers in lyophilized form. The infusion selection is reconstituted using a sterile carrier for injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The compositions of the invention may be administered alone or in combination with other adjuvants. Adjuvants that may be administered with the compositions of the invention include, but are not limited to, alum, alum plus deoxycholate (ImmunoAg), MTP-PE (Biocine Corp.), QS21 (GENENTECH™, Inc.), BCG, and MPL. In a specific embodiment, compositions of the invention are administered in combination with alum. In another specific embodiment, compositions of the invention are administered in combination with QS-21. Further adjuvants that may be administered with the compositions of the invention include, but are not limited to, Monophosphoryl lipid immunomodulator, AdjuVax 100a, QS-21, QS-18, CRL 1005, Aluminum salts, MF-59, and Virosomal adjuvant technology. Vaccines that may be administered with the compositions of the invention include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis, and/or PNEUMOVAX-23™. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In another specific embodiment, compositions of the invention are used in combination with PNEUMOVAX-23" to treat, prevent, and/or diagnose infection and/or any disease, disorder, and/or condition associated therewith. In one embodiment, compositions of the invention are used in combination with PNEUMOVAX-23™ to treat, prevent, and/or diagnose any Gram positive bacterial infection and/or any disease, disorder, and/or condition associated therewith. In another embodiment, compositions of the invention are used in combination with PNEUMOVAX-23™ to treat, prevent, and/or diagnose infection and/or any disease, disorder, and/or condition associated with one or more members of the genus *Enterococcus* and/or the genus *Streptococcus*. In another embodiment, compositions of the invention are used in any combination with PNEUMOVAX-23" to treat, prevent, and/or diagnose infection and/or any disease, disorder, and/or condition associated with one or more members of the Group B streptococci. In another embodiment, compositions of the invention are used in combination with PNEUMOVAX-23™ to treat, prevent, and/or diagnose infection and/or any disease, disorder, and/or condition associated with *Streptococcus pneumoniae*.

The compositions of the invention may be administered alone or in combination with other therapeutic agents, including but not limited to, chemotherapeutic agents, antibiotics, antivirals, steroidal and non-steroidal anti-inflammatories, conventional immunotherapeutic agents and cytokines. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with one or more members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911), APRIL (I. Exp. Med. 188(6):1185-1190), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12.

In a preferred embodiment, the compositions of the invention are administered in combination with CD40 ligand (CD40L), a soluble form of CD40L (e.g., AVREND™), bioloigically active fragments, variants, or derivatives of CD40L, anti-CD40L antibodies (e.g., agonistic or antagonistic antibodies), and/or anti-CD40 antibodies (e.g, agonistic or antagonistic antibodies).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPEVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carinii* pneumonia infection. In another specific embodiment, compositions of the invention are used in any combination with ESONIAZID™, RIFAMPIN™, PYRAZINAMIDE™, and/or ETHAMBUTOL™ to prophylactically treat, prevent, and/or diagnose an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, compositions of the invention are administered in combination with immunosuppressants. Immunosuppressants preparations that may be administered with the compositions of the invention include, but are not limited to, ORTHOCLONE™ (0KT3), SANDIMMUNE™/ NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, compositions of the invention are administered in combination with CHOP (cyclophosphamide, doxorubicin, vincristine, and prednisone) or any combination of the components of CHOP. In another embodiment, compositions of the invention are administered in combination with Rituximab. In a further embodiment, compositions of the invention are administered with Rituxmab and CHOP, or Rituxmab and any combination of the components of CHOP.

In an additional embodiment, the compositions of the invention are administered in combination with cytokines. Cytokines that may be administered with the compositions of the invention include, but are not limited to, GM-CSF, G-CSF, IL2, IL3, IL4, 115, IL6, IL7, IL 10, IL12, IL13, IL15, IL17, IL19, IL20, IL21, IL22, anti-CD40, CD40L, IFN-alpha, IFN-beta, IFN-gamma, TNF-alpha, and TNF-beta. In another embodiment, compositions of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, and IL-22.

In an additional embodiment, the compositions of the invention are administered with a chemokine. In another embodiment, the compositions of the invention are administered with chemokine beta-8, chemokine beta-1, and/or macrophage inflammatory protein-4. In a preferred embodiment, the compositions of the invention are administered with chemokine beta-8.

In an additional embodiment, the compositions of the invention are administered in combination with an IL-4 antagonist. IL-4 antagonists that may be administered with the compositions of the invention include, but are not limited to: soluble IL-4 receptor polypeptides, multimeric forms of soluble IL-4 receptor polypeptides; anti-IL-4 receptor antibodies that bind the IL-4 receptor without transducing the biological signal elicited by IL-4, anti-IL4 antibodies that block binding of IL-4 to one or more IL-4 receptors, and muteins of IL-4 that bind IL-4 receptors but do not transduce the biological signal elicited by IL-4. Preferably, the antibodies employed according to this method are monoclonal antibodies (including antibody fragments, such as, for example, those described herein).

In an additional embodiment, the compositions of the invention are administered in combination with hematopoietic growth factors. Hematopoietic growth factors that may be administered with the compositions of the invention include, but are not limited to, LEUKINE™ (SARGRAMOSTIM™) and NEUPOGEN™ (FELGRASTIM™).

In an additional embodiment, the compositions of the invention are administered in combination with fibroblast growth factors. Fibroblast growth factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

Additionally, the compositions of the invention may be administered alone or in combination with other therapeutic regimens, including but not limited to, radiation therapy. Such combinatorial therapy may be administered sequentially and/or concomitantly.

Agonists and Antagonists—Assays and Molecules

The invention also provides a method of screening compounds to identify those which enhance or block the action of IL17RLP on cells, such as its interaction with IL17RLP-binding molecules such as ligand molecules. An agonist is a compound which increases the natural biological functions of IL17RLP or which functions in a manner similar to IL17RLP, while antagonists decrease or eliminate such functions.

In another aspect of this embodiment the invention provides a method for identifying a ligand protein which binds specifically to a IL17RLP polypeptide. For example, a cellular compartment, such as a membrane or a preparation thereof, may be prepared from a cell that expresses a molecule that binds IL17RLP. The preparation is incubated with labeled IL17RLP and complexes of IL17RLP bound to the ligand or other binding protein are isolated and characterized according to routine methods known in the art. Alternatively, the IL17RLP polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds IL17RLP, such as a molecule of a signaling or regulatory pathway modulated by IL17RLP. The preparation is incubated with labeled IL17RLP in the absence or the presence of a candidate molecule which may be a IL17RLP agonist or antagonist. The ability of the candidate molecule to bind the binding molecule is reflected in decreased binding of the labeled ligand. Molecules which bind gratuitously, i.e., without inducing the effects of IL17RLP on binding the IL17RLP binding molecule, are most likely to be good antagonists. Molecules that bind well and elicit effects that are the same as or closely related to IL17RLP are agonists.

IL17RLP-like effects of potential agonists and antagonists may by measured, for instance, by determining activity of a second messenger system following interaction of the candidate molecule with a cell or appropriate cell preparation, and comparing the effect with that of IL17RLP or molecules that elicit the same effects as IL17RLP. Second messenger systems that may be useful in this regard include but are not limited to AMP guanylate cyclase, ion channel or phosphoinositide hydrolysis second messenger systems.

Another example of an assay for IL17RLP antagonists is a competitive assay that combines an IL17RLP ligand and a potential antagonist with membrane-bound IL17RLP receptor molecules or recombinant IL17RLP receptor molecules under appropriate conditions for a competitive inhibition assay. The IL17RLP ligand can be labeled, such as by radioactivity, such that the number of IL17RLP ligand molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, without inducing IL17RLP-induced activities, thereby preventing the action of IL17RLP by excluding the IL17RLP ligand from binding.

Other potential antagonists include antisense molecules. Antisense technology can be used to control gene expression through antisense DNA or RNA or through triple-helix formation. Antisense techniques are discussed in a number of studies (for example, Okano, J. Neurochem. 56:560 (1991); "Oligodeoxynucleotides as Antisense Inhibitors of Gene Expression." CRC Press, Boca Raton, Fla. (1988)). Triple helix formation is discussed in a number of studies, as well (for instance, Lee, et al., Nucleic Acids Research 6:3073 (1979); Cooney, et al., Science 241:456 (1988); Dervan, et al., Science 251:1360 (1991)). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of IL17RLP. The antisense RNA oligonucleotide hybridizes to the mRNA in vivo and blocks translation of the mRNA molecule into IL17RLP polypeptide. The oligonucleotides described above can also be delivered to cells such that the antisense RNA or DNA may be expressed in vivo to inhibit production of IL17RLP protein. The oligonucleotides described above can also be delivered to cells such that the antisense RNA or DNA may be expressed in vivo to inhibit production of IL17RLP.

In one embodiment, the IL17RLP antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the IL17RLP antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding IL17RLP, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature 29:304-310 (1981), the promoter contained in the 3' long terminal repeat of Rous sarcoma virus (Yamamoto et al., Cell 22:787-797 (1980), the herpes thymidine promoter (Wagner et al., Proc. Natl. Acad. Sci. U.S.A. 78:1441-1445 (1981), the regulatory sequences of the metallothionein gene (Brinster, et al., Nature 296:39-42 (1982)), etc.

The antisense nucleic acids of the invention comprise a sequence complementary to at least a portion of an RNA transcript of an IL17RLP gene. However, absolute complementarity, although preferred, is not required. A sequence "complementary to at least a portion of an RNA," referred to herein, means a sequence having sufficient complementarility to be able to hybridize with the RNA, forming a stable duplex; in the case of double stranded IL17RLP antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a IL17RLP RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of IL17RLP could be used in an antisense approach to inhibit translation of endogenous IL17RLP mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of IL17RLP mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., Proc. Natl. Acad. Sci. 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958-976 (1988)) or intercalating agents. (See, e.g., Zon, Pharm. Res. 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an alpha-anomeric oligonucleotide. An alpha-anomeric oligonucleotide forms specific double-stranded hybrids with complementary RNA in which, contrary to the usual beta-units, the strands run parallel to each other (Gautier et al., Nucl. Acids Res. 15:6625-6641 (1987)). The oligonucleotide is a 2-0-methylribonucleotide (Inoue et al., Nucl. Acids Res. 15:6131-6148 (1987)), or a chimeric RNA-DNA analogue (Inoue et al., FEBS Lett. 215:327-330 (1997)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448-7451 (1988)), etc.

While antisense nucleotides complementary to the IL17RLP coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science 247:1222-1225 (1990). While ribozymes that cleave mRNA at site specific recognition sequences can be used to destroy IL17RLP mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585-591 (1988). There are numerous potential hammerhead ribozyme cleavage sites within the nucleotide sequence of IL17RLP. Preferably, the ribozyme is engineered so that the cleavage recognition site is located near the 5' end of the IL17RLP mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express IL17RLP in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous IL17RLP messages and inhibit translation. Since ribozymes unlike antisense molecules, are catalytic, a lower intracellular concentration is required for efficiency.

Endogenous gene expression can also be reduced by inactivating or "knocking out" the IL17RLP gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In other embodiments, antagonists according to the present invention include soluble forms of IL17RLP (e.g., the extracellular domain of IL17RLP). Such soluble forms of the IL17RLP, which may be naturally occurring or synthetic, antagonize IL17RLP-mediated signaling by competing with native IL17RLP for binding to IL17RLP ligands (e.g., IL20 (See, International Application No. US98/14609)), and/or by forming a multimer that may or may not be capable of binding the ligand, but which is incapable of inducing signal transduction. Preferably, these antagonists inhibit IL17RLP-mediated stimulation of lymphocyte (e.g., T or B cell) proliferation, differentiation, and/or activation. Antagonists of the present invention also include, for example, anti-IL17RLP antibodies IL17RLP-Fc fusion proteins.

Antagonists of the present invention also include antibodies specific for IL17RLP polypeptides of the invention. Antibodies according to the present invention may be prepared by any of a variety of standard methods using IL17RLP immunogens of the present invention. As indicated, such IL17RLP immunogens include the complete IL17RLP polypeptides depicted in SEQ ED NO:2 and SEQ ED NO:18 (which may or may not include the leader sequence) and IL17RLP polypeptide fragments comprising, for example, the extracellular domain.

Polyclonal and monoclonal antibody agonists or antagonists according to the present invention can be raised according to the methods disclosed in Tartaglia and Goeddel, J. Biol. Chem. 267(7):4304-4307 (1992)); Tartaglia et al., *Cell* 73:213-216 (1993)), and PCT Application WO 94/09137 and are preferably specific to (i.e., bind uniquely to polypeptides of the invention having the amino acid sequence of SEQ ID NO:2. The term "antibody" (Ab) or "monoclonal antibody" (mAb) as used herein is meant to include intact molecules as well as fragments thereof (such as, for example, Fab and F(ab') fragments) which are capable of binding an antigen. Fab, Fab' and F(ab') fragments lack the Fc fragment intact antibody, clear more rapidly from the circulation, and may have less non-specific tissue binding of an intact antibody (Wahl et al., *J. Nucl. Med,* 24:316-325 (1983)).

In a preferred method, antibodies according to the present invention are mAbs. Such mAbs can be prepared using hybridoma technology (Kohler and Millstein, *Nature* 256:495-497 (1975) and U.S. Pat. No. 4,376,110; Harlow et al., *Antibodies*: A Laboratory Manual, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Proteins and other compounds which bind the IL17RLP domains are also candidate agonists and antagonists according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, *Cell* 75:791-803 (1993); Zervos et al., *Cell* 72:223-232 (1993)). Preferably, the yeast two-hybrid system is used according to the present invention to capture compounds which bind to the ligand binding domain, extracellular, intracellular, and transmembrane domains of IL17RLP. Such compounds are good candidate agonists and antagonists of the present invention.

For example, using the two-hybrid assay described above, the extracellular or intracellular domain of the IL17RLP receptor, or a portion thereof, may be used to identify cellular proteins which interact with the IL17RLP receptor in vivo. Such an assay may also be used to identify ligands with potential agonistic or antagonistic activity of IL17RLP receptor function. This screening assay has previously been used to identify protein which interact with the cytoplasmic domain of the murine TNF-RII and led to the identification of two receptor associated proteins. Rothe et al., *Cell* 78:681 (1994). Such proteins and amino acid sequences which bind to the cytoplasmic domain of the IL17RLP are good candidate agonists and/or antagonists of the present invention.

Other screening techniques include the use of cells which express the polypeptide of the present invention (for example, transfected CHO cells) in a system which measures extracellular changes caused by receptor activation, for example, as described in *Science,* 246:181-296 (1989). In another example, potential agonists or antagonists may be contacted with a cell which expresses the polypeptide of the present invention and a second messenger response, e.g., signal transduction may be measured to determine whether the potential antagonist or agonist is effective.

Agonists according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and alpha- and/or beta-amyloid peptide. (*Science* 267: 1457-1458 (1995)).

Preferred agonists are fragments of IL7RLP polypeptides of the invention which stimulate lymphocyte (e.g., T or B cell) proliferation, differentiation and/or activation. Further preferred agonists include polyclonal and monoclonal antibodies raised against the IL17RLP polypeptides of the invention, or a fragment thereof. Such agonist antibodies raised against a TNF-family receptor are disclosed in Tartaglia et al., *Proc. Natl. Acad Sci. USA* 88:9292-9296 (1991); and Tartaglia et al., *J. Biol. Chem.* 267:4304-4307 (1992). See, also, PCT Application WO 94/09137.

In an additional embodiment, immunoregulatory molecules such as, for example, IL2, IL3, IL4, IL5, IL6, IL7, IL10, IL12, IL13, IL15, anti-CD40, CD40L, IFN-gamma and TNF-alpha, may be used as agonists of IL17RLP polypeptides of the invention which stimulate lymphocyte (e.g., T or B cell) proliferation, differentiation and/or activation. In a specific embodiment, IL4 and/or IL10 are used to enhance the IL17RLP-mediated proliferation of T or B cells.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

In yet another embodiment of the invention, the activity of IL17RLP polypeptide can be reduced using a "dominant negative." To this end, constructs which encode defective IL17RLP polypeptide, such as, for example, mutants lacking all or a portion of any conserved domains, can be used in gene therapy approaches to diminish the activity of IL17RLP on appropriate target cells.

The agonists and antagonists may be employed in a composition with a pharmaceutically acceptable carrier, e.g., as described above.

The antagonists may be employed for instance to inhibit the activation of macrophages and their precursors, and of neutrophils, basophils, B lymphocytes and some T-cell subsets, e.g., activated and CD8 cytotoxic T cells and natural killer cells, in certain auto-immune and chronic inflammatory and infective diseases. Examples of auto-immune diseases include multiple sclerosis, and insulin-dependent diabetes. The antagonists may also be employed to treat infectious diseases including silicosis, sarcoidosis, idiopathic pulmonary fibrosis by preventing the activation of mononuclear phagocytes. They may also be employed to treat idiopathic hyper-eosinophilic syndrome by preventing eosinophil production. Antagonists may also be employed to treat rheumatoid arthritis by preventing the activation of monocytes in the synovial fluid in the joints of patients. Monocyte activation plays a significant role in the pathogenesis of both degenerative and inflammatory arthropathies. The antagonists may be employed to interfere with the deleterious cascades attributed primarily to IL-1 and TNF, which prevents the biosynthesis of other inflammatory cytokines. In this way, the antagonists may be employed to prevent inflammation. Antibodies against IL17RLP may be employed to bind to and inhibit IL17RLP activity to treat such conditions described above. Any of the above antagonists may be employed in a composition with a pharmaceutically acceptable carrier, e.g., as hereinafter described.

Gene Mapping (Chromosome Assays)

The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a IL17RLP protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15-25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Fluorescence in situ hybridization ("FISH") of a cDNA clone to a metaphase chromosomal spread can be used to provide a precise chromosomal location in one step. This technique can be used with probes from the cDNA as short as 50 or 60 bp (for a review of this technique, see Verma, et al. *Human Chromosomes: A Manual Of Basic Techniques*, Pergamon Press, New York (1988)).

Once a sequence has been mapped to a precise chromosomal location, the physical position of the sequence on the chromosome can be correlated with genetic map data. Such data are found, for example, on the World Wide Web (McKusick, V. *Mendelian Inheritance In Man*, available on-line through Johns Hopkins University, Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Utilizing the techniques described above, the chromosomal location of IL17RLP was determined with high confidence using a combination of somatic cell hybrids and radiation hybrids to chromosome position 3p21.1. It is noted that several chemokine receptors and trypsin inhibitors have been mapped in the 3p21.1, 3p21.2, and 3p21 regions.

Binding Peptides and Other Molecules

The invention also encompasses screening methods for identifying polypeptides and nonpolypeptides that bind IL17RLP polypeptides, and the IL17RLP binding molecules identified thereby. These binding molecules are useful, for example, as agonists and antagonists of the IL17RLP polypeptides. Such agonists and antagonists can be used, in accordance with the invention, in the therapeutic embodiments described in detail, below.

This method comprises the steps of:

contacting IL17RLP polypeptides or IL17RLP-like polypeptides with a plurality of molecules; and identifying a molecule that binds the IL17RLP polypeptides or IL17RLP-like polypeptides.

The step of contacting the IL17RLP polypeptides or IL17RLP-like polypeptides with the plurality of molecules may be effected in a number of ways. For example, one may contemplate immobilizing the IL17RLP polypeptides or IL17RLP-like polypeptides on a solid support and bringing a solution of the plurality of molecules in contact with the immobilized IL17RLP polypeptides or IL17RLP-like polypeptides. Such a procedure would be akin to an affinity chromatographic process, with the affinity matrix being comprised of the immobilized IL17RLP polypeptides or IL17RLP-like polypeptides. The molecules having a selective affinity for the IL17RLP polypeptides or IL17RLP-like polypeptides can then be purified by affinity selection. The nature of the solid support, process for attachment of the IL17RLP polypeptides or IL17RLP-like polypeptides to the solid support, solvent, and conditions of the affinity isolation or selection are largely conventional and well known to those of ordinary skill in the art.

Alternatively, one may also separate a plurality of polypeptides into substantially separate fractions comprising a subset of or individual polypeptides. For instance, one can separate the plurality of polypeptides by gel electrophoresis, column chromatography, or like method known to those of ordinary skill for the separation of polypeptides. The individual polypeptides can also be produced by a transformed host cell in such a way as to be expressed on or about its outer surface (e.g., a recombinant phage). Individual isolates can then be "probed" by the IL17RLP polypeptides or IL17RLP-like polypeptides, optionally in the presence of an inducer should one be required for expression, to determine if any selective affinity interaction takes place between the IL17RLP polypeptides or IL17RLP-like polypeptides and the individual clone. Prior to contacting the IL17RLP polypeptides or IL17RLP-like polypeptides with each fraction comprising individual polypeptides, the polypeptides could first be transferred to a solid support for additional convenience. Such a solid support may simply be a piece of filter membrane, such as one made of nitrocellulose or nylon. In this manner, positive clones could be identified from a collection of transformed host cells of an expression library, which harbor a DNA construct encoding a polypeptide having a selective affinity for IL17RLP polypeptides or IL17RLP-like polypeptides. Furthermore, the amino acid sequence of the polypeptide having a selective affinity for the IL17RLP polypeptides or IL17RLP-like polypeptides can be determined directly by conventional means or the coding sequence of the DNA encoding the polypeptide can frequently be determined more conveniently. The primary sequence can then be deduced from the corresponding DNA sequence. If the amino acid sequence is to be determined from the polypeptide itself, one may use microsequencing techniques. The sequencing technique may include mass spectroscopy.

In certain situations, it may be desirable to wash away any unbound IL17RLP polypeptides or IL17RLP-like polypeptides, or alternatively, unbound polypeptides, from a mixture of the IL17RLP polypeptides or IL17RLP-like polypeptides and the plurality of polypeptides prior to attempting to determine or to detect the presence of a selective affinity interaction. Such a wash step may be particularly desirable when the IL17RLP polypeptides or IL17RLP-like polypeptides or the plurality of polypeptides is bound to a solid support.

The plurality of molecules provided according to this method may be provided by way of diversity libraries, such as random or combinatorial peptide or nonpeptide libraries which can be screened for molecules that specifically bind IL17RLP polypeptides. Many libraries are known in the art that can be used, e.g., chemically synthesized libraries, recombinant (e.g., phage display libraries), and in vitro translation-based libraries. Examples of chemically synthesized libraries are described in Fodor et al., 1991, Science 251:767-773; Houghten et al., 1991, Nature 354:84-86; Lam et al., 1991, Nature 354:82-84; Medynski, 1994, Bio/Technology 12:709-710; Gallop et al., 1994, J. Medicinal Chemistry 37(9):1233-1251; Ohlmeyer et al., 1993, Proc. Natl. Acad. Sci. USA 90:10922-10926; Erb et al., 1994, Proc. Natl. Acad. Sci. USA 91:11422-11426; Houghten et al., 1992, Biotechniques 13:412; Jayawickreme et al., 1994, Proc. Natl. Acad. Sci. USA 91:1614-1618; Salmon et al., 1993, Proc. Natl. Acad. Sci. USA 90:11708-11712; PCT Publication No. WO 93/20242; and Brenner and Lerner, 1992, Proc. Natl. Acad. Sci. USA 89:5381-5383.

Examples of phage display libraries are described in Scott and Smith, 1990, Science 249:386-390; Devlin et al., 1990, Science, 249:404-406; Christian, R. B., et al., 1992, J. Mol. Biol. 227:711-718); Lenstra, 1992, J. Immunol. Meth. 152:149-157; Kay et al., 1993, Gene 128:59-65; and PCT Publication No. WO 94/18318 dated Aug. 18, 1994.

In vitro translation-based libraries include but are not limited to those described in PCT Publication No. WO 91/05058 dated Apr. 18, 1991; and Mattheakis et al., 1994, Proc. Natl. Acad. Sci. USA 91:9022-9026.

By way of examples of nonpeptide libraries, a benzodiazepine library (see e.g., Bunin et al., 1994, Proc. Natl. Acad. Sci. USA 91:4708-4712) can be adapted for use. Peptoid libraries (Simon et al., 1992, Proc. Natl. Acad. Sci. USA 89:9367-9371) can also be used. Another example of a library that can be used, in which the amide functionalities in peptides have been permethylated to generate a chemically transformed combinatorial library, is described by Ostresh et al. (1994, Proc. Natl. Acad. Sci. USA 91:11138-11142).

The variety of non-peptide libraries that are useful in the present invention is great For example, Ecker and Crooke, 1995, Bio/Technology 13:351-360 list benzodiazepines, hydantoins, piperazinediones, biphenyls, sugar analogs, beta-mercaptoketones, arylacetic acids, acylpiperidines, benzopyrans, cubanes, xanthines, aminimides, and oxazolones as among the chemical species that form the basis of various libraries.

Non-peptide libraries can be classified broadly into two types: decorated monomers and oligomers. Decorated monomer libraries employ a relatively simple scaffold structure upon which a variety functional groups is added. Often the scaffold will be a molecule with a known useful pharmacological activity. For example, the scaffold might be the benzodiazepine structure.

Non-peptide oligomer libraries utilize a large number of monomers that are assembled together in ways that create new shapes that depend on the order of the monomers. Among the monomer units that have been used are carbamates, pyrrolinones, and morpholinos. Peptoids, peptide-like oligomers in which the side chain is attached to the alpha amino group rather than the alpha carbon, form the basis of another version of non-peptide oligomer libraries. The first non-peptide oligomer libraries utilized a single type of monomer and thus contained a repeating backbone. Recent libraries have utilized more than one monomer, giving the libraries added flexibility.

Screening the libraries can be accomplished by any of a variety of commonly known methods. See, e.g., the following references, which disclose screening of peptide libraries: Parmley and Smith, 1989, Adv. Exp. Med. Biol. 251:215-218; Scott and Smith, 1990, Science 249:386-390; Fowlkes et al., 1992; BioTechniques 13:422-427; Oldenburg et al., 1992, Proc. Natl. Acad. Sci. USA 89:5393-5397; Yu et al., 1994, Cell 76:933-945; Staudt et al., 1988, Science 241:577-580; Bock et al., 1992, Nature 355:564-566; Tuerk et al., 1992, Proc. Natl. Acad. Sci. USA 89:6988-6992; Ellington et al., 1992, Nature 355:850-852; U.S. Pat. No. 5,096,815, U.S. Pat. No. 5,223,409, and U.S. Pat. No. 5,198,346, all to Ladner et al.; Rebar and Pabo, 1993, Science 263:671-673; and CT Publication No. WO 94/18318.

In a specific embodiment, screening to identify a molecule that binds IL17RLP polypeptides can be carried out by contacting the library members with a IL17RLP polypeptides or IL17RLP-like polypeptides immobilized on a solid phase and harvesting those library members that bind to the IL17RLP polypeptides or IL17RLP-like polypeptides. Examples of such screening methods, termed "panning" techniques are described by way of example in Parmley and Smith, 1988, Gene 73:305-318; Fowlkes et al., 1992, BioTechniques 13:422-427; PCT Publication No. WO 94/18318; and in references cited herein.

In another embodiment, the two-hybrid system for selecting interacting proteins in yeast (Fields and Song, 1989, Nature 340:245-246; Chien et al., 1991, Proc. Natl. Acad. Sci. USA 88:9578-9582) can be used to identify molecules that specifically bind to IL17RLP polypeptides or IL17RLP-like polypeptides.

Where the IL17RLP binding molecule is a polypeptide, the polypeptide can be conveniently selected from any peptide library, including random peptide libraries, combinatorial peptide libraries, or biased peptide libraries. The term "biased" is used herein to mean that the method of generating the library is manipulated so as to restrict one or more parameters that govern the diversity of the resulting collection of molecules, in this case peptides.

Thus, a truly random peptide library would generate a collection of peptides in which the probability of finding a particular amino acid at a given position of the peptide is the same for all 20 amino acids. A bias can be introduced into the library, however, by specifying, for example, that a lysine occur every fifth amino acid or that positions 4, 8, and 9 of a decapeptide library be fixed to include only arginine. Clearly, many types of biases can be contemplated, and the present invention is not restricted to any particular bias. Furthermore, the present invention contemplates specific types of peptide libraries, such as phage displayed peptide libraries and those that utilize a DNA construct comprising a lambda phage vector with a DNA insert.

As mentioned above, in the case of a IL17RLP binding molecule that is a polypeptide, the polypeptide may have about 6 to less than about 60 amino acid residues, preferably about 6 to about 10 amino acid residues, and most preferably, about 6 to about 22 amino acids. In another embodiment, a IL17RLP binding polypeptide has in the range of 15-100 amino acids, or 20-50 amino acids.

The selected IL17RLP binding polypeptide can be obtained by chemical synthesis or recombinant expression.

EXAMPLES

Having generally described the invention, the same will be more readily understood by reference to the following examples, which are provided by way of illustration and are not intended as limiting. Many of the following examples are set forth referring specifically to IL17RLP polynucleotides and polypeptides of the invention. Each example may also be practiced to generate and/or examine IL17RLP polynucleotides and/or polypeptides of the invention.

Example 1(a)

Expression and Purification of "His-Tagged" IL17RLP in E. coli

The bacterial expression vector pQE9 (pD10) is used for bacterial expression in this example. (QIAGEN, Inc., 9259 Eton Avenue, Chatsworth, Calif., 91311). pQE9 encodes ampicillin antibiotic resistance ("Ampr") and contains a bacterial origin of replication ("ori"), an WIG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the amino terminus of that polypeptide.

The DNA sequence encoding the desired portion of the IL17RLP protein comprising the extracellular domain of the IL17RLP amino acid sequence is amplified from the deposited cDNA clone using PCR oligonucleotide primers which anneal to the amino terminal sequences of the desired portion of the IL17RLP protein and to sequences in the deposited construct 3' to the cDNA coding sequence. Additional nucleotides containing restriction sites to facilitate cloning in the pQE9 vector are added to the 5' and 3' primer sequences, respectively.

For cloning the extracellular domain of the IL17RLP protein, the 5' primer has the sequence 5' CGC CCATGG CCG ACC GTT CAA TGT GGC TCT GAA AC 3' (SEQ ID NO:6) containing the underlined Nco I restriction site followed by 26 nucleotides of the amino terminal coding sequence of the mature IL17RLP sequence in SEQ ID NO:2. One of ordinary skill in the art would appreciate, of course, that the point in the protein coding sequence where the 5' primer begins may be varied to amplify a DNA segment encoding any desired portion of the complete IL17RLP protein shorter or longer than the extracellular domain of the protein. The 3' primer has the sequence 5' CGC AAGCTT CCA GCC TCC CGG CTT GC 3' (SEQ ID NO:7) containing the underlined Hind III restriction site followed by 17 nucleotides complementary to the 3' end of the coding sequence of the IL17RLP DNA sequence in FIGS. 1A, 1B, and 1C.

The amplified IL17RLP DNA fragment and the vector pQE9 are digested with Nco I and Hind III and the digested DNAs are then ligated together. Insertion of the IL17RLP DNA into the restricted pQE9 vector places the IL17RLP protein coding region downstream from the IPTG-inducible promoter and in-frame with an initiating AUG and the six histidine codons.

The ligation mixture is transformed into competent E coif cells using standard procedures such as those described by Sambrook and colleagues (Molecular Cloning: a Laboratory Manual, 2nd Ed.; Cold Spring Harbor Laboratory Press, Cold Spring Harbor, N.Y. (1989)). E. coli strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing IL17RLP protein, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-β-D-thiogalactopyranoside ("IPTG") is then added to a final concentration of 1 mM to induce transcription from the lac repressor sensitive promoter, by inactivating the lad repressor. Cells subsequently are incubated further for 3 to 4 hours. Cells then are harvested by centrifugation.

The cells are then stirred for 3-4 hours at 4° C. in 6M guanidine-HCl, pH 8. The cell debris is removed by centrifugation, and the supernatant containing the IL17RLP is loaded onto a nickel-nitrilo-tri-acetic acid ("Ni-NTA") affinity resin column (QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the IL17RLP is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Immidazole is removed by a final dialyzing step against PBS or 50 mM sodium acetate pH 6 buffer plus 200 mM NaCl. The purified protein is stored at 4° C. or frozen at −80° C.

The following alternative method may be used to purify IL17RLP expressed in *E. coli* when it is present in the form of inclusion bodies. Unless otherwise specified, all of the following steps are conducted at 4-10° C.

Upon completion of the production phase of the *E. coli* fermentation, the cell culture is cooled to 4-10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfluidics, Corp. or APV Gaulin, Inc.) twice at 4000-6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2-4 hours. After 7000×g centrifugation for 15 min., the pellet is discarded and the IL17RLP polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded IL17RLP polypeptide solution, a previously prepared tangential filtration unit equipped with 0.16 µm membrane filter with appropriate surface area (e.g., Filtron), equilibrated with 40 mM sodium acetate, pH 6.0 is employed. The filtered sample is loaded onto a cation exchange resin (e.g., Poros HS-50, Perspective Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the IL17RLP polypeptide are then pooled and mixed with 4 volumes of water. The diluted sample is then loaded onto a previously prepared set of tandem columns of strong anion (Poros HQ-50, Perspective Biosystems) and weak anion (Poros CM-20, Perspective Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the IL17RLP polypeptide (determined, for instance, by 16% SDS-PAGE) are then pooled.

The resultant IL17RLP polypeptide exhibits greater than 95% purity after the above refolding and purification steps. No major contaminant bands are observed from Commassie blue stained 16% SDS-PAGE gel when 5 µg of purified protein is loaded. The purified protein is also tested for endotoxin/LPS contamination, and typically the LPS content is less than 0.1 ng/ml according to LAL assays.

Example 2

Cloning and Expression of IL17RLP Protein in a Baculovirus Expression System

In this illustrative example, the plasmid shuttle vector pA2 is used to insert the cloned DNA encoding complete protein, including its naturally associated secretory signal (leader) sequence, into a baculovirus to express the mature IL17RLP protein, using standard methods as described by Summers and colleagues (*A Manual of Methods for Baculovirus Vectors and Insect Cell Culture Procedures*, Texas Agricultural Experimental Station Bulletin No. 1555 (1987)). This expression vector contains the strong polyhedrin promoter of the *Autographa californica* nuclear polyhedrosis virus (AcMNPV) followed by convenient restriction sites such as Bam HI, Xba I and Asp 718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, by Luckow and coworkers (*Virology* 170:31-39 (1989)).

The cDNA sequence encoding the extracellular domain of the IL17RLP protein in the deposited clone, including the AUG initiation codon and the naturally associated leader sequence shown in SEQ ID NO:2, is amplified using PCR oligonucleotide primers corresponding to the 5' and 3' sequences of the gene. The 5' primer has the sequence 5' CGC GGATCC ATG TCG CTC GTG CTG CTA AGC CTG G 3' (SEQ ID NO:8) containing the underlined Bam HI restriction enzyme site, an efficient signal for initiation of translation in eukaryotic cells (Kozak, M., *J. Mol. Biol.* 196:947-950 (1987)), followed by 25 of nucleotides of the sequence of the complete IL17RLP protein shown in FIGS. 1A, 1B, and 1C, beginning with the AUG initiation codon. The 3' primer has the sequence 5' CGC GGTACC CCA GCC TCC CGG CTT GC 3' (SEQ ID NO:9) containing the underlined Asp 718 restriction site followed by 17 nucleotides complementary to the 3' noncoding sequence in FIGS. 1A, 1B, and 1C.

The amplified fragment is isolated from a 1% agarose gel using a commercially available kit ("GENECLEAN™," BIO 101 Inc., La Jolla, Calif.). The fragment then is digested with Bam HI and Asp 718 and again is purified on a 1% agarose gel. This fragment is designated herein F1.

The plasmid is digested with the restriction enzymes Bam HI and Asp 718 and optionally, can be dephosphorylated using calf intestinal phosphatase, using routine procedures known in the art. The DNA is then isolated from a 1% agarose gel using a commercially available kit ("GENECLEAN™" BIO 101 Inc., La Jolla, Calif.). This vector DNA is designated herein "V1".

Fragment F1 and the dephosphorylated plasmid V1 are ligated together with T4 DNA ligase. *E. coli* H13101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human IL17RLP gene by digesting DNA from individual colonies using Bam HI and Asp 718 and then analyzing the digestion product by gel electrophoresis. The sequence of the cloned fragment is confirmed by DNA sequencing. This plasmid is designated herein pA2IL17RLP.

Five µg of the plasmid pA2IL17RLP is co-transfected with 1.0 µg of a commercially available linearized baculovirus DNA ("BACULOGOLD™ baculovirus DNA", Pharmingen, San Diego, Calif.), using the lipofection method described by Feigner and colleaguew (*Proc. Natl. Acad. Sci. USA* 84:7413-7417 (1987)). One µg of BACULOGOLD™ virus DNA and 5 µg of the plasmid pA2IL17RLP are mixed in a sterile well of a microtiter plate containing 50 µl of serum-free Grace's medium (LIFE TECHNOLOGIES™ Inc., Gaithersburg, Md.). Afterwards, 1.0 µl LIPOFECTIN™ plus 90 µl Grace's medium are added, mixed and incubated for 15 minutes at room temperature. Then the transfection mixture is added drop-wise to Sf9 insect cells (ATCC™ CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernatant is collected and a plaque assay is performed, as described by Summers and Smith (supra). An agarose gel with "Blue Gal" (LIFE TECHNOLOGIES™ Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by LIFE TECHNOLOGIES™ Inc., Gaithersburg, page 9-10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-IL17RLP.

To verify the expression of the IL17RLP gene Sf9 cells are grown in Grace's medium supplemented with 10% heat-inactivated FBS. The cells are infected with the recombinant baculovirus V-IL17RLP at a multiplicity of infection ("MOI") of about 2. If radiolabeled proteins are desired, 6 hours later the medium is removed and is replaced with SF900 II medium minus methionine and cysteine (available from LIFE TECHNOLOGIES™ Inc., Rockville, Md.). After 42 hours, 5 µCi of $^{35}$S-methionine and 5 µCi $^{35}$S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the extracellular domain of the IL17RLP protein, and thus the cleavage point and length of the naturally associated secretory signal peptide.

Example 3

Cloning and Expression of IL17RLP in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (PHARMACIA™, Uppsala, Sweden), pRSVcat (ATCC™ 37152), pSV2dhfr (ATCC™ 37146) and pBC12M1 (ATCC™ 67109). Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS; Murphy, et al., *Biochem J.* 227:277-279 (1991); Bebbington, et al., *Bio/Technology* 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen, et al., *Mol. Cell. Biol.* 5:438-447 (1985)) plus a fragment of the CMV-enhancer (Boshart, et al., *Cell* 41:521-530 (1985)). Multiple cloning sites, e.g., with the restriction enzyme cleavage sites Bam HI, Xba I and Asp 718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pIL17RLPHA, is made by cloning a portion of the cDNA encoding the extracelluar domain of the IL17RLP protein into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson and colleagues (*Cell* 37:767 (1984)). The fusion of the HA tag to the target protein allows easy detection and recovery of the recombinant protein with an antibody that recognizes the HA epitope. pcDNAIII contains, in addition, the selectable neomycin marker.

A DNA fragment encoding the extracellular domain of the IL17RLP polypeptide is cloned into the polylinker region of the vector so that recombinant protein expression is directed by the CMV promoter. The plasmid construction strategy is as follows. The IL17RLP cDNA of the deposited clone is amplified using primers that contain convenient restriction sites, much as described above for construction of vectors for expression of IL17RLP in *E. coli*. Suitable primers include the following, which are used in this example. The 5' primer, containing the underlined Bam HI site, a Kozak sequence, an AUG start codon, and 25 nucleotides of the 5' coding region of the extracellular domain of the IL17RLP polypeptide, has the following sequence: 5' GCC GGATCC GCC ACC ATG AAC TCC TTC TCC ACA AGC GCC TTC GGT CCA GTT GCC TTC TCC CTG GGG CTG CTC CTG GTG TTG CCT GCT GCC TTC CCT GCC CCA GTA TGT CGC TCG TGC TGC TAA GCC TGG 3' (SEQ ID NO: 10). The 3' primer, containing the underlined Asp 718 and 17 of nucleotides complementary to the 3' coding sequence immediately before the stop codon, has the following sequence: 5' GGC CG GGTACCC CAG CCT CCC GGC TTG C 3' (SEQ ID NO:11).

The PCR amplified DNA fragment and the vector, pcDNAI/Amp, are digested with Bam HI and Asp 718 and then ligated. The ligation mixture is transformed into *E. coli* strain SURE (STRATAGENE™ Cloning Systems, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the fragment encoding the extracellular domain of the IL17RLP polypeptide For expression of recombinant IL17RLP, COS cells are transfected with an expression vector, as described above, using DEAE-dextran, as described, for instance, by Sambrook and coworkers (*Molecular Cloning: a Laboratory Manual*, Cold Spring Laboratory Press, Cold Spring Harbor, N.Y. (1989)). Cells are incubated under conditions for expression of IL17RLP by the vector.

Expression of the IL17RLP-HA fusion protein is detected by radiolabeling and immunoprecipitation, using methods described in, for example Harlow and colleagues (*Antibodies: A Laboratory Manual*, 2nd Ed.; Cold Spring Harbor Laboratory Press, Cold Spring Harbor, N.Y. (1988)). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson and colleagues (supra). Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of IL17RLP polypeptide. Plasmid pC4 is a derivative of the plasmid pSV2-dhfr (ATCC™ Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, LIFE TECHNOLOGIES™) supplemented with the chemotherapeutic agent methotrexate. The amplification of the DHFR genes in cells resistant to methotrexate (MTX) has been well documented (see, e.g., Alt, F. W., et al., *J. Biol. Chem.* 253:1357-1370 (1978); Hamlin, J. L. and Ma, C. *Biochem. et Biophys. Acta,* 1097:107-143 (1990); Page, M. J. and Sydenham, M. A. *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Mol. Cell. Biol.* 5:438-447 (1985)) plus a fragment isolated from the enhancer of the immediate early gene of human cytomegalovirus (CMV; Boshart, et al., *Cell* 41:521-530 (1985)). Downstream of the promoter are the following single restriction enzyme cleavage sites that allow the integration of the genes: Bam HI, Xba I, and Asp 718. Behind these cloning sites the plasmid contains the 3' intron and polyadenylation site of the rat preproinsulin gene. Other high efficiency promoters can also be used for the expression, e.g., the human beta-actin promoter, the SV40 early or late promoters or the long terminal repeats from other retroviruses, e.g., HIV and HTLVI. CLONTECH™'s Tet-Off and Tet-On gene expression systems and similar systems can be used to express the IL17RLP polypeptide in a regulated way in mammalian cells (Gossen, M., and Bujard, H. *Proc. Natl. Acad. Sci. USA* 89:5547-5551 (1992)). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes Bam HI and Asp 718 and then dephosphorylated using calf intestinal phosphates by procedures known in the art. The vector is then isolated from a 1% agarose gel.

The DNA sequence encoding the extracellular domain of the IL17RLP polypeptide is amplified using PCR oligonucleotide primers corresponding to the 5' and 3' sequences of the desired portion of the gene. The 5' primer containing the underlined Bam HI site, a Kozak sequence, an AUG start codon, and 25 nucleotides of the 5' coding region of the extracellular domain of the IL17RLP polypeptide, has the following sequence: 5' CTA GCC GGATCC GCC ACC ATG TCG CTC GTG CTG CTA AGC CTG G 3' (SEQ ID NO:12). The 3' primer, containing the underlined Asp 718 and 17 of nucleotides complementary to the 3' coding sequence immediately before the stop codon as shown in FIGS. 1A, 1B, and 1C (SEQ ID NO:1), has the following sequence: 5' GGC CG GGTACCC CAG CCT CCC GGC TTG C 3' (SEQ ID NO:13).

The amplified fragment is digested with the endonucleases Bam HI and Asp 718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 µg of the plasmid pSVneo using LIPOFECTIN™ (Feigner, et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100-200 µM. Expression of the desired gene product is analyzed, for instance, by SDS-PAGE and Western blot or by reversed phase HPLC analysis.

Example 4

Tissue Distribution of IL17RLP mRNA Expression

Northern blot analysis is carried out to examine IL17RLP gene expression in human tissues, using methods described by, among others, Sambrook and colleagues (supra). A cDNA probe containing the entire nucleotide sequence of the IL17RLP protein (SEQ ID NO:1) is labeled with $^{32}P$ using the REDIPRIME™ DNA labeling system (Amersham Life Science), according to manufacturer's instructions. After labeling, the probe is purified using a CHROMA SPIN-100™ column (CLONTECH™ Laboratories, Inc.), according to manufacturer's protocol number PTI200-L The purified labeled probe is then used to examine various human tissues for IL17RLP mRNA.

Multiple Tissue Northern (MTN) blots containing various human tissues (H) or human immune system tissues (IM) are obtained from CLONTECH™ and are examined with the labeled probe using EXPRESSHYB™ hybridization solution (CLONTECH™) according to manufacturer's protocol number PT1190-1. Following hybridization and washing, the blots are mounted and exposed to film at −70° C. overnight, and films developed according to standard procedures.

In Northern blot experiments performed essentially as described above, expression of the IL17RLP transcript was detected in pancreas, kidney, liver, and fetal liver. Lower expression was also observed in other endocrine organs such as testis, colon, and small intestine. See also, Example 12.

Example 5

Blocking Effect of Soluble IL17RLP on
IL-20-Induced Neutrophil Migration and
Macrophage Activation in the Mouse Peritoneum An analysis of the use of soluble IL17RLP ("sIL17RLP") as an anti-inflammatory agent is performed through the use of a human IL-20 ("hIL-20")-induced inflammation model in mice. Our recent experiment indicate that, when given intraperitoneally, hIL-20 induces a significant migration of neutrophils into the mouse peritoneum at 4 hours after injection as observed by both FACS and Wright-Giemsa stained cytospin analysis. In addition, after hIL-20 challenge, peritoneal macrophages show activation signals by morphology. Soluble sIL17RLP is expected to bind hIL-20 and inhibit hIL-20-induced neutrophil migration and macrophage activation.

Initiation of the inflammation condition is induced by a single intraperitoneal injection of high (25 µg) and low doses (1-10 µg) of hIL-20 into BALB/c mice. Groups of 4 mice receive either 0.1 to 10 mg/kg of sIL17RLP, soluble human IL-17 receptor or negative control human receptor, intraperitoneally once between 0 and 2 hours prior to hIL-20 injection. The effect of sIL17RLP on neutrophil migration and macrophage activation in the peritoneum is analyzed at 4, 16, 24 or 48 hours by FACS and cytospin method. Briefly, for FACS analysis, collected peritoneal cells are stained with fluorescein phycoerythrin-conjugated antibodies against MHC class II (I-A/I-E) and FITC-conjugated anti-Mac-1 or anti-Gr1

(PharMingen (San Diego, Calif.)). Cells are then analyzed on a FACScan (Becton Dickinson, San Jose, Calif.), and the percentages of I-A/I-E hi+Mac-1+ macrophages and Gr1+ neutrophils are determined by two-color analysis. For cytospin method, peritoneal cells are spun down on to microscope slides and then differentiated by Wright-Giemsa staining. The percentages of activated macrophages and neutrophils are determined according to the cell morphology.

Example 6

Effect of Soluble IL17RLP on Adjuvant-Induced Arthritis

An analysis of the use of soluble IL17RLP ("sIL17RLP") to treat rheumatoid arthritis (RA) is performed through the use of an adjuvant-induced arthritis model (AIA) in rats. AIA is a well-characterized and reproducible animal model of rheumatoid arthritis, which is well known to one of ordinary skill in the art (Pearson, et al. *Ann. Rheum. Dis.* 15:379, (1956)); Pearson, et al., *Arthritis Rheum.* 2:440, (1959)). sIL17RLP is expected to bind to hIL-20 and inhibit IL-20-induced synoviocyte activation and cytokine production, which may involve in the perpetuation of chronic arthritis. Lewis rats (available from Charles River Lab, Raleigh, N.C.) are used as the common and responsive strains for adjuvant-induced arthritis in these experiments.

Initiation of the arthritis condition is induced by the intradermal injection of 0.1 ml adjuvant (5 mg/ml) into the base of the tail. Groups of 5 to 6 rats received either 0.1 to 10 mg/kg sIL17RLP or vehicle intra-articularly 10 days after the injection of adjuvant when the acute inflammation just begins. The effect of sIL17RLP on chronic arthritis is analyzed radiologically once each week between day 15-30 essentially as described by Taurog and colleagues (*J. Exp. Med.* 162:962, (1985)). Briefly, rats are anesthetized with ether or chloral hydrate and positioned so that both hind limbs are X-rayed together. The X-ray films are examined blindly using a scoring system of 0-3 for periosteal reaction, bony erosions, joint space narrowing and destruction. When there is a significant amount of joint damage in vehicle-treated rats, the animals are sacrificed. At this point, the paws are evaluated histologically for the relative degree of tissue damage and for the therapeutic effect sIL17RLP has elicited on these joints. Finally, sIL17RLP- and vehicle-treated animals undergo a clinical evaluation twice per week to assess hind paw volume using a plethysmometer system and body weight.

Alternatively, rheumatoid synoviocytes are isolated from RA patients undergoing knee or wrist synovectomy and cultured in 150 cm² flasks. Nonadherent cells are removed and adherent cells are trypsinized at confluence and passaged. Synoviocytes used between passages 3 and 8 constitute a homogenous population of fibroblast-like cells. Synoviocytes are cultured in 96-well plates in a final volume of 200 µl of the medium. Human IL-20 polypeptides (or human IL-17 as a control) are added at different concentrations to the medium at the onset of the culture. In experimental flasks, human sIL17RLP polypeptide is also added to the culture medium. Subsequently, cell-free supernatants are collected after 72 hr, and stored at −20° C. for further use in cytokine assays. Concentrations of IL-6 and IL-8 are measured by ELISA. A decrease in IL-6 and/or IL-8 levels in the culture supernatant indicates that the sIL17RLP polypeptide inhibits the IL-20-mediated increase in IL-6 and/or IL-8 production in this culture system. Consequently, sIL17RLP may be useful to treat rheumatoid arthritis and other related immunoregulatory disorders and diseases.

Example 7

Effect of Soluble IL17RLP in Treating Graft Versus Host Disease in Mice

An analysis of the use of soluble IL17RLP ("sIL17RLP") to treat graft-versus-host disease (GVHD) is performed through the use of a C57BL/6 parent into (BALB/c×C57BL/6) F1 mouse model. This parent into F1 mouse model is a well-characterized and reproducible animal model of GVHD in bone marrow transplant patients, which is well know to one of ordinary skill in the art (see, Gleichemann, et al., *Immunol. Today* 5:324, (1984)). IL17RLP is structurally related to the IL-17R which, in soluble form, has a beneficial effect on the prolongation of allograft survival in association with its inhibiting effect on alloantigen-induced lymphocyte proliferation. sIL17RLP is expected to inhibit the activation of the donor T cells to host MHC class II antigen (alloantigen) which play a crucial role in the pathogenesis of GVHD.

Initiation of the experimental GVHD condition is induced by the intravenous injection of ~1-3×10⁸ spleen cells from C57BL/6 mice into (BALB/c×C57BL/6) F1 mice (available from Jackson Lab, Bar Harbor, Me.). Groups of 6 to 8 mice received either 0.1 to 5.0 mg/kg of sIL17RLP or negative control intraperitoneally daily following the injection of spleen cells. The effect of sIL17RLP on lymphoid hypoplasia and atrophy of spleen is analyzed by FACS and histopathology at multiple time points (3-4) between days 10 and 30. Briefly, splenocytes are prepared from normal CBF1 mice, GVHD mice or sIL17RLP-treated mice, and stained with fluorescein phycoerythrin-conjugated anti-H-2 Kb, biotin-conjugated anti-14-2 Kd, and FITC-conjugated anti-CD4, anti-CD8, or anti-B220, followed by a CyChrome-conjugated avidin (PharMingen (San Diego, Calif.)). Cells are then analysis on a FACScan (Becton Dickinson, San Jose, Calif.). Recipient and donor lymphocytes are identified as H-2 Kb+Kd+ and H-1-2 Kb+ Kd− cells, respectively. Cell numbers of CD4+T, CD8+ T and B220+ B cells of recipient or donor origin are calculated from the total numbers of splenocytes recovered and the percentages of each subpopulation are determined by the three color analysis. Histological evaluation of the relative degree of tissue damage in other GVHD-associated organs (liver, skin and intestine) may be conducted after sacrificing the animals for the beneficial potential of sIL17RLP on these organs.

In addition, the effect of sIL17RLP on spontaneous proliferation and IL-2 production of host splenocytes is analyzed between day 2-10. Finally, sIL17RLP— and its negative control-treated animals undergo a clinical evaluation every other day to assess cachexia, body weight and lethality. Soluble sIL17RLP in combination therapy with immunosuppressive agents may also be examined in this GVHD murine model.

Example 8

Analysis of IL-17RLP Ligand Candidates

IL17RLP ligand candidates are screened for binding using BIACORE™ technology which enables one to monitor binding events between two or more molecules, in real time, without the use of labels. BIACORE™ technology relies on the phenomenon of surface plasmon resonance (SPR) which occurs when surface plasmon waves are excited at a metal/ liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal.

The conditioned culture supernatants from three IL-20 CHO (see copending U.S. patent application Ser. No. 09/115,832) clones (numbers 10, 16 and 22), as well as, IL-17 (purchased from R&D) were analyzed for binding to IL17-like receptors. The data indicate that compared to the negative control conditioned media (pC4 vector alone) that all clones showed greater binding. The binding was approximately 115 RU for clones 16 and 22, ~65 RU for clone 10 and ~20 RU for pC4. This binding was greater than that found for IL-17 which was ~60 RU measured at 25 ug/mL. The exact concentration of IL-20 in the culture supernatants is not known but is estimated to be comparable to IL-17, i.e., ~25 ug/mL. This result suggests that the IL-17 receptor binds both ligands, and may even bind IL-20 better.

The binding of IL-20 and IL-17 to IL-17 receptor (IL 17R-Fc) and IL17RLP fused to the human immunoglobulin domain (IL17RLP-Fc) after immobilization of the receptor on a BIACORE™ flow cell. Two CHO cell IL-20 preparations were first analyzed as they contain different N-terminal forms of the protein. IL-17 (R&D) ligand was also analyzed. The results indicate that IL-20 predominately bound to IL17RLP-Fc and to a much lesser extent to IL-17R. The dissociation of IL-20 from the IL17RLP-Fc appeared to be biphasic for both batches which might be due to the presence different N-terminally truncated forms of the protein present in both batches. In contrast, IL-17 bound almost exclusively to the IL-17R which little or no binding to IL17RLP-Fc.

Thus, these results suggest that IL-20 interacts with the IL-17 receptor and the IL17RLP described herein. As a result, IL17RLP, or soluble fragments thereof, may be useful to modulate the receptor activation pathways in which these receptors are involved. IL17RLP polypeptides of the invention may be used as an antagonist for binding IL-20 polypeptides and/or other related or unrelated polypeptides which interact with this receptor or the IL-20 ligand, e.g., IL-17. IL17RLP polypeptides of the invention may thus be useful in the diagnosis and/or treatment of immune disorders involving the IL-17 and IL17RLP molecules as known in the art and as described above.

Example 9

Gene Therapy Using the Endogenous IL17RLP Gene

Another method of gene therapy according to the present invention involves operably associating the endogenous IL17RLP sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932-8935 (1989); and Zijlstra et al., Nature 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous IL17RLP, flanking the promoter. The targeting sequence will be sufficiently near the 5' end of IL17RLP so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous IL17RLP sequence. This results in the expression of IL17RLP in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEMS pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the IL17RLP locus, plasmid pUC18 (MBI Fermentas, Amherst, N.Y.) is digested with HindIII. The CMV promoter is amplified by PCR with an XbaI site on the 5' end and a BamHI site on the 3' end. Two IL17RLP non-coding sequences are amplified via PCR: one IL17RLP non-coding sequence (IL17RLP fragment 1) is amplified with a HindIII site at the 5' end and an Xba site at the 3' end; the other IL17RLP non-coding sequence (IL17RLP fragment 2) is amplified with a BamHI site at the 5' end and a HindIII site at the 3' end. The CMV promoter and IL17RLP fragments are digested with the appropriate enzymes (CMV promoter—XbaI and BamHI; IL17RLP fragment 1-XbaI; IL17RLP fragment 2-BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C.

The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 10

Production of an Antibody

Hybridoma Technology

The antibodies of the present invention can be prepared by a variety of methods. (See, Current Protocols, Chapter 2.) As one example of such methods, cells expressing IL17RLP are administered to an animal to induce the production of sera containing polyclonal antibodies. In a preferred method, a preparation of IL17RLP protein is prepared and purified to render it substantially free of natural contaminants. Such a preparation is then introduced into an animal in order to produce polyclonal antisera of greater specific activity.

Monoclonal antibodies specific for protein IL17RLP are prepared using hybridoma technology. (Kohler et al., Nature 256:495 (1975); Kohler et al., Eur. Immunol. 6:511 (1976); Kohler et al., Eur. J. Immunol. 6:292 (1976); Hammerling et al in: Monoclonal Antibodies and T-Cell Hybridomas, Elsevier, N.Y., pp. 563-681 (1981)). In general, an animal (preferably a mouse) is immunized with IL17RLP polypeptide or, more preferably, with a secreted IL17RLP polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC™. After fusion, the resulting hybridoma cells are selectively maintained in HAT medium, and then cloned by limiting dilution as described by Wands et al. (Gastroenterology 80:225-232 (1981). The hybridoma cells obtained through such a selection are then assayed to identify clones which secrete antibodies capable of binding the IL17RLP polypeptide.

Alternatively, additional antibodies capable of binding to IL17RLP polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the IL17RLP protein-specific antibody can be blocked by IL17RLP. Such antibodies comprise anti-idiotypic antibodies to the IL17RLP protein-specific antibody and are used to immunize an animal to induce formation of further IL17RLP protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of Antibody Fragments Directed Against IL17RLP From a Library of scFvs Naturally occurring V-genes isolated from human PBLs are constructed into a library of antibody fragments which contain reactivities against IL17RLP to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing.

Example 11

Neutralization of IL17RLP/IL17RLP Ligand (e.g., IL20) Interaction with an Anti-IL17RLP Monoclonal Antibody Monoclonal antibodies are generated against IL17RLP protein according to the following method. Briefly, mice are given a subcutaneous injection (front part of the dorsum) of 50 micrograms of His-tagged IL17RLP protein produced by the method of Example 2 in 100 microliters of PBS emulsified in 100 microliters of complete Freunds adjuvant. Three additional subcutaneous injections of 25 micrograms of IL17RLP in incomplete Freunds adjuvant are given at 2-week intervals. The animals are rested for a month before they received the final intraperitoneal boost of 25 micrograms of IL17RLP in PBS. Four days later mice are sacrificed and splenocytes taken for fusion.

The process of "Fusion" is accomplished by fusing splenocytes from one spleen were with 2×10E7 P3X63Ag8.653 plasmacytoma cells using PEG 1500 (BOEHRINGER™ Mannheim), according to the manufacturer's modifications of an earlier described method. (See, Gefter, M. L., et al. *Somatic Cell Genet.* 3:231-36 (1977); BOEHRINGER™ Mannheim, PEG 1500 (Cat. No. 783641), product description.)

After fusion, the cells are resuspended in 400 ml of HAT medium supplemented with 20% FBS and 4% Hybridoma Supplement (BOEHRINGER™ Mannheim) and distributed to 96 well plates at a density of 200 microliters per well. At day 7 post-fusion, 100 microliters of medium is aspirated and replaced with 100 microliters of fresh medium. At day 14 post-fusion, the hybridomas are screened for antibody production.

Hybridoma supernatants are screened by ELISA for binding to IL17RLP protein immobilized on plates. Plates are coated with IL17RLP by overnight incubation of 100 microliters per well of IL17RLP in PBS at a concentration of 2 micrograms per ml. Hybridoma supernatants are diluted 1:10 with PBS and placed in individual wells of IL17RLP-coated plates and incubated overnight at 4° C. On the following day, the plates are washed 3 times with PBS containing 0.1% Tween-20 and developed using the anti-mouse IgG ABC system (Vector Laboratories). The color development reaction is stopped with the addition of 25 ml/well of 2M $E7SO_4$. The plates are then read at 450 nm.

Hybridoma supernatants are checked for Ig isotype using Isostrips. Cloning is done by the method of limiting dilutions on HT medium. About 3×10E6 cells in 0.9 ml of HBSS are injected in pristane-primed mice. After 7-9 days, ascitic fluid is collected using a 19 g needle. All antibodies are purified by protein G affinity chromatography using the Acta FPLC system (PHARMACIA™).

All purified monoclonal antibodies are tested for binding to different forms of IL17RLP (including His-tagged and protein produced from a baculoviral system (see Example 2)) in both Western blot analysis and ELISA. Antibodies are also tested for the ability to capture soluble IL17RLP from solution. Antibodies are tested for the ability to differentially recognize membrane-bound IL17RLP as compared to a soluble IL17RLP (e.g., an extracellular domain of IL17RLP). Antibodies are tested for the ability to neutralize IL17RLP receptor-ligand interactions.

Example 12

A Novel Cytokine Receptor-Ligand Pair: Identification, Molecular Characterization, and in Vivo Immunomodulatory Activity Cytokines are secreted regulatory peptides that mediate a wide range of biological activities by binding to specific cell surface receptors on target cells. Cytokine actions include control of cell proliferation and differentiation, regulation of hemopoiesis, immune and inflammatory responses (See e.g., Thomson, A. *The Cytokine Handbook,* 3rd Ed., Academic Press, New York, N.Y. (1998)). Cytokines are also major orchestrators of host defense processes and, as such, are involved in responses to exogenous as well as endogenous insults and in repair or restoration of tissue integrity.

Except for the presence of an N-terminal signal peptide usually required for secretion, the cytokines known thus far are members of many distinct and structurally unrelated families of molecules.

A novel homologue of Interleukin-17 ("IL-17") has been identified. (See, International Patent Application No. US98/14609; see also, Li, et al, *Proc. Natl. Acad. Sci.* 97:773-778 (2000)). IL-17 is a cytokine-inducing glycoprotein of 155 amino acids, produced predominantly by activated CD4+ T cells and double negative (CD4-CD8-) T cells exhibiting indirect proinflammatory and hematopoietic properties (See e.g., Yao, Z., et al., *J. Immunol.* 155:5483-5486 (1995); Fossiez, F., et al, *J. Exp. Med.* 183:2593-2603 (1996); Cai, X. Y., et al., *Immunol. Lett.* 62:51-58 (1998); Chabaud, M., et al, *J. Immunol.* 161:409-414 (1998); Jovanovic, D. V., et al., *J. Immunol.* 160:3513-3521 (1998)). In vivo, its expression has been reported elevated in the rheumatoid synovium, in multiple sclerosis blood and cerebrospinal fluid and in peripheral blood mononuclear cells following ischemic stroke (See e.g., Kotake, S., et al., *J. Clin. Invest* 103:1345-1352 (1999); Chabaud, M., et al., *Arthritis Rheum.* 42:963-970 (1999); Aarvak, T., et al., *Scand. J. Immunol.* 50:1-9 (1999); Matusevicius, D., et al., *Mult. Scler.* 5:101-104 (1999); Kostulas, N., et al., *Stroke* 30:2174-2179 (1999)). Is also produced by tumor-infiltrating lymphocytes and increases tumorigenicity of human cervical tumors in nude mice (See, Fridman, W. H., et al., *Res. Immunol.* 149:7-8 (1998); Tarour, E., et al., *Cancer*

*Res.* 59:3698-3704 (1999)). More recently, IL-17 has been implicated in allergic skin immune responses (See, Albanesi, C., et al., *J. Immunol.* 162:494-502 (1999)), neutrophil recruitment during airway inflammation (See, Antonysamy, M. A., et al., *Human Immunol.* 55(Suppl):1-15 (1997)), cardiac and renal allograft rejection (See, Laan, M., et al., *J. Immunol.* 162:2347-2352 (1999); Van Kooten, C., et al, *J. Am. Soc. Nephrol.* 9:1526-1534 (1998); Antonysamy, M. A., et al., *J. Immunol.* 162:577-584 (1999)) and granulopoiesis (See, Fine, J. S., et al., *J. Allergy Clin. Immunol.* 99:225 (1997); Schwarzenberger, P., et al., *J. Immunol.* 161:6383-6389 (1998)). In addition, it has been found to up-regulate nitric oxide production in human osteoarthritic cartilage and inflammatory cytokine production by rheumatoid arthritis synoviocytes (See, Attur, M. G., et al., *Arthritis Rheum.* 40:1050-1053 (1997); Amin, A. R., et al., *Curr. Opin. Rheumatol.* 10:263-268 (1998)), to stimulate osteoclastogenesis and the expression of several genes associated with inflammation and cartilage degradation in human chondrocytes (See, Lotz, M., et al., *Arthritis Rheum.* 39(Suppl.):559 (1996); Van bezooijen, R. L., et al., *J. Bone Miner. Res.* 14:1513-1521 (1999); Tali Shalom-Barak, T., et al., *J. Biol. Chem.* 173:27467-27473 (1998); Martel-Pelletier, J., et al., *Arthritis Rheum.* 42:2399-2409 (1999)), and to induce ICAM-1 expression in human bronchial epithelial cells (See, Kawaguchi, M., et al., *Cell* 46:659-667 (1986)).

Sequence and expression analysis—Full-length cDNAs for human IL-20 (SEQ ID NO:34) and IL17RLP (SEQ ID NOs:1 and 18) were identified, sequenced, and submitted to GenBank. The clones were assigned the accession numbers (AF212311) and (AF212365), respectively. DNA sequencing was performed using ABI 377 automated DNA sequencers and PE Biosystems Big Dye Terminator sequencing chemistries (Foster City, Calif.). Northern blot analysis of poly-A RNA samples was performed using CLONTECH™ (Palo Alto, Calif.) multiple tissue Northern blots. For analysis of murine IL-20 transcripts, total RNA was prepared from rodent organs, separated on agarose gels containing formamide and blotted onto Nylon filters Membranes were hybridized overnight in Hybrisol solution (Oncor), preheated to 42° C. before use, followed by two subsequent washes in 2×SSC/0.1% SDS and 0.2×SSC/0.1% SDS at the same temperature. Double-stranded cDNA probes, used at a minimum specific activity of $2 \times 10^9$ cpm/microgram, were generated by restriction digestion, $^{32}$P-labelled using the REDEPRIME™ random primer labelling system (Amersham/Arlington Heights, Ill.) and purified with NucTrap ion exchange push columns (STRATAGENE™, La Jolla, Calif.).

Mapping—The genomic position of the IL20 gene was determined with the standard G3 radiation hybrid panel (Research Genetics, Huntsville, Ala.). The panel DNAs were amplified by PCR using IL-20 gene specific primers 5'-GGC GGG CAG CAG CTG CAG GCT GAC C-3' (SEQ ID NO:19) and 5'-CTG GGC TGG CCC AGC CCC AGG AAG-3' (SEQ ID NO:20). The primers used for mapping of IL17RLPR were 5'-GAT CCT CCC GGA CTT CAA GAG GC-3' (SEQ ID NO:21) and 3'-GGA AAG GCC AGG CAG GCC TGG-3' (SEQ ID NO:22).

Antibody preparation—For bacterial production of IL-20, an open reading frame coding for the mature form of IL-20 (residues Q21-F180 of SEQ ID NO:2) as predicted by SignalP (See, Nielsen, H., et al., *Protein Eng.* 12:3-9 (1999)), was amplified by PCR and cloned as an Ndet-Asp718I restriction fragment (495-bp product) downstream of an inducible lacZ promoter. For efficient translation, the first 50 nucleotides of mature IL-20 were codon optimized for expression in *E. coli*. The primers used were: sense, 5'-GAC TCA TAT GCA GCC GCG TTC CCC GAA ATC CAA GCG TAA A-3; antisense, 5'-GAC TGG TAC CTT ATC AGA AGA TGC AGG TGC AGC-3'. The reading frame and adjacent areas were sequence confirmed following cloning. After transformation and expression in *E. coli*, IL-20 was present in the inclusion bodies. Inclusion bodies were solubilized with 4M guanidine HCl and dialyzed against 50 mM sodium acetate buffer, pH 5, containing 0.1 M NaCl. Antisera were prepared by immunizing rabbits with IL-20 (Q21-F180). The sera were used for immunoblot analysis after 1000-fold dilution.

Cell culture—In vitro cultures were grown in sterile disposable polystyrene (Corning Glass Works, Corning, N.Y.) in a humidified atmosphere with 5% $CO_2$. 293, CE-10, NIH3T3, WRL-68, Colo587, PANG-1, HeLa S3, K562, Raji and SW480 cell lines were obtained from the American Type Culture Collection (ATCC™).

Transient transfections—Plasmid DNA was transfected into 293T cells using LipofectAMINE reagent (LIFE TECHNOLOGIES™, Rockville, Md.) according to the manufacturer's instructions.

Generation of stably transfected CHO clones—The complete open reading frame of human IL-20 was amplified by PCR. The primers used were: sense, 5'-GAC TOG ATC CGC CAT CAT GGA CTG GCC TCA CAA CC-3 (SEQ ID NO:25); antisense, 5'-GAC TGG TAC CGG ATG GTC TCG GGC TGC TG-3' (SEQ ED NO:26). Full-length IL-20 was cloned as a Bam II-Asp718I restriction fragment into a CMV-Enhancer/RSV-LTR promoter-based expression vector. The clones were sequence confirmed before transfection into CHO cells. IL-20 positive CHO clones were selected by RT-PCR and amplified to 1 micromolar methotrexate. Conditioned media (CHO-5 serum-free media without methotrexate) from 7 CHO clones were analyzed for IL-20 expression by SDS-PAGE followed by silver staining. Three CHO clones with the highest expression were selected for continued amplification in the presence of 10 micromolar methotrexate.

Purification of IL-20—Four day conditioned media from IL-20 expressing clones was used for protein purification. The media was adjusted to 25 mM HEPES buffer, pH 7.2 and applied to the strong-cation exchange resin (Poros HS-50) using a BioCad 60 (PEPerseptive). The HS-50 bound material was eluted using a step gradient of NaCl in 25 mM HEPES buffer, pH 7.2 and fractions analyzed by SDS-PAGE. The 0.8M NaCl pool was applied to weak anion-exchanger (CM HyperD, BioSepra) and eluted with a NaCl gradient. The IL-20 positive fractions were pooled, subjected to size-exclusion chromatography on a Superdex 75 column (PHARMACIA™) equilibrated with PBS and pooled again. Protein concentration was determined using the BCA procedure (Pierce Chem. Co). Endotoxin was measured using the LAL assay (Cape Cod Assoc.).

Purification of epitope-tagged IL-20—For synthesis of N-terminal Flag fusion protein, the mature portion (nucleotides 105-584 of SEQ ID NO:34) coding region of IL-20 was amplified by PCR and cloned into pFLAG-CMV-I vector (SIGMA™, Saint Louis, Mo.) as an EcoRI-BamHI restriction fragment. The primers used were 5'-GCC CCG GAA TTC AAG GAG CCC CAA AAG CAA GAG G-3' (SEQ ID NO:27) (sense) and 5'-GCC CGC GGA TCC TCA GAA GAT GCA GGT GCA GCC-3' (SEQ ID NO:28) (antisense). Conditioned media from 293T cells transiently transfected with pFLAG-CMV-1:IL-20 was prepared and purified using anti-Flag affinity chromatography according to the manufacturer's instructions. Approximately 300 micrograms of purified protein was recovered from 500 ml of culture supernatant.

IL-17R and IL-17RLP Purification—The extracellular portion of each receptor was fused to a human Fc domain (heavy chain constant region of IgG1). The primers used for PCR amplification of the extracellular domain coding region of huIL-17R were 5'-GAT CGC GGA TCC GCC ATC ATG GGG GCC GCA CGC AGC CCG CCG TCC G-3' (SEQ ID NO:29) (sense) and 5'-GAT CGC GGA TCC CCG TCC GGA ATT GGT TCT GGA GTG TCT GGC ATT TCT G-3' (SEQ ID NO:30) (antisense), and 5'-GAG CGC AGA TCT GCC ACC ATG TCG CTC GTG CTG CTA AGC CTG G-3' (SEQ ID NO:31) (sense) and 5'-GGG GGG AGA TCT CCT CCC GGC TTG CTT TTG TTG TTA TC-3' (SEQ ID NO:32) (antisense) for huIL17RLP, respectively. Clones with correct insert orientation were selected by PCR screening and resequenced before use. Conditioned media from 293T cells transiently transfected with the IL17RLP (Met-(−19) through Gly-270 of SEQ ID NO:2)-Fc fusion or IL-17 receptor (Met-1 through Asp-315)-Fc were prepared. The Fc-protein was purified using a Protein A column (POROS), and approximately 150 micrograms of purified protein was recovered from 500 ml of culture supernatant.

Binding Analyses—IL-20 protein was dialyzed against 10 mM sodium acetate buffer, pH-5 and a BIACORE™ flow cell was prepared for each receptor at densities of 7900 and 9600 RU for IL-17R and IL17RLP, respectively. Various concentrations of purified IL-20 and IL-17 (R&D Systems, Minneapolis, Minn.) in 50 microliters hepes-buffered saline (HBS) buffer were examined for receptor binding at a flow rate of 15 microliters per minute. After injection of sample the flow cell was equilibrated with HBS. Flow cells were regenerated using two 40 sec pulses of 10 mM HCl.

Flow Cytometric Evaluation of IL17RLP transfectants—For detection of IL-20, cells ($10^6$ in 100 microliters) were incubated with either pre-immunized rabbit serum (1:100) or IL-20 immunized rabbit serum (1:100). Cells were washed, then incubated with PE conjugated goat anti-rabbit $F(ab)_2$. Cells were washed, resuspended in 5 micrograms per milliliter propidium iodide solution and acquired on the FACScan (Becton Dickinson Immunocytometry Systems, San Jose, Calif.). Alternatively, cells were first incubated 10 minutes at room temperature with 1 microgram soluble IL-20, then the anti IL-20 serum was added as described. Ability of soluble IL17RLP-Fc to block IL-20 binding to IL17RLP positive cells was also tested, using 1 microgram or 10 micrograms IL17RLP-Fc added in solution with the soluble IL-20. Analysis was performed using an electronic gate on propidium iodide negative live cells.

Peritoneal Exudate Cells—BALB/c mice (n=8 per group) were injected intraperitoneally with 0.2 ml of rhIL-20 at indicated amounts plus 50 micrograms of the human chemokine HCC-1 (See, Schulz-Knappe, P., et al., *Exp. Med.* 183: 295-299 (1996)) as a carrier. At 4 h after injection the mice were sacrificed by $CO_2$ asphyxiation. The peritoneal cavity was then exposed and the exudate collected by washing the cavity with 4 ml of PBS. Cell counts performed in triplicate on each peritoneal exudate sample were quantitiated by complete blood chemistry (CBC) analyzer and hemocytometer. Cytocentrifuge (Shandon, Inc., Pittsburgh, Pa.) smears of PEC from each mouse were stained with Wright's stain for differential counts. Total numbers of PMN accumulating in the peritoneal cavity were calculated by multiplying total PEC by the percent PMN determined from differential counts. Both percent and total values of PMN were expressed as the mean+SEM. Significance of difference was determined by an ANOVA t-test.

Reagents—Recombinant human IL-17 was from R&D Systems (Minneapolis, Minn.). Dextran sulfate sodium (DSS, 36,000-44,000 Mol. Wt) was purchased from American International Chemistry (Natick, Mass.). LipofectAMINE reagent and geneticin (G418) were from LIFE TECHNOLOGIES™ (Rockville, Md.). Indomethacin and methotrexate were obtained from SIGMA™ Chemical Company (St. Louis, Mo.).

Animals—Female Swiss Webster mice (20-25 g) and female Lewis rats (160-180 g) were obtained from Charles River Laboratories (Raleigh, N.C.) and kept under standard conditions for one week before being used in experiments. The animal protocols used in this study were reviewed and approved by the Human Genome Sciences, Inc, Institutional Animal Care and Use Committee.

Tissue Collection—Tissues from several models of inflammation were tested for expression of the IL17RLP. Models included murine colitis, rat jejunitis, mouse graft versus host disease and *Listeria* induced bacteremia in mice.

In the dextran sulfate sodium (DSS) induced murine colitis model, female Swiss Webster mice were given a four percent solution of DSS ad libitum for seven days. Animals were euthanized on day seven, and the distal third of the colon flushed with saline and snap frozen with liquid nitrogen in preparation for RNA extraction.

In indomethacin induced rat jejunitis, female Lewis rats were injected subcutaneously on day 0 and 1 with indomethacin. Indomethacin was prepared by solubilizing in absolute ethanol, sonication for 30 seconds and then diluted 1:4 vol/vol with five percent sodium bicarbonate to create a stock solution of 10 mg/ml. The stock solution was diluted further with five percent sodium bicarbonate, and rats were injected subcutaneously (sc) with a final dose of 8 mg/kg in a volume of 0.2 ml. On day 4, three days after the final indomethacin injection, rats were euthanized, and 10 cm of the small intestine removed, starting 20 cm up from the cecum. The intestinal tissue was flushed with saline and snap frozen with liquid nitrogen prior to RNA analysis.

Primary structure of IL-20—An EST coding for a putative signal peptide was initially discovered in a human thymus cDNA library. Three additional clones were subsequently identified in libraries from thymus tumor and from 9 and 12 week old human embryo tissue. All four clones were fully sequenced and found to be identical over the entire open reading frame. They are predicted to code for a protein of 184 amino acids with an N-terminal leader sequence of 20 amino acids (SEQ ID NO:35). The predicted molecular mass for this protein is 20.4 kDa, with an estimated isoelectric point of 924. There is one potential N-linked glycosylation site and eight cysteine residues. The short 3' untranslated region contains a single near-consensus polyadenylation site and is devoid of the characteristic AU-repeats found in several other cytokines, growth factors and protooncogenes (See, Shaw, G., et al., *Cell* 46:659-667 (1986)).

A comparison of both nucleotide and amino acid sequences with the GenBank or EMBL databases revealed significant homology of the translation product with the amino acid sequence of the recently described T cell-derived cytokine, IL-17. At the amino acid level, human IL-20 shared 21.3%, 19% and 20.7% identity with human, mouse and rat IL-17, respectively, and 21.9% identity with the product of the 13th ORF of Herpesvirus saimiri (HVS13). The degree of conservation is higher in the C-terminal portion of the protein, and six of the eight cysteines present in IL-20 are conserved and identically spaced between IL-20 and IL-17 (See, Yao, Z., et al. and Fossiez, F., et al., supra). A putative murine ortholog of IL-20 was identified in a mouse EST database and found to be 87.8% similar to the human IL-20 and 21.3%, 19.6%, 22% and 21.9% similar to the human, mouse, rat and viral IL-17 sequences.

The map position of the human IL-20 gene was determined by somatic cell hybrid and radiation hybrid mapping. Amplification of the standard G3 radiation hybrid panel using gene specific oligonucleotide primers showed linkage to the SHGC-33930, SHGC-4655 and SHGC-11215 markers on chromosome 6 at distances of 13, 14, and 18 centiRad, with LOD scores of 10. 13, 9.25, and 8.94, respectively, corresponding to a cytogenetic location at 6p21.2.

Cellular and tissue distribution of the hIL-20 mRNA—By Northern blot analysis of human tissues, a very strong signal at ca. 1.0 kb was seen in spinal cord, testis and small intestines, and less pronounced in prostate, colon mucosal lining, ovary and in the K-562 chronic myelogenous leukemia cell line. Furthermore, a weak transcript of similar length was routinely observed in trachea, uterus, adrenal gland, substantia nigra and fetal kidney. Even though IL-20 cDNA was initially isolated from thymus, the signal observed on all blots with spleen or thymus poly-A RNA was either feint or not visible. The tissue distribution of murine IL-20 was also determined. A ca. 1.0 kb band was observed on poly-A mouse RNA blots probed with a murine reading frame-specific cDNA probe. The signal was strongest in brain, heart and testis and weaker in lung, liver and skeletal muscle.

Molecular characterization of an IL-20 receptor—In order to identify target cell types that respond to IL-20, we searched for candidate receptors. Since IL-20 is distantly related to IL17, we screened the EST databases for novel homologs of the recently described murine and human IL-17 receptor amino acid sequences (See, Yao, Z., et al., *Immunity* 3:811-821 (1995); Yao, Z., et al., *Cytokine* 9:794-800 (1997)). A cDNA clone containing an open reading frame predicted to code for a type I transmembrane protein was identified in a library from human adult lung tissue. Overlapping clones were subsequently discovered in libraries from various other tissues, predominantly eosinophils, brain, pancreas, kidney, thyroid and osteoclastomas. A large open reading frame is predicted to encode a receptor of 426 amino acids. Computer-assisted analysis suggests that this protein has an N-terminal signal peptide with a cleavage site after Pro-(-3) of SEQ ID NO:2. The signal peptide is followed by a 273 amino acid residue extracellular domain (Arg-(-2) through Gly-270 of SEQ ID NO:2), a 22 amino acid residue transmembrane stretch (Trp-271 through Leu-292 of SEQ ID NO:2), and a 115 amino acid residue cytoplasmic tail (Met-293 through Leu-407 of SEQ ID NO:2). There are six potential N-linked glycosylation sites in the extracellular domain, at positions Asn-48; Asn-84; Asn-137; Asn-164; Asn-178; and Asn-264 of SEQ ID NO:2. The predicted molecular mass for this protein is 47.9 kDa, with an isoelectric point of 8.16. Overall, the IL17RLP protein sequence is 19.2% and 18.2% identical to the human and murine IL-17R sequences, respectively. There is no WSxWS motif in the extracellular domain (See, Baumgartner, J. W., et al., *J. Biol. Chem.* 269:29094-29101 (1994)). The cytoplasmic portion of this new receptor is much shorter than the unusually long tail described for IL-17R (See, Yao, Z., et al., *Cytokine* 9:794-800 (1997)). Furthermore, a segment (TPPPLR-PRKVW) (SEQ ID NO:33) located proximal to the IL-17R transmembrane domain, which is highly conserved among cytokine receptors (See, Baumgartner, J. W., et al., *J. Biol. Chem.* 269:29094-29101 (1994)), is absent.

By Northern blot analysis of human tissues using an open reading frame specific hybridization probe, two specific transcripts of ca 3.5 kb and 1.4 kb can be detected in several endocrine tissues, most pronounced in fetal and adult liver, kidney, pancreas, testis, colon and small intestines but are absent in peripheral blood leucocytes and lymphoid organs. Only a few of a large series of transformed human cell lines grown in culture expressed IL17RLP transcript detectable by Northern and real-time PCR analysis. These were predominantly derived from organs found to be positive for IL17RLP message above and included the WRL-68 human embryonic liver, Colo587 pancreas adenocarcinoma-mesothelioma, PANC-1 pancreatic epitheloid carcinoma, HeLa S3 cervical carcinoma, K562 leukemia, Raji Burkitts lymphoma and SW480 colorectal adenocarcinoma lines.

The map location of IL17RLP was determined at 3p21.1 by radiation hybrid mapping, with a LOD score of 12. It is noted that several chemokine receptors and trypsin inhibitors have been mapped in the 3p21.1, 3p21.2 and 3p21 regions.

Tissue distribution of rodent IL17RLP—Many cytokine receptors are not expressed constitutively, but their transcription and surface expression is dependent on specific activation mechanisms. To gain insight into possible roles of this novel cytokine receptor pair in disease processes, a partial cDNA clone for the putative murine IL17RLP ortholog was identified and hybridized with total RNA prepared from a series of rodent disease model organs. Because of the proinflammatory roles of IL-17, RNAs from several inflammatory models were used. These included kidney and liver RNAs from a murine model of graftversus-host disease, liver following *Listeria*-infection, as well as colon and intestinal tissues from DSS-induced colitis and from Indomethacin-induced intestinal inflammation in rats. Among the models tested, IL17RLP message was found to be significantly upregulated only in the intestines after Indomethacin treatment. However, the upregulation was drastic, from weak or undetectable in most untreated samples to a readily detectable or intense signal in total RNAs from several different treated animals. As seen above with the human probe and human tissues, two transcripts of 3.4 kb and 1.3 kb were observed.

Expression of recombinant IL-20 protein—Human IL-20 was cloned as described in experimental procedures and expressed in CHO cells under the control of an RSV-CMV hybrid promoter. Comparison of the protein pattern by SDS-PAGE analysis of conditioned media from IL-20 clones versus the control media revealed that several clones expressed a novel protein of ~20 kDa not present in control media transfected with expression vector plasmid only. One clone was chosen for scale-up and conditioned media were obtained after 4 days. Immunoblot analysis of conditioned media using a polyclonal antibody revealed the presence of several species of IL-20, which suggested the presence of proteolytic processing and/or differential glycosylation of the protein. IL-20 was purified to apparent homogeneity as described in Experimental Procedures. PAGE analysis of purified IL-20 under non-reducing conditions showed that, unlike IL-17, IL-20 migrates as a monomer and thus is not a disulfide-linked dimer under these conditions. However, when eluted from a Superdex 75 size exclusion column, IL-20 behaves as a dimer. Thus, native IL-20 appears to be a non-disulfide linked dimer.

The major bands were subjected to N-terminal sequence analysis. The 23/22 kDa species had four closely spaced N-termini starting at Arg-23, Ser-27, Arg-29 and Lys-30 of SEQ ID NO:35 (in roughly equal proportion), whereas the 18 kDa band had two N-termini starting at residues Leu-49 and Ser-51 of SEQ ID NO:35. The presence of truncated forms of the protein is suggestive of posttranslational proteolytic processing. This appears to be due to the action of a proprotein convertase-like activity as three of the N-terminal residues Arg-29, Ser-30 and Met-52 of SEQ ID NO:35 are preceded by basic residues. However, Ser-51 of SEQ ID NO:35 is preceded by Val and may not be processed by the same enzyme. When expressed in baculovirus, only one species was detected. The N-terminus of baculovirus expressed IL-20 was Arg-23 of SEQ ID NO:35, which is two residues downstream of the cleavage site predicted by SignalP (See, Nielsen, et al., supra.), Gln-21 of SEQ ID NO:35. Thus, IL-20 isolated from CHO conditioned media appears to occur in several forms due to posttranslational proteolysis. The effects of processing on biological activity are not yet known.

Binding experiments—Specific interaction of the extracellular domain of the novel receptor with soluble IL-20 purified as described above was demonstrated independently by three different methods. The predicted extracellular domains of human IL-17 receptor and of IL-20 receptor were expressed as chimeric proteins, fused to the heavy chain constant region of IgG1. When used as immobilized component in the BIA-CORE™ surface plasmon resonance analysis system, purified soluble IL-20 bound to IL17RLP, in a concentration-dependent manner. Very poor interaction of this receptor was observed with soluble recombinant human IL-17. In contrast, IL-17 bound well to IL-17 receptor under the same experimental conditions.

293T cells transiently transfected with human IL17RLP expression plasmid were used to measure cell surface binding of IL-20 by flow cytometry as detected by an IL-20 antibody. Significant binding of IL-20 was observed in the IL17RLP transfectants but was undetectable in untransfected cells. IL-20 antibody alone did not bind to untransfected or transfected cells. Furthermore, cell surface binding was inhibited by the addition of soluble IL17RLP-Fc fusion protein. This inhibition of binding was dose dependent, as the mean fluorescence peak was shifted back by 15% and 90% by the addition of 1 microgram and 10 micrograms of receptor protein, respectively.

Specific cell surface binding of epitope-tagged IL-20 was also demonstrated. The SW480 colorectal adenocarcinoma cell line, shown above to express IL17RLP transcript, was used in this experiment. Binding of N-terminal Flag-IL-20 fusion protein to these untransfected cells was detectable as a quantitative shift after staining with Flag- or IL20-specific antibody, in contrast to the only partial shift observed with the transfected cell population above.

Finally, binding of huIL-20 to huIL17RLP was confirmed by co-immunoprecipitation. Purified IL17RLP-Fc fusion protein was incubated with soluble CHO-derived recombinant human IL-20. Binding of IL-20 to IL17RLP was demonstrated by detection of IL-20 in the protein A agarose coprecipitate by Western immunostaining.

Neutrophil migration elicited by IL-20 in vivo—Treatment with IL-17 has been shown to activate the transcription factor NF-kappaB and to induce, cytokine secretion in fibroblasts (See, Yao, et al., *J. Immunol.* 155:5483-5486 (1995); Fossiez, et al., *J. Exp. Med.* 183:2593-2603 (1996)). In our hands, treatment with CHO-expressed and purified IL-20 did not activate NF-kappaB in NIH3T3 cells. Furthermore, no reproducible induction of cytokine message or protein (e.g., IL-6, IL-8, TNF-alpha, IFN-gamma, IL-3, G-CSF) was observed in HeLa, CHO or 293T cells after treatment with rhIL-20 in vitro.

To examine its possible physiological roles in vivo, recombinant human IL-20 was injected into BALB/c mice. As the abundance of IL-20 transcripts in RNA from colon mucosal lining and small intestines may suggest functions of the cytokine on the gastrointestinal tract walls, intra-peritoneal (i.p.) injection was chosen as the route of administration. The results demonstrate that i.p. injection of rhIL-20 consistently caused a dose-dependent influx of PMN into the peritoneal cavity within 4 hours. This influx of PMN was not a result of non-specific vascular leakage because very few RBC were observed in most cytopreparations. Red blood cells or clotting visible in some animals was attributed to vasculoepithelial injury during injection, and these preparations were excluded from analysis. Another cytokine, rhHCC-1 (Schulz-Knappe, P., et al., *Exp. Med.* 183:295-299 (1996)), showed no effect on PMN infiltration, even over a wide range of protein concentrations, and therefore was chosen to serve as protein carrier for the low dose study of IL-20. Peritoneal PMN infiltration was still marked in response to 100 ng of L-20 per mouse but became statistically insignificant at 10 ng. The results are not attributable to LPS contaminants since (a) the amount of LPS in rhIL-20 is ten fold lower than that of rhHCC-1, and (b) heating of rhIL-20 at 80° C. for 45 min completely abrogated its ability to cause PMN influx.

Several observations in this report suggest the physiological role of IL-20 to be distinct from IL-17 or other previously described secreted factors. First, while IL-17 is found to be expressed almost exclusively by CD4+ and DN activated T cells (See, Yao, et al., *J. Immunol.* 155:5483-5486 (1995)), IL-20 is highly transcribed in human and murine spinal cord, and low levels of expression can be found in many other organs. Second, the AU-rich repeats indicative of transient expression found in IL-17 and other cytokines are absent from the 3' untranslated realon of the IL-20 transcript (See, Shaw, G., et al., *Cell* 46:659-667 (1986)). IL-20 may thus be the translation product of a more stable message that in fact could give rise to a constitutive serum presence of the protein. Third, while a specific cell surface receptor for IL-17 is described to be expressed in virtually all cell types (See, Yao, Z., et al., *Immunity* 3:811-821 (1995)), the receptor for IL-20 discovered here shows a highly specific message expression pattern, largely restricted to kidney, liver, pancreas and intestines. Furthermore, the drastically shorter cytoplasmic tail of IL17RLP as compared to human and mouse IL-17R indicates that there may be principal differences in the corresponding downstream signalling processes.

Recombinant human IL-20 protein did not exert any detectable chemotactic activity upon peripheral blood neutrophils or eosinophils from several human donors. Moreover, IL17RLP message was undetectable in human neutrophils by either Northern or real-time PCR analysis, and neutrophils failed to bind epitope-tagged recombinant IL-20 by FACS analysis. Therefore, the dose-dependent neutrophil influx observed after i.p. injection is unlikely due to a direct activity on neutrophils. Rather, IL-20 binding to cell surface receptors on stromal or other connective tissue elements may trigger expression and secretion of chemoattractive factors from these cell types, leading to a guided local accumulation of poly morphonuclear leucocyte populations. Accordingly, our inability to observe transcription factor activation or mRNA and protein expression of several known chemokines in transformed cell lines in culture is most likely due to a requirement for a specific activation process to render cells responsive to IL-20. In addition, IL-20 could allow or enhance migration of polymorphonuclear cells into the gastrointestinal tract, or other epithelial structures by acting not on these invading cells directly, but via some effects on the local microvasculature of these tissues. However, even though recombinant expression of IL17RLP cDNA alone is sufficient to yield specific cell surface binding sites, it cannot be ruled out that IL-20 acts on these cells by additional receptors or receptor components.

Because of the similarity of IL-20 to the pro-inflammatory cytokine, IL-17, and its association with neutrophil chemotaxis, IL17RLP message distribution studies were conducted in target tissue from various models of inflammation. Among those models were DSS induced colitis and indomethacin induced jejunitis, both models of inflammatory bowel disease (IBD). Although Northern blot analysis showed no IL17RLP in the colons of DSS treated mice, IL17RLP was dramatically upregulated on day 4 in the mid bowel of rats receiving consecutive indomethacin injections on day 0 and 1. Indomethacin induced jejunitis is characterized by transmural lesions and an influx of neutrophils. Though there is little evidence for an immunologically driven mechanism of action, indomethacininduced IBD bears some resemblance to Crohn's disease, it's clinical counterpart, in that it: a) induces transmural lesions; b) causes non-bloody diarrhea; c) has a genetic component; d) is dependent on the presence of bacteria; e) causes granuloma formation and 1) is accompanied by inflammation (See, Kim, H, et al., *Scand J. Gastroenterol.* 27:529-537 (1992); Elson, C. O., et al., *Gatroenterol.* 109: 1344-1367 (1995)).

Thus, as described herein, IL-20 and IL17RLP is a novel cytokine ligand-receptor system that may be involved in specific local inflammatory processes and in the indirect recruitment of neutrophils to tissue repair and immune reactions at specific target organs.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith (in both paper and computer readable forms), and the Sequence Listings submitted with U.S. application Ser. No. 09/796,844, filed Mar. 2, 2001, U.S. Provisional Application Ser. No. 60/187,015, filed on Mar. 6, 2000, PCT Application Serial No. US00/05759, filed on Mar. 6, 2000; PCT Application Serial No. US99/21048, filed on Sep. 15, 1999; U.S. application Ser. No. 09/268,311, filed on Mar. 16, 1999; PCT Application Serial No. US98/19121, filed on Sep. 16, 1998, U.S. application Ser. No. 09/154,219, filed on Sep. 16, 1998, and U.S. Application Ser. No. 60/059,133, filed on Sep. 17, 1997, in both computer and paper forms are hereby incorporated by reference in their entireties.

What is claimed is:

1. A kit comprising (i) an isolated antibody or fragment thereof that binds specifically to an Interleukin 17 Receptor-Like Protein, wherein the Interleukin 17 Receptor-Like Protein consists of an amino acid sequence selected from the group consisting of:

(a) the amino acid sequence from position −19 to position +407 of SEQ ID NO:2;
  (b) the amino acid sequence from position −18 to position +407 of SEQ ID NO:2;
  (c) the amino acid sequence from position +1 to position +407 of SEQ ID NO:2;
  (d) the amino acid sequence from position +1 to position +271 of SEQ ID NO:2;
  (e) the amino acid sequence from position −5 to position +271 of SEQ ID NO:2;
  (f) the amino acid sequence of the full length protein encoded by the cDNA in ATCC Deposit No. 209198;
  (g) the amino acid sequence of the full length protein, excluding the N-terminal methionine residue, encoded by the cDNA in ATCC Deposit No. 209198; and
  (h) the amino acid sequence of the extracellular domain of the protein encoded by the cDNA in ATCC Deposit No. 209198; and (ii) an isolated polypeptide comprising a portion of SEQ ID NO:2 or a portion of the protein encoded by the cDNA in ATCC Deposit No. 209198 which binds specifically with said isolated antibody or fragment thereof.

2. The kit of claim 1, wherein said kit further comprises a control antibody which does not react with said polypeptide.

3. The kit of claim 1, wherein said antibody or fragment thereof is conjugated to a detectable substance.

4. The kit of claim 3, wherein said detectable substance is selected from the group consisting of a fluorescent compound, an enzymatic substrate, a radioactive compound and a luminescent compound.

5. The kit of claim 1, wherein said polypeptide is attached to a solid support.

6. The kit of claim 1, wherein said antibody or fragment thereof is attached to a solid support.

7. The kit of claim 1, wherein said antibody or fragment thereof is a monoclonal antibody.

8. The kit of claim 1, wherein the antibody or fragment thereof is a polyclonal antibody.

9. The kit of claim 1, wherein the antibody or fragment thereof is a human antibody.

10. The kit of claim 1, wherein the antibody or fragment thereof is a chimeric antibody, a humanized antibody, or a single chain antibody.

11. The kit of claim 1, wherein the fragment is a Fab fragment.

* * * * *

SEQUENCE LISTING

```
<160> NUMBER OF SEQ ID NOS: 35

<210> SEQ ID NO 1
<211> LENGTH: 1816
<212> TYPE: DNA
<213> ORGANISM: Homo sapiens
<220> FEATURE:
<221> NAME/KEY: CDS
<222> LOCATION: (10)..(1287)
<220> FEATURE:
<221> NAME/KEY: mat_peptide
<222> LOCATION: (67)..(1287)
<220> FEATURE:
<221> NAME/KEY: sig_peptide
<222> LOCATION: (10)..(66)

<400> SEQUENCE: 1 gcacgagcg atg tcg ctc gtg ctg cta agc ctg gcc gcg ctg tgc agg agc        51
          Met Ser Leu Val Leu Leu Ser Leu Ala Ala Leu Cys Arg Ser
              -15                      -10 gcc gta ccc cga gag ccg acc gtt caa tgt ggc tct gaa act ggg cca          99
Ala Val Pro Arg Glu Pro Thr Val Gln Cys Gly Ser Glu Thr Gly Pro
 -5              -1   1               5                  10 tct cca gag tgg atg cta caa cat gat cta atc ccc gga gac ttg agg         147
Ser Pro Glu Trp Met Leu Gln His Asp Leu Ile Pro Gly Asp Leu Arg
            15                  20                  25 gac ctc cga gta gaa cct gtt aca act agt gtt gca aca ggg gac tat         195
Asp Leu Arg Val Glu Pro Val Thr Thr Ser Val Ala Thr Gly Asp Tyr
        30                  35                  40 tca att ttg atg aat gta agc tgg gta ctc cgg gca gat gcc agc atc         243
Ser Ile Leu Met Asn Val Ser Trp Val Leu Arg Ala Asp Ala Ser Ile
    45                  50                  55 cgc ttg ttg aag gcc acc aag att tgt gtg acg ggc aaa agc aac ttc         291
Arg Leu Leu Lys Ala Thr Lys Ile Cys Val Thr Gly Lys Ser Asn Phe
60                  65                  70                  75 cag tcc tac agc tgt gtg agg tgc aat tac aca gag gcc ttc cag act         339
Gln Ser Tyr Ser Cys Val Arg Cys Asn Tyr Thr Glu Ala Phe Gln Thr
                80                  85                  90
```

```
cag acc aga ccc tct ggt ggt aaa tgg aca ttt tcc tac atc ggc ttc        387
Gln Thr Arg Pro Ser Gly Gly Lys Trp Thr Phe Ser Tyr Ile Gly Phe
            95                 100                 105 cct gta gag ctg aac aca gtc tat ttc att ggg gcc cat aat att cct        435
Pro Val Glu Leu Asn Thr Val Tyr Phe Ile Gly Ala His Asn Ile Pro
        110                 115                 120 aat gca aat atg aat gaa gat ggc cct tcc atg tct gtg aat ttc acc        483
Asn Ala Asn Met Asn Glu Asp Gly Pro Ser Met Ser Val Asn Phe Thr
    125                 130                 135 tca cca ggc tgc cta gac cac ata atg aaa tat aaa aaa aag tgt gtc        531
Ser Pro Gly Cys Leu Asp His Ile Met Lys Tyr Lys Lys Lys Cys Val
140                 145                 150                 155 aag gcc gga agc ctg tgg gat ccg aac atc act gct tgt aag aag aat        579
Lys Ala Gly Ser Leu Trp Asp Pro Asn Ile Thr Ala Cys Lys Lys Asn
                160                 165                 170 gag gag aca gta gaa gtg aac ttc aca acc act ccc ctg gga aac aga        627
Glu Glu Thr Val Glu Val Asn Phe Thr Thr Thr Pro Leu Gly Asn Arg
            175                 180                 185 tac atg gct ctt atc caa cac agc act atc atc ggg ttt tct cag gtg        675
Tyr Met Ala Leu Ile Gln His Ser Thr Ile Ile Gly Phe Ser Gln Val
        190                 195                 200 ttt gag cca cac cag aag aaa caa acg cga gct tca gtg gtg att cca        723
Phe Glu Pro His Gln Lys Lys Gln Thr Arg Ala Ser Val Val Ile Pro
    205                 210                 215 gtg act ggg gat agt gaa ggt gct acg gtg cag ctg act cca tat ttt        771
Val Thr Gly Asp Ser Glu Gly Ala Thr Val Gln Leu Thr Pro Tyr Phe
220                 225                 230                 235 cct act tgt ggc agc gac tgc atc cga cat aaa gga aca gtt gtg ctc        819
Pro Thr Cys Gly Ser Asp Cys Ile Arg His Lys Gly Thr Val Val Leu
                240                 245                 250 tgc cca caa aca ggc gtc cct ttc cct ctg gat aac aac aaa agc aag        867
Cys Pro Gln Thr Gly Val Pro Phe Pro Leu Asp Asn Asn Lys Ser Lys
            255                 260                 265 ccg gga ggc tgg ctg cct ctc ctc ctg ctg tct ctg ctg gtg gcc aca        915
Pro Gly Gly Trp Leu Pro Leu Leu Leu Leu Ser Leu Leu Val Ala Thr
        270                 275                 280 tgg gtg ctg gtg gca ggg atc tat cta atg tgg agg cac gaa agg atc        963
Trp Val Leu Val Ala Gly Ile Tyr Leu Met Trp Arg His Glu Arg Ile
    285                 290                 295 aag aag act tcc ttt tct acc acc aca cta ctg ccc ccc att aag gtt       1011
Lys Lys Thr Ser Phe Ser Thr Thr Thr Leu Leu Pro Pro Ile Lys Val
300                 305                 310                 315 ctt gtg gtt tac cca tct gaa ata tgt ttc cat cac aca att tgt tac       1059
Leu Val Val Tyr Pro Ser Glu Ile Cys Phe His His Thr Ile Cys Tyr
                320                 325                 330 ttc act gaa ttt ctt caa aac cat tgc aga agt gag gtc atc ctt gaa       1107
Phe Thr Glu Phe Leu Gln Asn His Cys Arg Ser Glu Val Ile Leu Glu
            335                 340                 345 aag tgg cag aaa aag aaa ata gca gag atg ggt cca gtg cag tgg ctt       1155
Lys Trp Gln Lys Lys Lys Ile Ala Glu Met Gly Pro Val Gln Trp Leu
        350                 355                 360 gcc act caa aag aag gca gca gac aaa gtc gtc ttc ctt ctt tcc aat       1203
Ala Thr Gln Lys Lys Ala Ala Asp Lys Val Val Phe Leu Leu Ser Asn
    365                 370                 375 gac gtc aac agt gtg tgc gat ggt acc tgt ggc aag agc gag ggc agt       1251
Asp Val Asn Ser Val Cys Asp Gly Thr Cys Gly Lys Ser Glu Gly Ser
380                 385                 390                 395 ccc agt gag aac tct caa gac tct tcc cct tgc ctt taacctttc             1297
Pro Ser Glu Asn Ser Gln Asp Ser Ser Pro Cys Leu
                400                 405
```

-continued

```
tgcagtgatc taagaagcca gattcatctg cacaaatacg tggtggtcta ctttagagag    1357
attgatacaa agacgatta caatgctctc agtgtctgcc ccaagtacca cctcatgaag     1417
gatgccactg ctttctgtgc agaacttctc catgtcaagt agcaggtgtc agcaggaaaa    1477
agatcacaag cctgccacga tggctgctgc tccttgtagc ccacccatga gaagcaagwg    1537
accttaaagg cttcctatcc caccaattac agggaaaaaa cgtgtgatga tcctgaagct    1597
tactatgcag cctacaaaca gccttagtaa ttaaaacatt ttataccaat aaaattttca    1657
aatattgcta actaatgtag cattaactaa cgattggaaa ctacatttac aacttcaaag    1717
ctgttttata catagaaatc aattacagtt ttaattgaaa actataacca ttttgataat    1777
gcaacaataa agcatcttca gccaaaaaaa aaaaaaaaa                          1816
```

<210> SEQ ID NO 2
<211> LENGTH: 426
<212> TYPE: PRT
<213> ORGANISM: Homo sapiens

<400> SEQUENCE: 2

```
Met Ser Leu Val Leu Leu Ser Leu Ala Ala Leu Cys Arg Ser Ala Val
        -15                 -10                  -5

Pro Arg Glu Pro Thr Val Gln Cys Gly Ser Glu Thr Gly Pro Ser Pro
    -1   1               5                  10

Glu Trp Met Leu Gln His Asp Leu Ile Pro Gly Asp Leu Arg Asp Leu
         15                  20                  25

Arg Val Glu Pro Val Thr Thr Ser Val Ala Thr Gly Asp Tyr Ser Ile
 30                  35                  40                  45

Leu Met Asn Val Ser Trp Val Leu Arg Ala Asp Ala Ser Ile Arg Leu
                 50                  55                  60

Leu Lys Ala Thr Lys Ile Cys Val Thr Gly Lys Ser Asn Phe Gln Ser
             65                  70                  75

Tyr Ser Cys Val Arg Cys Asn Tyr Thr Glu Ala Phe Gln Thr Gln Thr
         80                  85                  90

Arg Pro Ser Gly Gly Lys Trp Thr Phe Ser Tyr Ile Gly Phe Pro Val
     95                 100                 105

Glu Leu Asn Thr Val Tyr Phe Ile Gly Ala His Asn Ile Pro Asn Ala
110                 115                 120                 125

Asn Met Asn Glu Asp Gly Pro Ser Met Ser Val Asn Phe Thr Ser Pro
                130                 135                 140

Gly Cys Leu Asp His Ile Met Lys Tyr Lys Lys Cys Val Lys Ala
            145                 150                 155

Gly Ser Leu Trp Asp Pro Asn Ile Thr Ala Cys Lys Lys Asn Glu Glu
        160                 165                 170

Thr Val Glu Val Asn Phe Thr Thr Thr Pro Leu Gly Asn Arg Tyr Met
    175                 180                 185

Ala Leu Ile Gln His Ser Thr Ile Gly Phe Ser Gln Val Phe Glu
190                 195                 200                 205

Pro His Gln Lys Lys Gln Thr Arg Ala Ser Val Val Ile Pro Val Thr
                210                 215                 220

Gly Asp Ser Glu Gly Ala Thr Val Gln Leu Thr Pro Tyr Phe Pro Thr
            225                 230                 235

Cys Gly Ser Asp Cys Ile Arg His Lys Gly Thr Val Val Leu Cys Pro
        240                 245                 250

Gln Thr Gly Val Pro Phe Pro Leu Asp Asn Asn Lys Ser Lys Pro Gly
    255                 260                 265
```

```
Gly Trp Leu Pro Leu Leu Leu Ser Leu Leu Val Ala Thr Trp Val
270                 275                 280                 285

Leu Val Ala Gly Ile Tyr Leu Met Trp Arg His Glu Arg Ile Lys Lys
        290                 295                 300

Thr Ser Phe Ser Thr Thr Thr Leu Leu Pro Pro Ile Lys Val Leu Val
        305                 310                 315

Val Tyr Pro Ser Glu Ile Cys Phe His His Thr Ile Cys Tyr Phe Thr
        320                 325                 330

Glu Phe Leu Gln Asn His Cys Arg Ser Glu Val Ile Leu Glu Lys Trp
        335                 340                 345

Gln Lys Lys Lys Ile Ala Glu Met Gly Pro Val Gln Trp Leu Ala Thr
350                 355                 360                 365

Gln Lys Lys Ala Ala Asp Lys Val Val Phe Leu Leu Ser Asn Asp Val
        370                 375                 380

Asn Ser Val Cys Asp Gly Thr Cys Gly Lys Ser Glu Gly Ser Pro Ser
        385                 390                 395

Glu Asn Ser Gln Asp Ser Ser Pro Cys Leu
        400                 405

<210> SEQ ID NO 3
<211> LENGTH: 426
<212> TYPE: PRT
<213> ORGANISM: Homo sapiens

<400> SEQUENCE: 3

Met Ser Leu Val Leu Leu Ser Leu Ala Ala Leu Cys Arg Ser Ala Val
1               5                   10                  15

Pro Arg Glu Pro Thr Val Gln Cys Gly Ser Glu Thr Gly Pro Ser Pro
            20                  25                  30

Glu Trp Met Leu Gln His Asp Leu Ile Pro Gly Asp Leu Arg Asp Leu
        35                  40                  45

Arg Val Glu Pro Val Thr Thr Ser Val Ala Thr Gly Asp Tyr Ser Ile
    50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
            100                 105                 110

Arg Pro Ser Gly Gly Lys Trp Thr Phe Ser Tyr Ile Gly Phe Pro Val
        115                 120                 125

Glu Leu Asn Thr Val Tyr Phe Ile Gly Ala His Asn Ile Pro Asn Ala
130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Cys Val Lys Ala
                165                 170                 175

Gly Ser Leu Trp Asp Pro Asn Ile Thr Ala Cys Lys Lys Asn Glu Glu
        180                 185                 190

Thr Val Glu Val Asn Phe Thr Thr Thr Pro Leu Gly Asn Arg Tyr Met
        195                 200                 205

Ala Leu Ile Gln His Ser Thr Ile Ile Gly Phe Ser Gln Val Phe Glu
        210                 215                 220

Pro His Gln Lys Lys Gln Thr Arg Ala Ser Val Val Ile Pro Val Thr
225                 230                 235                 240
```

```
Gly Asp Ser Glu Gly Ala Thr Val Gln Leu Thr Pro Tyr Phe Pro Thr
                245                 250                 255

Cys Gly Ser Asp Cys Ile Arg His Lys Gly Thr Val Val Leu Cys Pro
            260                 265                 270

Gln Thr Gly Val Pro Phe Pro Leu Asp Asn Asn Lys Ser Lys Pro Gly
        275                 280                 285

Gly Trp Leu Pro Leu Leu Leu Ser Leu Leu Val Ala Thr Trp Val
    290                 295                 300

Leu Val Ala Gly Ile Tyr Leu Met Trp Arg His Glu Arg Ile Lys Lys
305                 310                 315                 320

Thr Ser Phe Ser Thr Thr Thr Leu Leu Pro Pro Ile Lys Val Leu Val
                325                 330                 335

Val Tyr Pro Ser Glu Ile Cys Phe His His Thr Ile Cys Tyr Phe Thr
            340                 345                 350

Glu Phe Leu Gln Asn His Cys Arg Ser Glu Val Ile Leu Glu Lys Trp
        355                 360                 365

Gln Lys Lys Lys Ile Ala Glu Met Gly Pro Val Gln Trp Leu Ala Thr
    370                 375                 380

Gln Lys Lys Ala Ala Asp Lys Val Val Phe Leu Leu Ser Asn Asp Val
385                 390                 395                 400

Asn Ser Val Cys Asp Gly Thr Cys Gly Lys Ser Glu Gly Ser Pro Ser
                405                 410                 415

Glu Asn Ser Gln Asp Ser Ser Pro Cys Leu
                420                 425

<210> SEQ ID NO 4
<211> LENGTH: 409
<212> TYPE: DNA
<213> ORGANISM: Homo sapiens
<220> FEATURE:
<221> NAME/KEY: misc_feature
<222> LOCATION: (17)
<223> OTHER INFORMATION: n equals a, t, g or c
<220> FEATURE:
<221> NAME/KEY: misc_feature
<222> LOCATION: (65)
<223> OTHER INFORMATION: n equals a, t, g or c
<220> FEATURE:
<221> NAME/KEY: misc_feature
<222> LOCATION: (148)
<223> OTHER INFORMATION: n equals a, t, g or c
<220> FEATURE:
<221> NAME/KEY: misc_feature
<222> LOCATION: (160)
<223> OTHER INFORMATION: n equals a, t, g or c
<220> FEATURE:
<221> NAME/KEY: misc_feature
<222> LOCATION: (362)
<223> OTHER INFORMATION: n equals a, t, g or c
<220> FEATURE:
<221> NAME/KEY: misc_feature
<222> LOCATION: (373)
<223> OTHER INFORMATION: n equals a, t, g or c
<220> FEATURE:
<221> NAME/KEY: misc_feature
<222> LOCATION: (388)
<223> OTHER INFORMATION: n equals a, t, g or c
<220> FEATURE:
<221> NAME/KEY: misc_feature
<222> LOCATION: (406)
<223> OTHER INFORMATION: n equals a, t, g or c

<400> SEQUENCE: 4
aattcggcac gagattnatc tgcacaaata cgtggtggtc tactttagag agattgatac      60
aaaanacgat tacaatgctc tcagtgtctg ccccaagtac cacctcatga aggatgccac     120
```

-continued

```
tgctttctgt gcagaacttc tccatgtnaa gtagcaggtn tcagcaggaa aaagatcaca    180
agcctgccac gatggctgct gctccttgta gcccacccat gagaagcaag agaccttaaa    240
ggcttcctat cccaccaatt acagggaaaa aacgtgtgat gatcctgaag ctttactatg    300
cagcctacaa acagccttag taattaaaac attttatac ccataaaatt tttcaaatat    360
tngttaacta atngtagcat taactaangt ttgggaacta catttncaa               409
```

<210> SEQ ID NO 5
<211> LENGTH: 327
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (120)..(121)
<223> OTHER INFORMATION: n is a, c, g, or t
<220> FEATURE:
<221> NAME/KEY: misc_feature
<222> LOCATION: (128)..(128)
<223> OTHER INFORMATION: n is a, c, g, or t
<220> FEATURE:
<221> NAME/KEY: misc_feature
<222> LOCATION: (163)..(163)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:

```
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (277)..(277)
<223> OTHER INFORMATION: n is a, c, g, or t
<220> FEATURE:
<221> NAME/KEY: misc_feature
<222> LOCATION: (279)..(280)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (289)..(289)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (302)..(302)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t

<400> SEQUENCE: 5
aattcggcan agcccggcga tgtcgctcgt gctgctagnc tngnngcgct gtncaggagc      60
gccgtacccc gagagccgac cgttcaatgt ggctctgaaa ctgggncatc tccagagtgn    120
nttgctanaa catgatctaa tcccgggaga cttgagggac ctncgagtag agnctgttac    180
aactagtgtt gcaacagggg actattcaan ttgatgaatg tanctgggta ctncgggnag    240
ntgccancat ncgtttttttg naggctnang tttngtntnn cgggnaaang tantntcagt    300
cntanagtgt tngaggtgca ttaaaaa                                        327

<210> SEQ ID NO 6
<211> LENGTH: 35
<212> TYPE: DNA
<213> ORGANISM: Homo sapiens

<400> SEQUENCE: 6
cgcccatggc cgaccgttca atgtggctct gaaac                               35
```

<210> SEQ ID NO 7
<211> LENGTH: 35
<212> TYPE: DNA
<213> ORGANISM: Homo sapiens

<400> SEQUENCE: 7
cgcccatggc cgaccgttca atgtggctct gaaac                          35

<210> SEQ ID NO 8
<211> LENGTH: 34
<212> TYPE: DNA
<213> ORGANISM: Homo sapiens

<400> SEQUENCE: 8
cgcggatcca tgtcgctcgt gctgctaagc ctgg                           34

<210> SEQ ID NO 9
<211> LENGTH: 26
<212> TYPE: DNA
<213> ORGANISM: Homo sapiens

<400> SEQUENCE: 9
cgcggtaccc cagcctcccg gcttgc                                    26

<210> SEQ ID NO 10
<211> LENGTH: 129
<212> TYPE: DNA
<213> ORGANISM: Homo sapiens

<400> SEQUENCE: 10
gccggatccg ccaccatgaa ctccttctcc acaagcgcct tcggtccagt tgccttctcc    60
ctggggctgc tcctggtgtt gcctgctgcc ttccctgccc cagtatgtcg ctcgtgctgc   120
taagcctgg                                                          129

<210> SEQ ID NO 11
<211> LENGTH: 28
<212> TYPE: DNA
<213> ORGANISM: Homo sapiens

<400> SEQUENCE: 11
ggccgggtac cccagcctcc cggcttgc                                  28

<210> SEQ ID NO 12
<211> LENGTH: 43
<212> TYPE: DNA
<213> ORGANISM: Homo sapiens

<400> SEQUENCE: 12
ctagccggat ccgccaccat gtcgctcgtg ctgctaagcc tgg                 43

<210> SEQ ID NO 13
<211> LENGTH: 28
<212> TYPE: DNA
<213> ORGANISM: Homo sapiens

<400> SEQUENCE: 13
ggccgggtac cccagcctcc cggcttgc                                  28

<210> SEQ ID NO 14
<211> LENGTH: 17
<212> TYPE: PRT
<213> ORGANISM: Homo sapiens -continued

```
<400> SEQUENCE: 14

Pro Arg Glu Pro Thr Val Gln Cys Gly Ser Glu Thr Gly Pro Ser Pro
 1               5                  10                  15

Glu

<210> SEQ ID NO 15
<211> LENGTH: 10
<212> TYPE: PRT
<213> ORGANISM: Homo sapiens

<400> SEQUENCE: 15

Leu Asp His Ile Met Lys Tyr Lys Lys Lys
 1               5                  10

<210> SEQ ID NO 16
<211> LENGTH: 10
<212> TYPE: PRT
<213> ORGANISM: Homo sapiens

<400> SEQUENCE: 16

Lys Lys Asn Glu Glu Thr Val Glu Val Asn
 1               5                  10

<210> SEQ ID NO 17
<211> LENGTH: 1918
<212> TYPE: DNA
<213> ORGANISM: Homo sapiens
<220> FEATURE:
<221> NAME/KEY: CDS
<222> LOCATION: (111)..(1409)
<220> FEATURE:
<221> NAME/KEY: misc_feature
<222> LOCATION: (29)
<223> OTHER INFORMATION: n equals a, t, g or c
<220> FEATURE:
<221> NAME/KEY: misc_feature
<222> LOCATION: (101)
<223> OTHER INFORMATION: n equals a, t, g or c

<400> SEQUENCE: 17
aagctcgaaa ttaaccctca ctaaagggna acaaaagctg agctccacc gcggtggcgg      60 ccgctctaga actagtggat cccccgggct gcaggaattc ngcacgagcg atg tcg     116
                                                        Met Ser
                                                          1 ctc gtg ctg cta agc ctg gcc gcg ctg tgc agg agc gcc gta ccc cga   164
Leu Val Leu Leu Ser Leu Ala Ala Leu Cys Arg Ser Ala Val Pro Arg
         5                  10                  15 gag ccg acc gtt caa tgt ggc tct gaa act ggg cca tct cca gag tgg   212
Glu Pro Thr Val Gln Cys Gly Ser Glu Thr Gly Pro Ser Pro Glu Trp
 20                  25                  30 atg cta caa cat gat cta atc ccc gga gac ttg agg gac ctc cga gta   260
Met Leu Gln His Asp Leu Ile Pro Gly Asp Leu Arg Asp Leu Arg Val
 35                  40                  45                  50 gaa cct gtt aca act agt gtt gca aca ggg gac tat tca att ttg atg   308
Glu Pro Val Thr Thr Ser Val Ala Thr Gly Asp Tyr Ser Ile Leu Met
                 55                  60                  65 aat gta agc tgg gta ctc cgg gca gat gcc agc atc cgc ttg ttg aag   356
Asn Val Ser Trp Val Leu Arg Ala Asp Ala Ser Ile Arg Leu Leu Lys
             70                  75                  80 gcc acc aag att tgt gtg acg ggc aaa agc aac ttc cag tcc tac agc   404
Ala Thr Lys Ile Cys Val Thr Gly Lys Ser Asn Phe Gln Ser Tyr Ser
         85                  90                  95 tgt gtg agg tgc aat tac aca gag gcc ttc cag act cag acc aga ccc   452
Cys Val Arg Cys Asn Tyr Thr Glu Ala Phe Gln Thr Gln Thr Arg Pro
```

-continued

```
                100                 105                 110
tct ggt ggt aaa tgg aca ttt tcc tac atc ggc ttc cct gta gag ctg          500
Ser Gly Gly Lys Trp Thr Phe Ser Tyr Ile Gly Phe Pro Val Glu Leu
115                 120                 125                 130 aac aca gtc tat ttc att ggg gcc cat aat att cct aat gca aat atg          548
Asn Thr Val Tyr Phe Ile Gly Ala His Asn Ile Pro Asn Ala Asn Met
                135                 140                 145 aat gaa gat ggc cct tcc atg tct gtg aat ttc acc tca cca ggc tgc          596
Asn Glu Asp Gly Pro Ser Met Ser Val Asn Phe Thr Ser Pro Gly Cys
            150                 155                 160 cta gac cac ata atg aaa tat aaa aaa aag tgt gtc aag gcc gga agc          644
Leu Asp His Ile Met Lys Tyr Lys Lys Lys Cys Val Lys Ala Gly Ser
        165                 170                 175 ctg tgg gat ccg aac atc act gct tgt aag aag aat gag gag aca gta          692
Leu Trp Asp Pro Asn Ile Thr Ala Cys Lys Lys Asn Glu Glu Thr Val
180                 185                 190 gaa gtg aac ttc aca acc act ccc ctg gga aac aga tac atg gct ctt          740
Glu Val Asn Phe Thr Thr Thr Pro Leu Gly Asn Arg Tyr Met Ala Leu
195                 200                 205                 210 atc caa cac agc act atc atc ggg ttt tct cag gtg ttt gag cca cac          788
Ile Gln His Ser Thr Ile Ile Gly Phe Ser Gln Val Phe Glu Pro His
                215                 220                 225 cag aag aaa caa acg cga gct tca gtg gtg att cca gtg act ggg gat          836
Gln Lys Lys Gln Thr Arg Ala Ser Val Val Ile Pro Val Thr Gly Asp
            230                 235                 240 agt gaa ggt gct acg gtg cag ctg act cca tat ttt cct act tgt ggc          884
Ser Glu Gly Ala Thr Val Gln Leu Thr Pro Tyr Phe Pro Thr Cys Gly
        245                 250                 255 agc gac tgc atc cga cat aaa gga aca gtt gtg ctc tgc cca caa aca          932
Ser Asp Cys Ile Arg His Lys Gly Thr Val Val Leu Cys Pro Gln Thr
260                 265                 270 ggc gtc cct ttc cct ctg gat aac aac aaa agc aag ccg gga ggc tgg          980
Gly Val Pro Phe Pro Leu Asp Asn Asn Lys Ser Lys Pro Gly Gly Trp
275                 280                 285                 290 ctg cct ctc ctc ctg ctg tct ctg ctg gtg gcc aca tgg gtg ctg gtg         1028
Leu Pro Leu Leu Leu Leu Ser Leu Leu Val Ala Thr Trp Val Leu Val
                295                 300                 305 gca ggg atc tat cta atg tgg agg cac gaa agg atc aag aag act tcc         1076
Ala Gly Ile Tyr Leu Met Trp Arg His Glu Arg Ile Lys Lys Thr Ser
            310                 315                 320 ttt tct acc acc aca cta ctg ccc ccc att aag gtt ctt gtg gtt tac         1124
Phe Ser Thr Thr Thr Leu Leu Pro Pro Ile Lys Val Leu Val Val Tyr
        325                 330                 335 cca tct gaa ata tgt ttc cat cac aca att tgt tac ttc act gaa ttt         1172
Pro Ser Glu Ile Cys Phe His His Thr Ile Cys Tyr Phe Thr Glu Phe
340                 345                 350 ctt caa aac cat tgc aga agt gag gtc atc ctt gaa aag tgg cag aaa         1220
Leu Gln Asn His Cys Arg Ser Glu Val Ile Leu Glu Lys Trp Gln Lys
355                 360                 365                 370 aag aaa ata gca gag atg ggt cca gtg cag tgg ctt gcc act caa aag         1268
Lys Lys Ile Ala Glu Met Gly Pro Val Gln Trp Leu Ala Thr Gln Lys
                375                 380                 385 aag gca gca gac aaa gtc gtc ttc ctt ctt tcc aat gac gtc aac agt         1316
Lys Ala Ala Asp Lys Val Val Phe Leu Leu Ser Asn Asp Val Asn Ser
            390                 395                 400 gtg tgc gat ggt acc tgt ggc aag agc gag ggc agt ccc agt gag aac         1364
Val Cys Asp Gly Thr Cys Gly Lys Ser Glu Gly Ser Pro Ser Glu Asn
        405                 410                 415 tct caa gac tct tcc ccc ttg cct tta acc ttt tct gca gtg atc             1409
Ser Gln Asp Ser Ser Pro Leu Pro Leu Thr Phe Ser Ala Val Ile
```

```
                420         425         430
taagaagcca gattcatctg cacaaatacg tggtggtcta ctttagagag attgatacaa        1469
aagacgatta caatgctctc agtgtctgcc ccaagtacca cctcatgaag gatgccactg        1529
ctttctgtgc agaacttctc catgtcaagt agcaggtgtc agcaggaaaa agatcacaag        1589
cctgccacga tggctgctgc tccttgtagc ccacccatga gaagcaagag accttaaagg        1649
cttcctatcc caccaattac agggaaaaaa cgtgtgatga tcctgaagct tactatgcag        1709
cctacaaaca gccttagtaa ttaaaacatt ttataccaat aaaattttca atatattgcta       1769 actaatgtag cattaactaa cgattggaaa ctacatttac aacttcaaag ctgttttata        1829
catagaaatc aattacagtt ttaattgaaa actataacca ttttgataat gcaacaataa        1889
agcatcttca gccaaaaaaa aaaaaaaaa                                          1918
```

<210> SEQ ID NO 18
<211> LENGTH: 433
<212> TYPE: PRT
<213> ORGANISM: Homo sapiens
<400> SEQUENCE: 18

```
Met Ser Leu Val Leu Ser Leu Ala Ala Leu Cys Arg Ser Ala Val
 1               5                  10                  15

Pro Arg Glu Pro Thr Val Gln Cys Gly Ser Glu Thr Gly Pro Ser Pro
            20                  25                  30

Glu Trp Met Leu Gln His Asp Leu Ile Pro Gly Asp Leu Arg Asp Leu
        35                  40                  45

Arg Val Glu Pro Val Thr Thr Ser Val Ala Thr Gly Asp Tyr Ser Ile
    50                  55                  60

Leu Met Asn Val Ser Trp Val Leu Arg Ala Asp Ala Ser Ile Arg Leu
65                  70                  75                  80

Leu Lys Ala Thr Lys Ile Cys Val Thr Gly Lys Ser Asn Phe Gln Ser
                85                  90                  95

Tyr Ser Cys Val Arg Cys Asn Tyr Thr Glu Ala Phe Gln Thr Gln Thr
            100                 105                 110

Arg Pro Ser Gly Gly Lys Trp Thr Phe Ser Tyr Ile Gly Phe Pro Val
        115                 120                 125

Glu Leu Asn Thr Val Tyr Phe Ile Gly Ala His Asn Ile Pro Asn Ala
    130                 135                 140

Asn Met Asn Glu Asp Gly Pro Ser Met Ser Val Asn Phe Thr Ser Pro
145                 150                 155                 160

Gly Cys Leu Asp His Ile Met Lys Tyr Lys Lys Cys Val Lys Ala
                165                 170                 175

Gly Ser Leu Trp Asp Pro Asn Ile Thr Ala Cys Lys Lys Asn Glu Glu
            180                 185                 190

Thr Val Glu Val Asn Phe Thr Thr Thr Pro Leu Gly Asn Arg Tyr Met
        195                 200                 205

Ala Leu Ile Gln His Ser Thr Ile Ile Gly Phe Ser Gln Val Phe Glu
    210                 215                 220

Pro His Gln Lys Lys Gln Thr Arg Ala Ser Val Val Ile Pro Val Thr
225                 230                 235                 240

Gly Asp Ser Glu Gly Ala Thr Val Gln Leu Thr Pro Tyr Phe Pro Thr
                245                 250                 255

Cys Gly Ser Asp Cys Ile Arg His Lys Gly Thr Val Val Leu Cys Pro
            260                 265                 270

Gln Thr Gly Val Pro Phe Pro Leu Asp Asn Asn Lys Ser Lys Pro Gly
```

-continued

```
                      275                 280                 285
Gly Trp Leu Pro Leu Leu Leu Ser Leu Leu Val Ala Thr Trp Val
            290                 295                 300
Leu Val Ala Gly Ile Tyr Leu Met Trp Arg His Glu Arg Ile Lys Lys
305                 310                 315                 320
Thr Ser Phe Ser Thr Thr Leu Leu Pro Pro Ile Lys Val Leu Val
                325                 330                 335
Val Tyr Pro Ser Glu Ile Cys Phe His His Thr Ile Cys Tyr Phe Thr
            340                 345                 350
Glu Phe Leu Gln Asn His Cys Arg Ser Glu Val Ile Leu Glu Lys Trp
                355                 360                 365
Gln Lys Lys Lys Ile Ala Glu Met Gly Pro Val Gln Trp Leu Ala Thr
            370                 375                 380
Gln Lys Lys Ala Ala Asp Lys Val Val Phe Leu Leu Ser Asn Asp Val
385                 390                 395                 400
Asn Ser Val Cys Asp Gly Thr Cys Gly Lys Ser Glu Gly Ser Pro Ser
                405                 410                 415
Glu Asn Ser Gln Asp Ser Ser Pro Leu Pro Leu Thr Phe Ser Ala Val
            420                 425                 430
Ile

<210> SEQ ID NO 19
<211> LENGTH: 25
<212> TYPE: DNA
<213> ORGANISM: Homo sapiens

<400> SEQUENCE: 19
ggcgggcagc agctgcaggc tgacc                                          25

<210> SEQ ID NO 20
<211> LENGTH: 24
<212> TYPE: DNA
<213> ORGANISM: Homo sapiens

<400> SEQUENCE: 20
ctgggctggc ccagccccag gaag                                           24

<210> SEQ ID NO 21
<211> LENGTH: 23
<212> TYPE: DNA
<213> ORGANISM: Homo sapiens

<400> SEQUENCE: 21
gatcctcccg gacttcaaga ggc                                            23

<210> SEQ ID NO 22
<211> LENGTH: 21
<212> TYPE: DNA
<213> ORGANISM: Homo sapiens

<400> SEQUENCE: 22
ggaaaggcca ggcaggcctg g                                              21

<210> SEQ ID NO 23
<211> LENGTH: 40
<212> TYPE: DNA
<213> ORGANISM: Homo sapiens

<400> SEQUENCE: 23
gactcatatg cagccgcgtt ccccgaaatc caagcgtaaa                          40
```

<210> SEQ ID NO 24
<211> LENGTH: 33
<212> TYPE: DNA
<213> ORGANISM: Homo sapiens

<400> SEQUENCE: 24
gactggtacc ttatcagaag atgcaggtgc agc                                    33

<210> SEQ ID NO 25
<211> LENGTH: 35
<212> TYPE: DNA
<213> ORGANISM: Homo sapiens

<400> SEQUENCE: 25
gactggatcc gccatactgg actggcctca caacc                                  35

<210> SEQ ID NO 26
<211> LENGTH: 29
<212> TYPE: DNA
<213> ORGANISM: Homo sapiens

<400> SEQUENCE: 26
gactggtacc ggatggtctc gggctgctg                                         29

<210> SEQ ID NO 27
<211> LENGTH: 34
<212> TYPE: DNA
<213> ORGANISM: Homo sapiens

<400> SEQUENCE: 27
gccccggaat tcaaggagcc ccaaaagcaa gagg                                   34

<210> SEQ ID NO 28
<211> LENGTH: 33
<212> TYPE: DNA
<213> ORGANISM: Homo sapiens

<400> SEQUENCE: 28
gcccgcggat cctcagaaga tgcaggtgca gcc                                    33

<210> SEQ ID NO 29
<211> LENGTH: 46
<212> TYPE: DNA
<213> ORGANISM: Homo sapiens

<400> SEQUENCE: 29
gatcgcggat ccgccatcat gggggccgca cgcagcccgc cgtccg                      46

<210> SEQ ID NO 30
<211> LENGTH: 49
<212> TYPE: DNA
<213> ORGANISM: Homo sapiens

<400> SEQUENCE: 30
gatcgcggat ccccgtccgg aattggttct ggagtgtctg gcatttctg                   49

<210> SEQ ID NO 31
<211> LENGTH: 43
<212> TYPE: DNA
<213> ORGANISM: Homo sapiens

<400> SEQUENCE: 31
gagcgcagat ctgccaccat gtcgctcgtg ctgctaagcc tgg                         43

<210> SEQ ID NO 32
<211> LENGTH: 38
<212> TYPE: DNA
<213> ORGANISM: Homo sapiens

<400> SEQUENCE: 32 gggggagat ctcctcccgg cttgcttttg ttgttatc                              38

<210> SEQ ID NO 33
<211> LENGTH: 11
<212> TYPE: PRT
<213> ORGANISM: Homo sapiens

<400> SEQUENCE: 33

Thr Pro Pro Pro Leu Arg Pro Arg Lys Val Trp
 1               5                  10

<210> SEQ ID NO 34
<211> LENGTH: 705
<212> TYPE: DNA
<213> ORGANISM: Homo sapiens
<220> FEATURE:
<221> NAME/KEY: CDS
<222> LOCATION: (45)..(584)
<220> FEATURE:
<221> NAME/KEY: sig_peptide
<222> LOCATION: (45)..(104)
<220> FEATURE:
<221> NAME/KEY: mat_peptide
<222> LOCATION: (105)..(584)

<400> SEQUENCE: 34
tccaggcggg cagcagctgc aggctgacct tgcagcttgg cgga atg gac tgg cct       56
                                                Met Asp Trp Pro
                                                -20 cac aac ctg ctg ttt ctt ctt acc att tcc atc ttc ctg ggg ctg ggc      104
His Asn Leu Leu Phe Leu Leu Thr Ile Ser Ile Phe Leu Gly Leu Gly
    -15                 -10                 -5                  -1 cag ccc agg agc ccc aaa agc aag agg aag ggg caa ggg cgg cct ggg      152
Gln Pro Arg Ser Pro Lys Ser Lys Arg Lys Gly Gln Gly Arg Pro Gly
 1               5                  10                  15 ccc ctg gcc cct ggc cct cac cag gtg cca ctg gac ctg gtg tca cgg      200
Pro Leu Ala Pro Gly Pro His Gln Val Pro Leu Asp Leu Val Ser Arg
             20                  25                  30 atg aaa ccg tat gcc cgc atg gag gag tat gag agg aac atc gag gag      248
Met Lys Pro Tyr Ala Arg Met Glu Glu Tyr Glu Arg Asn Ile Glu Glu
         35                  40                  45 atg gtg gcc cag ctg agg aac agc tca gag ctg gcc cag aga aag tgt      296
Met Val Ala Gln Leu Arg Asn Ser Ser Glu Leu Ala Gln Arg Lys Cys
     50                  55                  60 gag gtc aac ttg cag ctg tgg atg tcc aac aag agg agc ctg tct ccc      344
Glu Val Asn Leu Gln Leu Trp Met Ser Asn Lys Arg Ser Leu Ser Pro
 65                  70                  75                  80 tgg ggc tac agc atc aac cac gac ccc agc cgt atc ccc gtg gac ctg      392
Trp Gly Tyr Ser Ile Asn His Asp Pro Ser Arg Ile Pro Val Asp Leu
                 85                  90                  95 ccg gag gca cgg tgc ctg tgt ctg ggc tgt gtg aac ccc ttc acc atg      440
Pro Glu Ala Arg Cys Leu Cys Leu Gly Cys Val Asn Pro Phe Thr Met
            100                 105                 110 cag gag gac cgc agc atg gtg agc gtg ccg gtg ttc agc cag gtt cct      488
Gln Glu Asp Arg Ser Met Val Ser Val Pro Val Phe Ser Gln Val Pro
        115                 120                 125 gtg cgc cgc cgc ctc tgc ccg cca ccg ccc cgc aca ggg cct tgc cgc      536

-continued

```
                 Val Arg Arg Arg Leu Cys Pro Pro Pro Arg Thr Gly Pro Cys Arg
                     130             135             140 cag cgc gca gtc atg gag acc atc gct gtg ggc tgc acc tgc atc ttc        584
Gln Arg Ala Val Met Glu Thr Ile Ala Val Gly Cys Thr Cys Ile Phe
145             150             155             160 tgaattacct ggcccagaag ccaggccagc agcccgagac catcctcctt gcacctttgt      644
gccaagaaag gcctatgaaa agtaaacact gactttgaa agcaaaaaaa aaaaaaaaa        704 a                                                                     705

<210> SEQ ID NO 35
<211> LENGTH: 180
<212> TYPE: PRT
<213> ORGANISM: Homo sapiens

<400> SEQUENCE: 35

Met Asp Trp Pro His Asn Leu Leu Phe Leu Leu Thr Ile Ser Ile Phe
-20             -15             -10                  -5

Leu Gly Leu Gly Gln Pro Arg Ser Pro Lys Ser Arg Lys Gly Gln
            -1  1                5               10

Gly Arg Pro Gly Pro Leu Ala Pro Gly Pro His Gln Val Pro Leu Asp
            15              20              25

Leu Val Ser Arg Met Lys Pro Tyr Ala Arg Met Glu Glu Tyr Glu Arg
            30              35              40

Asn Ile Glu Glu Met Val Ala Gln Leu Arg Asn Ser Ser Glu Leu Ala
45              50              55              60

Gln Arg Lys Cys Glu Val Asn Leu Gln Leu Trp Met Ser Asn Lys Arg
            65              70              75

Ser Leu Ser Pro Trp Gly Tyr Ser Ile Asn His Asp Pro Ser Arg Ile
            80              85              90

Pro Val Asp Leu Pro Glu Ala Arg Cys Leu Cys Leu Gly Cys Val Asn
            95              100             105

Pro Phe Thr Met Gln Glu Asp Arg Ser Met Val Ser Val Pro Val Phe
    110             115             120

Ser Gln Val Pro Val Arg Arg Arg Leu Cys Pro Pro Pro Arg Thr
125             130             135             140

Gly Pro Cys Arg Gln Arg Ala Val Met Glu Thr Ile Ala Val Gly Cys
                145             150             155

Thr Cys Ile Phe
            160
```